United States Patent
Fink et al.

(10) Patent No.: US 10,744,150 B2
(45) Date of Patent: Aug. 18, 2020

(54) CYCLIC DINUCLEOTIDES AS ANTICANCER AGENTS

(71) Applicant: BRISTOL-MYERS SQUIBB COMPANY, Princeton, NJ (US)

(72) Inventors: Brian E. Fink, Yardley, PA (US); Dharmpal S. Dodd, Monmouth Junction, NJ (US); Lan-ying Qin, Plainsboro, NJ (US); Zheming Ruan, Dayton, NJ (US); Yufen Zhao, Pennington, NJ (US); Lalgudi S. Harikrishnan, Skillman, NJ (US); Muthoni G. Kamau, Lawrenceville, NJ (US); Steven J. Walker, Portage, MI (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/047,071

(22) Filed: Jul. 27, 2018

(65) Prior Publication Data

US 2019/0030057 A1    Jan. 31, 2019

Related U.S. Application Data

(60) Provisional application No. 62/538,329, filed on Jul. 28, 2017.

(51) Int. Cl.

| | |
|---|---|
| C07H 19/20 | (2006.01) |
| C07H 19/23 | (2006.01) |
| C07H 19/207 | (2006.01) |
| C07H 19/14 | (2006.01) |
| C07H 21/04 | (2006.01) |
| A61K 31/7084 | (2006.01) |
| A61P 35/02 | (2006.01) |
| A61P 35/00 | (2006.01) |
| A61K 45/06 | (2006.01) |

(52) U.S. Cl.
CPC .......... *A61K 31/7084* (2013.01); *A61K 45/06* (2013.01); *A61P 35/00* (2018.01); *A61P 35/02* (2018.01); *C07H 19/14* (2013.01); *C07H 19/20* (2013.01); *C07H 19/207* (2013.01); *C07H 19/23* (2013.01); *C07H 21/04* (2013.01)

(58) Field of Classification Search
CPC ...... C07H 19/20; C07H 19/23; C07H 19/207; C07H 19/14; C07H 21/04
See application file for complete search history.

(56) References Cited

U.S. PATENT DOCUMENTS 7,709,458 B2    5/2010    Karaolis et al.
2008/0286296 A1    11/2008    Ebensen et al.

FOREIGN PATENT DOCUMENTS

| WO | WO 2014/189805 A1 | 11/2014 |
| WO | WO 2015/185565 A1 | 12/2015 |
| WO | WO 2016/096174 A1 | 6/2016 |

OTHER PUBLICATIONS

Vargas et al. Eur. J. Cancer. 2017, 75, 86-97 (Year: 2017).*

(Continued)

*Primary Examiner* — Matthew P Coughlin
(74) *Attorney, Agent, or Firm* — Elliott Korsen

(57) ABSTRACT

The present invention is directed to compounds of the formulae I, II and III as shown below

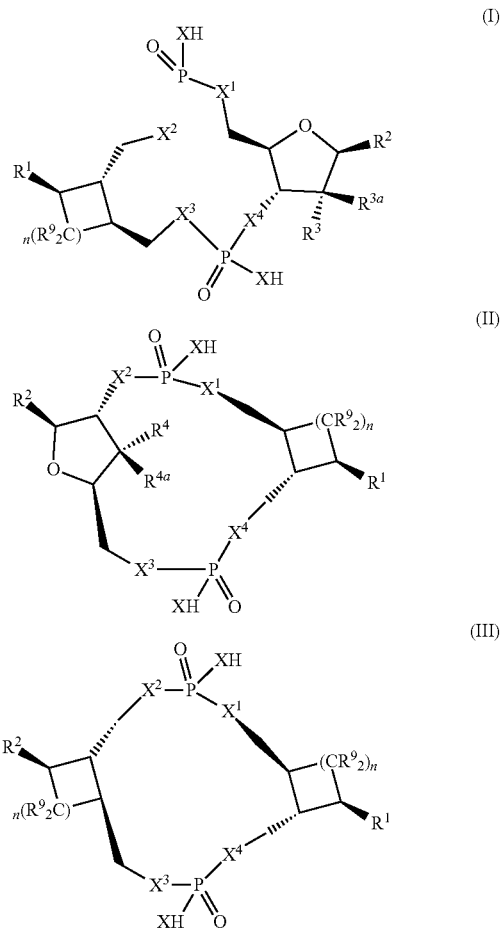

wherein all substituents are defined herein, as well as pharmaceutically acceptable compositions comprising compounds of the invention and methods of using said compositions in the treatment of various disorders.

54 Claims, No Drawings
Specification includes a Sequence Listing.

(56) References Cited

OTHER PUBLICATIONS

Luo et al. Cell, 2009, 136, pp. 823-837 (Year: 2009).*
U.S. Appl. No. 62/552,680, filed Aug. 31, 2017, Expired.
PCT/US2018/048666, Filing date: Aug. 30, 2018, Pending.
U.S. Appl. No. 62/552,689, filed Aug. 31, 2017, Expired.
PCT/US2018/048662, Filing date: Aug. 30, 2018, Pending.
U.S. Appl. No. 62/552,701, filed Aug. 31, 2017, Expired.
PCT/US2018/048658, Filing date: Aug. 30, 2018, Pending.
U.S. Appl. No. 62/570,386, filed Oct. 10, 2017, Expired.
PCT/US2018/054944, Filing date: Sep. 10, 2018, Pending.
U.S. Appl. No. 62/572,884, filed Oct. 16, 2017, Expired.
PCT/US2018/056030, Filing date: Oct. 16, 2018, Pending.
U.S. Appl. No. 62/277,273, filed Jan. 11, 2016, Expired.
U.S. Appl. No. 62/436,759, filed Dec. 20, 2016, Expired.
U.S. Appl. No. 62/436,795, filed Dec. 20, 2016, Expired.
U.S. Appl. No. 15/748,685, filed Jan. 30, 2018, Pending.
U.S. Appl. No. 16/069,201, filed Jul. 11, 2018, Pending.
PCT/US2017/013066, Filing date: Jan. 11, 2017, Published.
PCT/US2017/013049, Filing date: Jan. 11, 2017, Published.
U.S. Appl. No. 62/640,325, filed Mar. 8, 2018, Pending.
U.S. Appl. No. 62/629,956, filed Feb. 13, 2018, Pending.

* cited by examiner

CYCLIC DINUCLEOTIDES AS ANTICANCER AGENTS

CROSS-REFERENCE TO RELATED APPLICATIONS

This application claims the benefit of U.S. Provisional Application No. 62/538,329, filed Jul. 28, 2017, the disclosure of which is incorporated herein by reference in its entirety.

FIELD OF THE INVENTION

The invention provides novel compounds, pharmaceutical compositions comprising the compounds, and methods of using them, for example, for the treatment or prophylaxis of certain cancers and to their use in therapy.

BACKGROUND OF THE INVENTION

Immunotherapy is a rapidly expanding area of medical treatment in which a patient's immune system is deliberately activated, suppressed or otherwise modulated for a positive therapeutic effect. Immunotherapy agents include such things as cells, antigens, antibodies, nucleic acids, proteins, peptides, naturally occurring ligands and synthetically prepared molecules. Cytokines are small glycoprotein molecules known for their role in causing immune response through complex signaling networks. Cytokines have been explored as immunotherapy agents but their direct administration is hampered by many factors including their short half-life in blood which can only be compensated with frequent and often high doses. One highly promising approach is cytokine induction in which the patient is treated with an immunomodulatory agent that triggers the production of one or more therapeutically beneficial cytokines in their body.

One agent in the production of cytokines is the adaptor protein STING (STimulator of INterferon Genes; also known as MPYS, TMEM173, MITA and ERIS). STING is an intracellular receptor situated on the endoplasmic reticulum. The binding to STING by an agonist activates a signaling pathway culminating in the induction of Type I IFNs, which are secreted and protect the secreting and nearby cells. STING can be activated by two different pathways, each involving a different type of cyclic dinucleotide ("CDN") agonist. In the first pathway, the agonist is an exogenous CDN used by bacterial pathogens as a second messenger (Burdette et al. 2013). In the second pathway the enzyme cyclic GMP-AMP synthase (cGAS) detects cytosolic DNA and, in response, synthesizes a CDN that functions as an endogenous STING agonist (Ablasser et al. 2013; Gao et al. 2013; Sun et al. 2013).

Activation of STING results in up-regulation of IRF3 and NF-κB pathways leading to induction of Interferon-3 and other cytokines. STING is crucial for responses to cytosolic DNA of pathogen or host origin.

Two exogenous bacterial STING agonist CDNs are 3'3'-cGAMP and c-GMP. The endogenous STING agonist CDN made by cGAS is 2'3'-cGAMP. The bacterial CDNs are characterized by two 3'5' phosphodiester bridges, while the cGAS-produced CDN is characterized by one 2'5' and one 3'5' phosphodiester bridge. As a shorthand, the former CDNs are referred to as 3'3' CDNs and the latter as 2'3' CDNs. For historical reasons, 3'3' CDNs also are referred to as the "canonical" form and 2'3' CDNs are referred to as the "non-canonical" form.

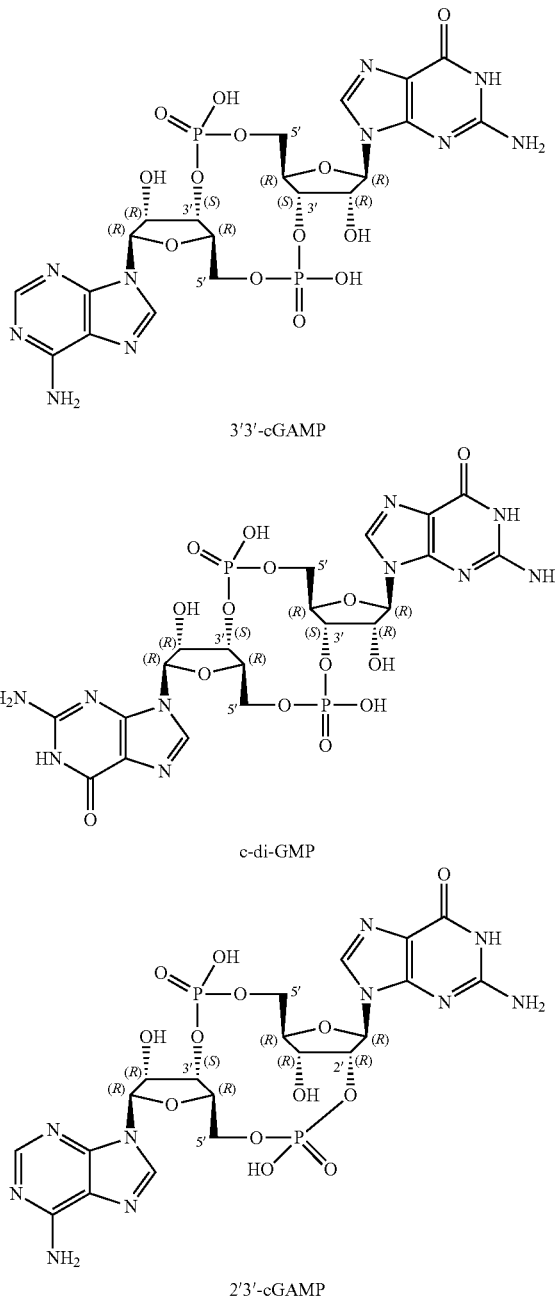

3'3'-cGAMP c-di-GMP

2'3'-cGAMP

In addition to protecting an organism against pathogen infection, STING activation has also been reported to be beneficial in the treatment of inflammatory diseases and, in an area of particular current interest, cancer. Administration of a synthetic CDN in combination with the cancer vaccine STINGVAX demonstrated enhanced antitumor efficacy in multiple therapeutic models (Fu et al. 2015). Administration of STING agonists alone has been reported to show potent antitumor immune efficacy in a mouse model (Corrales et al. 2015a). For reviews on the role of STING in infection, inflammation, and/or cancer, see Ahn et al. 2015; Corrales et al. 2015b and 2016; and Barber 2015.

The present invention, therefore, provides novel cyclic dinucleotides which may be useful for the treatment of cancer.

SUMMARY OF THE INVENTION

There are provided compounds of formulae (I), (II) and (III)

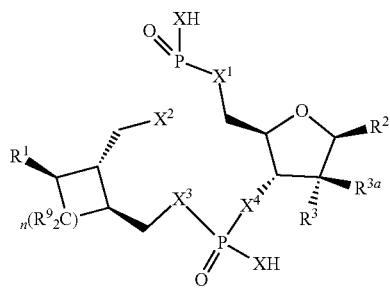

(I)

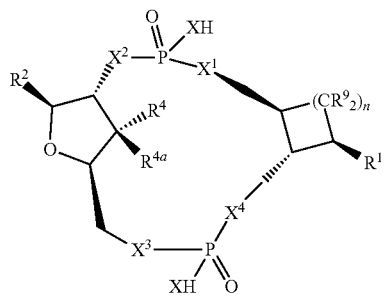

(II)

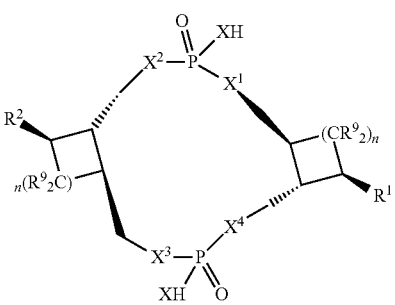

(III)

wherein all substituents are defined herein.

In another aspect, there is provided a pharmaceutical composition comprising a compound of the invention or a pharmaceutically acceptable salt thereof and one or more pharmaceutically acceptable carriers, diluents or excipients.

In another aspect, there is provided a method of treating cancer which comprises administering to a subject in need thereof a therapeutically effective amount of an activator of STING (of Formula I).

DETAILED DESCRIPTION OF THE INVENTION

The following are aspects and embodiments of the present invention, as well as additional aspects and embodiments that can be within the scope of those shown. The aspects of the invention are not limited to those described below.

A compound of formula I

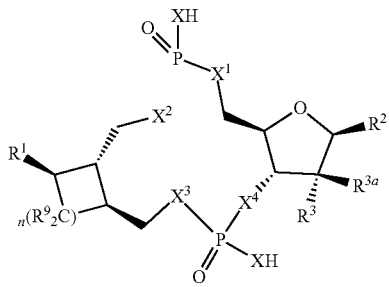

(I)

wherein
X is O or S;
$X^1$, $X^2$, $X^3$ and $X^4$ are each independently O or NH;
$R^1$ and $R^2$ are independently

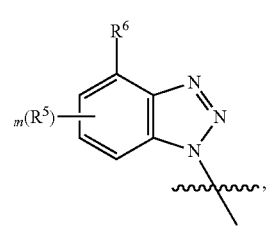

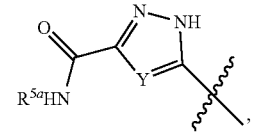

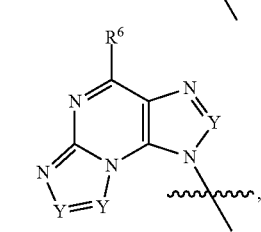

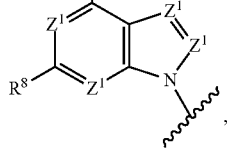

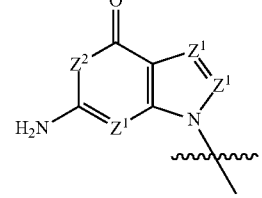

or $Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;
$R^{a1}$ is H or $C_{1-3}$ alkyl;
$R^3$ is H, $CH_3$, halogen, $NH_2$ or OH;
$R^{3a}$ is H, $CH_3$, halogen, $NH_2$ or OH; or
$R^3$ and $R^{3a}$ may be taken together to form a 3-4 membered carbocycle; or
$R^3$ and $R^{3a}$ may be taken together to form a $C=CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^5$ or N;

m is 0, 1, 2 or 3;

n is 0 or 1; when n=0, the ring is a 3-membered cyclopropyl ring;

or a pharmaceutically acceptable salt, tautomer or stereoisomer thereof.

The compound according to formula I wherein
$R^1$ is

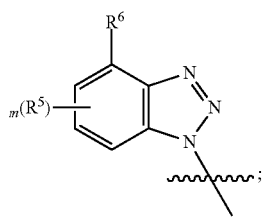

$R^2$ is

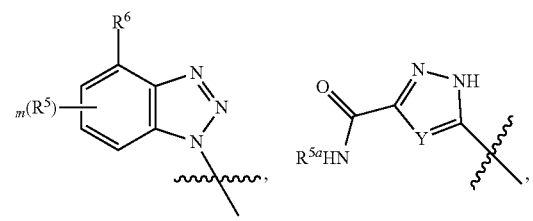

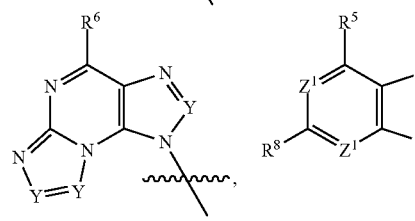

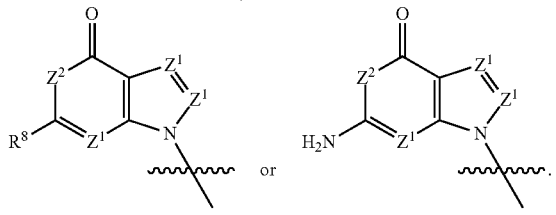

The compound according to formula I wherein
$R^1$ is

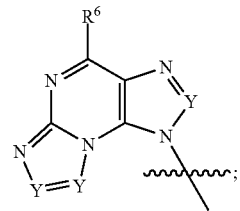

$R^2$ is

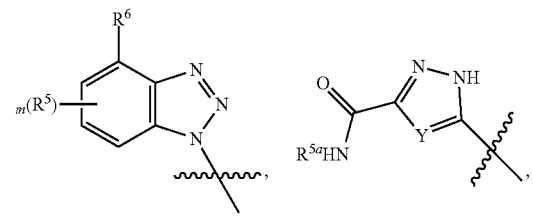

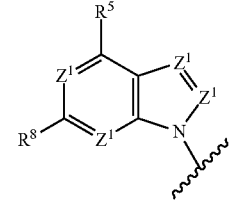

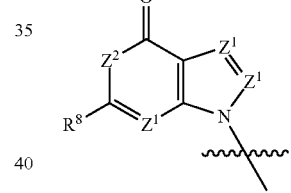

The compound according to formula I wherein
$R^1$ is

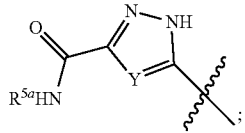

and
$R^2$ is

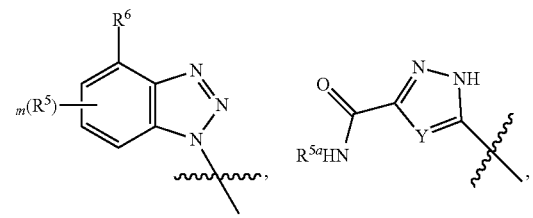

-continued
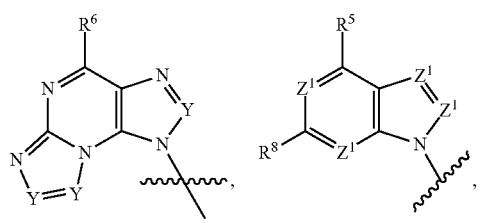
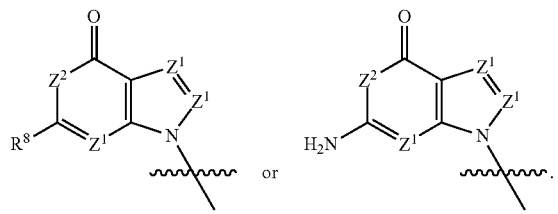
The compound according to formula I wherein R¹ is
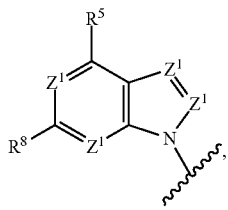
and
R² is
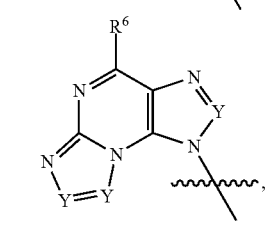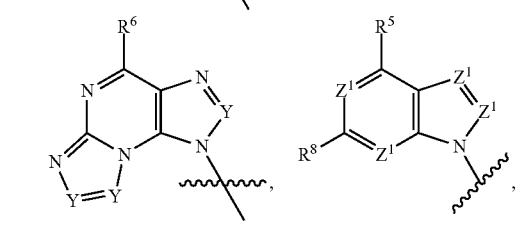
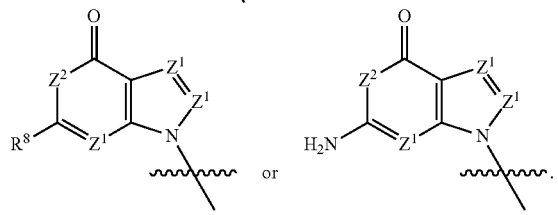
The compound according to formula I wherein R¹ is
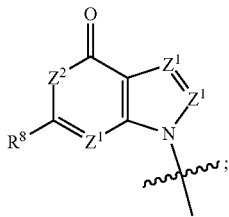
and
R² is
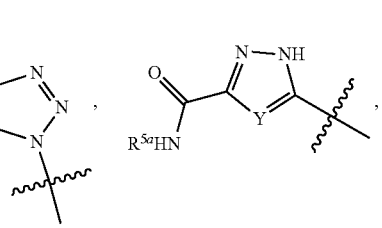
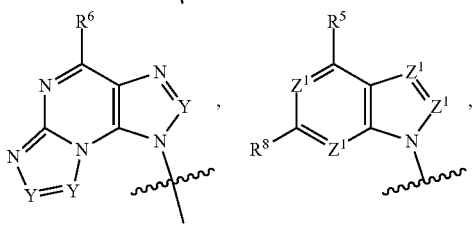
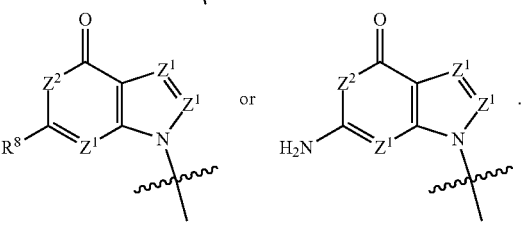
The compound according to formula I wherein R¹ is
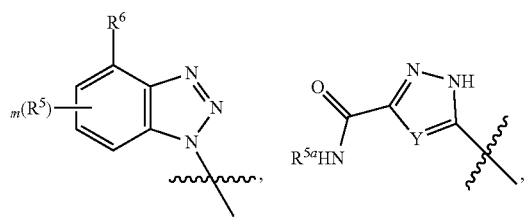
and
R² is
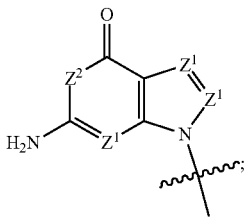
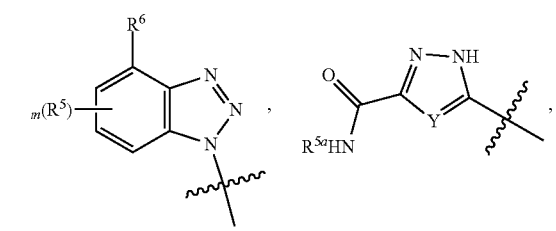

-continued
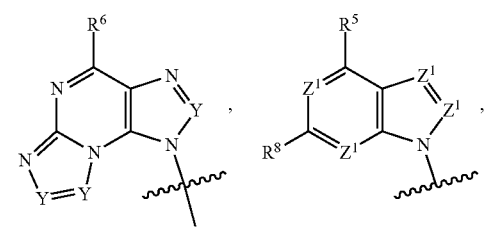
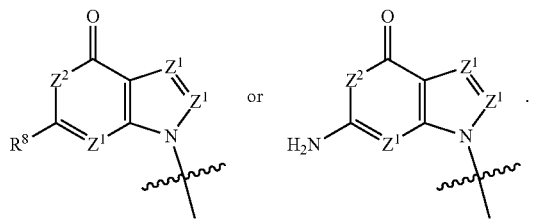 or
The compound according to formula I wherein R¹ is
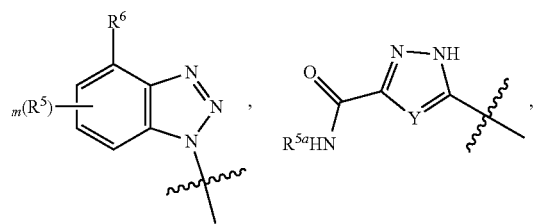
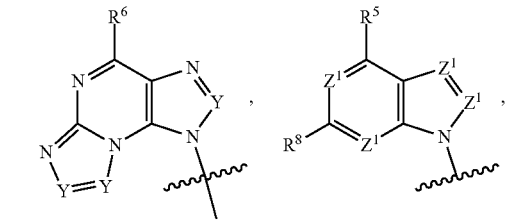
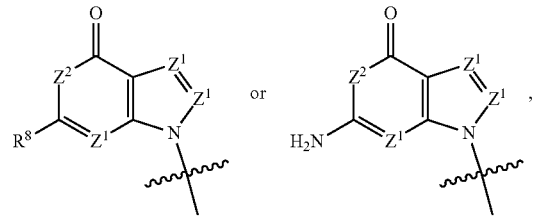 or ,
R² is
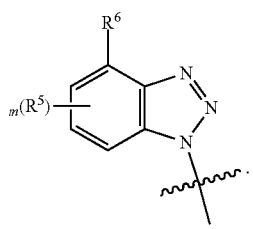.
The compound according to formula I wherein R¹ is
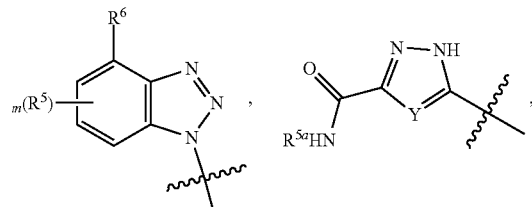,
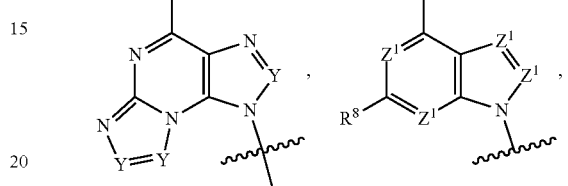,
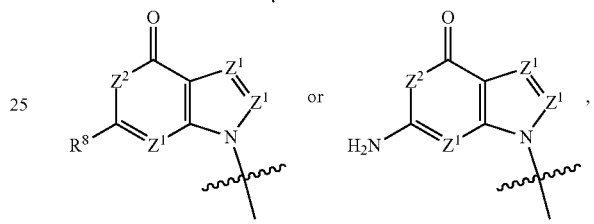 or ,
and
R² is
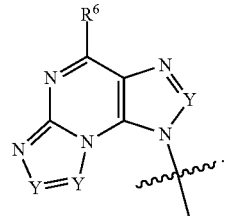.
The compound according to formula I wherein R¹ is
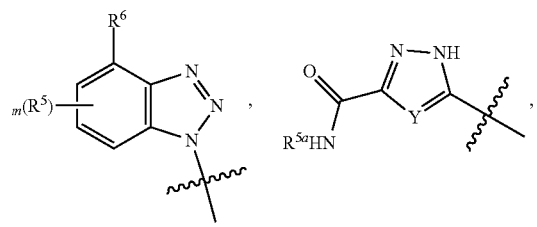,
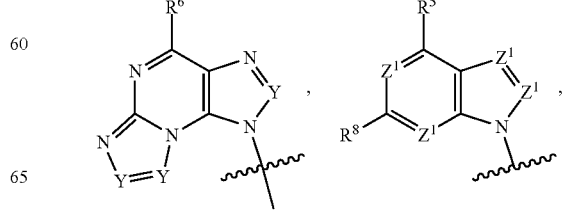, -continued
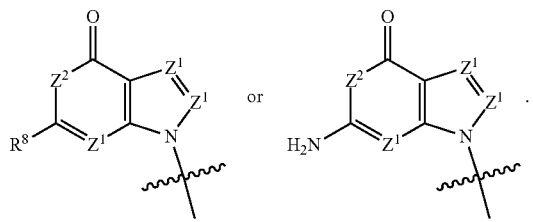
and
R² is
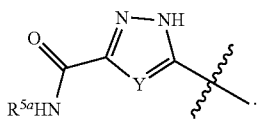
The compound according to formula I wherein
R¹ is
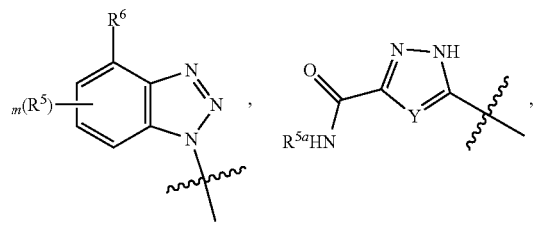
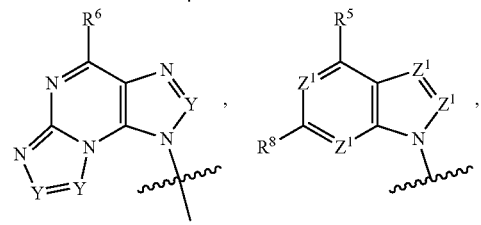
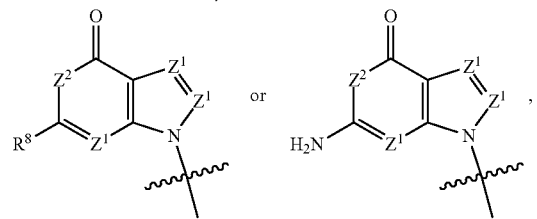
and
R² is
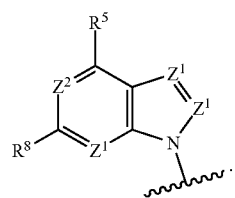
The compound according to formula I wherein
R¹ is
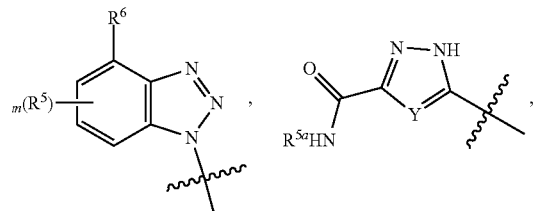
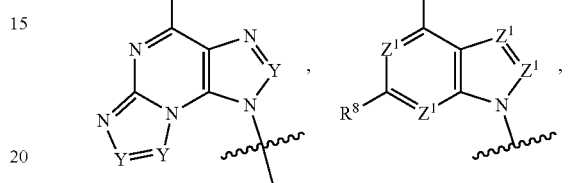
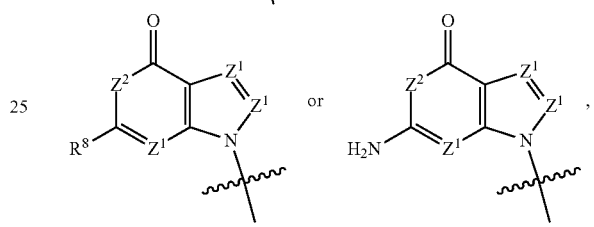
and
R² is
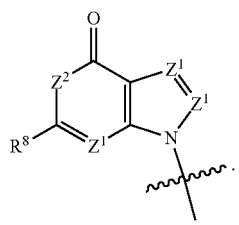
The compound according to formula I wherein
R¹ is
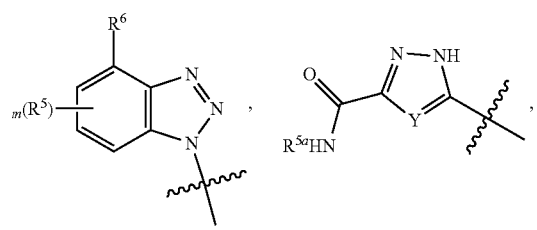
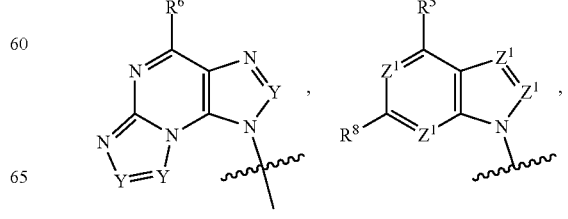

13

-continued

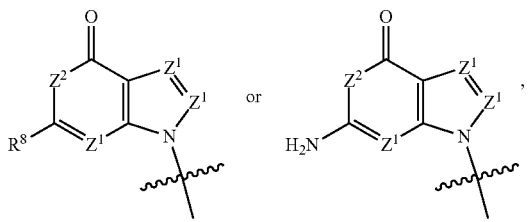

and

R² is

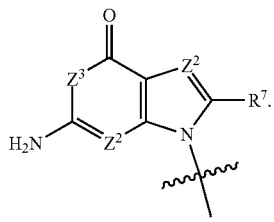

The compound of the formula

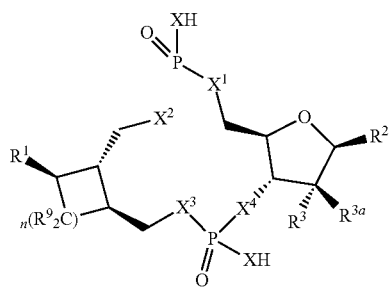         (I)

wherein

X is S;

X¹, X², X³ and X⁴ are each independently O or NH;

R¹ and R² are independently

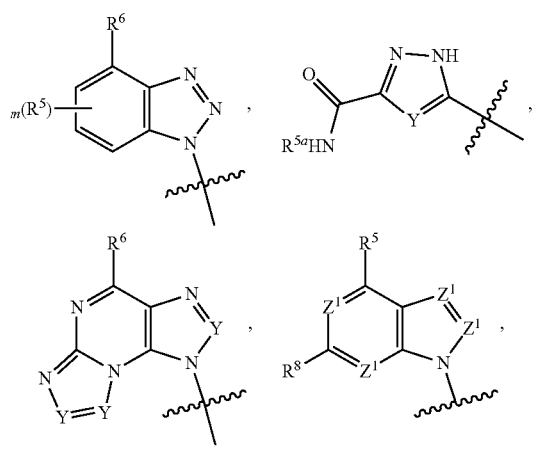

14

-continued

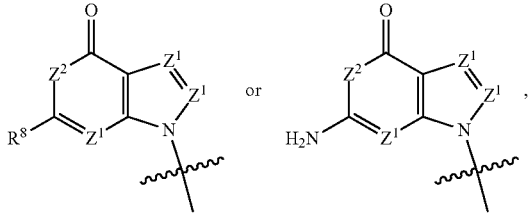

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2$$R^{a1}$, —$NR^{a1}$S(O)$_2$$NR^{a1}R^{a1}$, —S(O)$R^{a1}$, —S(O)$NR^{a1}R^{a1}$, —S(O)$_2$$R^{a1}$ or S(O)$_2$$NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2$$R^{a1}$ or S(O)$_2$$NR^{a1}R^{a1}$;

$R^{a1}$ is H or $C_{1-3}$ alkyl;

$R^3$ is H, $CH_3$, halogen, $NH_2$ or OH;

$R^{3a}$ is H, $CH_3$, halogen, $NH_2$ or OH; or $R^3$ and $R^{3a}$ may be taken together to form a 3-4 membered carbocycle; or $R^3$ and $R^{3a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2$$R^{a1}$, —$NR^{a1}$S(O)$_2$$NR^{a1}R^{a1}$, —S(O)$R^{a1}$, —S(O)$NR^{a1}R^{a1}$, —S(O)$_2$$R^{a1}$ or S(O)$_2$$NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2$$R^{a1}$, —$NR^{a1}$S(O)$_2$$NR^{a1}R^{a1}$, —S(O)$R^{a1}$, —S(O)$NR^{a1}R^{a1}$, —S(O)$_2$$R^{a1}$ or S(O)$_2$$NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2$$R^{a1}$, —$NR^{a1}$S(O)$_2$$NR^{a1}R^{a1}$, —S(O)$R^{a1}$, —S(O)$NR^{a1}R^{a1}$, —S(O)$_2$$R^{a1}$ or S(O)$_2$$NR^{a1}R^{a1}$;

$R^9$ is H, halogen or methyl;

Y is $CR^5$ or N;

m is 0, 1, 2 or 3;

n is 0 or 1; when n=0, the ring is a 3-membered cyclopropyl ring;

or a pharmaceutically acceptable salt, tautomer or stereoisomer thereof.

The compound of the formula

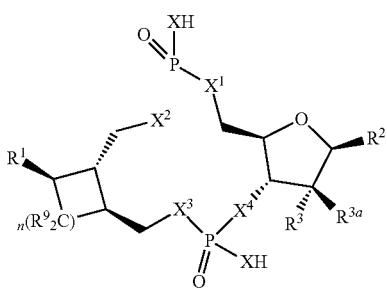

(I)

wherein
X is O;
X¹, X², X³ and X⁴ are each independently O or NH;
R¹ and R² are independently

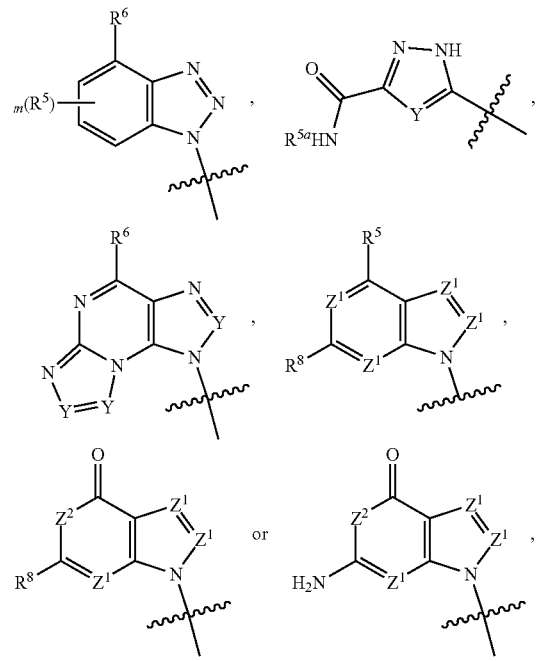

Z¹ is N or CR$^a$;
Z² is NR$^b$;
R$^a$ is H, halogen, C$_{1-6}$ alkyl substituted with 0-6 R⁵, C$_{3-6}$ cycloalkyl substituted with 0-6 R⁵, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^b$ is H, C$_{1-6}$ alkyl substituted with 0-6 R⁵, C$_{3-6}$ cycloalkyl substituted with 0-6 R⁵, —C(O)R$^{a1}$, —C(O)NR$^{a1}$R$^{a1}$, —S(O)$_2$R$^{a1}$ or S(O)$_2$NR$^{a1}$R$^{a1}$;
R$^{a1}$ is H or C$_{1-3}$ alkyl;
R³ is H, CH$_3$, halogen, NH$_2$ or OH;
R$^{3a}$ is H, CH$_3$, halogen, NH$_2$ or OH; or
R³ and R$^{3a}$ may be taken together to form a 3-4 membered carbocycle; or
R³ and R$^{3a}$ may be taken together to form a C=CH$_2$ substituent;

R⁵ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^{5a}$ is H or C$_{1-3}$ alkyl;
R⁶ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R⁸ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R⁹ is H, halogen or methyl;
Y is CR⁵ or N;
m is 0, 1, 2 or 3;
n is 0 or 1; when n=0, the ring is a 3-membered cyclopropyl ring;
or a pharmaceutically acceptable salt, tautomer or stereoisomer thereof.

The compound of the formula

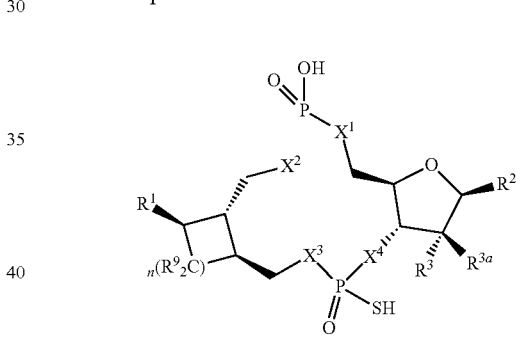

wherein
X¹, X², X³ and X⁴ are each independently O or NH;
R¹ and R² are independently

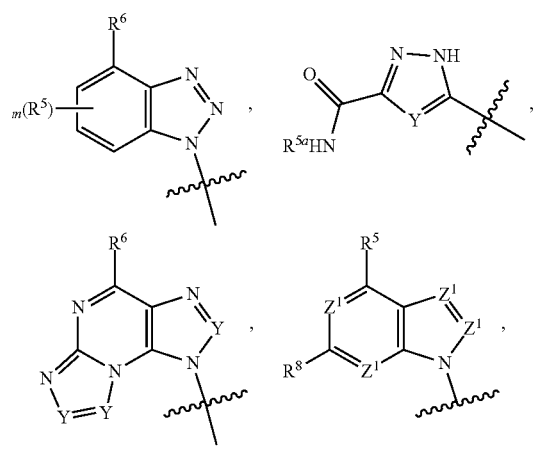

17

-continued $Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H or $C_{1-3}$ alkyl;

$R^3$ is H, $CH_3$, halogen, $NH_2$ or OH;

$R^{3a}$ is H, $CH_3$, halogen, $NH_2$ or OH; or $R^3$ and $R^{3a}$ may be taken together to form a 3-4 membered carbocycle; or $R^3$ and $R^{3a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^5$ or N;

m is 0, 1, 2 or 3;

n is 0 or 1; when n=0, the ring is a 3-membered cyclopropyl ring;

or a pharmaceutically acceptable salt, tautomer or stereoisomer thereof.

18

The compound of the formula wherein $X^1$, $X^2$, $X^3$ and $X^4$ are each independently O or NH;

$R^1$ and $R^2$ are independently $Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H or $C_{1-3}$ alkyl;

$R^3$ is H, $CH_3$, halogen, $NH_2$ or OH;

$R^{3a}$ is H, $CH_3$, halogen, $NH_2$ or OH; or $R^3$ and $R^{3a}$ may be taken together to form a 3-4 membered carbocycle; or $R^3$ and $R^{3a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1; when n=0, the ring is a 3-membered cyclopropyl ring;

or a pharmaceutically acceptable salt, tautomer or stereoisomer thereof.

The compound of the formula

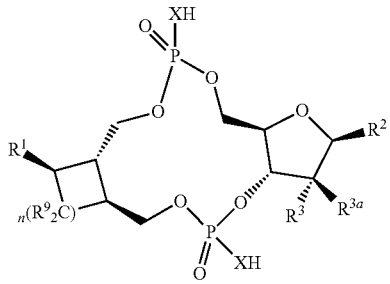

wherein

X is O or S;

R$^1$ and R$^2$ are independently

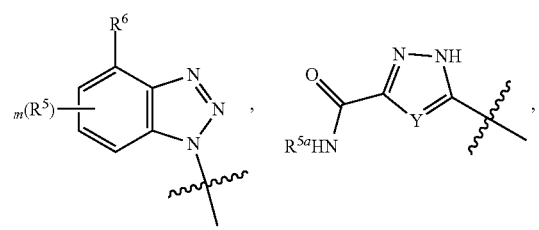

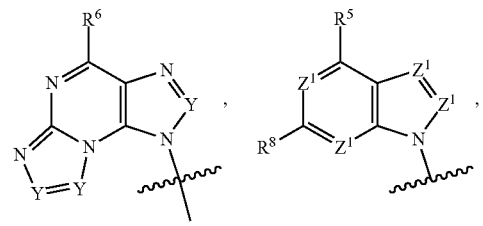

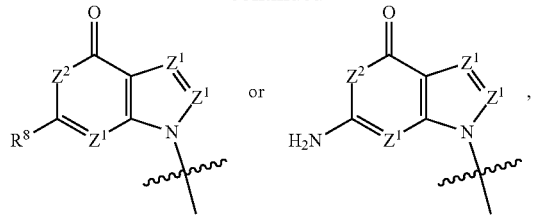

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^3$ is H, CH$_3$, halogen, NH$_2$ or OH;

R$^{3a}$ is H, CH$_3$, halogen, NH$_2$ or OH; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

Y is CH or N;

m is 0, 1, 2 or 3;

n is 0 or 1; when n=0, the ring is a 3-membered cyclopropyl ring;

or a pharmaceutically acceptable salt, tautomer or stereoisomer thereof.

The compound of the formula

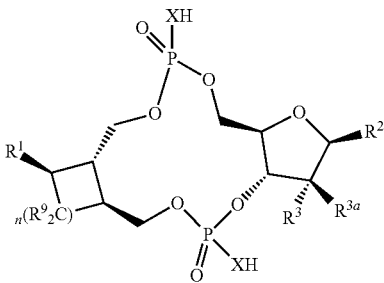

wherein
X is O or S;
$R^1$ and $R^2$ are independently

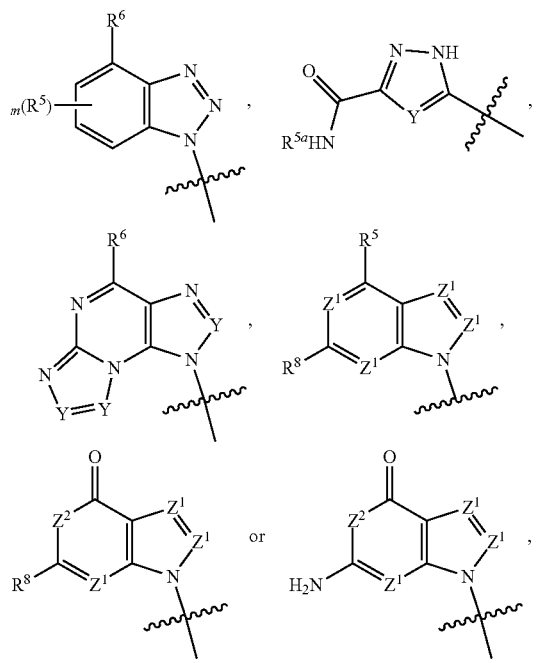

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —NR$^{a1}R^{a1}$, —NR$^{a1}$C(O)$R^{a1}$, —NR$^{a1}$COOR$^{a1}$, —NR$^{a1}$C(O)NR$^{a1}R^{a1}$, —NR$^{a1}$S(O)$_2R^{a1}$, —NR$^{a1}$S(O)$_2$NR$^{a1}R^{a1}$, —S(O)$R^{a1}$, —S(O)NR$^{a1}R^{a1}$, —S(O)$_2R^{a1}$ or S(O)$_2$NR$^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)NR$^{a1}R^{a1}$, —S(O)$_2R^{a1}$ or S(O)$_2$NR$^{a1}R^{a1}$;
$R^{a1}$ is H or $C_{1-3}$ alkyl;
$R^3$ is F;
$R^5$ is H, halogen, $C_{1-3}$ alkyl, CN, $NO_2$, OH, $OR^{a1}$, $SR^{a1}$, —C(O)NR$^{a1}R^{a1}$, —COOR$^{a1}$, —OC(O)$R^{a1}$, —OC(O)NR$^{a1}R^{a1}$, —NR$^{a1}R^{a1}$, —NR$^{a1}$C(O)$R^{a1}$, —NR$^{a1}$COOR$^{a1}$, —NR$^{a1}$C(O)NR$^{a1}R^{a1}$, —NR$^{a1}$S(O)$_2R^{a1}$, —NR$^{a1}$S(O)$_2$NR$^{a1}R^{a1}$, —S(O)$R^{a1}$, —S(O)NR$^{a1}R^{a1}$, —S(O)$_2R^{a1}$ or S(O)$_2$NR$^{a1}R^{a1}$;

$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)NR$^{a1}R^{a1}$, —COOR$^{a1}$, —OC(O)$R^{a1}$, —OC(O)NR$^{a1}R^{a1}$, —NR$^{a1}R^{a1}$, —NR$^{a1}$C(O)$R^{a1}$, —NR$^{a1}$COOR$^{a1}$, —NR$^{a1}$C(O)NR$^{a1}R^{a1}$, —NR$^{a1}$S(O)$_2R^{a1}$, —NR$^{a1}$S(O)$_2$NR$^{a1}R^{a1}$, —S(O)$R^{a1}$, —S(O)NR$^{a1}R^{a1}$, —S(O)$_2R^{a1}$ or S(O)$_2$NR$^{a1}R^{a1}$;
$R^8$ is H, halogen, $C_{1-3}$ alkyl, CN, $NO_2$, OH, $OR^{a1}$, $SR^{a1}$, —C(O)NR$^{a1}R^{a1}$, —COOR$^{a1}$, —OC(O)$R^{a1}$, —OC(O)NR$^{a1}R^{a1}$, —NR$^{a1}R^{a1}$, —NR$^{a1}$C(O)$R^{a1}$, —NR$^{a1}$COOR$^{a1}$, —NR$^{a1}$C(O)NR$^{a1}R^{a1}$, —NR$^{a1}$S(O)$_2R^{a1}$, —NR$^{a1}$S(O)$_2$NR$^{a1}R^{a1}$, —S(O)$R^{a1}$, —S(O)NR$^{a1}R^{a1}$, —S(O)$_2R^{a1}$ or S(O)$_2$NR$^{a1}R^{a1}$;
$R^9$ is H, halogen or methyl;
Y is $CR^5$ or N;
m is 0, 1, 2 or 3;
n is 0 or 1; when n=0, the ring is a 3-membered cyclopropyl ring;
or a pharmaceutically acceptable salt, tautomer or stereoisomer thereof.

The compound of the formula

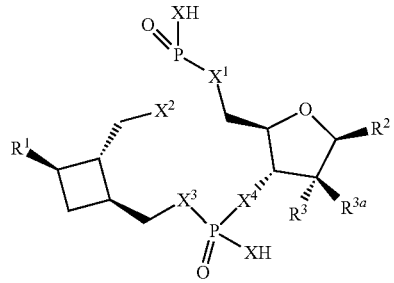

wherein
X is O or S;
$X^1$, $X^2$, $X^3$ and $X^4$ are each independently O or NH;
$R^1$ and $R^2$ are independently

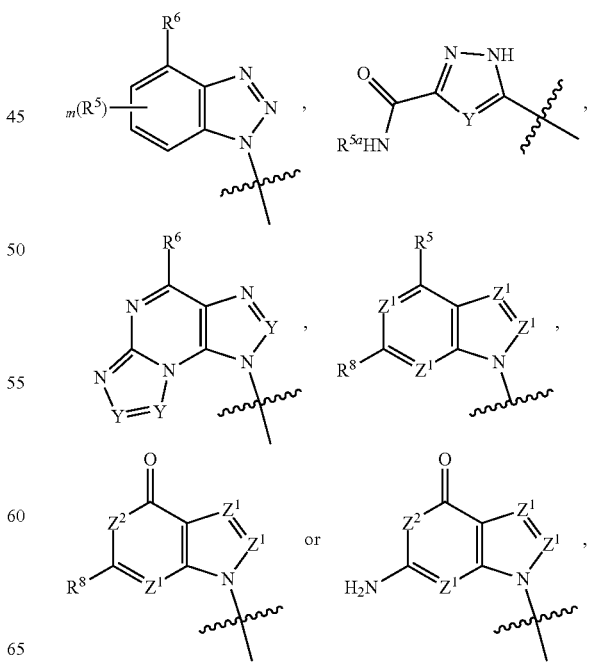

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;

$R^{a1}$ is H or $C_{1-3}$ alkyl;

$R^3$ is H, $CH_3$, halogen, $NH_2$ or OH;

$R^{3a}$ is H, $CH_3$, halogen, $NH_2$ or OH; or $R^3$ and $R^{3a}$ may be taken together to form a 3-4 membered carbocycle; or $R^3$ and $R^{3a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

Y is $CR^5$ or N;

m is 0, 1, 2 or 3;

or a pharmaceutically acceptable salt, tautomer or stereoisomer thereof.

The compound of the formula

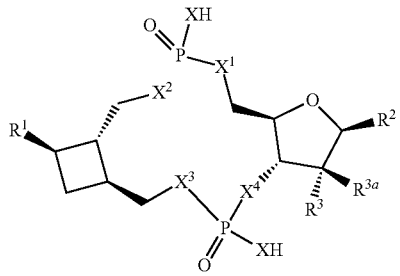

(I)

wherein

X is S;

$X^1$, $X^2$, $X^3$ and $X^4$ are each independently O or NH;

$R^1$ and $R^2$ are independently

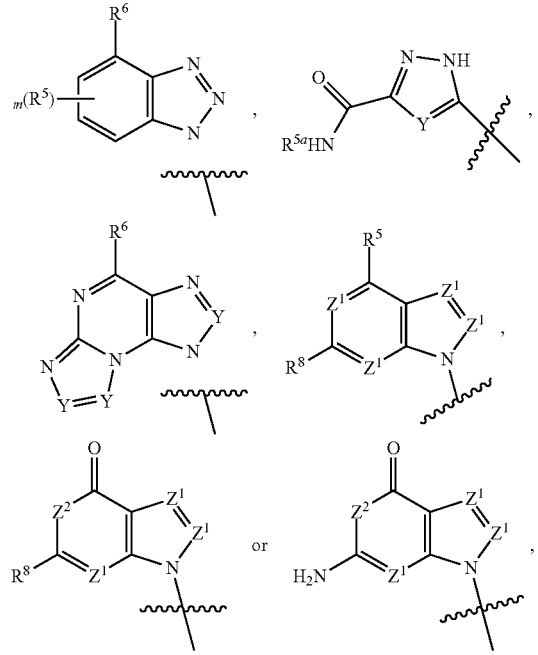

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;

$R^{a1}$ is H or $C_{1-3}$ alkyl;

$R^3$ is H, $CH_3$, halogen, $NH_2$ or OH;

$R^{3a}$ is H, $CH_3$, halogen, $NH_2$ or OH; or $R^3$ and $R^{3a}$ may be taken together to form a 3-4 membered carbocycle; or $R^3$ and $R^{3a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

Y is $CR^5$ or N;

m is 0, 1, 2 or 3;

or a pharmaceutically acceptable salt, tautomer or stereoisomer thereof.

The compound of the formula

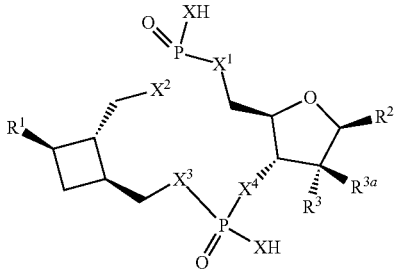

wherein

X is O;

X$^1$, X$^2$, X$^3$ and X$^4$ are each independently O or NH;

R$^1$ and R$^2$ are independently

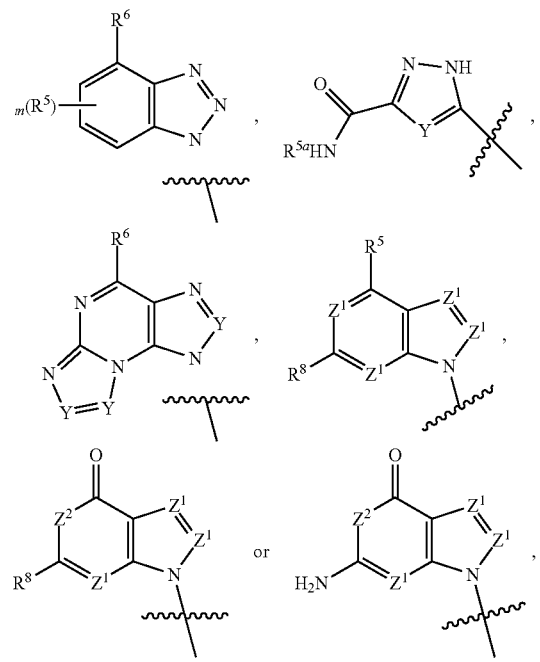

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^3$ is H, CH$_3$, halogen, NH$_2$ or OH;

R$^{3a}$ is H, CH$_3$, halogen, NH$_2$ or OH; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

The compound of the formula

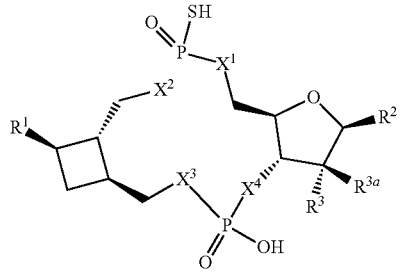

wherein

X$^1$, X$^2$, X$^3$ and X$^4$ are each independently O or NH;

R$^1$ and R$^2$ are each independently

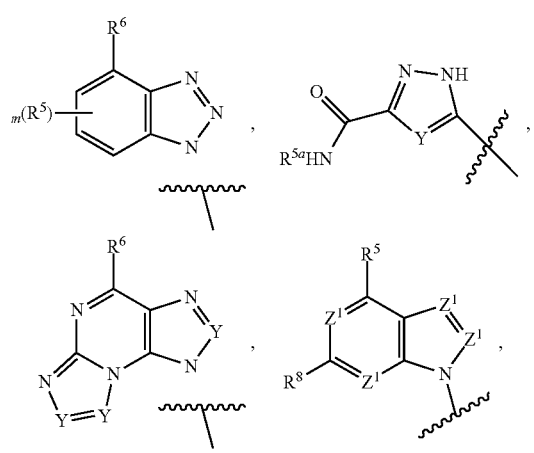

-continued

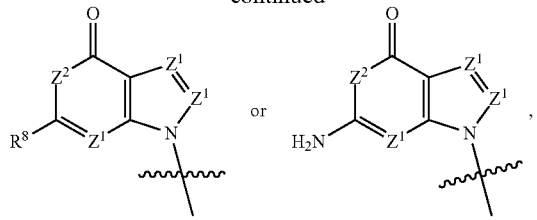

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;
$R^{a1}$ is H or $C_{1-3}$ alkyl;
$R^3$ is H, $CH_3$, halogen, $NH_2$ or OH;
$R^{3a}$ is H, $CH_3$, halogen, $NH_2$ or OH; or
$R^3$ and $R^{3a}$ may be taken together to form a 3-4 membered carbocycle; or
$R^3$ and $R^{3a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
Y is $CR^5$ or N;
m is 0, 1, 2 or 3;
or a pharmaceutically acceptable salt, tautomer or stereoisomer thereof.

The compound of the formula

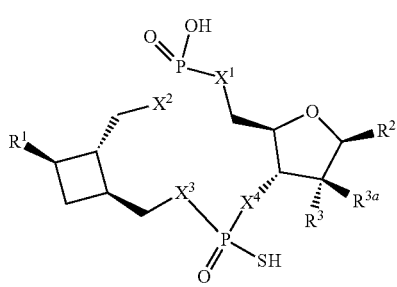

wherein
$X^1$, $X^2$, $X^3$ and $X^4$ are each independently O or NH;

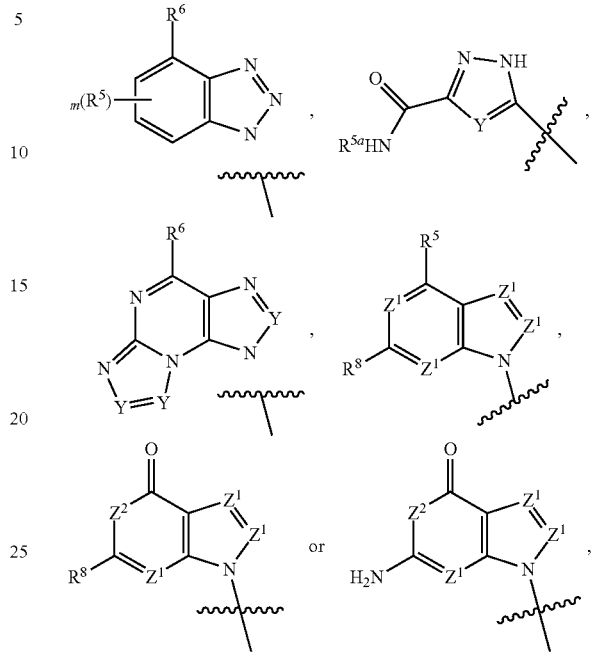

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;
$R^{a1}$ is H or $C_{1-3}$ alkyl;
$R^3$ is H, $CH_3$, halogen, $NH_2$ or OH;
$R^{3a}$ is H, $CH_3$, halogen, $NH_2$ or OH; or
$R^3$ and $R^{3a}$ may be taken together to form a 3-4 membered carbocycle; or
$R^3$ and $R^{3a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

Y is CR⁵ or N;

m is 0, 1, 2 or 3;

or a pharmaceutically acceptable salt, tautomer or stereoisomer thereof.

The compound of the formula

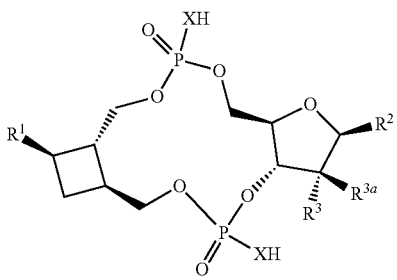

wherein

X is O or S;

R¹ and R² are each independently

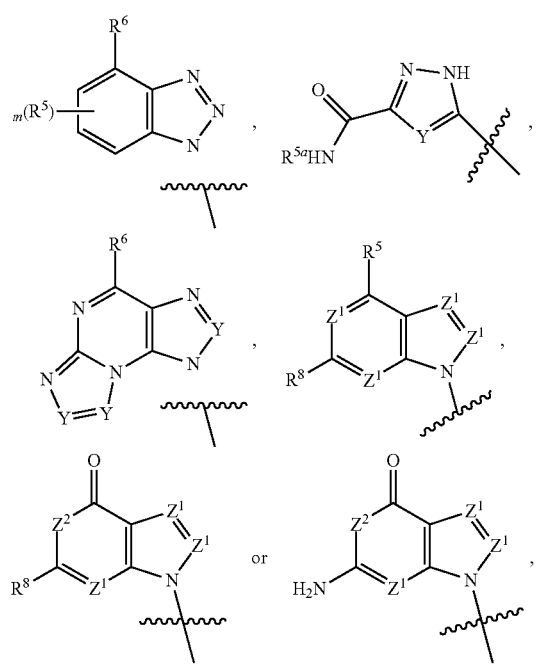

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^b$ is H, substituted with 0-6 $R^5$, $C_{3-6}$ cycloalkyl substituted with 0-6 $R^5$, —C(O)R$^{a1}$, —C(O)NR$^{a1}$R$^{a1}$, -, —S(O)$_2$R$^{a1}$ or S(O)$_2$NR$^{a1}$R$^{a1}$;

$R^{a1}$ is H or $C_{1-3}$ alkyl;

R³ is H, CH₃, halogen, NH₂ or OH;

R³ᵃ is H, CH₃, halogen, NH₂ or OH; or

R³ and R³ᵃ may be taken together to form a 3-4 membered carbocycle; or

R³ and R³ᵃ may be taken together to form a C=CH₂ substituent;

$R^5$ is H, halogen, $C_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^{5a}$ is H or $C_{1-3}$ alkyl;

$R^6$ is H, halogen, $C_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^8$ is H, halogen, $C_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR⁵ or N;

m is 0, 1, 2 or 3;

or a pharmaceutically acceptable salt, tautomer or stereoisomer thereof.

The compound of the formula

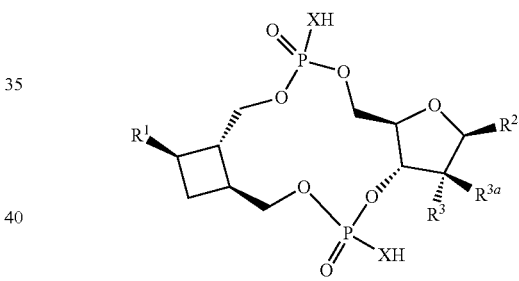

wherein

X is S;

R¹ and R² are each independently

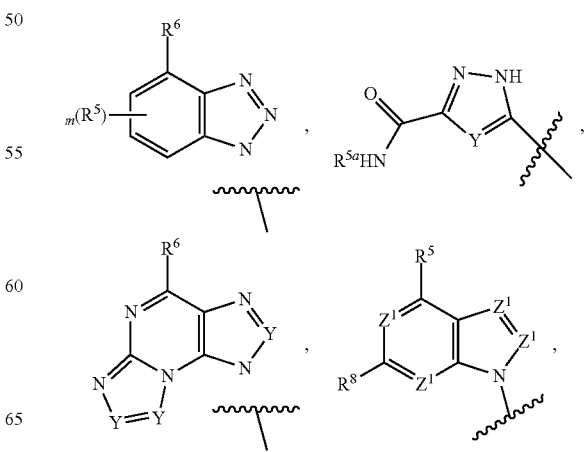

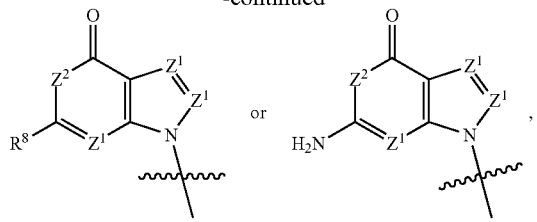

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl;
$R^3$ is H, $CH_3$, halogen, $NH_2$ or OH;
$R^{3a}$ is H, $CH_3$, halogen, $NH_2$ or OH; or
$R^3$ and $R^{3a}$ may be taken together to form a 3-4 membered carbocycle; or
$R^3$ and $R^{3a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
Y is $CR^5$ or N;
m is 0, 1, 2 or 3;
or a pharmaceutically acceptable salt, tautomer or stereoisomer thereof.

The compound of the formula

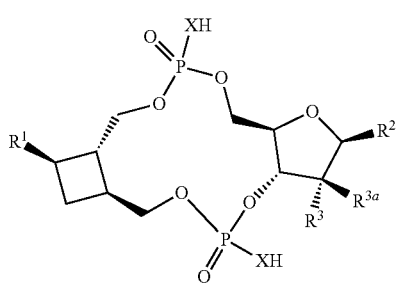

wherein
X is O;
$R^1$ and $R^2$ are each independently

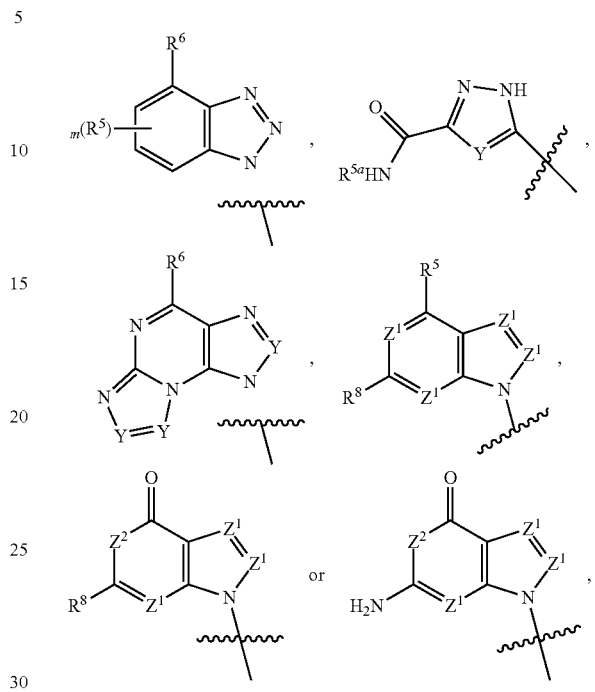

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl;
$R^3$ is H, $CH_3$, halogen, $NH_2$ or OH;
$R^{3a}$ is H, $CH_3$, halogen, $NH_2$ or OH; or
$R^3$ and $R^{3a}$ may be taken together to form a 3-4 membered carbocycle; or
$R^3$ and $R^{3a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

The compound of the formula

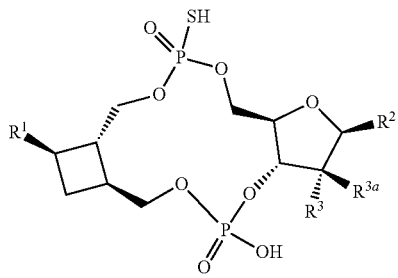

wherein
R$^1$ and R$^2$ are each independently

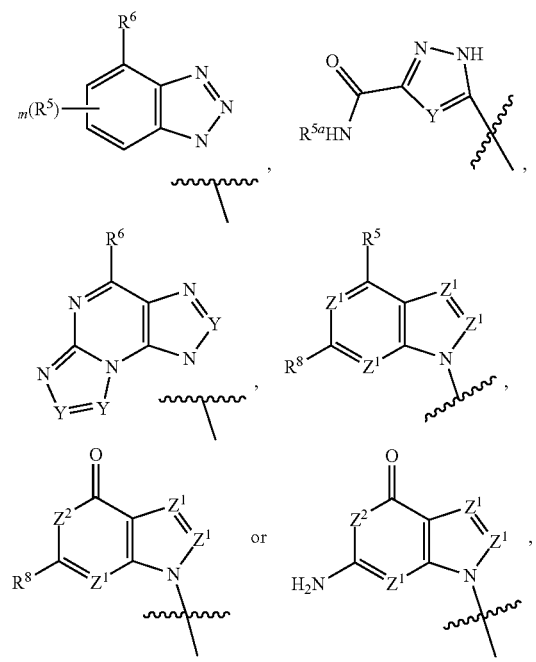

Z$^1$ is N or CR$^a$;
Z$^2$ is NR$^b$;
R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^3$ is H, CH$_3$, halogen, NH$_2$ or OH;

R$^{3a}$ is H, CH$_3$, halogen, NH$_2$ or OH; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

The compound of the formula

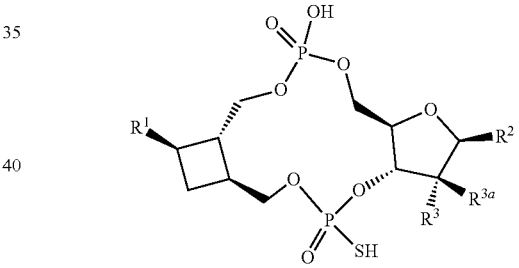

wherein
R$^1$ and R$^2$ are each independently

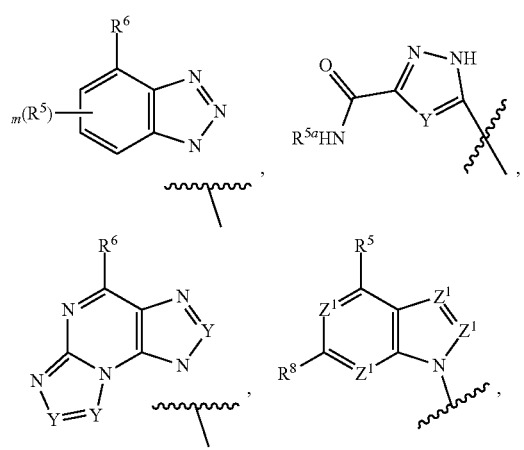

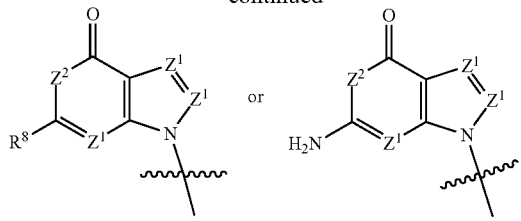

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H or $C_{1-3}$ alkyl;
$R^3$ is H, $CH_3$, halogen, $NH_2$ or OH;
$R^{3a}$ is H, $CH_3$, halogen, $NH_2$ or OH; or
$R^3$ and $R^{3a}$ may be taken together to form a 3-4 membered carbocycle; or
$R^3$ and $R^{3a}$ may be taken together to form a $C=CH_2$ substituent;
$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
Y is $CR^5$ or N;
m is 0, 1, 2 or 3;
or a pharmaceutically acceptable salt, tautomer or stereoisomer thereof.

The compound of the formula

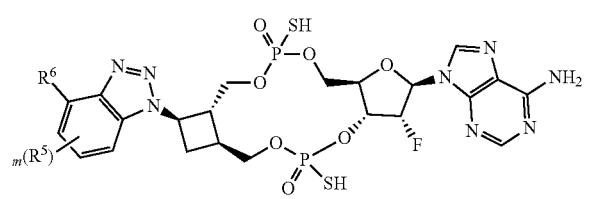

or a pharmaceutically acceptable salt, tautomer or stereoisomer thereof.

A compound of the formula

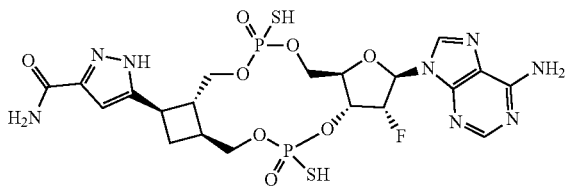 [SMILES: NC(=O)c1cc([C@@H]2C[C@@H]3COP(=O)(S)O[C@H]4[C@@H](F)[C@H](n5cnc6c(N)ncnc65)O[C@@H]4COP(=O)(S)OC[C@H]32)[nH]n1]

or a pharmaceutically acceptable salt, tautomer or stereoisomer thereof.

A compound of the formula

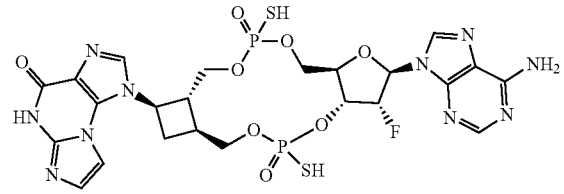 [SMILES: Nc1ncnc2c1ncn2[C@@H]1O[C@@H]2COP(=O)(S)OC[C@@H]3[C@@H](COP(=O)(S)O[C@H]2[C@H]1F)C[C@H]3n1cnc2c(=O)[nH]c3nccn3c21]

or a pharmaceutically acceptable salt, tautomer or stereoisomer thereof.

A compound of the formula

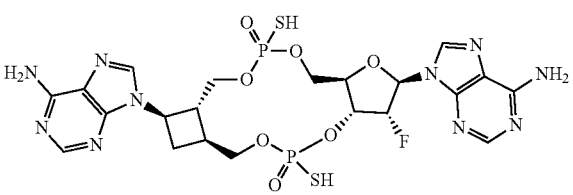 [SMILES: Nc1ncnc2c1ncn2[C@@H]1C[C@@H]2COP(=O)(S)O[C@H]3[C@@H](F)[C@H](n4cnc5c(N)ncnc54)O[C@@H]3COP(=O)(S)OC[C@H]21]

or a pharmaceutically acceptable salt, tautomer or stereoisomer thereof.

A compound of formula II

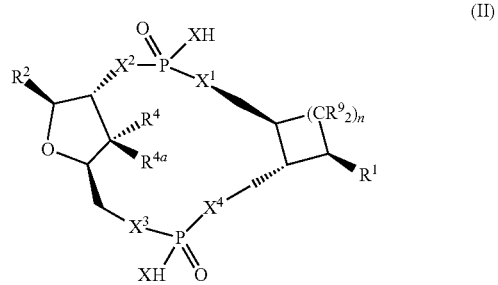

(II)

wherein
X is O or S;
$X^1$, $X^2$, $X^3$ and $X^4$ are each independently O or NH;
$R^1$ and $R^2$ are each independently

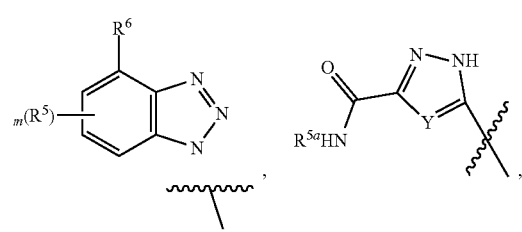

-continued

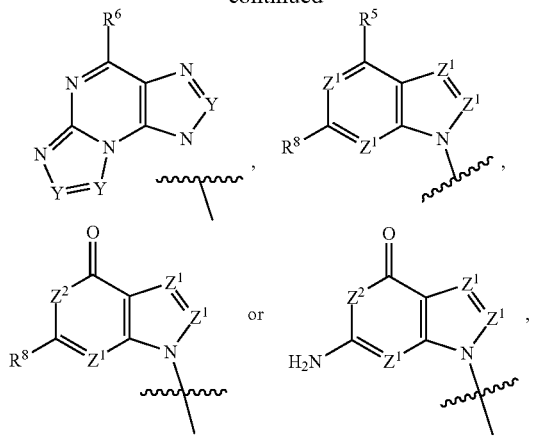

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H or $C_{1-3}$ alkyl;

$R^4$ is H, $CH_3$, halogen, $NH_2$ or OH;

$R^{4a}$ is H, $CH_3$, halogen, $NH_2$ or OH; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^5$ or N;

m is 0, 1, 2 or 3;

n is 0 or 1; when n=0, the ring is a 3-membered cyclopropyl ring;

or a pharmaceutically acceptable salt, tautomer or stereoisomer thereof.

The compound according to formula II wherein $R^1$ is

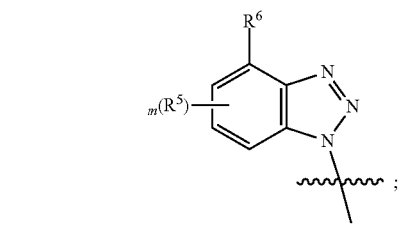

and $R^2$ is

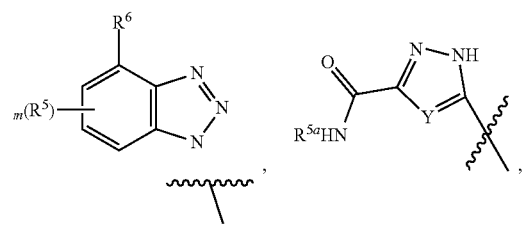

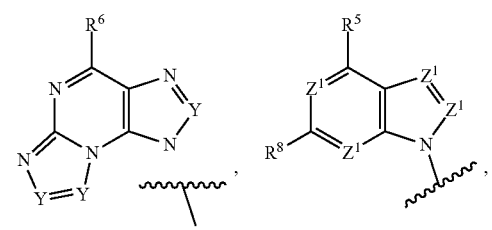

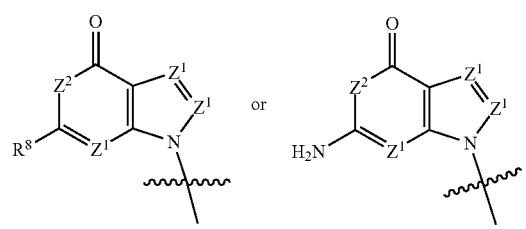

The compound according to formula II wherein $R^1$ is

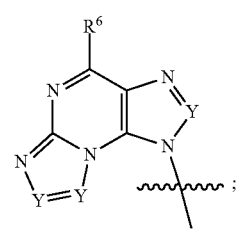

and
R² is
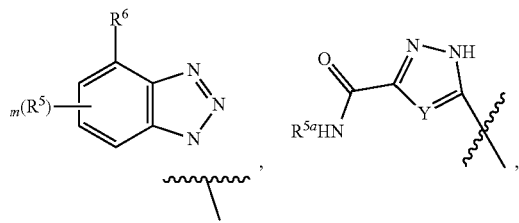
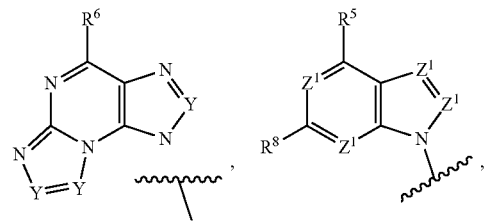
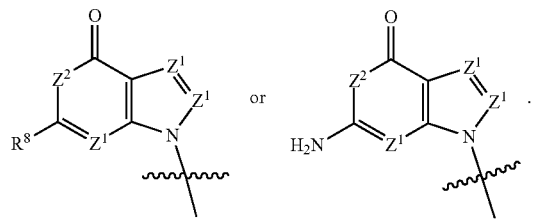
The compound according to formula II wherein R¹ is
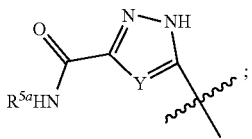
and
R² is
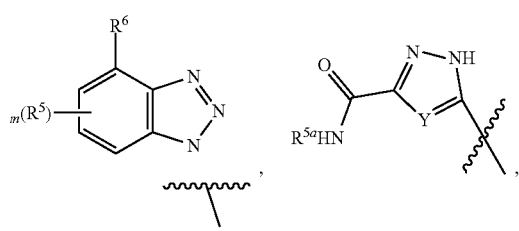
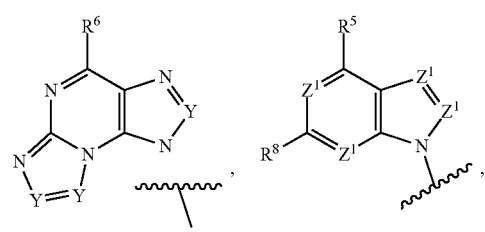 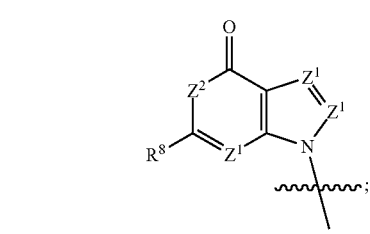
-continued
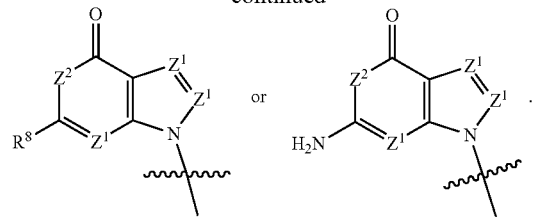
The compound according to formula II wherein R¹ is
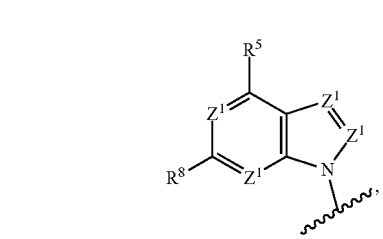
and
R² is
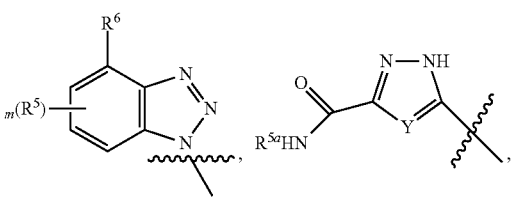
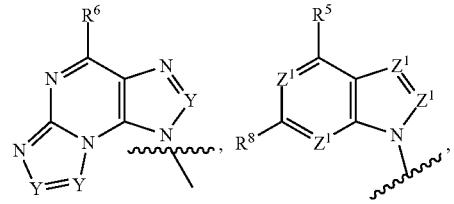
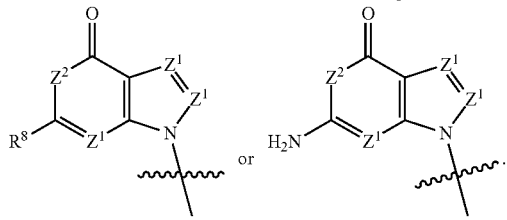
The compound according to formula II wherein R¹ is
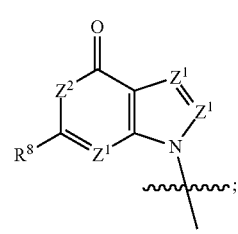

and
R² is
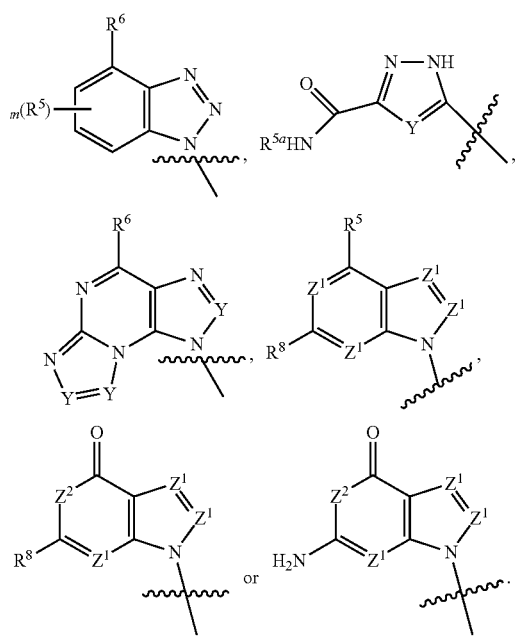
The compound according to formula II wherein R¹ is
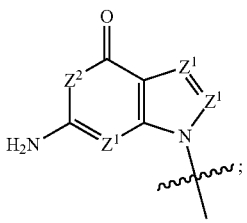
and
R² is
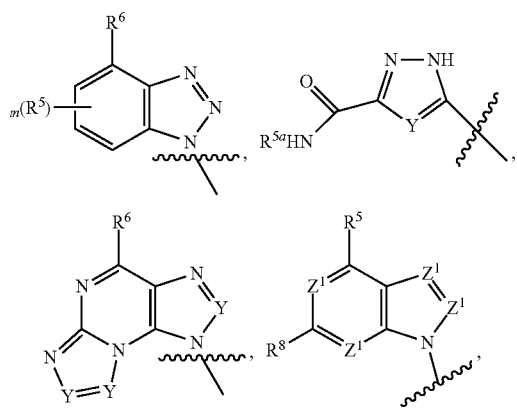
-continued
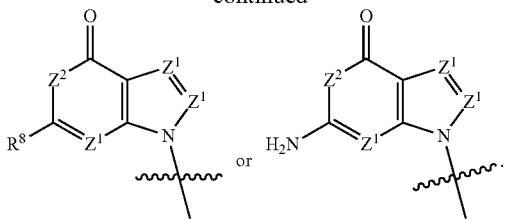
The compound according to formula II wherein R¹ is
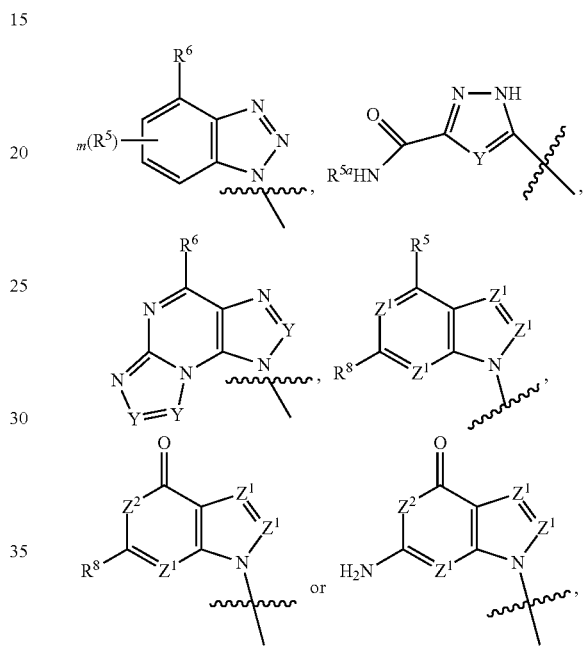
and
R² is
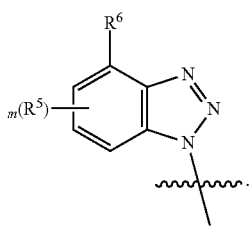
The compound according to formula II wherein R¹ is
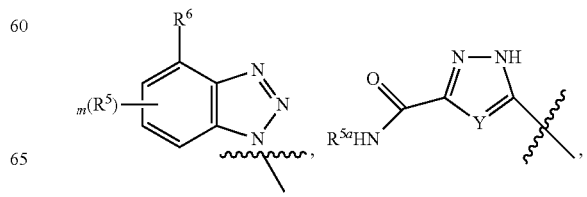

-continued
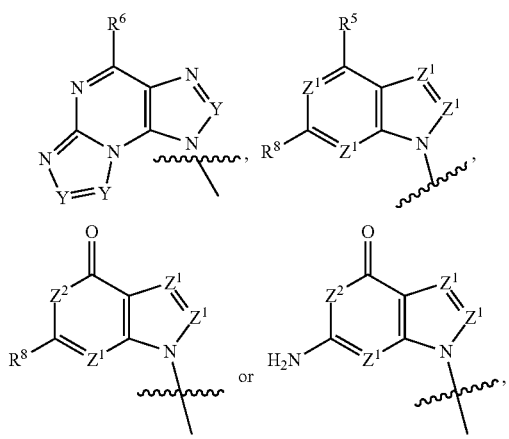
and
R² is
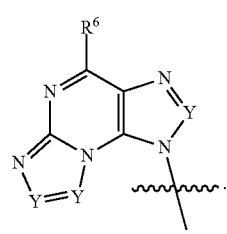
The compound according to formula II wherein
R¹ is
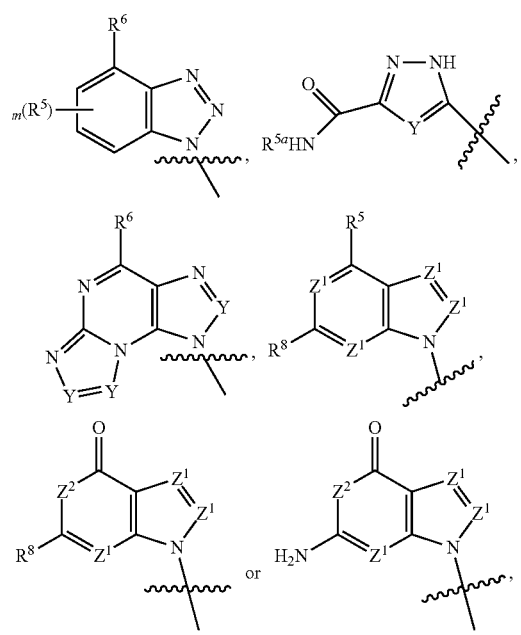
and
R² is
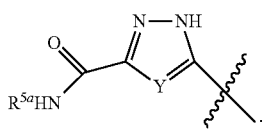
The compound according to formula II wherein
R¹ is
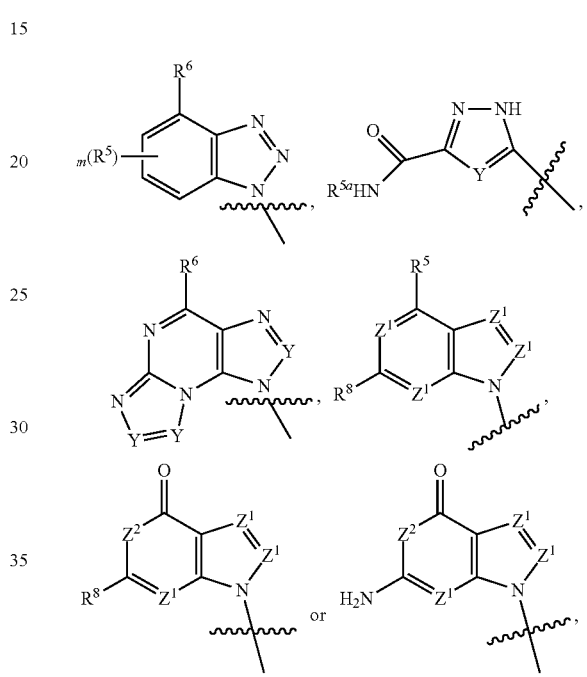
and
R² is
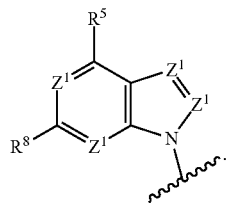
The compound according to formula II wherein
R¹ is
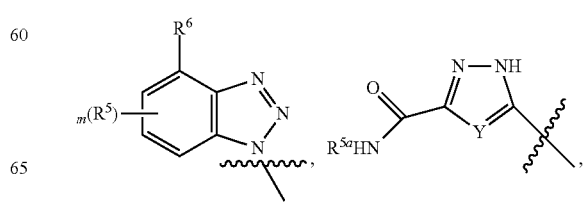

-continued

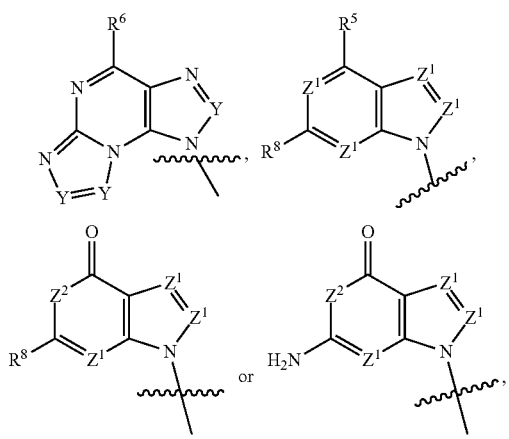

and
R² is

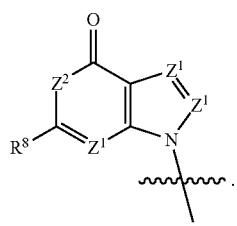

The compound according to formula II wherein R¹ is

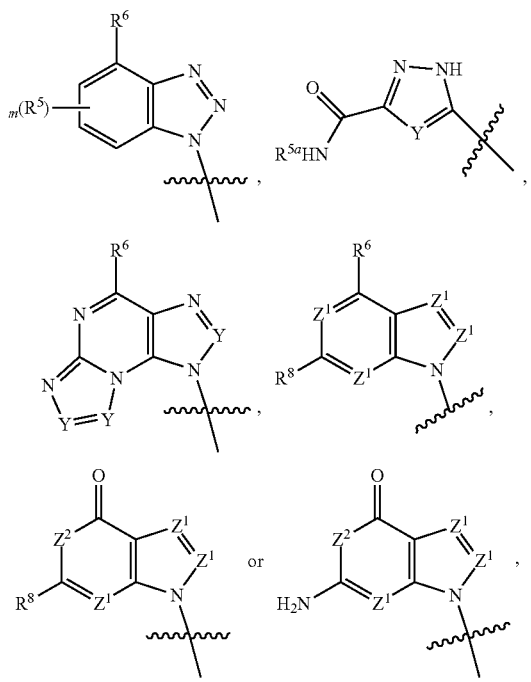

and
R² is

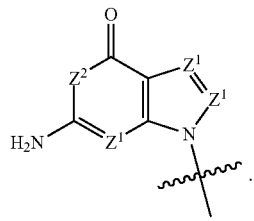

The compound of the formula

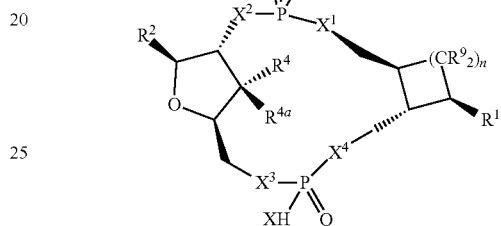

(II)

wherein
X is S;
X¹, X², X³ and X⁴ are each independently O or NH;
R¹ and R² are each independently

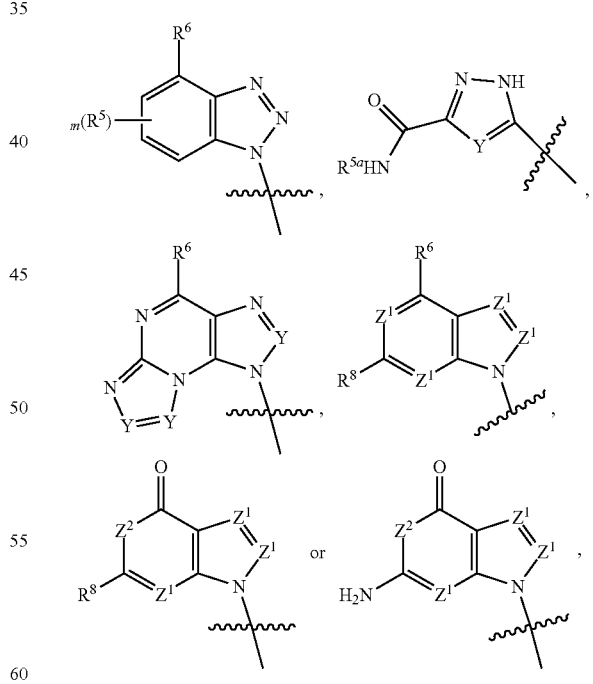

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, NO₂, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^4$ is H, CH$_3$, halogen, NH$_2$ or OH;

R$^{4a}$ is H, CH$_3$, halogen, NH$_2$ or OH; or

R$^4$ and R$^{4a}$ may be taken together to form a 3-4 membered carbocycle; or

R$^4$ and R$^{4a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1; when n=0, the ring is a 3-membered cyclopropyl ring;

or a pharmaceutically acceptable salt, tautomer or stereoisomer thereof.

The compound of the formula

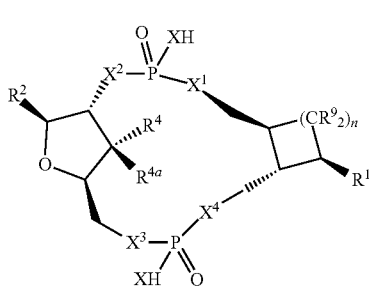

(II)

wherein

X is O;

X$^1$, X$^2$, X$^3$ and X$^4$ are each independently O or NH;

R$^1$ and R$^2$ are each independently

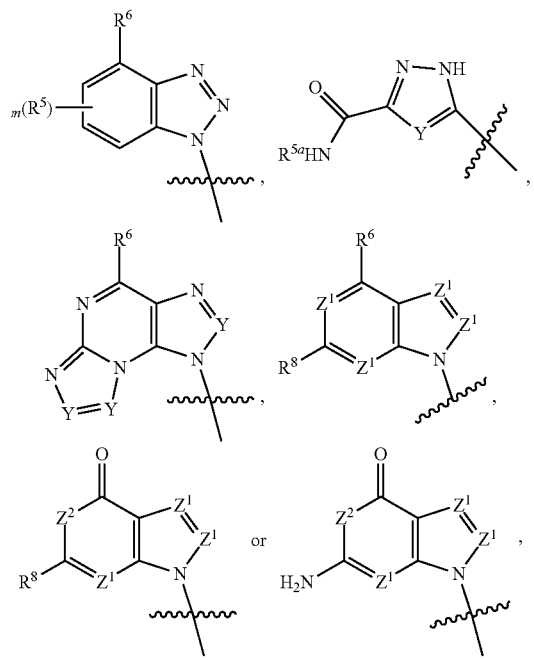

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^4$ is H, CH$_3$, halogen, NH$_2$ or OH;

R$^{4a}$ is H, CH$_3$, halogen, NH$_2$ or OH; or

R$^4$ and R$^{4a}$ may be taken together to form a 3-4 membered carbocycle; or

R$^4$ and R$^{4a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1; when n=0, the ring is a 3-membered cyclopropyl ring;

or a pharmaceutically acceptable salt, tautomer or stereoisomer thereof.

The compound of the formula

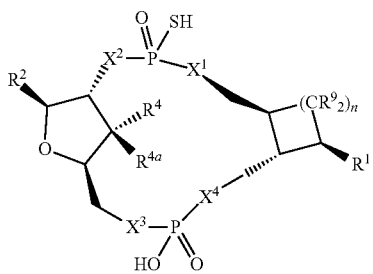

wherein

X$^1$, X$^2$, X$^3$ and X$^4$ are each independently O or NH;

R$^1$ and R$^2$ are each independently

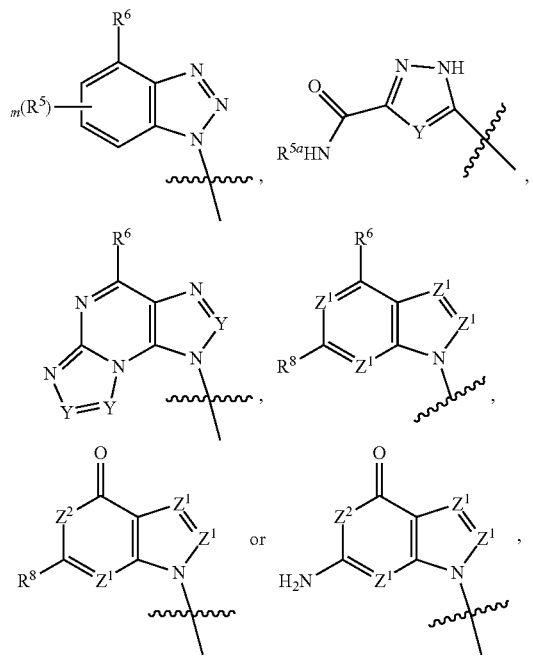

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^4$ is H, CH$_3$, halogen, NH$_2$ or OH;

R$^{4a}$ is H, CH$_3$, halogen, NH$_2$ or OH; or

R$^4$ and R$^{4a}$ may be taken together to form a 3-4 membered carbocycle; or

R$^4$ and R$^{4a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1; when n=0, the ring is a 3-membered cyclopropyl ring;

or a pharmaceutically acceptable salt, tautomer or stereoisomer thereof.

The compound of the formula

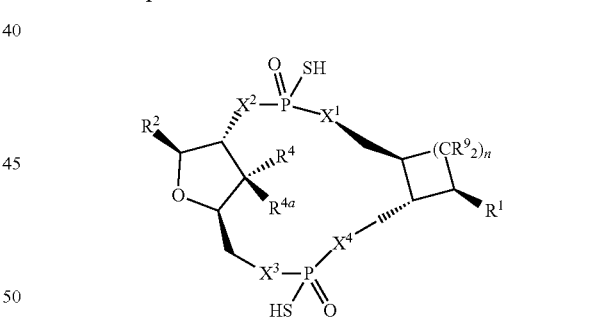

wherein

X$^1$, X$^2$, X$^3$ and X$^4$ are each independently O or NH;

R$^1$ and R$^2$ are each independently

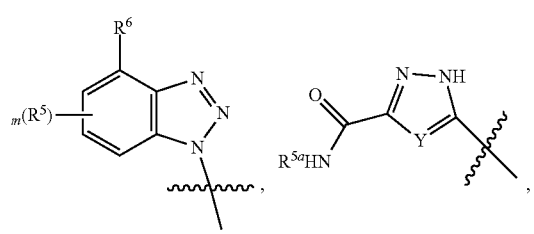

-continued

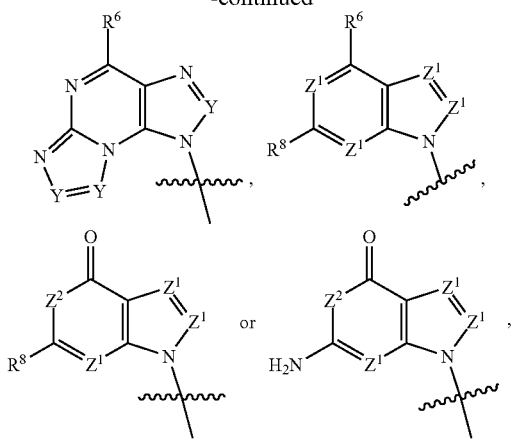

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, $—C(O)R^{a1}$, $—C(O)NR^{a1}R^{a1}$, $—S(O)_2R^{a1}$ or $S(O)_2NR^{a1}R^{a1}$;
$R^{a1}$ is H or $C_{1-3}$ alkyl;
$R^4$ is H, $CH_3$, halogen, $NH_2$ or OH;
$R^{4a}$ is H, $CH_3$, halogen, $NH_2$ or OH; or
$R^4$ and $R^{4a}$ may be taken together to form a 3-4 membered carbocycle; or
$R^4$ and $R^{4a}$ may be taken together to form a $C═CH_2$ substituent;
$R^5$ is H, halogen, $C_{1-3}$ alkyl, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;
$R^9$ is H, halogen or methyl;
Y is $CR^5$ or N;
m is 0, 1, 2 or 3;
n is 0 or 1; when n=0, the ring is a 3-membered cyclopropyl ring;
or a pharmaceutically acceptable salt, tautomer or stereoisomer thereof.

The compound of the formula

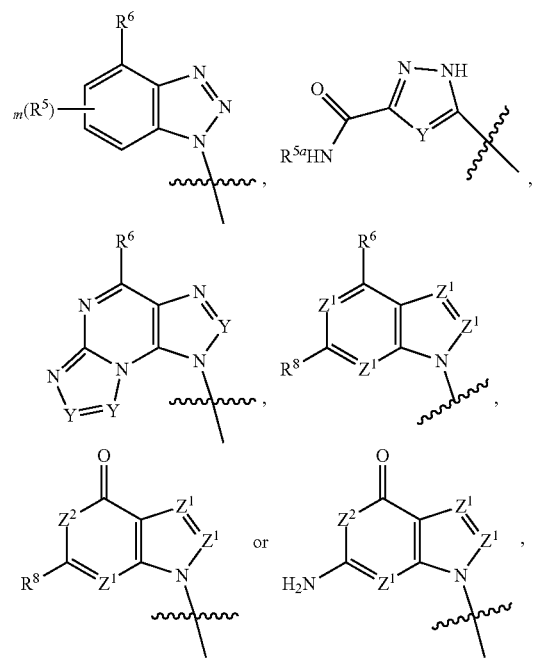

wherein
X is O or S;
$R^1$ and $R^2$ are each independently $Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, $—NR^{a1}C(O)NR^{a1}R^{a1}$, $—NR^{a1}S(O)_2R^{a1}$, $—NR^{a1}S(O)_2NR^{a1}R^{a1}$, $—S(O)R^{a1}$, $—S(O)NR^{a1}R^{a1}$, $—S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, $—C(O)R^{a1}$, $—C(O)NR^{a1}R^{a1}$, $—S(O)_2R^{a1}$ or $S(O)_2NR^{a1}R^{a1}$;
$R^{a1}$ is H or $C_{1-3}$ alkyl;
$R^4$ is H, $CH_3$, halogen, $NH_2$ or OH;
$R^{4a}$ is H, $CH_3$, halogen, $NH_2$ or OH; or
$R^4$ and $R^{4a}$ may be taken together to form a 3-4 membered carbocycle; or
$R^4$ and $R^{4a}$ may be taken together to form a $C═CH_2$ substituent;
$R^5$ is H, halogen, $C_{1-3}$ alkyl, CN, $NO_2$, OH, $OR^{a1}$, $SR^{a1}$, $—C(O)NR^{a1}R^{a1}$, $—COOR^{a1}$, $—OC(O)R^{a1}$, $—OC(O)NR^{a1}R^{a1}$, $—NR^{a1}R^{a1}$, $—NR^{a1}C(O)R^{a1}$, $—NR^{a1}COOR^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1; when n=0, the ring is a 3-membered cyclopropyl ring;

or a pharmaceutically acceptable salt, tautomer or stereoisomer thereof.

The compound of the formula

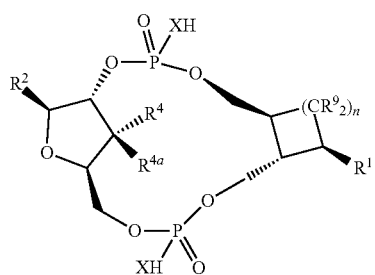

wherein

X is O or S;

X$^1$, X$^2$, X$^3$ and X$^4$ are each independently O or NH;

R$^1$ and R$^2$ are each independently

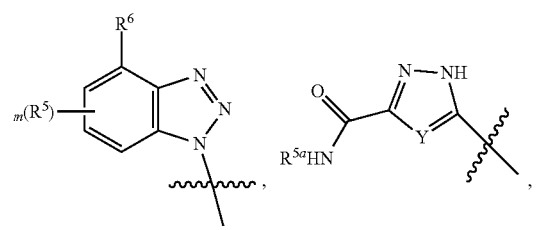

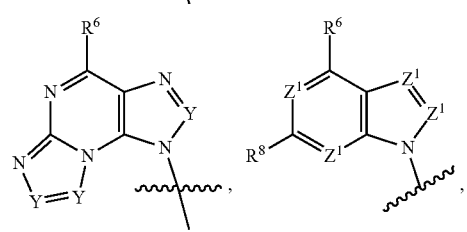

-continued

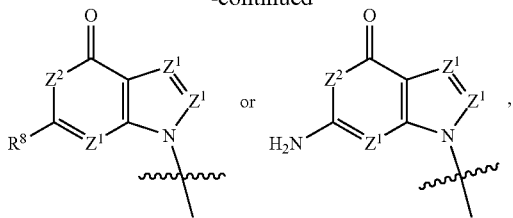

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^4$ is F;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1; when n=0, the ring is a 3-membered cyclopropyl ring;

or a pharmaceutically acceptable salt, tautomer or stereoisomer thereof.

The compound of the formula (II)

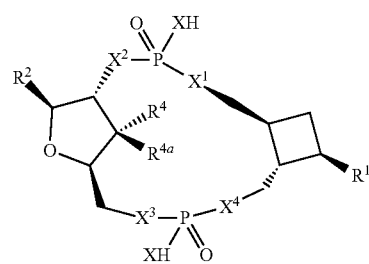

wherein
X is O or S;
$X^1$, $X^2$, $X^3$ and $X^4$ are each independently O or NH;
$R^1$ and $R^2$ are each independently

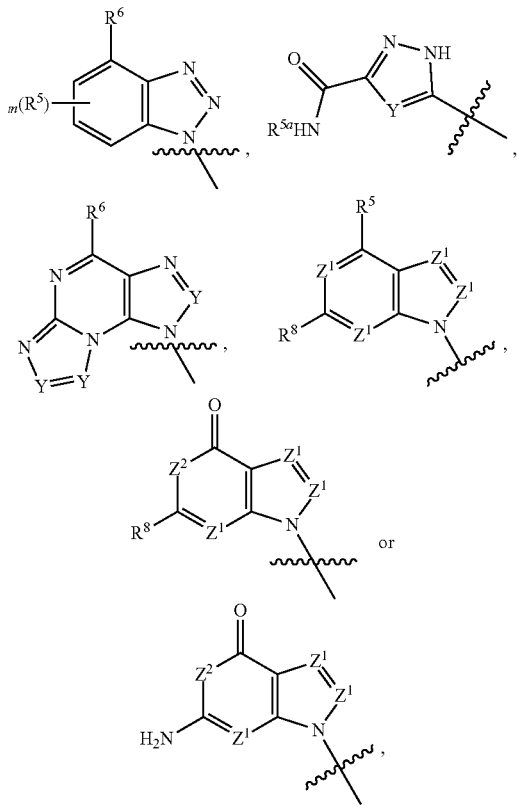

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H or $C_{1-3}$ alkyl;
$R^4$ is H, $CH_3$, halogen, $NH_2$ or OH;
$R^{4a}$ is H, $CH_3$, halogen, $NH_2$ or OH; or
$R^4$ and $R^{4a}$ may be taken together to form a 3-4 membered carbocycle; or
$R^4$ and $R^{4a}$ may be taken together to form a $C=CH_2$ substituent;
$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}$ $S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
Y is $CR^5$ or N;
m is 0, 1, 2 or 3;
or a pharmaceutically acceptable salt, tautomer or stereoisomer thereof.

The compound of the formula

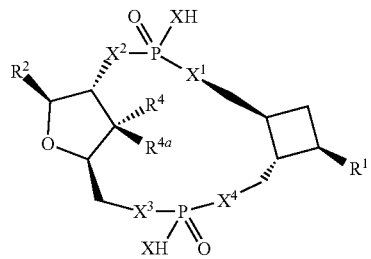

wherein
X is S;
$X^1$, $X^2$, $X^3$ and $X^4$ are each independently O or NH;
$R^1$ and $R^2$ are each independently

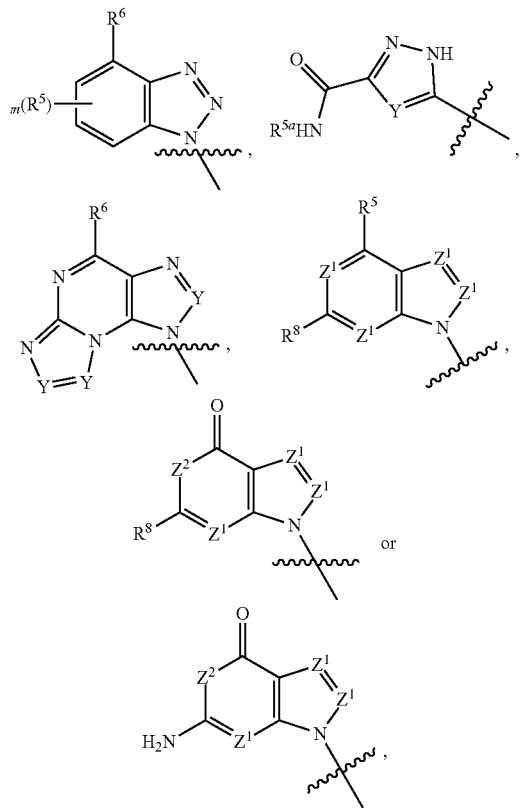

$Z^1$ is N or $CR^a$;
$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^b$ is H, $C_{1-6}$ alkyl substituted with 0-6 $R^5$, $C_{3-6}$ cycloalkyl substituted with 0-6 $R^5$, —C(O)R$^{a1}$, —C(O)NR$^{a1}$R$^{a1}$, —S(O)$_2$R$^{a1}$ or S(O)$_2$NR$^{a1}$R$^{a1}$;

$R^{a1}$ is H or $C_{1-3}$ alkyl;

$R^4$ is H, CH$_3$, halogen, NH$_2$ or OH;

$R^{4a}$ is H, CH$_3$, halogen, NH$_2$ or OH; or $R^4$ and $R^{4a}$ may be taken together to form a 3-4 membered carbocycle; or $R^4$ and $R^{4a}$ may be taken together to form a C=CH$_2$ substituent;

$R^5$ is H, halogen, $C_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^{5a}$ is H or $C_{1-3}$ alkyl;

$R^6$ is H, halogen, $C_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^8$ is H, halogen, $C_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

The compound of the formula

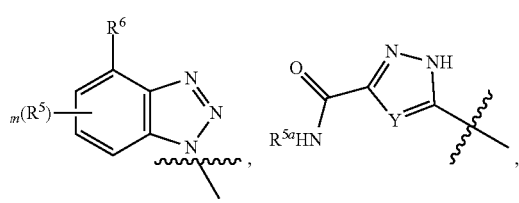

wherein

X is O;

$X^1$, $X^2$, $X^3$ and $X^4$ are each independently O or NH;

$R^1$ and $R^2$ are each independently

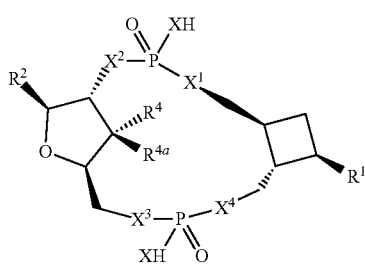

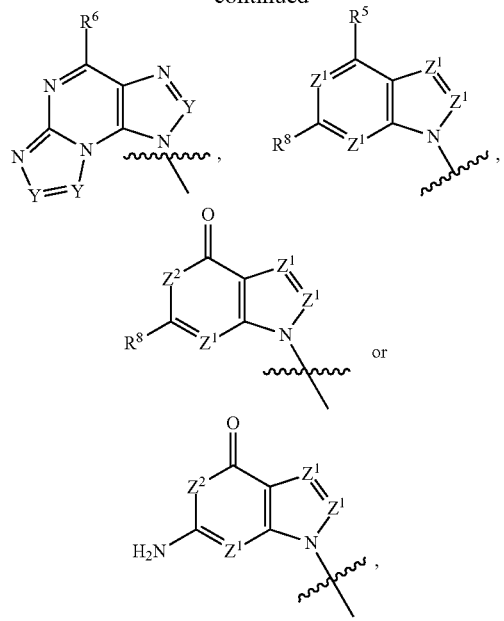

$Z^1$ is N or CR$^a$;

$Z^2$ is NR$^b$;

$R^a$ is H, halogen, $C_{1-6}$ alkyl substituted with 0-6 $R^5$, $C_{3-6}$ cycloalkyl substituted with 0-6 $R^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^b$ is H, $C_{1-6}$ alkyl substituted with 0-6 $R^5$, $C_{3-6}$ cycloalkyl substituted with 0-6 $R^5$, —C(O)R$^{a1}$, —C(O)NR$^{a1}$R$^{a1}$, —S(O)$_2$R$^{a1}$ or S(O)$_2$NR$^{a1}$R$^{a1}$;

$R^{a1}$ is H or $C_{1-3}$ alkyl;

$R^4$ is H, CH$_3$, halogen, NH$_2$ or OH;

$R^{4a}$ is H, CH$_3$, halogen, NH$_2$ or OH; or $R^4$ and $R^{4a}$ may be taken together to form a 3-4 membered carbocycle; or $R^4$ and $R^{4a}$ may be taken together to form a C=CH$_2$ substituent;

$R^5$ is H, halogen, $C_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^{5a}$ is H or $C_{1-3}$ alkyl;

$R^6$ is H, halogen, $C_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^8$ is H, halogen, $C_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

The compound of the formula

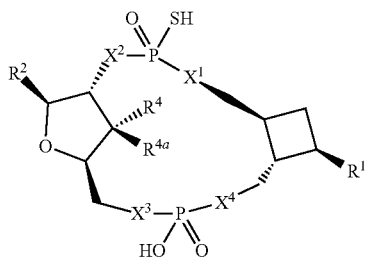

wherein $X^1$, $X^2$, $X^3$ and $X^4$ are each independently O or NH;

$R^1$ and $R^2$ are each independently

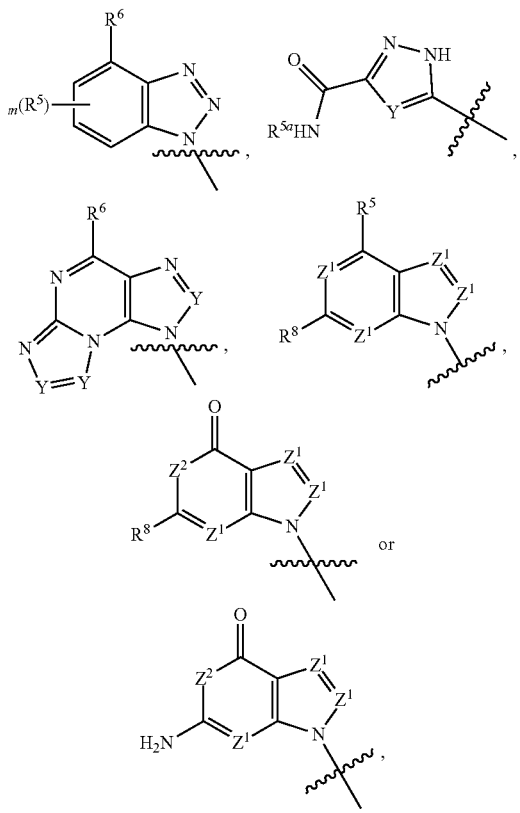

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —NR$^{a1}R^{a1}$, —NR$^{a1}$C(O)$R^{a1}$, —NR$^{a1}$COOR$^{a1}$, —NR$^{a1}$C(O)NR$^{a1}R^{a1}$, —NR$^{a1}$S(O)$_2R^{a1}$, —NR$^{a1}$S(O)$_2$NR$^{a1}R^{a1}$, —S(O)$R^{a1}$, —S(O)NR$^{a1}R^{a1}$, —S(O)$_2R^{a1}$ or S(O)$_2$NR$^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)NR$^{a1}R^{a1}$, —S(O)$_2R^{a1}$ or S(O)$_2$NR$^{a1}R^{a1}$;

$R^{a1}$ is H or $C_{1-3}$ alkyl;

$R^4$ is H, $CH_3$, halogen, $NH_2$ or OH;

$R^{4a}$ is H, $CH_3$, halogen, $NH_2$ or OH; or $R^4$ and $R^{4a}$ may be taken together to form a 3-4 membered carbocycle; or $R^4$ and $R^{4a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)NR$^{a1}R^{a1}$, —COOR$^{a1}$, —OC(O)$R^{a1}$, —OC(O)NR$^{a1}R^{a1}$, —NR$^{a1}R^{a1}$, —NR$^{a1}$C(O)$R^{a1}$, —NR$^{a1}$COOR$^{a1}$, —NR$^{a1}$C(O)NR$^{a1}R^{a1}$, —NR$^{a1}$S(O)$_2R^{a1}$, —NR$^{a1}$S(O)$_2$NR$^{a1}R^{a1}$, —S(O)$R^{a1}$, —S(O)NR$^{a1}R^{a1}$, —S(O)$_2R^{a1}$ or S(O)$_2$NR$^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)NR$^{a1}R^{a1}$, —COOR$^{a1}$, —OC(O)$R^{a1}$, —OC(O)NR$^{a1}R^{a1}$, —NR$^{a1}R^{a1}$, —NR$^{a1}$C(O)$R^{a1}$, —NR$^{a1}$COOR$^{a1}$, —NR$^{a1}$C(O)NR$^{a1}R^{a1}$, —NR$^{a1}$S(O)$_2R^{a1}$, —NR$^{a1}$S(O)$_2$NR$^{a1}R^{a1}$, —S(O)$R^{a1}$, —S(O)NR$^{a1}R^{a1}$, —S(O)$_2R^{a1}$ or S(O)$_2$NR$^{a1}R^{a1}$;

$R^8$ is H, halogen, $C_{1-3}$ alkyl, CN, $NO_2$, OH, $OR^{a1}$, $SR^{a1}$, —C(O)NR$^{a1}R^{a1}$, —COOR$^{a1}$, —OC(O)$R^{a1}$, —OC(O)NR$^{a1}R^{a1}$, —NR$^{a1}R^{a1}$, —NR$^{a1}$C(O)$R^{a1}$, —NR$^{a1}$COOR$^{a1}$, —NR$^{a1}$C(O)NR$^{a1}R^{a1}$, —NR$^{a1}$S(O)$_2R^{a1}$, —NR$^{a1}$S(O)$_2$NR$^{a1}R^{a1}$, —S(O)$R^{a1}$, —S(O)NR$^{a1}R^{a1}$, —S(O)$_2R^{a1}$ or S(O)$_2$NR$^{a1}R^{a1}$;

Y is $CR^5$ or N;

m is 0, 1, 2 or 3;

or a pharmaceutically acceptable salt, tautomer or stereoisomer thereof.

The compound of the formula

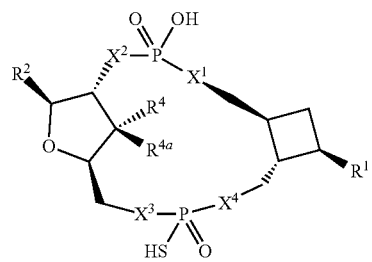

wherein $X^1$, $X^2$, $X^3$ and $X^4$ are each independently O or NH;

$R^1$ and $R^2$ are each independently

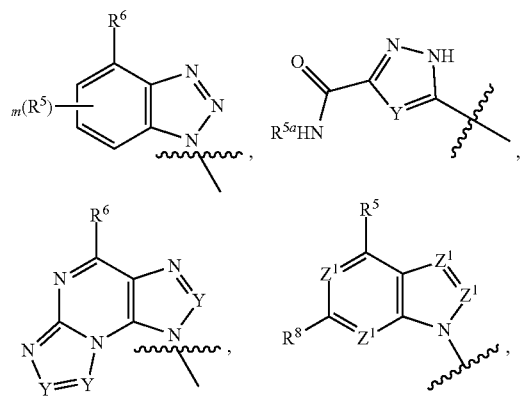

-continued

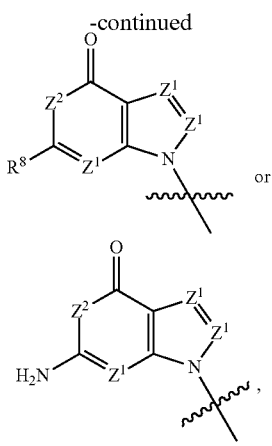

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H or $C_{1-3}$ alkyl;

$R^4$ is H, $CH_3$, halogen, $NH_2$ or OH;

$R^{4a}$ is H, $CH_3$, halogen, $NH_2$ or OH; or $R^4$ and $R^{4a}$ may be taken together to form a 3-4 membered carbocycle; or $R^4$ and $R^{4a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

Y is $CR^5$ or N;

m is 0, 1, 2 or 3;

or a pharmaceutically acceptable salt, tautomer or stereoisomer thereof.

The compound of the formula

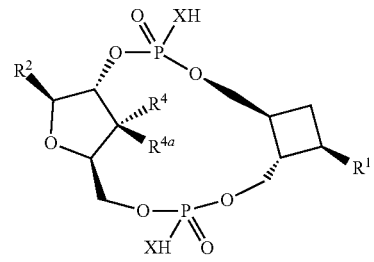

wherein

X is O or S;

$R^1$ and $R^2$ are each independently

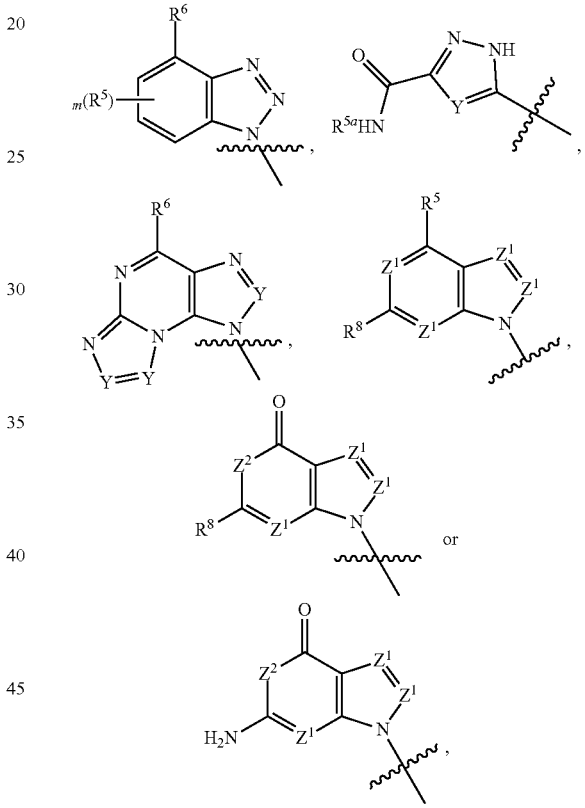

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H or $C_{1-3}$ alkyl;

$R^4$ is H, $CH_3$, halogen, $NH_2$ or OH;

$R^{4a}$ is H, $CH_3$, halogen, $NH_2$ or OH; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

Y is $CR^5$ or N;

m is 0, 1, 2 or 3;

or a pharmaceutically acceptable salt, tautomer or stereoisomer thereof.

The compound of the formula

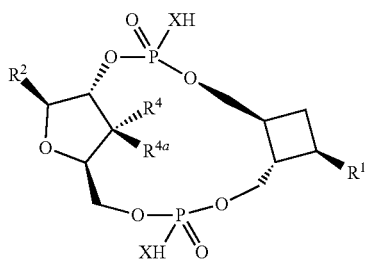

wherein
X is S;
$R^1$ and $R^2$ are each independently

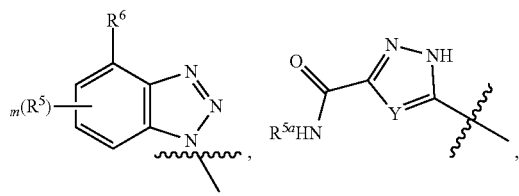

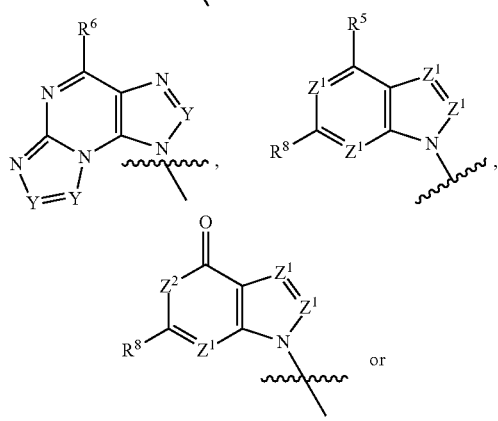

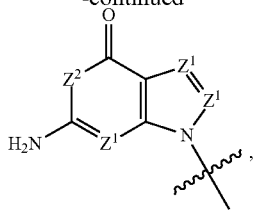

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H or $C_{1-3}$ alkyl;

$R^4$ is H, $CH_3$, halogen, $NH_2$ or OH;

$R^{4a}$ is H, $CH_3$, halogen, $NH_2$ or OH; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

Y is $CR^5$ or N;

m is 0, 1, 2 or 3;

or a pharmaceutically acceptable salt, tautomer or stereoisomer thereof.

The compound of the formula

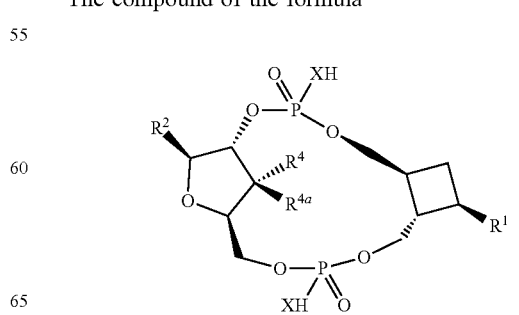

wherein

X is O;

R¹ and R² are each independently

[Structures shown: benzotriazole with R⁶ and m(R⁵) substituents; triazole carboxamide with R⁵ªHN and Y; triazolopyrimidine with R⁶ and Y; indazole/benzimidazole with R⁵, Z¹, Z¹, R⁸; keto-bicyclic with Z², Z¹, Z¹, R⁸; keto-bicyclic with Z², Z¹, Z¹, H₂N]

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, NO₂, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)₂$R^{a1}$, —$NR^{a1}$S(O)₂$NR^{a1}R^{a1}$, —S(O)$R^{a1}$, —S(O)$NR^{a1}R^{a1}$, —S(O)₂$R^{a1}$ or S(O)₂$NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)₂$R^{a1}$ or S(O)₂$NR^{a1}R^{a1}$;

$R^{a1}$ is H or $C_{1-3}$ alkyl;

$R^4$ is H, CH₃, halogen, NH₂ or OH;

$R^{4a}$ is H, CH₃, halogen, NH₂ or OH; or $R^4$ and $R^{4a}$ may be taken together to form a 3-4 membered carbocycle; or $R^4$ and $R^{4a}$ may be taken together to form a C=CH₂ substituent;

$R^5$ is H, halogen, $C_{1-3}$ alkyl, CN, NO₂, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)₂$R^{a1}$, —$NR^{a1}$S(O)₂$NR^{a1}R^{a1}$, —S(O)$R^{a1}$, —S(O)$NR^{a1}R^{a1}$, —S(O)₂$R^{a1}$ or S(O)₂$NR^{a1}R^{a1}$;

$R^{5a}$ is H or $C_{1-3}$ alkyl;

$R^6$ is H, halogen, $C_{1-3}$ alkyl, CN, NO₂, OH, $OR^{a1}$, $SR^{a1}$, —C(O)$NR^{a1}R^{a1}$, —COO$R^{a1}$OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)₂$R^{a1}$, —$NR^{a1}$S(O)₂$NR^{a1}R^{a1}$, —S(O)$R^{a1}$, —S(O)$NR^{a1}R^{a1}$, —S(O)₂$R^{a1}$ or S(O)₂$NR^{a1}R^{a1}$;

$R^8$ is H, halogen, $C_{1-3}$ alkyl, CN, NO₂, OH, $OR^{a1}$, $SR^{a1}$, —C(O)$NR^{a1}R^{a1}$, —COO$R^{a1}$OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)₂$R^{a1}$, —$NR^{a1}$S(O)₂$NR^{a1}R^{a1}$, —S(O)$R^{a1}$, —S(O)$NR^{a1}R^{a1}$, —S(O)₂$R^{a1}$ or S(O)₂$NR^{a1}R^{a1}$;

Y is $CR^5$ or N;

m is 0, 1, 2 or 3;

or a pharmaceutically acceptable salt, tautomer or stereoisomer thereof.

The compound of the formula

[Cyclic phosphate structure shown with R², R⁴, R⁴ª, R¹ substituents, O, SH, OH, P=O groups]

wherein

R¹ and R² are each independently

[Same set of structures as above: benzotriazole, triazole carboxamide, triazolopyrimidine, indazole derivatives, keto-bicyclics]

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, NO₂, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)₂$R^{a1}$, —$NR^{a1}$S(O)₂$NR^{a1}R^{a1}$, —S(O)$R^{a1}$, —S(O)$NR^{a1}R^{a1}$, —S(O)₂$R^{a1}$ or S(O)₂$NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)₂$R^{a1}$ or S(O)₂$NR^{a1}R^{a1}$;

$R^{a1}$ is H or $C_{1-3}$ alkyl;

$R^4$ is H, CH₃, halogen, NH₂ or OH;

$R^{4a}$ is H, CH₃, halogen, NH₂ or OH; or $R^4$ and $R^{4a}$ may be taken together to form a 3-4 membered carbocycle; or $R^4$ and $R^{4a}$ may be taken together to form a C=CH$_2$ substituent;

$R^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^{5a}$ is H or C$_{1-3}$ alkyl;

$R^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

The compound of the formula

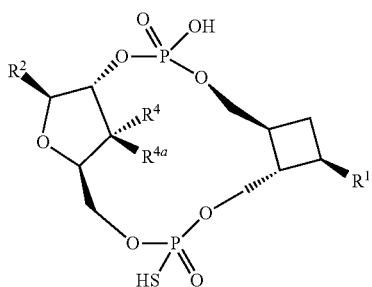

wherein $R^1$ and $R^2$ are each independently

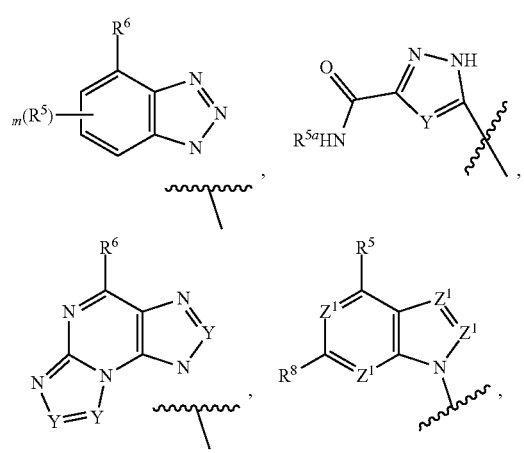

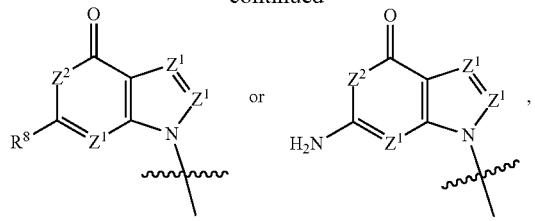

$Z^1$ is N or CR$^a$;

$Z^2$ is NR$^b$;

$R^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

$R^{a1}$ is H or C$_{1-3}$ alkyl;

$R^4$ is H, CH$_3$, halogen, NH$_2$ or OH;

$R^{4a}$ is H, CH$_3$, halogen, NH$_2$ or OH; or $R^4$ and $R^{4a}$ may be taken together to form a 3-4 membered carbocycle; or $R^4$ and $R^{4a}$ may be taken together to form a C=CH$_2$ substituent;

$R^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^{5a}$ is H or C$_{1-3}$ alkyl;

$R^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

The compound of the formula

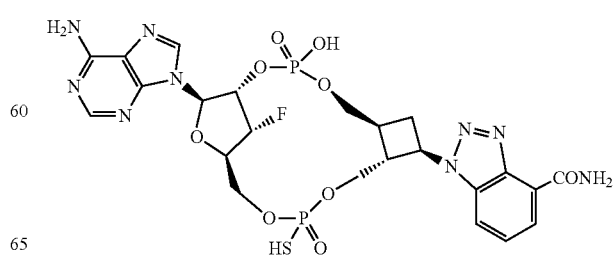

or a pharmaceutically acceptable salt, tautomer or stereoisomer thereof.

The compound of the formula

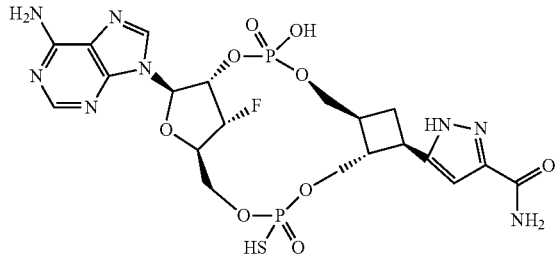

or a pharmaceutically acceptable salt, tautomer or stereoisomer thereof.

The compound of the formula

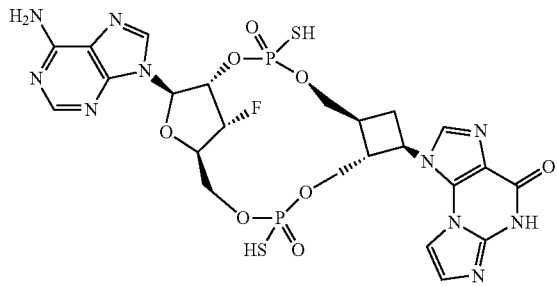

or a pharmaceutically acceptable salt, tautomer or stereoisomer thereof.

The compound of the formula

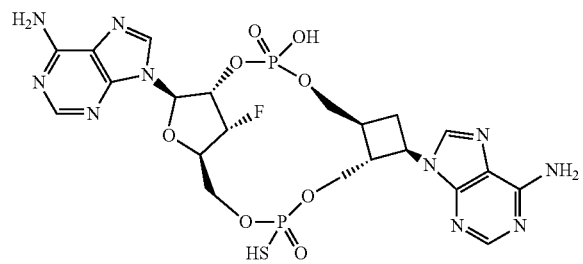

or a pharmaceutically acceptable salt, tautomer or stereoisomer thereof.

A compound of formula III

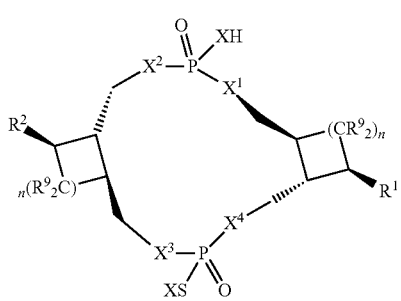

(III)

wherein
X is O or S;
$X^1$, $X^2$, $X^3$ and $X^4$ are each independently O or NH;
$R^1$ and $R^2$ are each independently

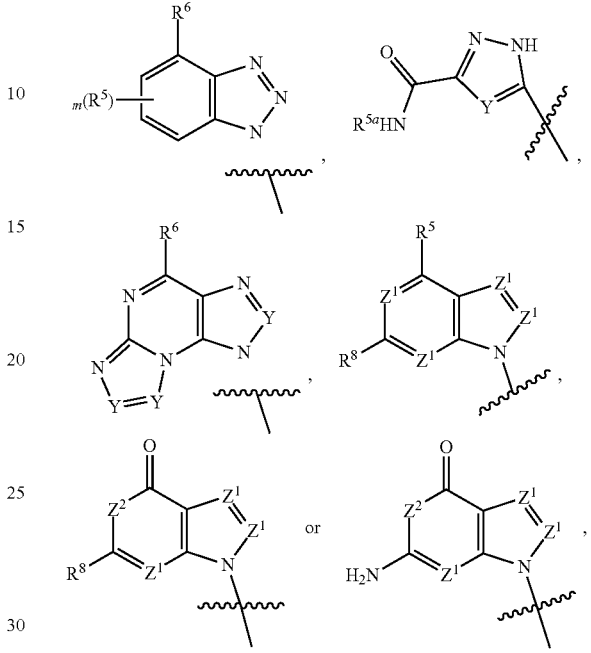

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl;
$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, halogen or methyl;
Y is $CR^5$ or N;
m is 0, 1, 2 or 3;

n is 0 or 1; when n=0, the ring is a 3-membered cyclopropyl ring;
or a pharmaceutically acceptable salt, tautomer or stereoisomer thereof.
The compound according to formula III wherein
R¹ is
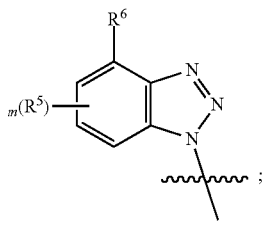
and
R² is
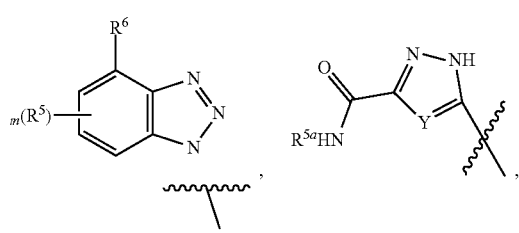
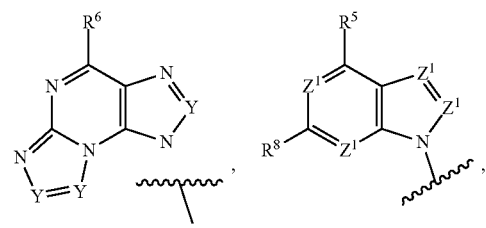
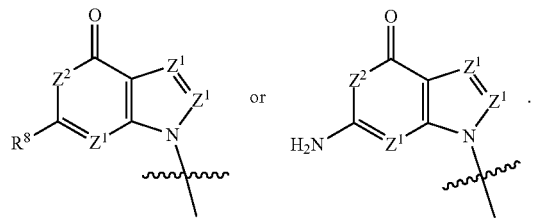
The compound according to formula III wherein
R¹ is
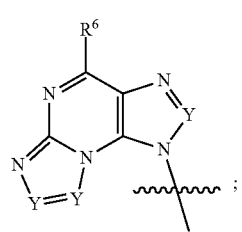
and
R² is
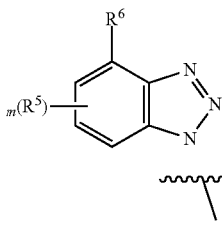 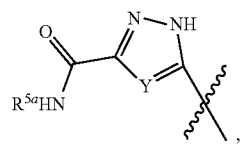
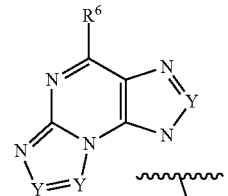 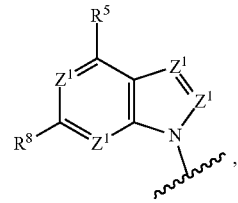
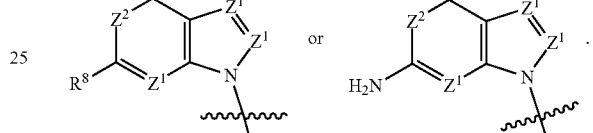
The compound according to formula III wherein
R¹ is
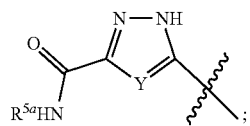
and
R² is
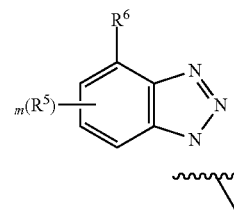 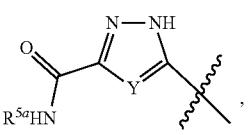
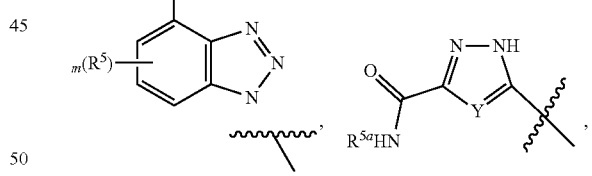
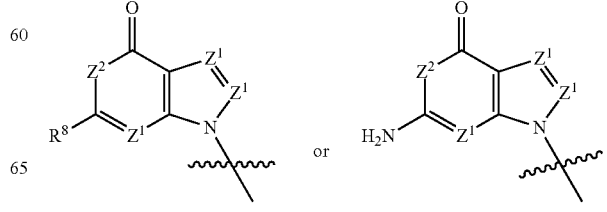

The compound according to formula III wherein
R¹ is
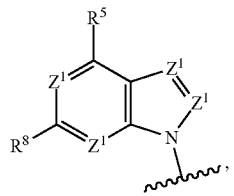
and
R² is
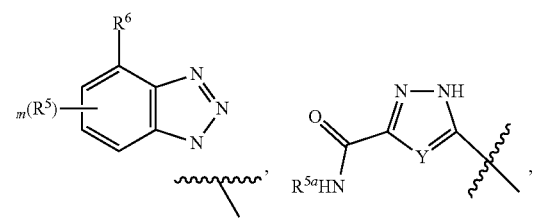
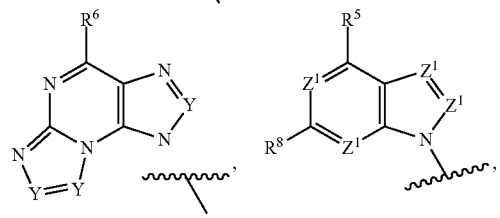
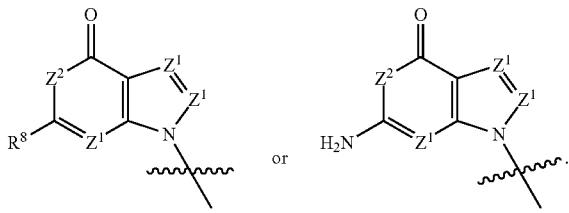
The compound according to formula III wherein
R¹ is
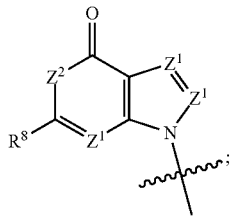
and
R² is
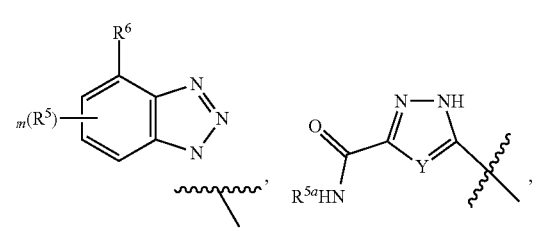
-continued
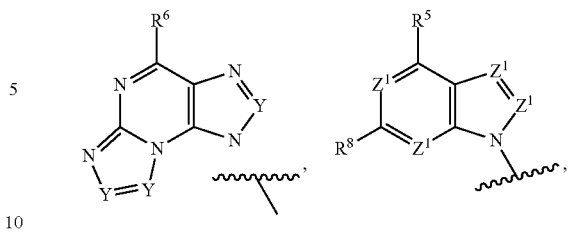
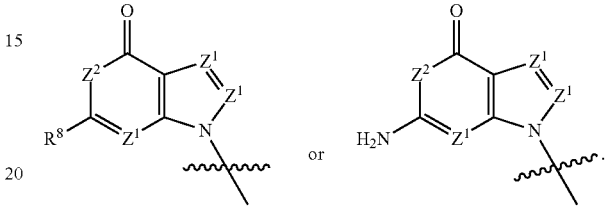
The compound according to formula III wherein
R¹ is
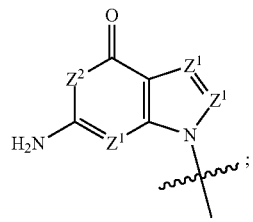
and
R² is
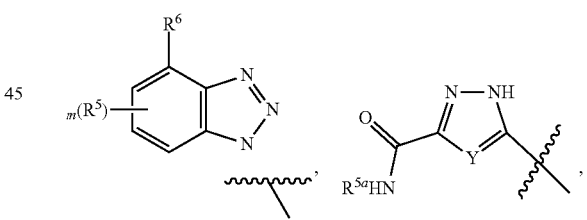
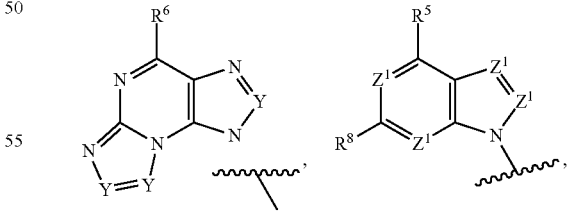
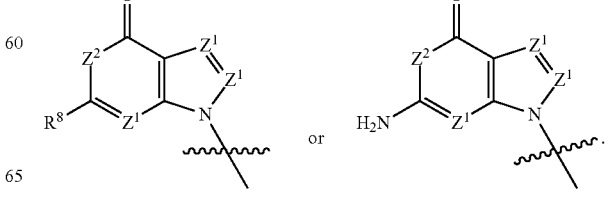

The compound according to formula III wherein R¹ is
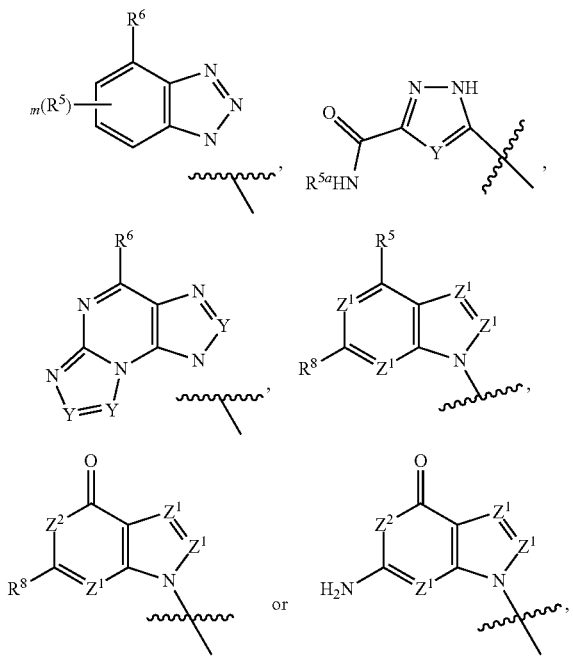
and
R² is
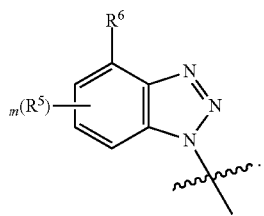
The compound according to formula III wherein R¹ is
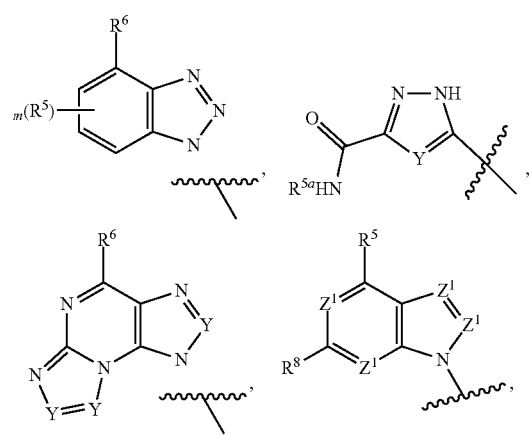
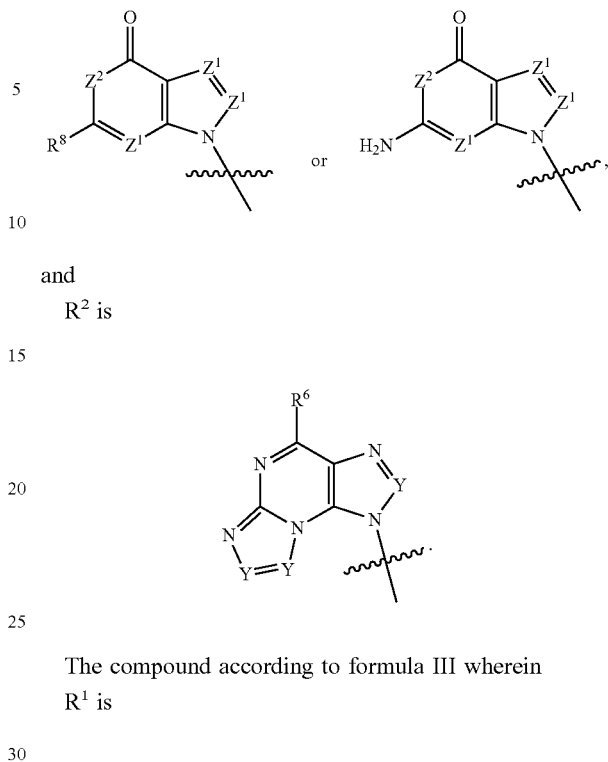
and
R² is
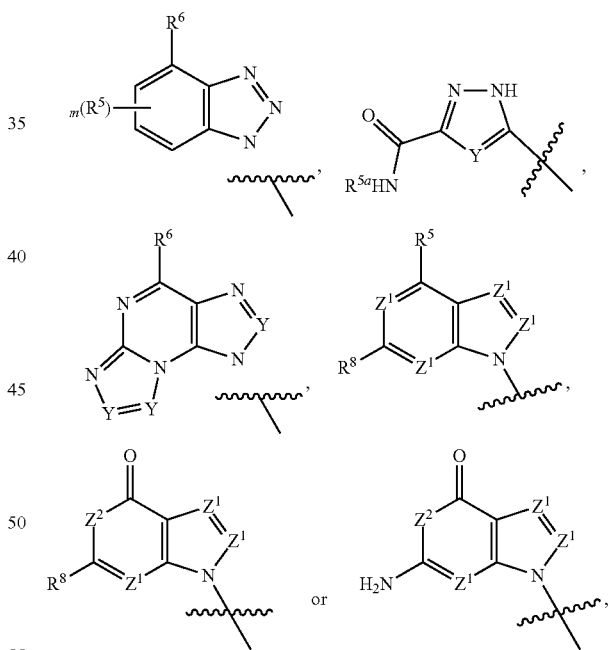
The compound according to formula III wherein R¹ is
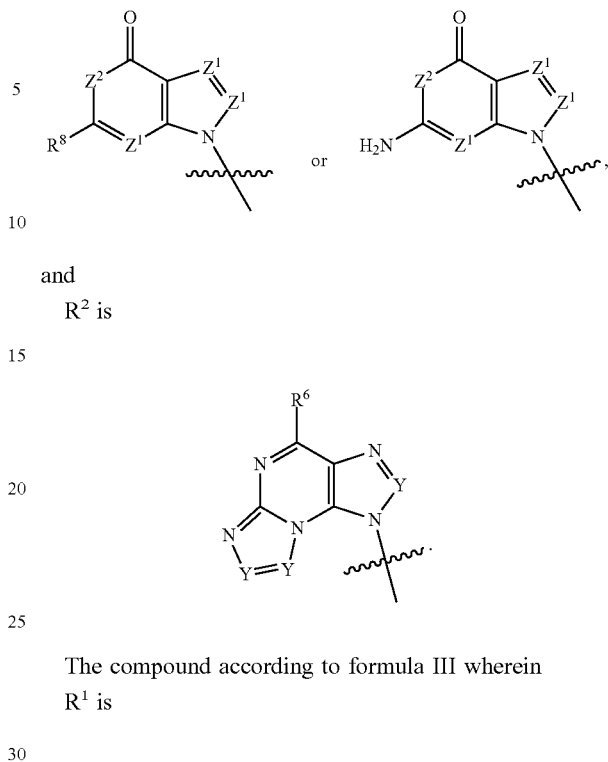
and
R² is
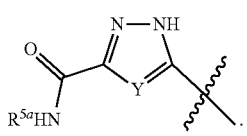

The compound according to formula III wherein
R¹ is
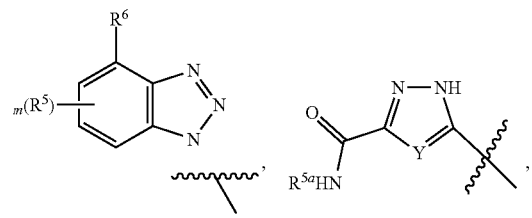
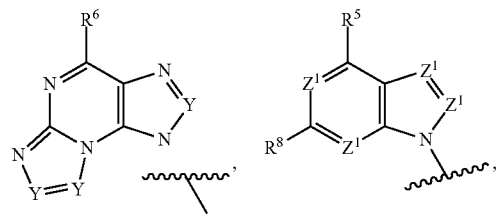
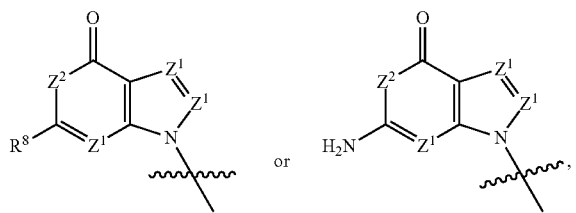
and
R² is
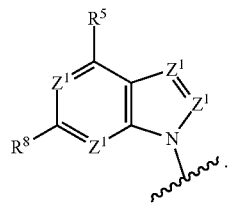
The compound according to formula III wherein
R¹ is
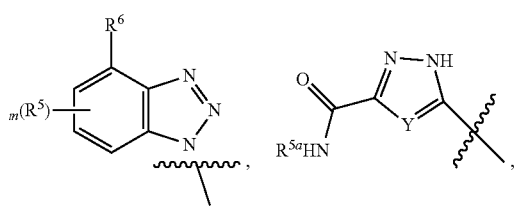
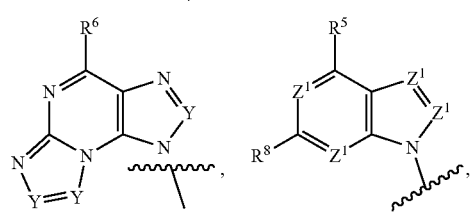
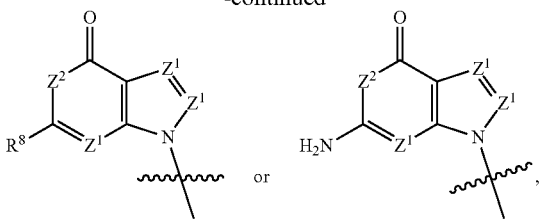
and
R² is
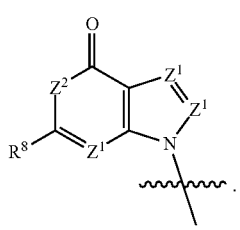
The compound according to formula III wherein
R¹ is
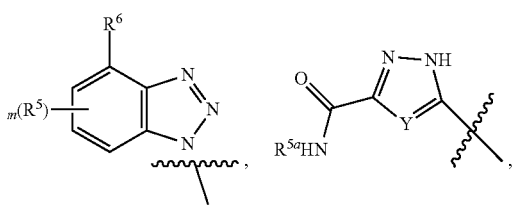
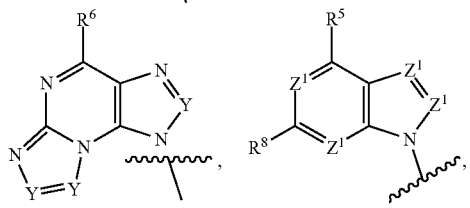
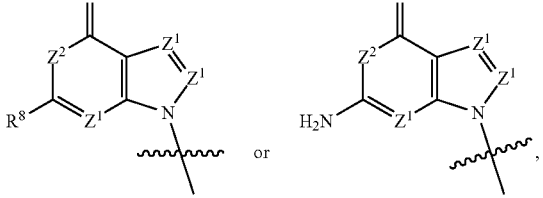
and
R² is
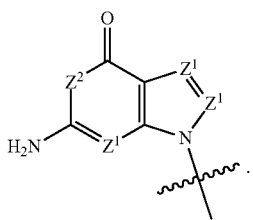

The compound according to formula III

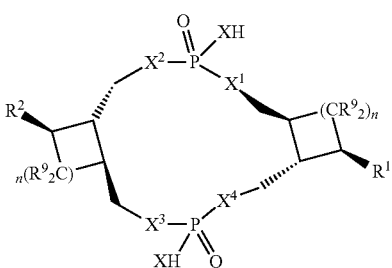

wherein
X is S;
$X^1$, $X^2$, $X^3$ and $X^4$ are each independently O or NH;
$R^1$ and $R^2$ are independently

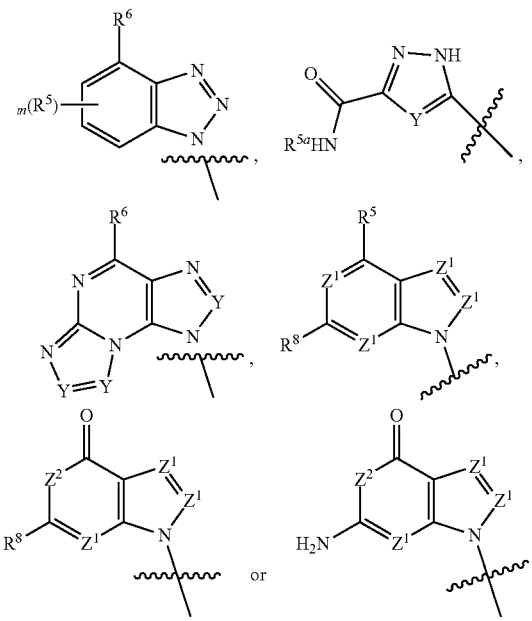

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl;
$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, halogen or methyl;
Y is $CR^5$ or N;
m is 0, 1, 2 or 3;
n is 0 or 1; when n=0, the ring is a 3-membered cyclopropyl ring;
or a pharmaceutically acceptable salt, tautomer or stereoisomer thereof.

The compound according to formula III

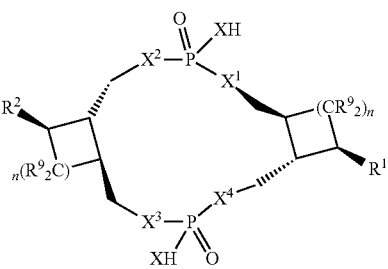

wherein
X is O;
$X^1$, $X^2$, $X^3$ and $X^4$ are each independently O or NH;
$R^1$ and $R^2$ are independently

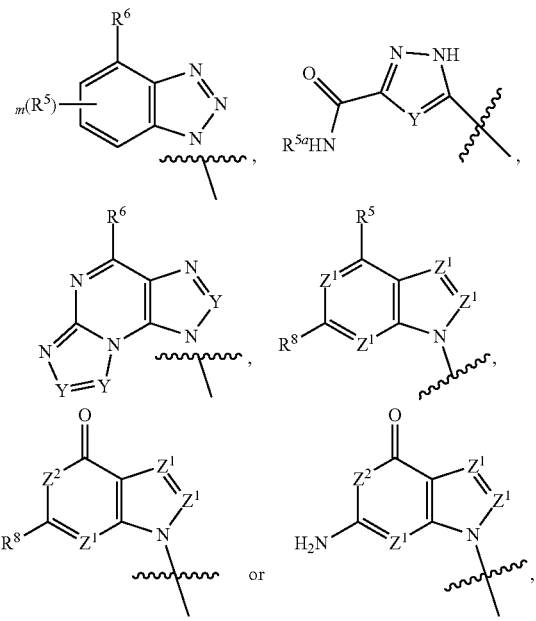

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC (O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1; when n=0, the ring is a 3-membered cyclopropyl ring;

or a pharmaceutically acceptable salt, tautomer or stereoisomer thereof.

The compound of the formula

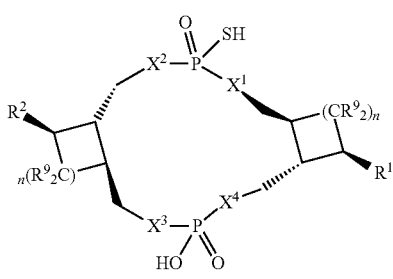

wherein

X$^1$, X$^2$, X$^3$ and X$^4$ are each independently O or NH;

R$^1$ and R$^2$ are independently

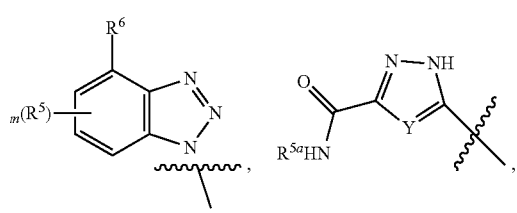

-continued

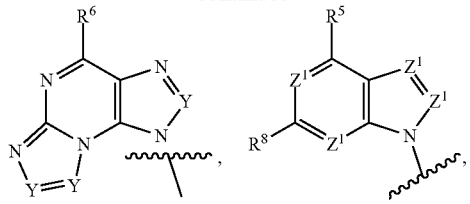

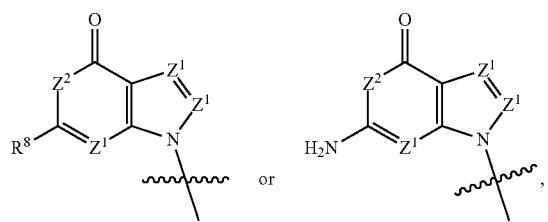

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1; when n=0, the ring is a 3-membered cyclopropyl ring;

or a pharmaceutically acceptable salt, tautomer or stereoisomer thereof.

The compound of the formula

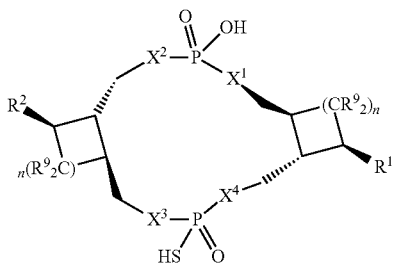

wherein
$X^1$, $X^2$, $X^3$ and $X^4$ are each independently O or NH;
$R^1$ and $R^2$ are each independently

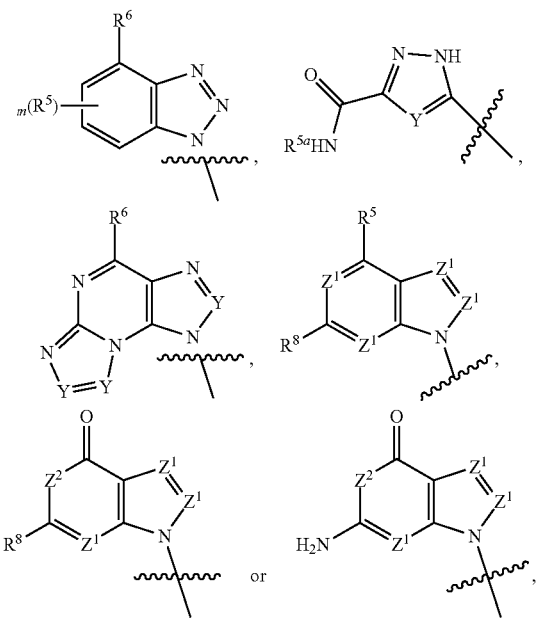

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, halogen or methyl;
Y is $CR^5$ or N;
m is 0, 1, 2 or 3;
n is 0 or 1; when n=0, the ring is a 3-membered cyclopropyl ring;
or a pharmaceutically acceptable salt, tautomer or stereoisomer thereof.

The compound of the formula

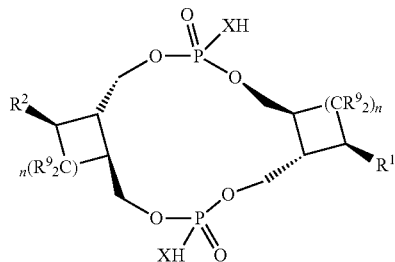

wherein
X is O or S;
$R^1$ and $R^2$ are each independently

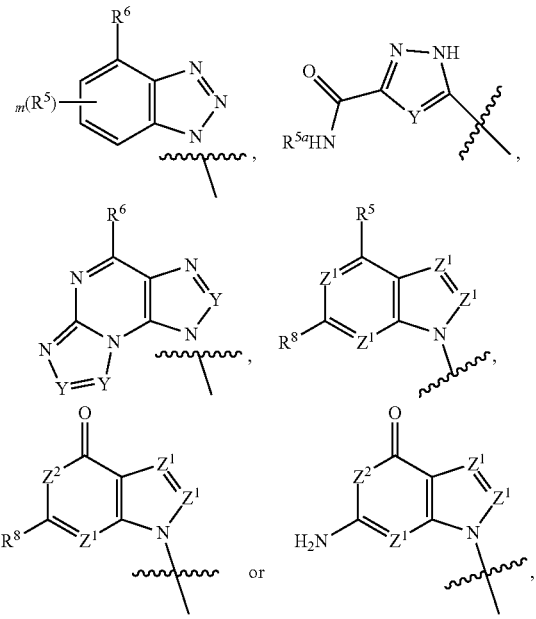

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1; when n=0, the ring is a 3-membered cyclopropyl ring;

or a pharmaceutically acceptable salt, tautomer or stereoisomer thereof.

The compound of the formula

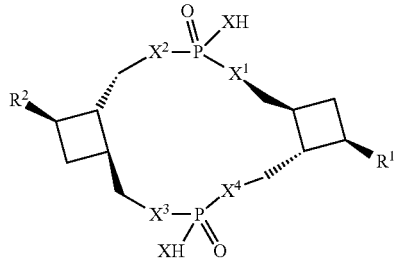

wherein
X is O or S;
X$^1$, X$^2$, X$^3$ and X$^4$ are each independently O or NH;
R$^1$ and R$^2$ are independently

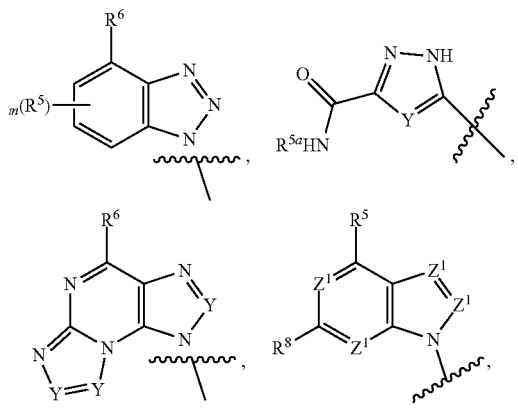

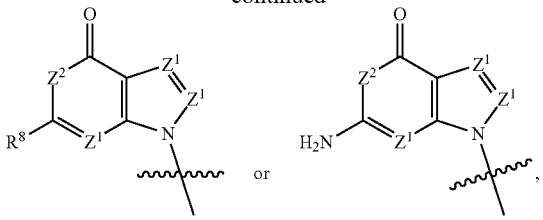

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

The compound of the formula

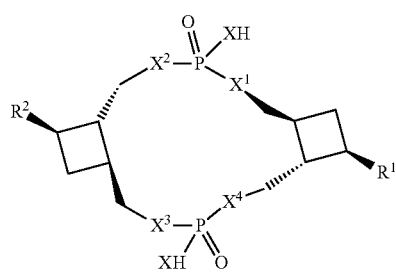

wherein
X is S;
$X^1$, $X^2$, $X^3$ and $X^4$ are each independently O or NH;
$R^1$ and $R^2$ are independently

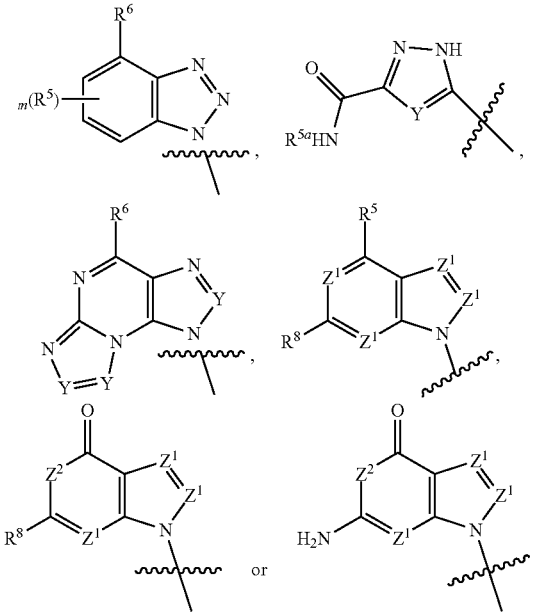

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;
$R^{a1}$ is H or $C_{1-3}$ alkyl;
$R^5$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
Y is $CR^5$ or N;
m is 0, 1, 2 or 3;
or a pharmaceutically acceptable salt, tautomer or stereoisomer thereof.

The compound of the formula

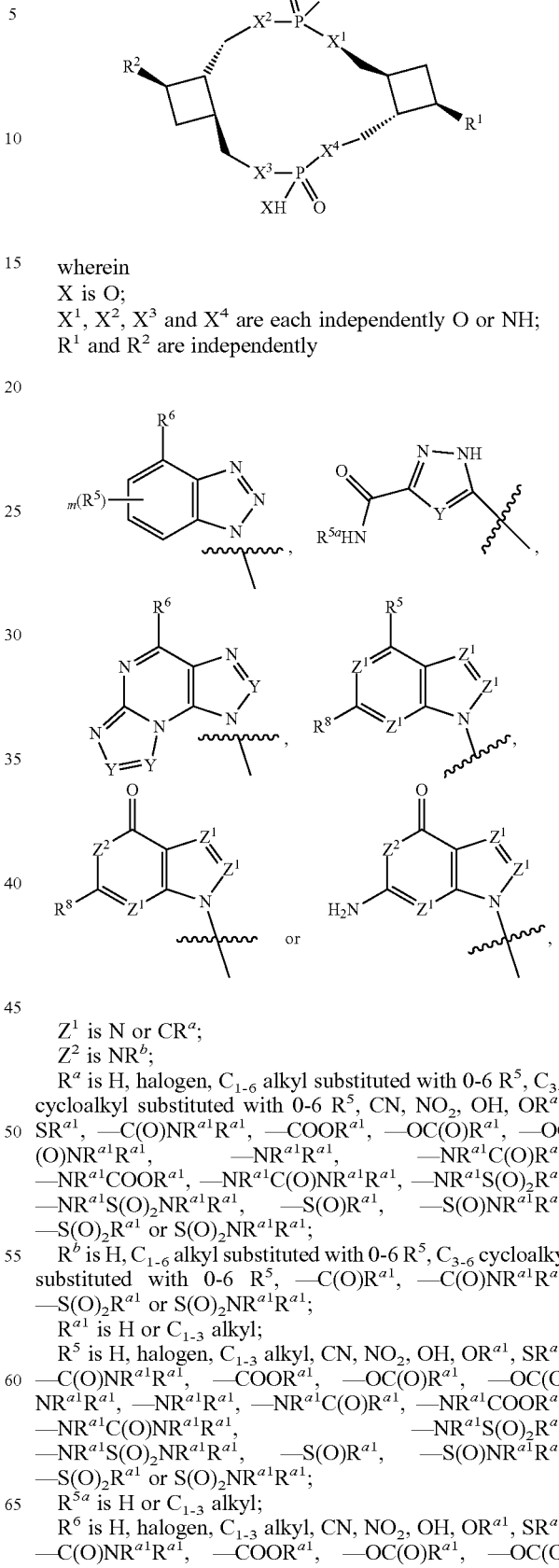

wherein
X is O;
$X^1$, $X^2$, $X^3$ and $X^4$ are each independently O or NH;
$R^1$ and $R^2$ are independently $Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;
$R^{a1}$ is H or $C_{1-3}$ alkyl;
$R^5$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)$ $NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

Y is $CR^5$ or N;

m is 0, 1, 2 or 3;

or a pharmaceutically acceptable salt, tautomer or stereoisomer thereof.

The compound of the formula

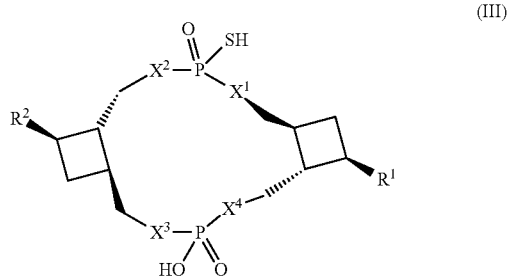 (III)

wherein $X^1$, $X^2$, $X^3$ and $X^4$ are each independently O or NH;

$R^1$ and $R^2$ are independently

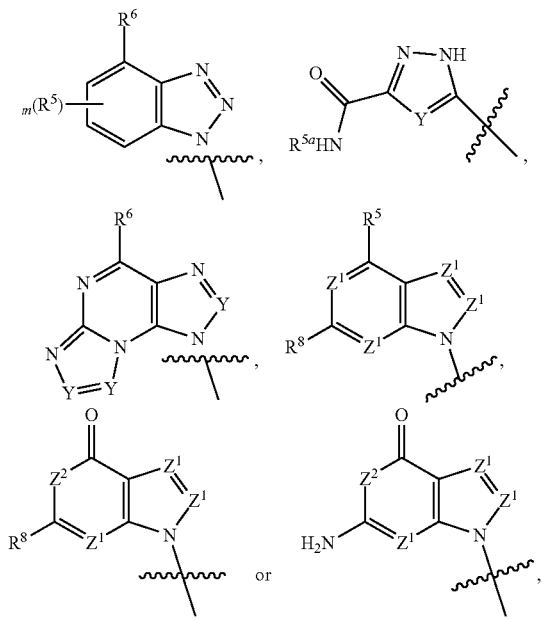

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H or $C_{1-3}$ alkyl;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

Y is $CR^5$ or N;

m is 0, 1, 2 or 3;

or a pharmaceutically acceptable salt, tautomer or stereoisomer thereof.

The compound of the formula

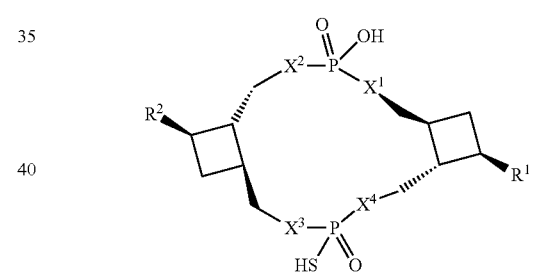

wherein $X^1$, $X^2$, $X^3$ and $X^4$ are each independently O or NH;

$R^1$ and $R^2$ are each independently

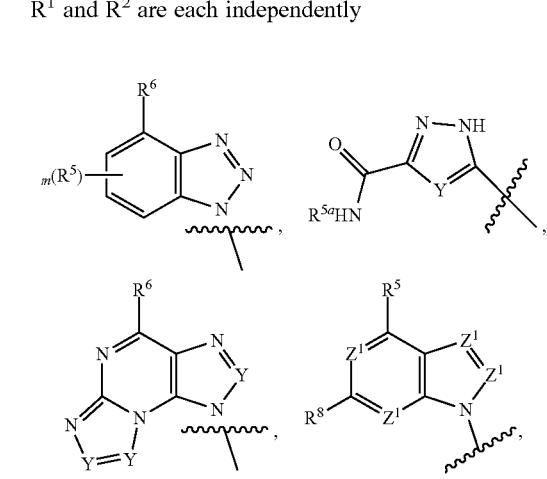

-continued

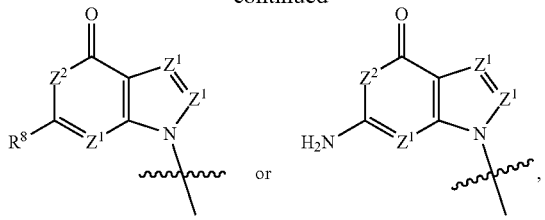

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H or $C_{1-3}$ alkyl;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

Y is $CR^5$ or N;

m is 0, 1, 2 or 3;

or a pharmaceutically acceptable salt, tautomer or stereoisomer thereof.

The compound of the formula

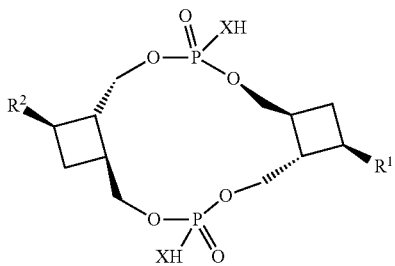

wherein

X is O or S;

$R^1$ and $R^2$ are each independently

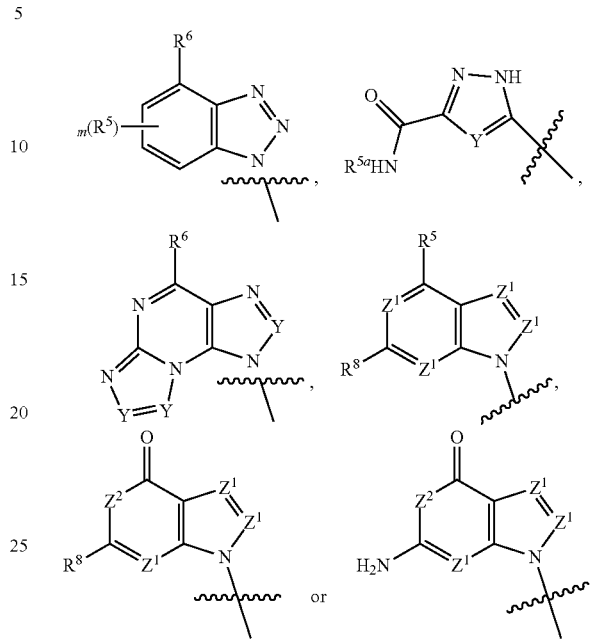

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H or $C_{1-3}$ alkyl;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

Y is $CR^5$ or N;

m is 0, 1, 2 or 3;

or a pharmaceutically acceptable salt, tautomer or stereoisomer thereof.

The compound of the formula

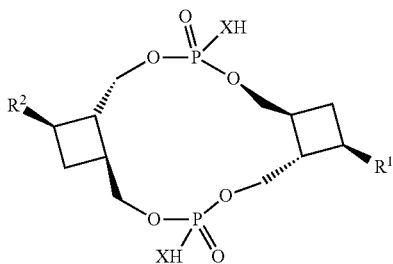

wherein
X is S;
$R^1$ and $R^2$ are independently

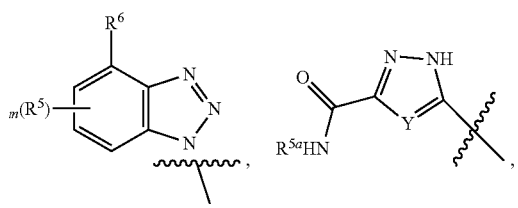

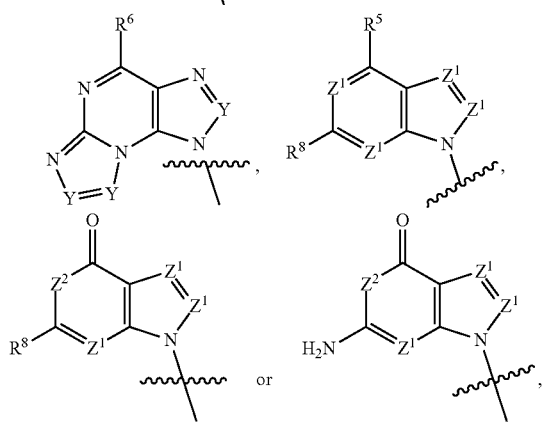

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl;
$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
Y is $CR^5$ or N;
m is 0, 1, 2 or 3;
or a pharmaceutically acceptable salt, tautomer or stereoisomer thereof.

The compound of the formula

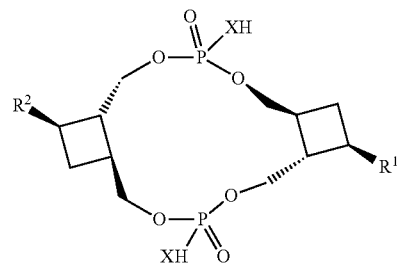

wherein
X is O;
$R^1$ and $R^2$ are independently

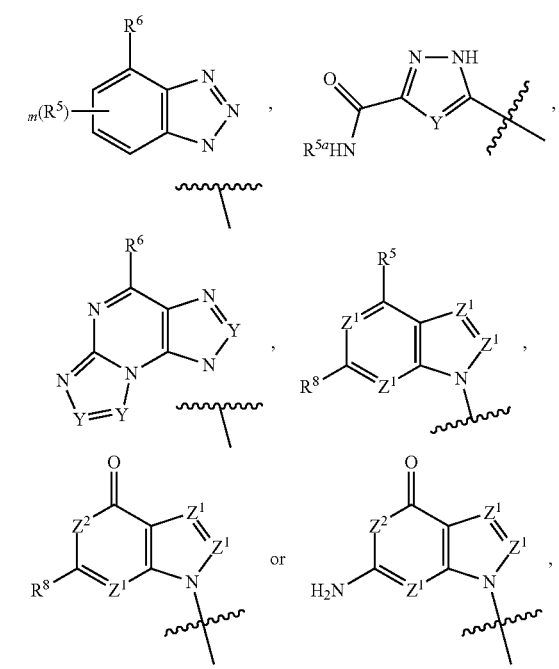

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)N$R^{a1}R^{a1}$, —S(O)$_2R^{a1}$ or S(O)$_2$N$R^{a1}R^{a1}$;

$R^{a1}$ is H or $C_{1-3}$ alkyl;

$R^5$ is H, halogen, $C_{1-3}$ alkyl, CN, NO$_2$, OH, O$R^{a1}$, S$R^{a1}$, —C(O)N$R^{a1}R^{a1}$, —COO$R^{a1}$, —OC(O)$R^{a1}$, —OC(O)N$R^{a1}R^{a1}$, —N$R^{a1}R^{a1}$, —N$R^{a1}$C(O)$R^{a1}$, —N$R^{a1}$COO$R^{a1}$, —N$R^{a1}$C(O)N$R^{a1}R^{a1}$, —N$R^{a1}$S(O)$_2R^{a1}$, —N$R^{a1}$S(O)$_2$N$R^{a1}R^{a1}$, —S(O)$R^{a1}$, —S(O)N$R^{a1}R^{a1}$, —S(O)$_2R^{a1}$ or S(O)$_2$N$R^{a1}R^{a1}$;

$R^{5a}$ is H or $C_{1-3}$ alkyl;

$R^6$ is H, halogen, $C_{1-3}$ alkyl, CN, NO$_2$, OH, O$R^{a1}$, S$R^{a1}$, —C(O)N$R^{a1}R^{a1}$, —COO$R^{a1}$, —OC(O)$R^{a1}$, —OC(O)N$R^{a1}R^{a1}$, —N$R^{a1}R^{a1}$, —N$R^{a1}$C(O)$R^{a1}$, —N$R^{a1}$COO$R^{a1}$, —N$R^{a1}$C(O)N$R^{a1}R^{a1}$, —N$R^{a1}$S(O)$_2R^{a1}$, —N$R^{a1}$S(O)$_2$N$R^{a1}R^{a1}$, —S(O)$R^{a1}$, —S(O)N$R^{a1}R^{a1}$, —S(O)$_2R^{a1}$ or S(O)$_2$N$R^{a1}R^{a1}$;

$R^8$ is H, halogen, $C_{1-3}$ alkyl, CN, NO$_2$, OH, O$R^{a1}$, S$R^{a1}$, —C(O)N$R^{a1}R^{a1}$, —COO$R^{a1}$, —OC(O)$R^{a1}$, —OC(O)N$R^{a1}R^{a1}$, —N$R^{a1}R^{a1}$, —N$R^{a1}$C(O)$R^{a1}$, —N$R^{a1}$COO$R^{a1}$, —N$R^{a1}$C(O)N$R^{a1}R^{a1}$, —N$R^{a1}$S(O)$_2R^{a1}$, —N$R^{a1}$S(O)$_2$N$R^{a1}R^{a1}$, —S(O)$R^{a1}$, —S(O)N$R^{a1}R^{a1}$, —S(O)$_2R^{a1}$ or S(O)$_2$N$R^{a1}R^{a1}$;

Y is C$R^5$ or N;

m is 0, 1, 2 or 3;

or a pharmaceutically acceptable salt, tautomer or stereoisomer thereof.

The compound of the formula

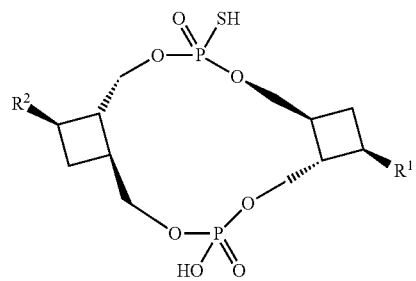

wherein $R^1$ and $R^2$ are independently

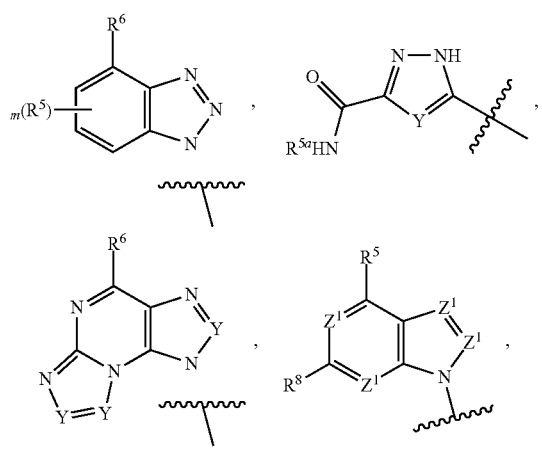

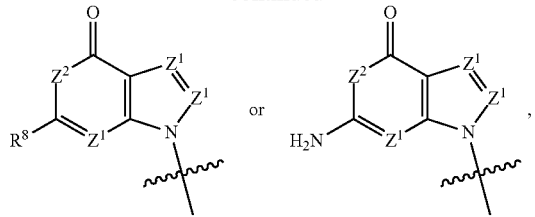

$Z^1$ is N or C$R^a$;

$Z^2$ is N$R^b$;

$R^a$ is H, halogen, $C_{1-6}$ alkyl substituted with 0-6 $R^5$, $C_{3-6}$ cycloalkyl substituted with 0-6 $R^5$, CN, NO$_2$, OH, O$R^{a1}$, S$R^{a1}$, —C(O)N$R^{a1}R^{a1}$, —COO$R^{a1}$, —OC(O)$R^{a1}$, —OC(O)N$R^{a1}R^{a1}$, —N$R^{a1}R^{a1}$, —N$R^{a1}$C(O)$R^{a1}$, —N$R^{a1}$COO$R^{a1}$, —N$R^{a1}$C(O)N$R^{a1}R^{a1}$, —N$R^{a1}$S(O)$_2R^{a1}$, —N$R^{a1}$S(O)$_2$N$R^{a1}R^{a1}$, —S(O)$R^{a1}$, —S(O)N$R^{a1}R^{a1}$, —S(O)$_2R^{a1}$ or S(O)$_2$N$R^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)N$R^{a1}R^{a1}$, —S(O)$_2R^{a1}$ or S(O)$_2$N$R^{a1}R^{a1}$;

$R^{a1}$ is H or $C_{1-3}$ alkyl;

$R^5$ is H, halogen, $C_{1-3}$ alkyl, CN, NO$_2$, OH, O$R^{a1}$, S$R^{a1}$, —C(O)N$R^{a1}R^{a1}$, —COO$R^{a1}$, —OC(O)$R^{a1}$, —OC(O)N$R^{a1}R^{a1}$, —N$R^{a1}R^{a1}$, —N$R^{a1}$C(O)$R^{a1}$, —N$R^{a1}$COO$R^{a1}$, —N$R^{a1}$C(O)N$R^{a1}R^{a1}$, —N$R^{a1}$S(O)$_2R^{a1}$, —N$R^{a1}$S(O)$_2$N$R^{a1}R^{a1}$, —S(O)$R^{a1}$, —S(O)N$R^{a1}R^{a1}$, —S(O)$_2R^{a1}$ or S(O)$_2$N$R^{a1}R^{a1}$;

$R^{5a}$ is H or $C_{1-3}$ alkyl;

$R^6$ is H, halogen, $C_{1-3}$ alkyl, CN, NO$_2$, OH, O$R^{a1}$, S$R^{a1}$, —C(O)N$R^{a1}R^{a1}$, —COO$R^{a1}$, —OC(O)$R^{a1}$, —OC(O)N$R^{a1}R^{a1}$, —N$R^{a1}R^{a1}$, —N$R^{a1}$C(O)$R^{a1}$, —N$R^{a1}$COO$R^{a1}$, —N$R^{a1}$C(O)N$R^{a1}R^{a1}$, —N$R^{a1}$S(O)$_2R^{a1}$, —N$R^{a1}$S(O)$_2$N$R^{a1}R^{a1}$, —S(O)$R^{a1}$, —S(O)N$R^{a1}R^{a1}$, —S(O)$_2R^{a1}$ or S(O)$_2$N$R^{a1}R^{a1}$;

$R^8$ is H, halogen, $C_{1-3}$ alkyl, CN, NO$_2$, OH, O$R^{a1}$, S$R^{a1}$, —C(O)N$R^{a1}R^{a1}$, —COO$R^{a1}$, —OC(O)$R^{a1}$, —OC(O)N$R^{a1}R^{a1}$, —N$R^{a1}R^{a1}$, —N$R^{a1}$C(O)$R^{a1}$, —N$R^{a1}$COO$R^{a1}$, —N$R^{a1}$C(O)N$R^{a1}R^{a1}$, —N$R^{a1}$S(O)$_2R^{a1}$, —N$R^{a1}$S(O)$_2$N$R^{a1}R^{a1}$, —S(O)$R^{a1}$, —S(O)N$R^{a1}R^{a1}$, —S(O)$_2R^{a1}$ or S(O)$_2$N$R^{a1}R^{a1}$;

Y is C$R^5$ or N;

m is 0, 1, 2 or 3;

or a pharmaceutically acceptable salt, tautomer or stereoisomer thereof.

The compound of the formula

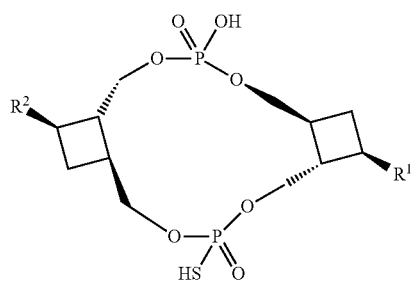

wherein
R¹ and R² are each independently

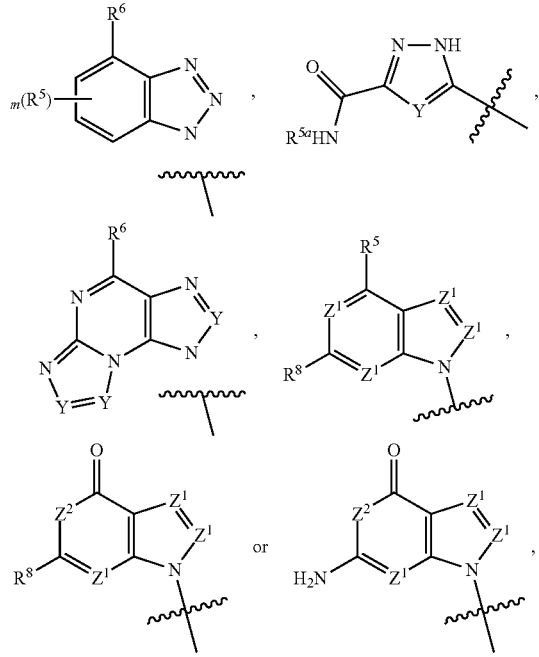

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl;
$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
Y is $CR^5$ or N;
m is 0, 1, 2 or 3;
or a pharmaceutically acceptable salt, tautomer or stereoisomer thereof.

In another aspect, there is provided a compound selected from the exemplified examples or a pharmaceutically acceptable salt, tautomer or stereoisomer thereof.

In another aspect, there is provided a compound selected from
(1R,6S,8R,9R,15R,17R,18R)-8,17-bis(6-amino-9H-purin-9-yl)-18-fluoro-3,12-disulfanyl-2,4,11,13,16-pentaoxa-3λ⁵,12λ⁵-diphosphatricyclo[13.3.0.0⁶,⁹]octadecane-3,12-dione;
(1R,6S,8R,9R,15R,17R,18R)-17-(6-amino-9H-purin-9-yl)-18-fluoro-3,12-dihydroxy-8-{4-hydroxy-1H-imidazo[2,1-b]purin-1-yl}-2,4,11,13,16-pentaoxa-3λ⁵,12λ⁵-diphosphatricyclo[13.3.0.0⁶,⁹]octadecane-3,12-dithione;
(1R,6S,8R,9R,15R,17R,18R)-8,17-bis(6-amino-9H-purin-9-yl)-3,12,18-trihydroxy-2,4,11,13,16-pentaoxa-3λ⁵,12λ⁵-diphosphatricyclo[13.2.1.0⁶,⁹]octadecane-3,12-dithione;
9-[(1R,6S,8R,9R,15R,17R,18R)-17-(6-amino-9H-purin-9-yl)-18-fluoro-3,12-dihydroxy-3,12-disulfanylidene-2,4,11,13,16-pentaoxa-3λ⁵,12λ⁵-diphosphatricyclo[13.3.0.0⁶,⁹]octadecan-8-yl]-6,9-dihydro-1H-purin-6-one;
(1S,6S,8R,9R,15R,17R)-8-(6-amino-9H-purin-9-yl)-17-{4-chloro-7H-pyrrolo[2,3-d]pyrimidin-7-yl}-3-hydroxy-12-sulfanyl-3-sulfanylidene-2,4,11,13,16-pentaoxa-3λ⁵,12λ⁵-diphosphatricyclo[13.3.0.0⁶,⁹]octadecan-12-one;
(1R,6S,8R,9R,15R,17R,18S)-8-(6-amino-9H-purin-9-yl)-17-{4-chloro-7H-pyrrolo[2,3-d]pyrimidin-7-yl}-18-fluoro-3,12-dihydroxy-2,4,11,13,16-pentaoxa-3λ⁵,12λ⁵-diphosphatricyclo[13.3.0.0⁶,⁹]octadecane-3,12-dithione;
(1R,6S,8R,9R,15R,17R,18S)-17-{4-amino-7H-pyrrolo[2,3-d]pyrimidin-7-yl}-8-(6-amino-9H-purin-9-yl)-18-fluoro-3,12-dihydroxy-2,4,11,13,16-pentaoxa-3λ⁵,12λ⁵-diphosphatricyclo[13.3.0.0⁶,⁹]octadecane-3,12-dithione
1-[(1R,6S,8R,9R,15R,17R,18R)-8-(6-amino-9H-purin-9-yl)-18-fluoro-3,12-dihydroxy-3,12-disulfanylidene-2,4,11,13,16-pentaoxa-3λ⁵,12λ⁵-diphosphatricyclo[13.3.0.0⁶,⁹]octadecan-17-yl]-1H,4H,5H-imidazo[2,1-b]purin-4-one;
(1R,6S,8R,9R,15R,17R,18R)-8,17-bis(6-amino-9H-purin-9-yl)-18-fluoro-3,12-dihydroxy-2,4,11,13,16-pentaoxa-3λ⁵,12λ⁵-diphosphatricyclo[13.3.0.0⁶,⁹]octadecane-3,12-dione;
1-[(1S,6S,8R,9R,15R,17R,18R)-8-(6-amino-9H-purin-9-yl)-18-fluoro-3,12-dihydroxy-3,12-disulfanylidene-2,4,11,13,16-pentaoxa-3λ⁵,12λ⁵-diphosphatricyclo[13.2.1.0⁶,⁹]octadecan-17-yl]-1H-1,2,3-benzotriazole-4-carboxamide;
1-[(1R,6S,8R,9R,15R,17R,18R)-8-(6-amino-9H-purin-9-yl)-18-fluoro-3,12-dihydroxy-3,12-disulfanylidene-2,4,11,13,16-pentaoxa-3λ⁵,12λ⁵-diphosphatricyclo[13.3.0.0⁶,⁹]octadecan-17-yl]-1H-1,2,3-benzotriazole-4-carboxamide;
1-[(1R,6S,8R,9R,15R,17R,18R)-17-(6-amino-9H-purin-9-yl)-18-fluoro-3,12-dihydroxy-3,12-disulfanylidene-2,4,11,13,16-pentaoxa-3λ⁵,12λ⁵-diphosphatricyclo[13.3.0.0⁶,⁹]octadecan-8-yl]-1H-1,2,3-benzotriazole-4-carboxamide;
(1R,6S,8R,9R,15R,17R,18R)-18-hydroxy-8-(6-hydroxy-9H-purin-9-yl)-17-{4-oxo-1H,4H,5H-imidazo[2,1-b]purin-1-yl}-3,12-disulfanyl-2,4,11,13,16-pentaoxa-3λ⁵,12λ⁵-diphosphatricyclo[13.2.1.0⁶,⁹]octadecane-3,12-dione;
(1R,6S,8R,9R,15R,17R,18R)-8-(6-amino-9H-purin-9-yl)-3,12,18-trihydroxy-17-{4-hydroxy-1H-imidazo[2,1-b]purin-1-yl}-2,4,11,13,16-pentaoxa-3λ⁵,12λ⁵-diphosphatricyclo[13.2.1.0⁶,⁹]octadecane-3,12-dithione;

(1S,6S,8R,9R,15R,17R,18R)-8-(6-amino-9H-purin-9-yl)-3,12,18-trihydroxy-17-(6-hydroxy-9H-purin-9-yl)-2,4,11,13,16-pentaoxa-3λ⁵,12λ⁵-diphosphatricyclo[13.3.0.0⁶,⁹]octadecane-3,12-dithione;

(1R,6S,8R,9R,15R,17R,18S)-8,17-bis(6-amino-9H-purin-9-yl)-18-fluoro-3,12-dihydroxy-2,4,11,13,16-pentaoxa-3λ⁵,12λ⁵-diphosphatricyclo[13.3.0.0⁶,⁹]octadecane-3,12-dithione; and 2-amino-9-[(1R,6S,8R,9R,15R,17R,18R)-17-(6-amino-9H-purin-9-yl)-18-fluoro-3,12-dihydroxy-3,12-disulfanylidene-2,4,11,13,16-pentaoxa-3λ⁵,12λ⁵-diphosphatricyclo[13.3.0.0⁶,⁹]octadecan-8-yl]-6,9-dihydro-1H-purin-6-one or a pharmaceutically acceptable salt, tautomer or stereoisomer thereof.

In another aspect, there is provided a compound selected from

1

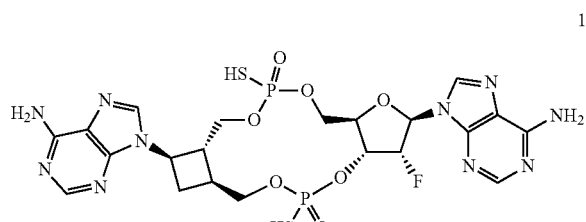

3

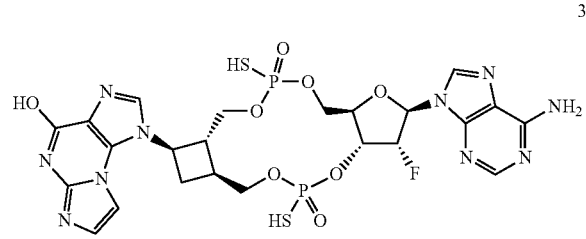

5

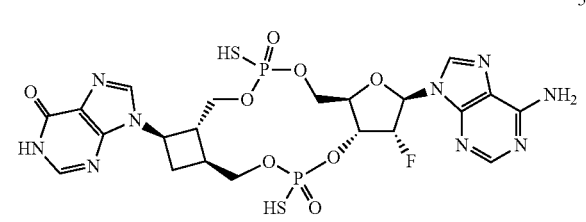

6

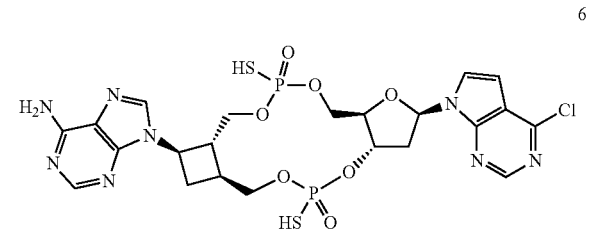

7

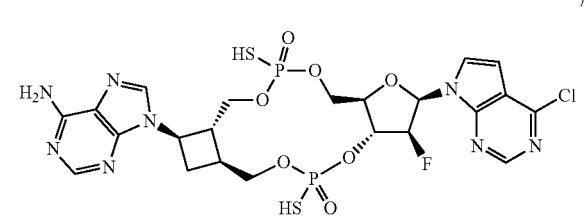

8

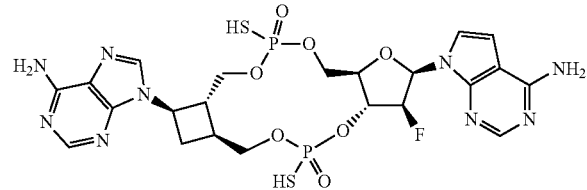

9

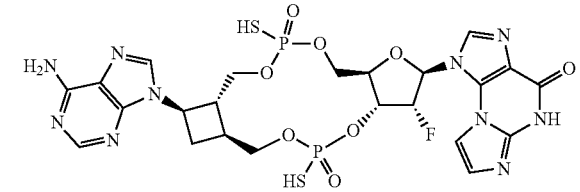

10

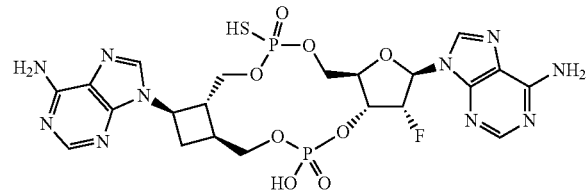

12

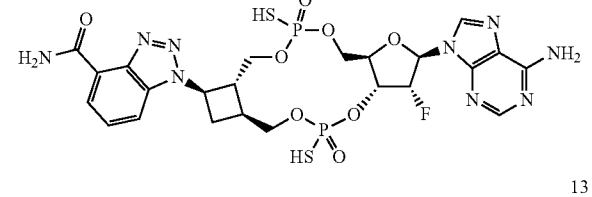

13

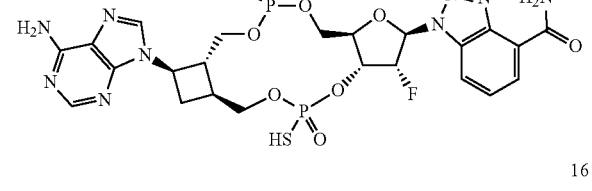

16

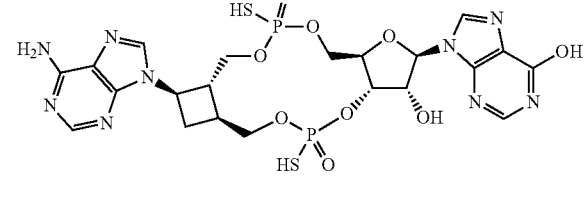

17

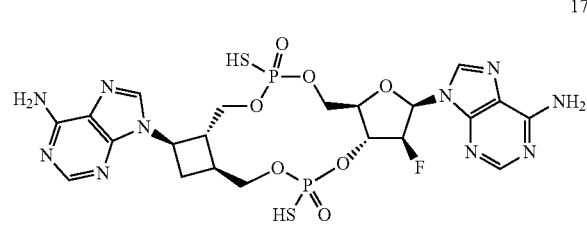

-continued

18

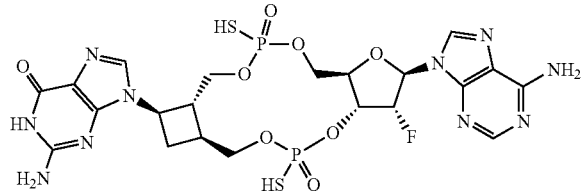

or a pharmaceutically acceptable salt, tautomer or stereoisomer thereof.

In another aspect, there is provided a compound selected from any subset list of compounds within the scope of any of the above aspects.

OTHER EMBODIMENTS OF THE INVENTION

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including small cell lung cancer, non-small cell lung cancer, colorectal cancer, melanoma, renal cell carcinoma, head and neck cancer, Hodgkin's lymphoma, bladder cancer, esophageal carcinoma, gastric carcinoma, ovarian carcinoma, cervical carcinoma, pancreatic carcinoma, prostate carcinoma, breast cancers, urinary carcinoma, brain tumors such as glioblastoma, non-Hodgkin's lymphoma, acute lymphatic leukemia (ALL), chronic lymphatic leukemia (CLL), acute myeloid leukemia (AML), chronic myeloid leukemia (CML), hepatocellular carcinoma, multiple myeloma, gastrointestinal stromal tumors, mesothelioma, and other solid tumors or other hematological cancers In another embodiment, the invention provides a method for the treatment and/or prophylaxis of various types of cancer, including without limitation, small cell lung cancer, non-small cell lung cancer, colorectal cancer, melanoma, renal cell carcinoma, head and neck cancer, Hodgkin's lymphoma or bladder cancer.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

Therapeutic Applications

The cyclic dinucleotides of the invention induce Type I interferons and/or pro-inflammatory cytokines in vitro in human cells, animal cells and human blood. The cytokine-inducting activity of these CDNs requires the presence of STING, as confirmed by in vitro experiments in human or animal cells.

The CDNs of the invention are agonists of the receptor STING.

The term "agonist" refers to any substance that activates a biologic receptor in vitro or in vivo to provoke a physiological response.

"STING" is an abbreviation of "stimulator of interferon genes", which is also known as "endoplasmic reticulum interferon stimulator (ERIS)", "mediator of IRF3 activation (MITA)", "MPYS" or "transmembrane protein 173 (TM173)". STING is a transmembrane receptor protein that in humans is encoded by the gene TMEM173. Activation of STING by cyclic dinucleotides (CDN) leads to activation of the IRF3 and NF-κB pathways and consequently, to induction of Type I interferons and of pro-inflammatory cytokines, respectively.

Another object of the present invention is the cyclic dinucleotides of Formula (I), for use in a therapeutic treatment in humans or animals. In particular, the compounds of the present invention may be used for therapeutic or diagnostic applications in human or animal health.

The term "therapeutic agent" refers to one or more substances that are administered to a human or animal in order to achieve some kind of therapeutic effect in that human or animal, including to prevent, cure, or mitigate the effects of, infection or disease, and/or to otherwise improve the health of that human or animal.

The term "monotherapy" refers to the use of a single substance and/or strategy to treat a human or animal in any clinical or medical context, as opposed to the use of multiple substances and/or strategies to treat a human or animal in the same clinical or medical context, regardless of whether the multiple substances and/or strategies are used sequentially in any order or concurrently.

The term "chemotherapeutic agent" herein refers to one or more chemical substances that are administered to a human or animal in order to kill tumors, or slow or stop the growth of tumors, and/or slow or stop the division of cancerous cells and/or prevent or slow metastasis. Chemotherapeutic agents are often administered to treat cancer, but are also indicated for other diseases.

The term "chemotherapy" refers to medical treatment of a human or animal with one or more chemotherapeutic agents (see definition above).

The term "chemoimmunotherapy" refers to the combined use, whether sequentially in any order or concurrently, of chemotherapy substances and/or strategies, and immunotherapy substances and/or strategies. Chemoimmunotherapy is often employed to treat cancer, but can also be employed to treat other diseases.

The term "immune system" refers to the ensemble, or to any one or more components, of the molecules, substances (e.g. bodily fluids), anatomic structures (e.g. cells, tissue and organs) and physiologic processes involved in preventing infection in the body, in protecting the body during infection or during disease, and/or in helping the body to recuperate after infection or disease. A complete definition of "immune system" is beyond the scope of this patent; however, this term should be understood by any ordinary practitioner in the field.

The term "immune agent" refers to any endogenous or exogenous substance that can interact with any one or more components of the immune system. The term "immune agent" includes antibodies, antigens, vaccines and their constituent components, nucleic acids, synthetic drugs, natural or synthetic organic compounds, cytokines, natural or modified cells, synthetic analogs thereof, and/or fragments thereof.

The term "antagonist" refers to any substance that inhibits, counteracts, downregulates, and/or desensitizes a biologic receptor in vitro or in vivo to provoke a physiological response.

The term "immunotherapy" refers to any medical treatment in which one or more components of a human's or animal's immune system is deliberately modulated in order to directly or indirectly achieve some therapeutic benefit, including systemic and/or local effects, and preventative and/or curative effects. Immunotherapy can involve administering one or more immune agents (see definition above), either alone or in any combination, to a human or animal subject by any route (e.g. orally, intravenously, dermally, by injection, by inhalation, etc.), whether systemically, locally or both.

"Immunotherapy" can involve provoking, increasing, decreasing, halting, preventing, blocking or otherwise modulating the production of cytokines, and/or activating or deactivating cytokines or immune cells, and/or modulating the levels of immune cells, and/or delivering one or more therapeutic or diagnostic substances to a particular location in the body or to a particular type of cell or tissue, and/or destroying particular cells or tissue. Immunotherapy can be used to achieve local effects, systemic effects or a combination of both.

The term "immunosuppressed" describes the state of any human or animal subject whose immune system is functionally diminished, deactivated or otherwise compromised, or in whom one or more immune components is functionally diminished, deactivated or otherwise compromised.

"Immunosuppression" can be the cause, consequence or byproduct of disease, infection, exhaustion, malnutrition, medical treatment or some other physiologic or clinical state.

The terms "immunomodulating substance", "immunomodulatory substance", "immunomodulatory agent" and "immunomodulator", used here synonymously, refer to any substance that, upon administration to a human or animal, directly influences the functioning of the immune system of that human or animal. Examples of common immunomodulators include, but are not limited to, antigens, antibodies and small-molecule drugs.

The term "vaccine" refers to a biological preparation administered to a human or animal in order to elicit or enhance a specific immune system response and/or protection against one or more antigens in that human or animal.

The term "vaccination" refers to treatment of a human or animal with a vaccine or to the act of administering a vaccine to a human or animal.

The term "adjuvant" refers to a secondary therapeutic substance that is administered together (either sequentially in any order, or concurrently) with a primary therapeutic substance to achieve some kind of complimentary, synergic or otherwise beneficial effect that could not be achieved through use of the primary therapeutic substance alone. An adjuvant can be used together with a vaccine, chemotherapy, or some other therapeutic substance. Adjuvants can enhance the efficacy of the primary therapeutic substance, reduce the toxicity or side effects of the primary therapeutic substance, or provide some kind of protection to the subject that receives the primary therapeutic substance, such as, but not limited to, improved functioning of the immune system.

In one embodiment, the cyclic dinucleotide of Formula (I) can be administered as immunotherapy to a human or an animal to induce in vivo production of one or more cytokines that are therapeutically beneficial to that human or animal. This type of immunotherapy could be used alone or in combination with other treatment strategies, whether sequentially in any order, or concurrently. It could be used to prevent, cure, and/or mitigate the effects of infection or disease in that human or animal, and/or to modulate the immune system of that human or animal to achieve some other therapeutic benefit.

In one particular embodiment, the cyclic dinucleotides of the present invention can be used for cytokine induction immunotherapy of immunosuppressed individuals.

In this example, a cyclic dinucleotide of Formula (I) would be administered to an immunosuppressed human or animal subject to induce in vivo production of one or more cytokines that directly or indirectly enhance the immune system of that human or animal. Subjects that might benefit from such treatment include those suffering from autoimmune disorders, immune system deficiencies or defects, microbial or viral infections, infectious diseases, or cancer.

The present invention thus discloses a method for inducing cytokine in immunosuppressed individuals, said method comprising administering to a patient in need thereof a cyclic dinucleotide of Formula (I) or a pharmaceutically acceptable salt or prodrug thereof.

In another embodiment, the cyclic dinucleotides of the present invention can be used for cytokine induction immunotherapy in combination with chemotherapy. In this example, a cyclic dinucleotide of Formula (I) would be administered together with one or more chemotherapeutic agents, sequentially in any order or concomitantly, to a cancer patient to stop the growth of, shrink and/or destroy tumors in that patient. The chemoimmunotherapy resulting from the combination of cytokine induction, provided by the compound(s) of the present invention, and cytotoxicity, provided by the chemotherapeutic agent(s), might be less toxic to the patient, cause fewer side effects in the patient and/or exhibit greater anti-tumor efficacy than would the chemotherapeutic agent(s) when used as monotherapy.

The present invention thus discloses a method for treating cancer, said method comprising administering to a patient in need thereof: a chemotherapeutic agent; and a cyclic dinucleotide of Formula (I) or a pharmaceutically acceptable salt or prodrug thereof.

Another object of the present invention is the cyclic dinucleotides of Formula (I) for use in the treatment of a bacterial infection, a viral infection or a cancer.

As used herein, "cancer" refers to the physiological condition in subjects that is characterized by unregulated or dysregulated cell growth or death. The term "cancer" includes solid tumors and blood-born tumors, whether malignant or benign.

In a preferred embodiment, the cancer is from the following group: small cell lung cancer, non-small cell lung cancer, colorectal cancer, melanoma, renal cell carcinoma, head and neck cancer, Hodgkin's lymphoma or bladder cancer.

The present invention thus discloses a method for treating a bacterial infection, a viral infection or a cancer, said method comprising administering to a patient in need thereof a cyclic dinucleotide of Formula (I) or a pharmaceutically acceptable salt or prodrug thereof.

Another object of the present invention is the cyclic dinucleotides of Formula (I) for use in the treatment of a pathology that may be alleviated by the induction of an immune response via the STING pathway.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colorectal cancers, blood cancers, lung cancers and bone cancers. Examples of such cancer types include neuroblastoma, intestinal carcinoma such as rectal carcinoma, colon carcinomas, familiar adenomatous polyposis carcinoma and hereditary non-polyposis colorectal cancer, esophageal carcinoma, labial carcinoma, larynx carcinoma, nasopharyngeal cancers, oral cavity cancers, salivary gland carcinoma, peritoneal cancers, soft tissue sarcoma, urothelial cancers, sweat gland carcinoma, gastric carcinoma, adenocarcinoma, medullary thyroid carcinoma, papillary thyroid carcinoma, renal carcinoma, kidney parenchymal carcinoma, ovarian carcinoma, cervical carcinoma, uterine corpus carcinoma, endometrial carcinoma, pancreatic carcinoma, prostate carcinoma, testis carcinoma, breast cancers including HER2 Negative, urinary carcinoma, melanoma, brain tumors such as glioblastoma, astrocytoma, meningioma, medulloblastoma and peripheral neuroectodermal tumors, Hodgkin's lymphoma, non-Hodgkin's lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, multiple myeloma, seminoma, osteosarcoma, chondrosarcoma, anal canal cancers, adrenal cortex carcinoma, chordoma, fallopian tube cancer, gastrointestinal stromal tumors, myeloproliferative diseases, mesothelioma, biliary tract cancers, Ewing sarcoma and other rare tumor types.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergistic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s) of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. The PD-1 antibody can be selected from Opdivo (nivolumab), Keytruda (pembrolizumab), PDR001 (Novartis; see WO2015/112900), MEDI-0680 (AMP-514) (AstraZeneca; see WO2012/145493), REGN-2810 (Sanofi/Regeneron; see WO2015/112800), JS001 (Taizhou Junshi), BGB-A317 (Beigene; see WO2015/35606), INCSHR1210 (SHR-1210) (Incyte/Jiangsu Hengrui Medicine; see WO2015/085847), TSR-042 (ANB001) (Tesara/AnaptysBio; see WO2014/179664), GLS-010 (Wuxi/Harbin Gloria Pharmaceuticals), AM-0001 (Armo/Ligand), or STI-1110 (Sorrento; see WO2014/194302). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In one aspect,

In another aspect, the immuno-oncology agent is a PD-L1 antagonist, such as an antagonistic PD-L1 antibody. The PD-L1 antibody can be selected from Tecentriq (atezolizumab), durvalumab, avelumab, STI-1014 (Sorrento; see WO2013/181634), or CX-072 (CytomX; see WO2016/149201).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO006/105021, WO009/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intratumoral routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intratumoral, intravenous or epidural injection as, for example, a sterile solution or suspension, or sustained release formulation; (3) topical application, for example, as a cream, ointment, or a controlled release patch or spray applied to the skin; or intratumorally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Formulations of the present invention include those suitable for oral, intratumoral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

In some cases, in order to prolong the effect of a drug, it is desirable to slow the absorption of the drug from subcutaneous, intratumoral or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans-(or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (—) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

Additionally, the phosphorothioate group can be drawn as either

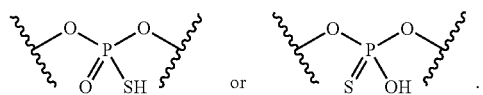 [SMILES: *OP(=O)(S)O* ; *OP(O)(=S)O*]

The term "counter ion" is used to represent a negatively charged species such as chloride, bromide, hydroxide, acetate, and sulfate or a positively charged species such as sodium (Na+), potassium (K+), ammonium (R$_n$NH$_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, CF$_3$, CF$_2$CF$_3$, CN, halogen, haloalkyl, NO$_2$, sulfone, sulfoxide, ester, sulfonamide, carboxamide, alkoxy, alkoxyether, alkenyl, alkynyl, OH, C(O)alkyl, CO$_2$H, phenyl, heteroaryl, —O-phenyl, and —O— heteroaryl. Preferred examples of EWG include, but are not limited to, CF$_3$, CF$_2$CF$_3$, CN, halogen, SO$_2$(C$_{1-4}$ alkyl), CONH(C$_{1-4}$ alkyl), CON(C$_{1-4}$ alkyl)$_2$, and heteroaryl. More preferred examples of EWG include, but are not limited to, CF$_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^1$H (hydrogen), $^2$H (deuterium) and $^3$H (tritium). They are also commonly denoted as D for deuterium and T for tritium. In the application, $CD_3$ denotes a methyl group wherein all of the hydrogen atoms are deuterium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, $22^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK ($2^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, $3^{rd}$ edition, Academic Press, San Diego, Calif. (2008).

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated by reference in their entirety.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Fourth Edition, Wiley and Sons, 2007).

Compounds of Formula (I) may be prepared by reference to the methods illustrated in the following Schemes. As shown therein, the end product is a compound having the same structural formula as Formula (I)-(III). It will be understood that any compound of Formula (I)-(III) may be produced by the schemes and by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

Scheme 1

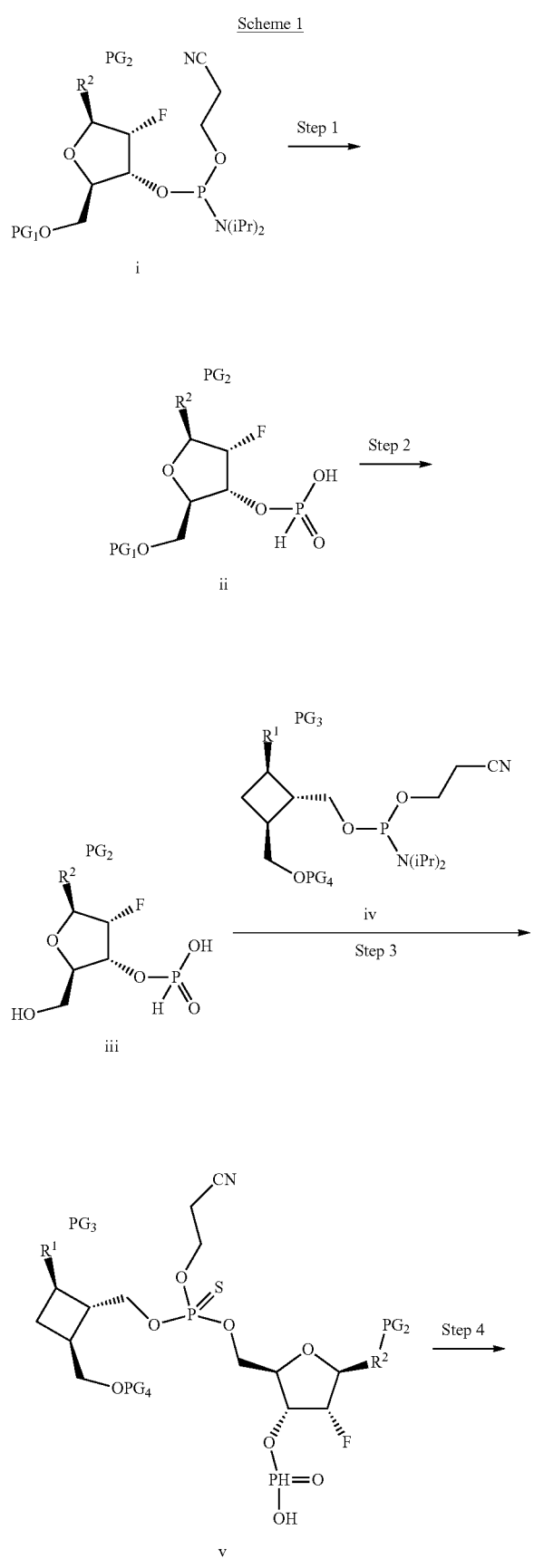

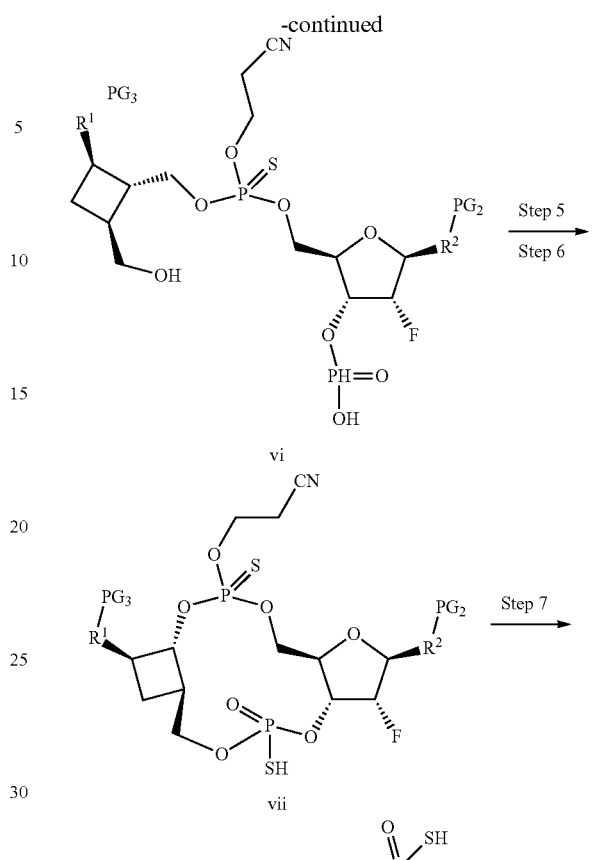

One method for preparation of examples of the present disclosure is described in Scheme 1. The method starts from a 2'-F ribo-nucleoside (i), wherein the nucleobase ($R^1$ or $R^2$) is appropriately protected ($PG_2$ or $PG_3$), such as with a benzoyl group, and the 5'-hydroxy group is appropriately protected ($PG_1$), such as with a DMTr ether, and the 3'-position is a phosphoramidite functionality. In step 1, treatment with appropriate reagents, such as pyridine trifluoroacetate followed by butylamine, affords the H-phosphonate (ii). Subsequent removal of the 5'-OH protecting group in step 2, under acidic conditions ($PG_1$=DMTr) affords compounds of formula iii. The resulting compound of formula iii may be reacted with a fully protected phosphoramidite (iv) in step 3 and then immediately sulfurized, for example with DDTT, to provide compounds of formula v. Removal of the protecting group from the second ribo-nucleoside in step 4, under appropriate conditions (for example trimethylamine trihydrofluoride when $PG_4$=TBDPS) provides compounds of formula vi. Treatment of compounds vi with an appropriate cyclization reagent in step 5, such as DMOCP followed immediately with a sulfurizing reagent, such as 3H-1,2-benzodithiol-3-one in step 6 affords compounds of formula vii. Compounds of formula vii may be treated with an appropriate reagent, for example $NH_4OH/MeOH$, to remove the cyanoethyl protecting group and the protecting groups of the nucleobase (for example, when $PG_2$ and $PG_3$=benzoyl) to afford compounds of formula (I).

Additional Examples of the present invention may be prepared according to Scheme 2.

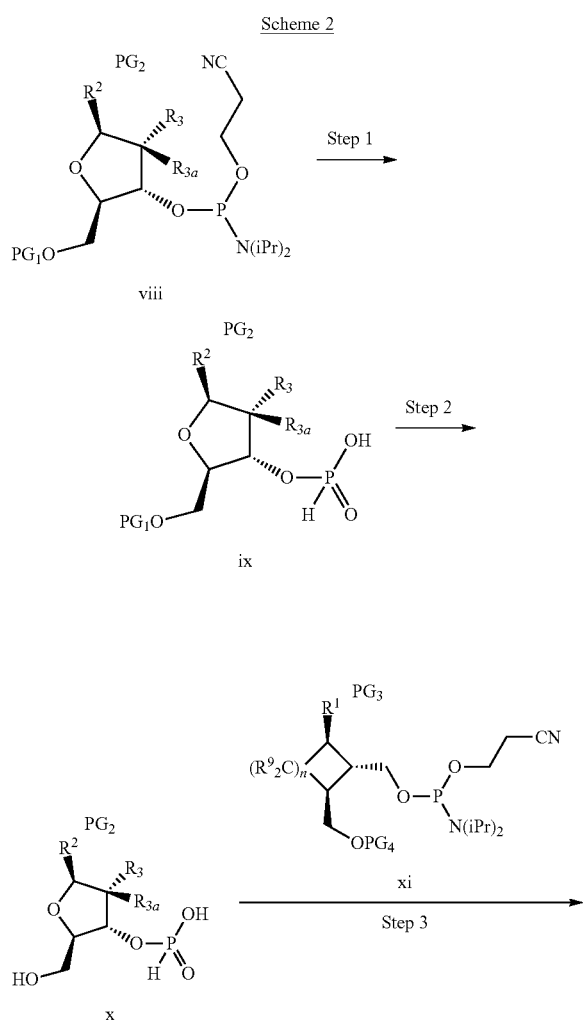

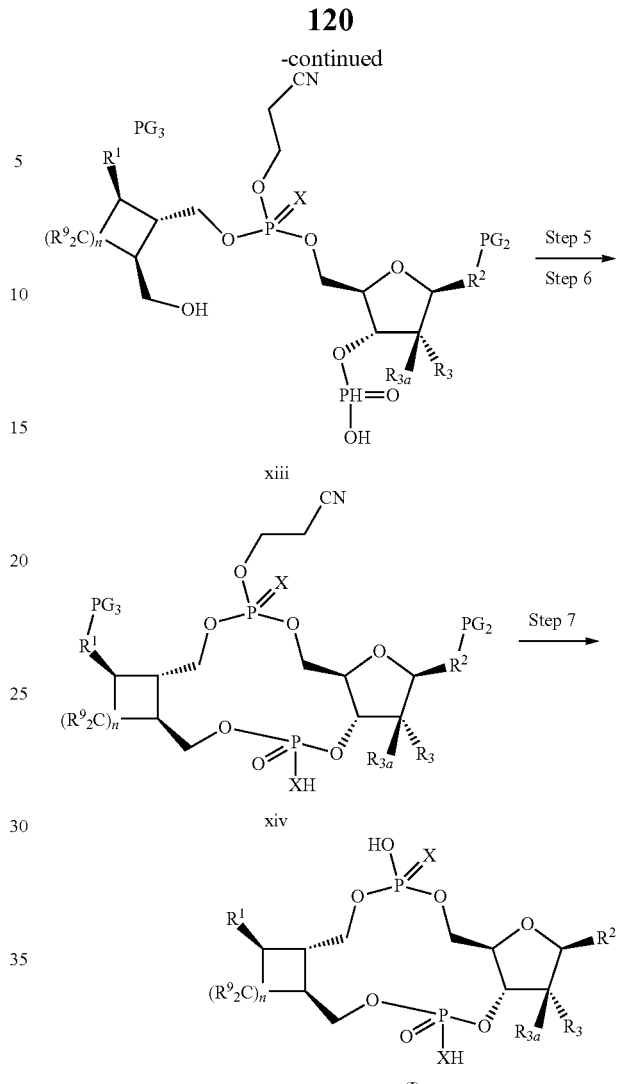

The method starts from an appropriately substituted cycloalkyl or ribo-nucleoside (viii), wherein the nucleobase ($R^1$ or $R^2$) is appropriately protected ($PG_2$ or $PG_3$), such as with a benzoyl group, and the 5'-hydroxy group is appropriately protected ($PG_1$), such as with a DMTr ether, and the 3'-position is a phosphoramidite functionality. In step 1, treatment with appropriate reagents, such as pyridine trifluoroacetate followed by butylamine, affords the H-phosphonate (ix). Subsequent removal of the 5'-OH protecting group in step 2, under acidic conditions ($PG_1$=DMTr) affords compounds of formula x. The resulting compound of formula x may be reacted with a fully protected phosphoramidite (xi) in step 3 followed by oxidation with, for example, t-butylhydroperoxide (X=O) or sulfurization with, for example DDTT (X=S), to provide compounds of formula xii. Removal of the protecting group from xii in step 4, under appropriate conditions (for example triethylamine trihydrofluoride when $PG_4$=TBDPS) provides compounds of formula xiii. Treatment of compounds xiii with an appropriate cyclization reagent in step 5, such as DMOCP followed by oxidation with, for example, t-butylhydroperoxide (X=O) or sulfurization with, for example DDTT (X=S) in step 6 affords compounds of formula xiv. Compounds of formula xiv may be treated with an appropriate reagent to remove the remaining protecting groups of the nucleobase, for example NH₄OH/MeOH (PG₂ and PG₃=benzoyl) to afford compounds of formula (I).

An additional method for preparation of examples of the present disclosure is described in Scheme 3.

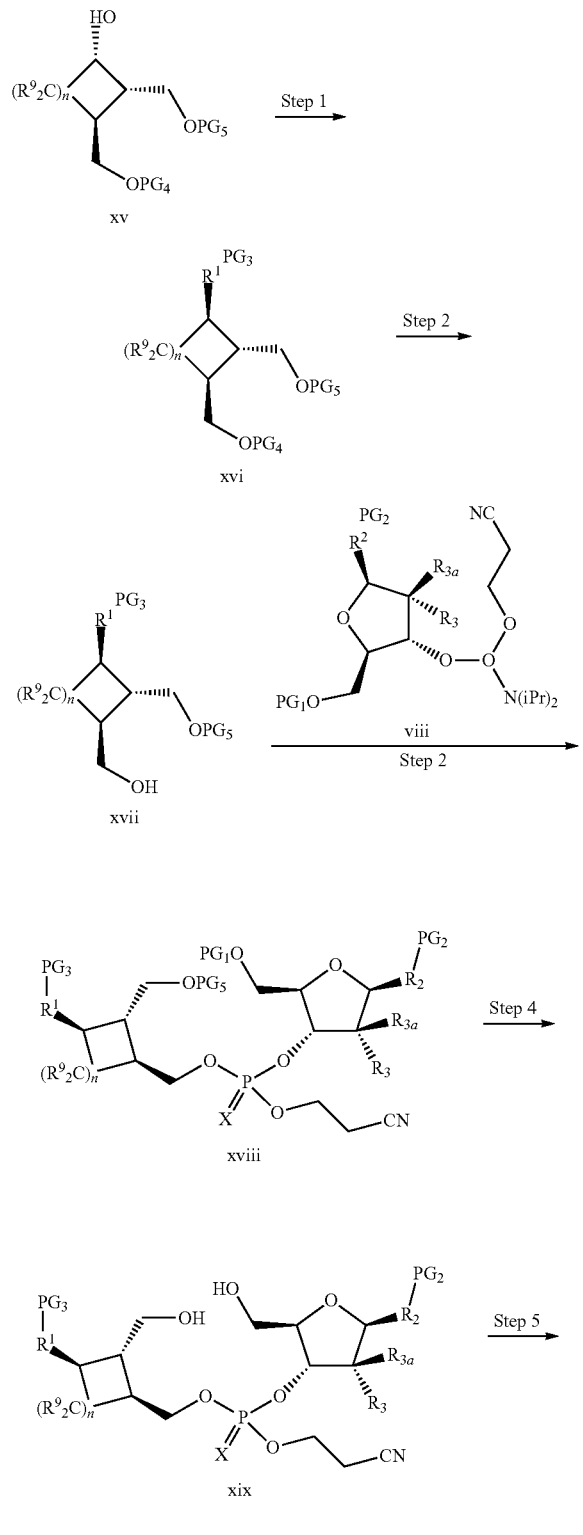

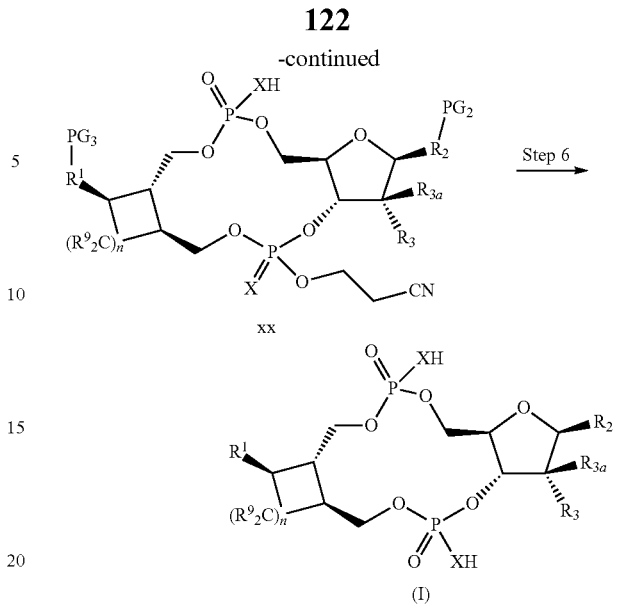

Compounds of formula xvi may be prepared from an appropriately protected compound of formula xv through a number of ways known to those skilled in the art. For example, treatment of xv (where PG₅=Trityl and PG₄=Ac) with an appropriate heterocyclic compound under Mitsunobu conditions provides compounds of formula xvi. Selective removal of one protecting group, for example where PG₄=Ac, may be accomplished under a number of conditions, for example by treatment with ammonia or MeMgCl, to afford compounds of formula xvii. Coupling of compounds of formula xvii with an appropriately protected phosphoramidite (viii) followed by oxidation with, for example, t-butylhydroperoxide (X=O) or sulfurization with, for example DDTT (X=S) provides compounds of formula xviii. Subsequent removal of protecting groups (for example PG₅=Trityl or TBDPS, PG₁=DMTr) under a variety of conditions known to one skilled in the art (for example with TFA) provides compounds of formula xix. Macrocyclization of compounds of formula xix may be accomplished in a number of ways known to those skilled in the art. For example, treatment with diphenyl phosphite, followed by oxidation with, for example, t-butylhydroperoxide (X=O) or sulfurization with, for example DDTT (X=S) provides compounds of formula xx. Removal of all remaining protecting group provides compounds of general formula (I).

An additional method for preparation of examples of the present disclosure is described in Scheme 4.

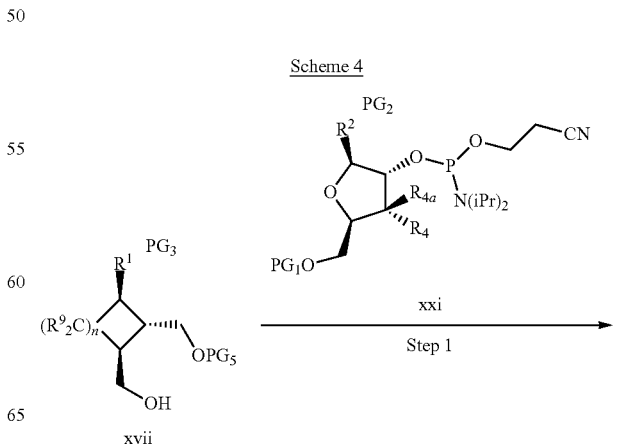

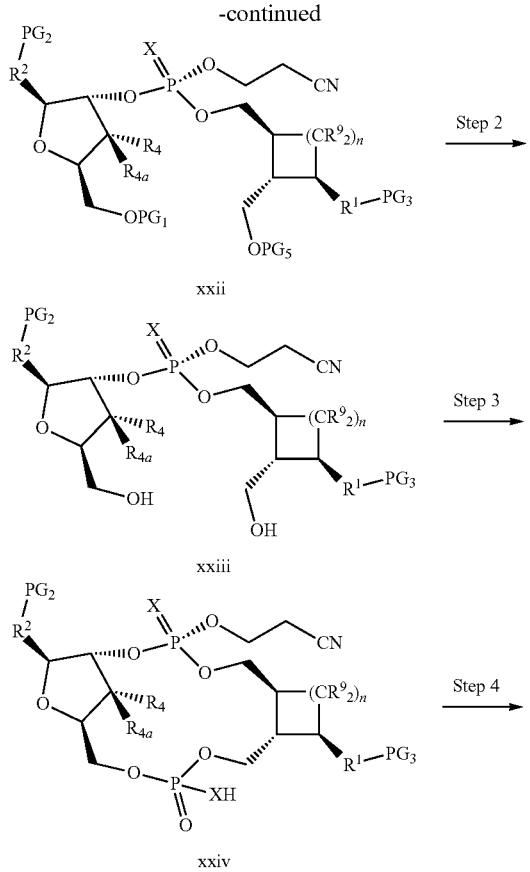

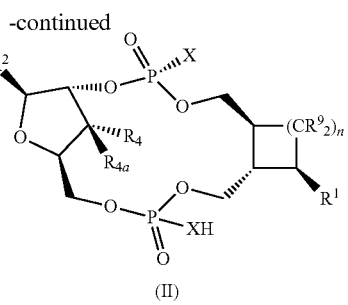

The reaction of compounds of formula xvii may also be carried out with phosphoramidites of formula xxi, followed by oxidation with, for example, t-butylhydroperoxide (X=O) or sulfurization with, for example DDTT (X=S) to afford compounds of general formula xxii. Subsequent removal of protecting groups (for example PG$_5$=Trityl or TBS, PG$_1$=DMTr) under a variety of conditions know to one skilled in the art (for example with TFA) provides compounds of formula xxiii. Macrocyclization of compounds of formula xxiii may be accomplished in a number of ways known to those skilled in the art. For example, treatment with diphenyl phosphite, followed by oxidation with, for example, t-butylhydroperoxide (X=O) or sulfurization with, for example DDTT (X=S) provides compounds of formula xxiv. Removal of all remaining protecting group provides compounds of general formula (II).

Alternatively, an additional method for the preparation of examples of the present disclosure is described in Scheme 5.

Scheme 5

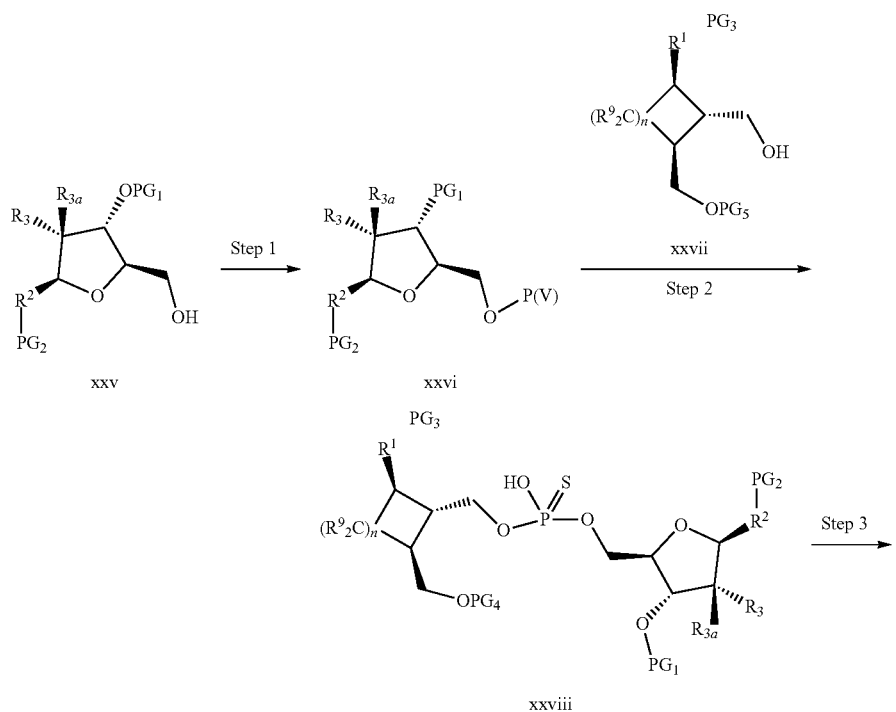

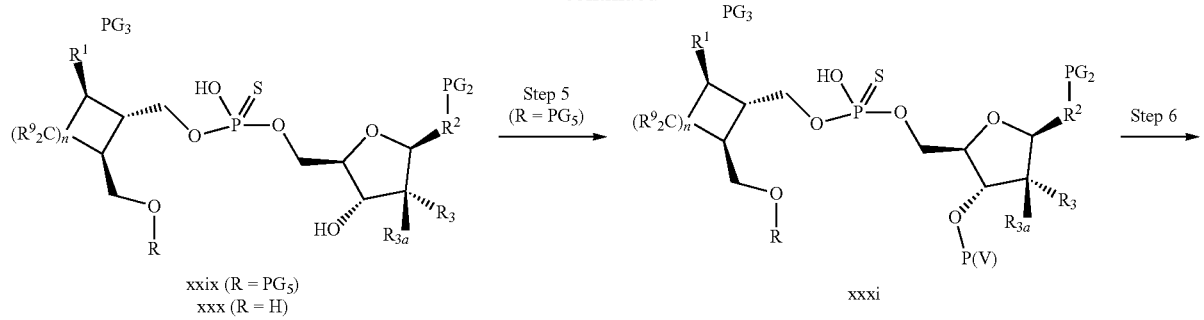

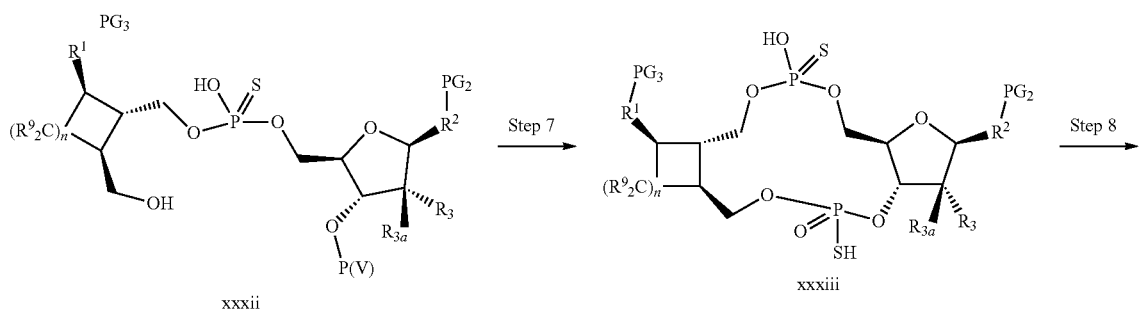

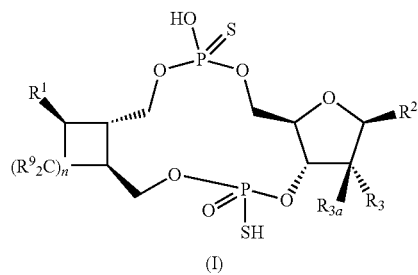

The method starts from an appropriately substituted natural or modified nucleoside (xxv), wherein the nucleobase ($R^2$) is appropriately protected (PG=protecting group), such as with a benzoyl group. In Step 1, treatment of xxv with an appropriate organophosphorus (V) reagent, for example one of those listed in Table 1, in an appropriate solvent (such as acetonitrile or dimethylformamide), with an appropriate base (for example DBU) affords compounds of formula xxvi. Treatment with an appropriately protected alcohol (for example xxvii) in Step 2, in an appropriate solvent (for example acetonitrile or dimethylformamide) in the presence of a base (for example DBU) affords compounds of formula xxviii. In Step 3, one or both protecting groups ($PG_1$ and $PG_5$) may be removed under conditions known to one skilled in the art to afford alcohol (xxix) or a diol (xxx). Compounds of formula xxx may be treated with an appropriate organophosphorus (V) reagent, for example one of those listed in Table 1, in an appropriate solvent (such as acetonitrile or dimethylformamide), with an appropriate base (for example DBU) to afford compounds of formula xxxiii. Alternatively, one may treat compounds of formula xxix with an appropriate organophosphorus (V) reagent, for example one of those listed in Table 1, in an appropriate solvent (such as acetonitrile of dimethylformamide), with an appropriate base (for example DBU) to afford compounds of formula xxxi. In Step 6, the protecting group (R=$PG_5$) may be removed to afford the alcohol xxxii. Treatment of xxxii, in Step 7, with an appropriate base (for example DBU) affords compounds of formula xxxiii. Removal of the remaining protecting groups, if necessary, affords compounds of formula (I).

An additional method for the preparation of examples of the present disclosure is described in Scheme 6.

Scheme 6

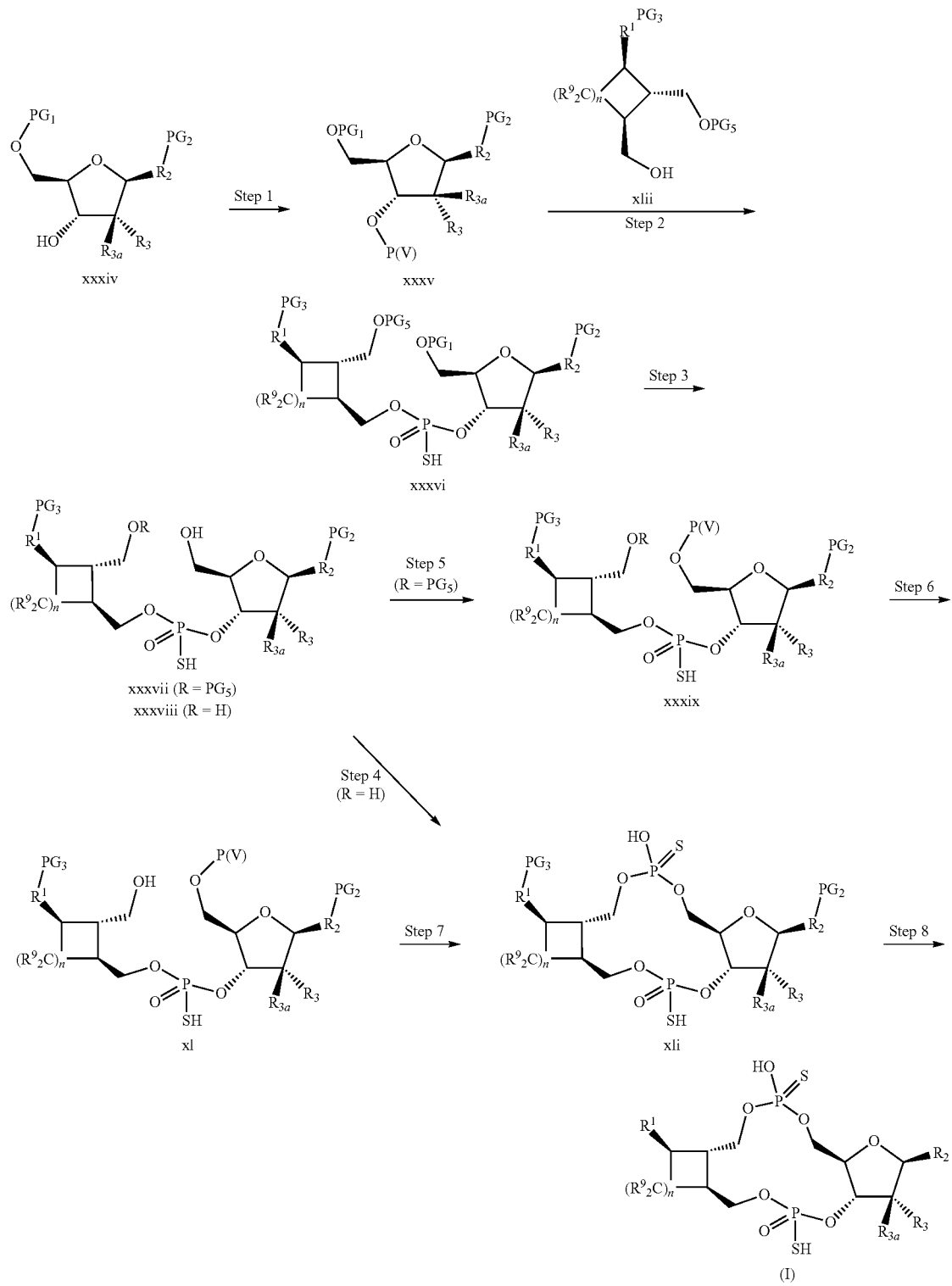

The method starts from an appropriately substituted natural or modified nucleoside (xxxiv), wherein the nucleobase ($R^2$) is appropriately protected (PG=appropriate organophosphorus (V) reagent, for example one of those listed in Table 1, in an appropriate solvent (such as acetonitrile or dimethylformamide), with an appropriate base (for example DBU) affords compounds of formula xxxv. Treatment with an appropriately protected alcohol (for example xlii) in Step 2, in an appropriate solvent (for example acetonitrile or dimethylformamide) in the presence of a base (for example DBU) affords compounds of formula xxxvi. In Step 3, one or both protecting groups ($PG_1$ and $PG_5$) may be removed under conditions known to one skilled in the art to afford alcohol (xxxvii) or a diol (xxxviii). Compounds of formula xxxviii may be treated with an appropriate organophosphorus (V) reagent, for example one of those listed in Table 1, in an appropriate solvent (such as acetonitrile or dimethylformamide), with an appropriate base (for example DBU) to afford compounds of formula xli. Alternatively, one may treat compounds of formula xxxvii with an appropriate organophosphorus (V) reagent, for example one of those listed in Table 1, in an appropriate solvent (such as acetonitrile of dimethylformamide), with an appropriate base (for example DBU) to afford compounds of formula xxxix. In Step 6, the protecting group (R=$PG_5$) may be removed to afford the alcohol xl. Treatment of xl, in Step 7, with an appropriate base (for example DBU) affords compounds of formula xli. Removal of the remaining protecting groups, if necessary, affords compounds of formula (I).

An additional method for preparation of examples of the present disclosure is described in Scheme 7.

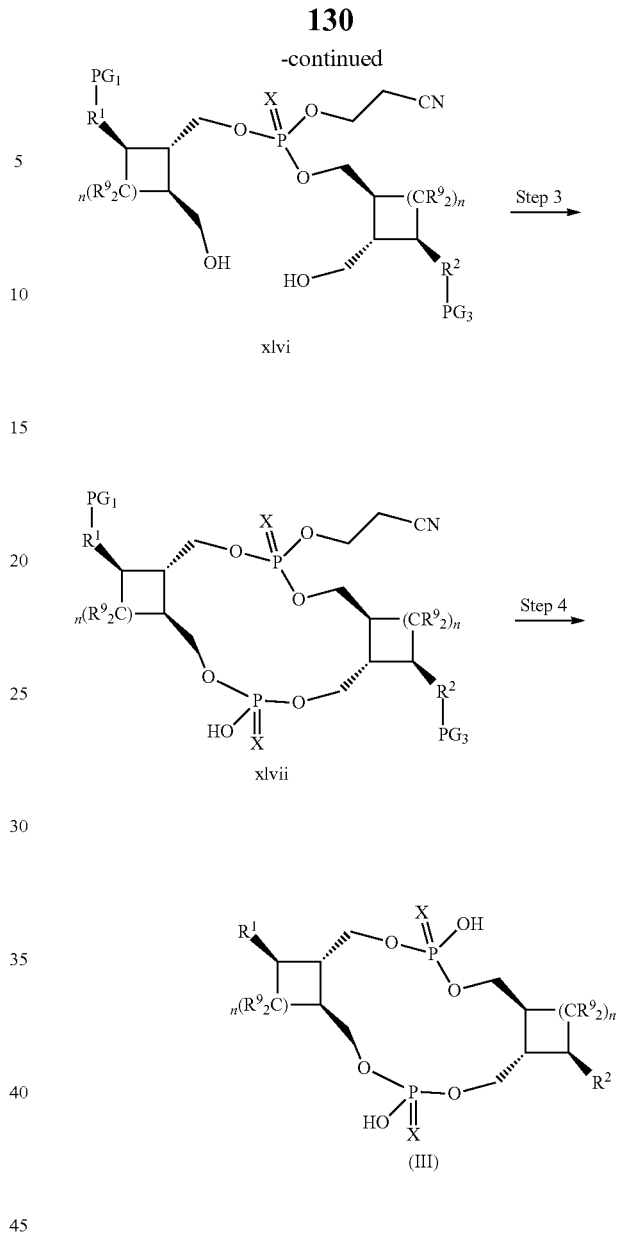

The method starts from an appropriately protected phosphoramidite (xliii) prepared by methods known to those skilled in the art. Coupling of compounds of formula xliii with an appropriately protected alcohol (xliv) followed by oxidation with, for example, t-butylhydroperoxide (X=O) or sulfurization with, for example DDTT (X=S) provides compounds of formula xvl. Subsequent removal of protecting groups (for example $PG_4$=Trityl or TBDPS, $PG_2$=DMTr) under a variety of conditions known to one skilled in the art (for example with TFA) provides compounds of formula xlvi. Macrocyclization of compounds of formula xlvi may be accomplished in a number of ways known to those skilled in the art. For example, treatment with diphenyl phosphite, followed by oxidation with, for example, t-butylhydroperoxide (X=O) or sulfurization with, for example DDTT (X=S) provides compounds of formula xvlii. Removal of all remaining protecting group provides compounds of general formula (III).

TABLE 1

Organophosphorus Reagents and Corresponding —P(V) groups

| Organophosphorus (V) Reagent | —P(V) |
| --- | --- |

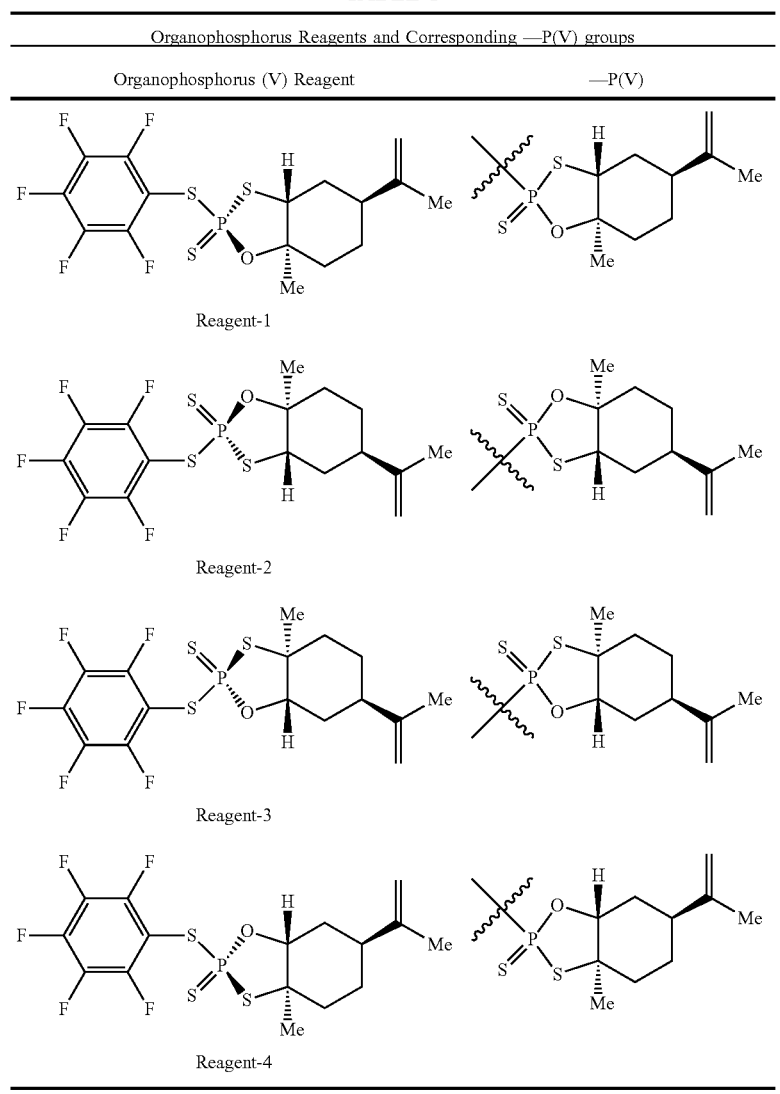

Reagent-1

Reagent-2

Reagent-3

Reagent-4

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

Abbreviations

The following abbreviations may be used in the example section below and elsewhere herein:

| Abbreviation | Full Name |
| --- | --- |
| Ac | acetyl |
| ACN | acetonitrile |
| aq. | aqueous |
| DCM | dichloromethane |
| DDTT | ((dimethylamino-methylidene)amino)-3H-1,2,4-dithiazoline-3-thione |
| DMSO | dimethyl sulfoxide |
| DMOCP | 2-chloro-5,5-dimethyl-1,3,2-dioxaphosphorinane 2-oxide |
| DMTr | 4,4'-dimethoxytrityl |
| EtOAc | ethyl acetate |
| Et$_3$N or TEA | triethylamine |
| EtOH | ethanol |
| HPLC | high-performance liquid chromatography |
| iPr | isopropyl |
| MeOH | methanol |
| RT | room temperature |
| satd. or sat'd | saturated |
| TBDPS | tert-butyldiphenylsilyl |
| TBS | tButyldimethylsilyl |
| TFA | Trifluoroacetic acid |
| $t_R$ | retention time |
| Trt | trityl |

Examples 1-1 and 1-2

(1R,6S,8R,9R,15R,17R,18R)-8,17-bis(6-amino-9H-purin-9-yl)-18-fluoro-12-hydroxy-3-sulfanyl-12-sulfanylidene-2,4,11,13,16-pentaoxa-3$\lambda^5$,12$\lambda^5$-diphosphatricyclo[13.3.0.0$^{6,9}$]octadecan-3-one

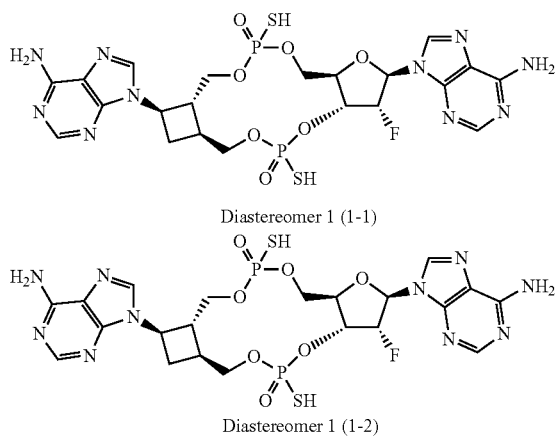

Diastereomer 1 (1-1)

Diastereomer 1 (1-2)

Preparation of Intermediate 1A:

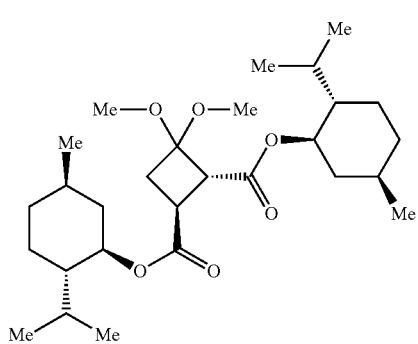

To a −78° C. solution of bis((1R,2S,5R)-2-isopropyl-5-methylcyclohexyl) fumarate (5 g, 12.7 mmol) in toluene (64 mL) was added diethylaluminium chloride (25 mL, 25 mmoL) dropwise, under nitrogen. The reaction was stirred at −78° C. for 10 min, then 1,1-dimethoxyethene (1.3 mL, 14 mmol) was added and the reaction stirred for an additional 10 min. The reaction was quenched with dropwise addition of 1 mL methanol and 1 mL of 15% aqueous sodium hydroxide. Methanol (2.5 mL) was added and the mixture was stirred for 10 min. To the mixture was added 1 g of magnesium sulfate and the mixture was stirred at room temperature for 30 min. The suspension was filtered through a pad of Celite and the filtrate was concentrated in vacuo to give the crude. The crude material was purified by flash chromatography over 120 g of silica gel (20 min gradient, with 0-10% ethyl acetate in hexanes) and was then recrystallize from 95:5 methanol:water to give Intermediate 1A (5.6 g, 91%) as a white solid. $^1$H NMR (400 MHz, CHLOROFORM-d) δ 4.85-4.66 (m, 2H), 3.56-3.49 (m, 1H), 3.36-3.28 (m, 3H), 3.16 (s, 3H), 2.61 (dd, J=11.9, 10.7 Hz, 1H), 2.22-2.15 (m, 1H), 2.11-1.96 (m, 2H), 1.93-1.80 (m, 1H), 1.75-1.65 (m, 3H), 1.62-1.34 (m, 8H), 1.12-0.84 (m, 18H), 0.80-0.75 (m, 6H).

Preparation of Intermediate 1B:

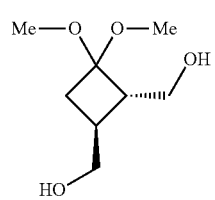

To a 0° C. solution of Intermediate 1A (17 g, 35.4 mmol) in THF (88 mL) was added lithium aluminum hydride (2.0 g, 53.0 mmol). The reaction was slowly warmed to RT, then heated at 55° C. for 5 h, followed by stirring at RT for 16 h. The solution was cooled to 0° C., quenched with 5 mL water, 5 mL 15% aq NaOH, slowly warmed to RT and stirred for 10 min. Water (20 mL) was added, and the mixture was stirred at RT for 10 min. To this mixture was added 10 g MgSO$_4$, and stirring continued for 10 min. It was then filtered through a pad of Celite and the filtrate was concentrated in vacuo. The resulting material was dissolved in 200 mL of hexanes and extracted with water (3×150 mL). The combined aqueous extracts were saturated with ammonium sulfate. The aqueous phase was extracted (3×125 mL) with ethyl acetate, and the combined organic layers were dried (sodium sulfate), filtered and concentrated in vacuo to give Intermediate 1B (3.7 g, 60%) as a clear, colorless oil. $^1$H NMR (400 MHz, CHLOROFORM-d) δ 3.84-3.71 (m, 3H), 3.56 (dd, J=10.4, 8.3 Hz, 1H), 3.21 (d, J=2.2 Hz, 6H), 2.49-2.24 (m, 2H), 2.23-1.95 (m, 2H), 1.72 (ddd, J=12.4, 7.6, 1.0 Hz, 2H).

Preparation of Intermediate 1C

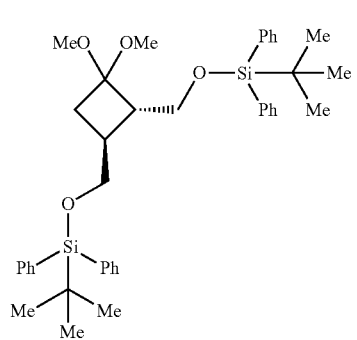

To a solution Intermediate 1B (1 g, 5.7 mmol) and imidazole (0.97 g, 14 mmol) in DCM (28 mL) was added tert-butylchlorodiphenylsilane (3 mL, 11.6 mmol) at room temperature. The reaction mixture was stirred at room temperature for 16 h. The resulting mixture was washed with water and 50% aqueous sodium bicarbonate, then dried (sodium sulfate), filtered and concentrated in vacuo. The crude material was purified by flash chromatography over 80 g of silica gel (20 min gradient, with 0-10% ethyl acetate in hexanes) to afford Intermediate 1C (3.7 g, 100%) as a clear, colorless oil. $^1$H NMR (400 MHz, CHLOROFORM-d) δ 7.74-7.62 (m, 8H), 7.45-7.32 (m, 12H), 3.88 (dd, J=10.3, 8.4 Hz, 1H), 3.72-3.58 (m, 3H), 3.20 (d, J=8.8 Hz, 6H), 2.51-2.45 (m, 1H), 2.25 (dd, J=11.7, 8.8 Hz, 1H), 1.90-1.74 (m, 2H), 1.03 (d, J=4.2 Hz, 18H).

Preparation of Intermediate 1D:

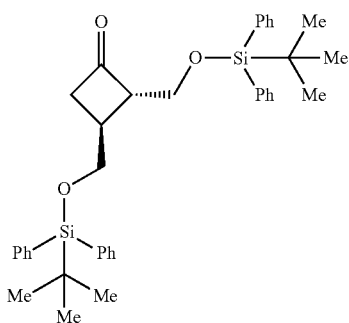

A mixture of Intermediate 1C (3.6 g, 5.5 mmol) and tosic acid (0.10 g, 0.55 mmol) in 28 mL of acetone was stirred at room temperature for 3 days. The solvent was removed in vacuo. The mixture was partitioned between EtOAc and water, the organic layers were separated, and the aqueous phase was extracted with EtOAc. The combined organic layers were dried (sodium sulfate), filtered and concentrated in vacuo. The crude material was purified by flash chromatography over 80 g of silica gel (20 min gradient, with 0-30% ethyl acetate in hexanes) to afford Intermediate 1D (3.3 g, 97%) as a clear, colorless oil. $^1$H NMR (400 MHz, CHLOROFORM-d) δ 7.69-7.63 (m, 8H), 7.47-7.35 (m, 12H), 3.99 (dd, J=10.6, 4.0 Hz, 1H), 3.92-3.82 (m, 2H), 3.71 (dd, J=10.6, 3.8 Hz, 1H), 3.34-3.28 (m, 1H), 3.04-2.80 (m, 2H), 1.33-1.27 (m, 1H), 1.10-0.98 (m, 18H).

Preparation of Intermediate 1E:

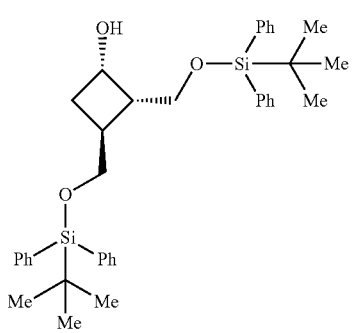

To a −78° C. solution of Intermediate 1D (3.3 g, 5.4 mmol) in 27 mL of THF was added L-Selectride (5.9 mL, 5.9 mmol) dropwise, under nitrogen. The reaction was stirred at −78° C. for 20 min, and then was quenched slowly with water. Hydrogen peroxide was added (0.55 mL, 5.4 mmol), and the mixture was stirred at room temperature for 10 min. To this mixture was added 50% aqueous sodium bicarbonate and it was stirred at room temperature for 10 min. The mixture was extracted with EtOAc, and the combined organic layers were dried (sodium sulfate) and concentrated in vacuo. The crude material was purified by flash chromatography over 80 g of silica gel (15 min gradient, with 0-30% ethyl acetate in hexanes) to afford Intermediate 1E (2.38 g, 73%) as a clear, colorless oil. $^1$H NMR (400 MHz, CHLOROFORM-d) δ 7.79-7.54 (m, 8H), 7.48-7.28 (m, 12H), 4.54-4.46 (m, 1H), 4.03-3.90 (m, 1H), 3.68-3.55 (m, 2H), 3.19 (d, J=7.5 Hz, 1H), 2.53 (br s, 1H), 2.38 (dquin, J=10.4, 5.3 Hz, 1H), 2.28-2.19 (m, 1H), 2.16-2.12 (m, 1H), 1.11-1.08 (m, 9H), 1.05-1.04 (s, 9H).

Preparation of Intermediate 1F:

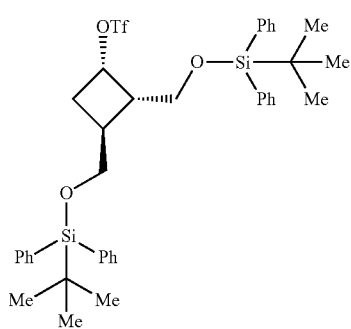

To a 0° C. solution of Intermediate 1E (0.38 g, 0.62 mmol) and pyridine (0.08 mL, 0.94 mmol) in 2 mL of dichloromethane was added a solution of triflic anhydride (0.13 mL, 0.75 mmol) in 1 mL of dichloromethane. The reaction mixture was stirred at 0° C. for 10 min and then quenched with ice water and diluted with 10 mL of dichloromethane. The solution was washed with 5 mL of 5% aqueous sodium bisulfate. The organic layer was separated, dried (sodium sulfate), and concentrated in vacuo. The crude Intermediate 1F was carried on to next step without further purification.

Preparation of Intermediate 1G:

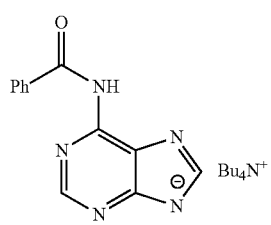

To a suspension of N-(9H-purin-6-yl)benzamide (2 g, 8.36 mmol) in DCM (41.8 mL) was added tetrabutylammonium hydroxide (40% aq) (5.45 mL, 8.36 mmol) at RT.

After 5 minutes the reaction became a turbid solution. The solvent was removed in vacuo and the resulting material was azeotroped 2×30 mL with toluene and 30 mL of EtOAc to give an off-white solid. The solid was triturated with Et$_2$O and then collected by vacuum filtration to give Intermediate 1G (4 g, 8 mmol) as an off-white solid. $^1$H NMR (400 MHz, DMSO-d$_6$) δ 8.30 (s, 1H), 8.10 (br d, J=7.2 Hz, 2H), 7.90 (s, 1H), 7.56-7.42 (m, 3H), 3.21-3.11 (m, 8H), 1.57 (quin, J=7.9 Hz, 8H), 1.31 (sxt, J=7.3 Hz, 8H), 0.94 (t, J=7.3 Hz, 12H).

Preparation of Intermediate 1H:

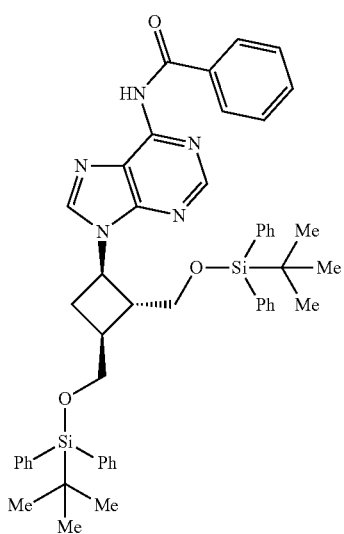

To a 0° C. suspension of Intermediate 1G (1.56 g, 3.24 mmol) in THF (32 mL) was added a solution of Intermediate 1F (2.4 g, 3.2 mmol) in 2 mL of dichloromethane over 5 min. The reaction was warmed to RT and stirred for 16 h. The mixture was partitioned between ethyl acetate and water, and the organic layer was washed with water and brine, and then dried (sodium sulfate) and concentrated in vacuo. The crude material was purified by flash chromatography over 40 g of silica gel (15 min gradient, with 0-100% ethyl acetate in hexanes) to afford Intermediate 1H (0.49 g, 18%) as an oil. LCMS, $[M+H]^+=830$ Preparation of Intermediate 1I:

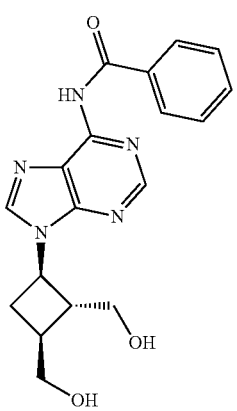

A mixture of Intermediate 1H (0.44 g, 0.53 mmol) and triethylamine trihydrofluoride (0.34 mL, 2.1 mmol) in acetonitrile (2.6 mL) was stirred in a teflon flask at RT for 16 h. The solvent was then removed in vacuo. The crude material was purified by flash chromatography over 12 g of silica gel (10 min gradient, with 0-20% methanol in dichloromethane) to afford Intermediate 1I (0.126 g, 67%) as a white foam. LCMS: $[M+H]^+=354$.

Preparation of Intermediate 1J:

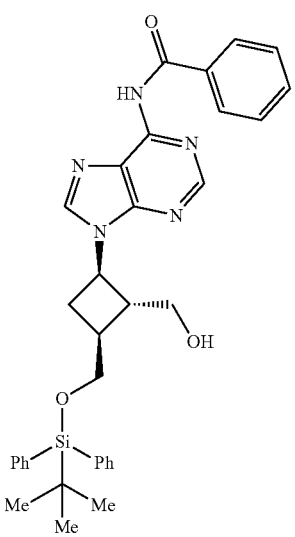

To a biphasic mixture of Intermediate 1I (0.64 g, 1.8 mmol) in DMF (5.7 mL)/DIPEA (3.2 mL, 18 mmol) was added TBDPS-Cl (0.93 mL, 3.6 mmol) at room temperature and the reaction was stirred at room temperature for 16 h. The mixture was partitioned between ethyl acetate and water, and the organic layer was washed with 1N HCl followed by saturated sodium bicarbonate, and then dried (sodium sulfate) and concentrated in vacuo. The crude material was purified by flash chromatography over 40 g of silica gel (20 min gradient, with 0-20% methanol in dichloromethane) to afford a mixture of products. The mixture was further purified by reverse-phase ISCO over 150 g Gold C18 with 25-100% solvent A: (95% water containing 0.05% TFA: 5% ACN), solvent B (95% ACN: 5% water containing 0.05% TFA) to afford Intermediate 1J (0.22 g) as a white foam. LCMS, $[M+H]^+=592$ Preparation of Intermediate 1K:

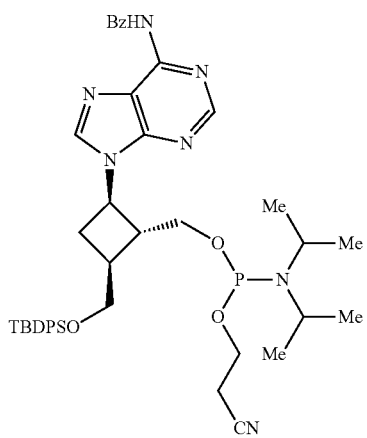

To a solution of Intermediate 1J (0.061 g, 0.10 mmol) in DCM (0.51 mL) was added a solution of 1H-imidazole-4,5-dicarbonitrile (8.5 mg, 0.072 mmol) in 0.2 mL ACN. To the reaction was added 3-((bis(diisopropylamino)phosphanyl) oxy)propanenitrile (0.049 mL, 0.155 mmol) dropwise and the reaction was stirred at RT for 16 h. The mixture was diluted with dichloromethane, washed with 50% aqueous sodium bicarbonate, dried (sodium sulfate) and concentrated in vacuo. The crude material was purified by flash chromatography over 4 g of silica gel (10 min gradient, with 0-100% ethyl acetate in hexanes) to afford Intermediate 1K (0.072 g) as a solid.

Preparation of Intermediate 1L:

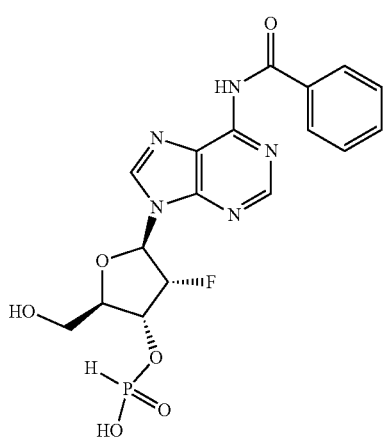

1L

A solution of (2R,3R,4R,5R)-5-(6-benzamido-9H-purin-9-yl)-2-((bis(4-methoxyphenyl)(phenyl)methoxy)methyl)-4-fluorotetrahydrofuran-3-yl 2-cyanoethyl diisopropylphosphoramidite (Sigma-Aldrich, 2 g, 2.3 mmol) in ACN (5 mL) was treated with water (0.05 mL, 2.7 mmol), followed by pyridine trifluoroacetate (0.53 g, 2.7 mmol) The colorless solution was stirred for 10 min. and then concentrated in vacuo to afford a light pink foam. The resulting solid was dissolved in MeCN (5 mL) and concentrated to dryness. The resulting material was again dissolved in MeCN (5 mL). A solution of DBU (2.75 mL, 18.3 mmol) in ACN (6 mL) and nitromethane (1 mL, 18.3 mmol) was prepared. To this DBU solution was added the ACN solution from above in one portion and the mixture was stirred for 20 min. The reaction was then poured into a 15 wt % aqueous solution of KH$_2$PO$_4$ (25 mL) and 2-MeTHF (20 mL) and agitated. The aqueous layer was extracted with 2-MeTHF (20 mL) and the combined organic layers were washed with a 15 wt % aqueous solution of KH$_2$PO$_4$ (2×20 mL), then a solution of brine (20 mL). The organic layer was dried over sodium sulfate, filtered and concentrated in vacuo. The resulting gel was dried by azeotropic distillation with 2-MeTHF (30-40 mL/g total, charged in 8-10 mL amounts). The crude material was then dissolved in DCM (20 mL). Methanol (1 mL) was added, followed by dichloroacetic acid (0.8 mL, 10.8 mmol). The reaction was stirred for 3 h. To this mixture was added pyridine (2 mL, 27 mmol) and then the mixture was concentrated in vacuo to a gel-like residue. Dimethoxyethane (10 mL) was added and a white solid precipitated. The solids were collected by filtration and re-suspended in DME (2.5 mL/g) and agitated carefully with a spatula on the filter. The solids were again filtered and the process was repeated two more times to afford Intermediate 1L as a white powder (1 g, 72%).

Preparation of Intermediate 1M:

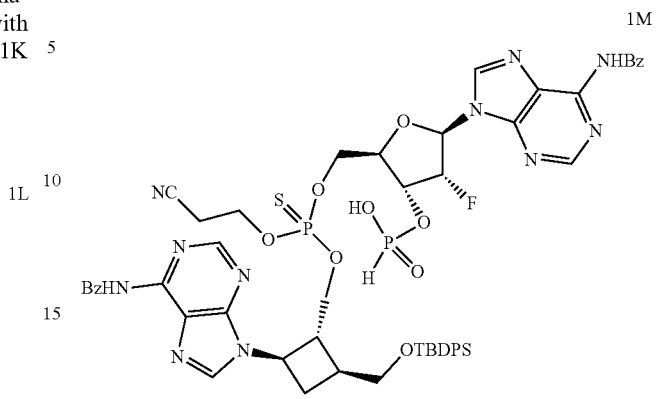

1M

Intermediate 1K (0.12 g, 0.150 mmol) was azeotroped with ACN (3×1 mL) and then dissolved in 0.5 mL of ACN. Intermediate 1L (0.08 g, 0.173 mmol) and pyridine trifluoroacetate (0.04 g, 0.225 mmol) were combined and azeotroped with pyridine (2×0.5 mL) and then 1 mL of ACN and then dissolved in 0.5 mL of ACN. To this solution, under nitrogen was added the solution of Intermediate 1K from above. The reaction was stirred at RT for 1 h. To the reaction was added (E)-N,N-dimethyl-N'-(3-thioxo-3H-1,2,4-dithiazol-5-yl)formimidamide (0.032 g, 0.158 mmol) and the resulting bright yellow solution was stirred at RT for 20 min. The mixture was partitioned between EtOAc and 10% aqueous sodium bicarbonate. The layers were separated and the aqueous layer was extracted 2×5 mL with EtOAc. The combined organic layers were dried (sodium sulfate) and concentrated in vacuo. The material was purified by reverse-phase ISCO over 150 g C18 column with 25-100% solvent A: (water:ACN:ammonium acetate 95/5/0.01M) solvent B(ACN:water:ammonium acetate 95/5/0.01M) to afford Intermediate 1M (0.054 g) as a white solid following lyophilization. LCMS, [M+H]$^+$=1161.5.

Preparation of Intermediate 1N:

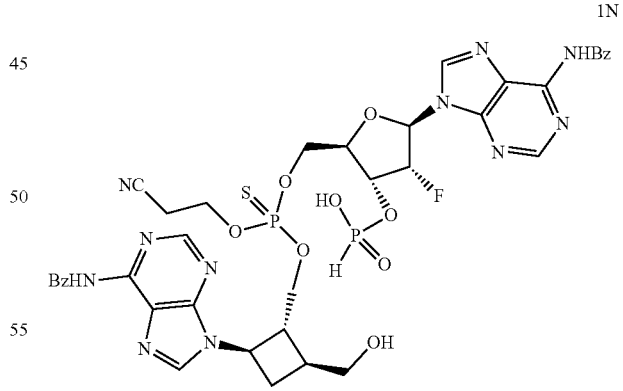

1N

To a solution of Intermediate 1M (0.06 g, 0.053 mmol) in ACN (2 mL) was added triethylamine trihydrofluoride (0.086 ml, 0.526 mmol) at RT. The reaction was stirred at RT for 6 h, and then heated to 50° C. for 5 h. The reaction was quenched with calcium carbonate (0.16 g, 1.58 mmol) and was then stirred at RT for 10 min. The resulting solids were filtered off, and the filtrate was concentrated in vacuo. The crude material was purified by reverse phase ISCO over a 50 g C18 column with 0-100% water:ACN:ammonium acetate 95/5/0.01M to ACN:water:ammonium acetate 95/5/0.01M) to give Intermediate 1N (20 mg) as a white solid following lyophilization. LCMS, [M+H]⁺=922.2.

Preparation of Intermediate 1O:

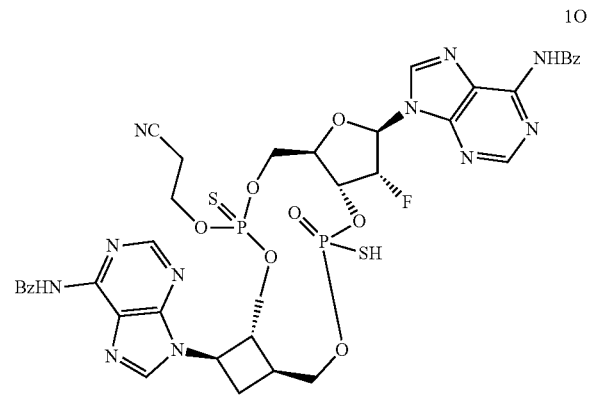

Intermediate 1N (0.02 g, 0.022 mmol) was azeotroped with pyridine (5×1 mL) and then dissolved in pyridine (2 mL). 2-Chloro-5,5-dimethyl-1,3,2-dioxaphosphinane 2-oxide (0.012 g, 0.065 mmol) was azeotroped with pyridine (5×1 mL) and then dissolved in pyridine (2 mL) and cooled to 0° C. The solution of Intermediate 1N from above was then added dropwise over a period of 20 min. The reaction was slowly warmed to room temperature and then stirred for 30 min. To the reaction was added (E)-N,N-dimethyl-N'-(3-thioxo-3H-1,2,4-dithiazol-5-yl)formimidamide (5.8 mg, 0.03 mmol) and water (8 ptL, 0.4 mmol) and the reaction was stirred at RT for 30 min. The solvent was removed in vacuo. The crude mixture was purified by reverse phase ISCO over 50 g of C18 with 0-100% water:ACN:ammonium acetate 95/5/0.01M to ACN:water:ammonium acetate 95/5/0.01M) to give Intermediate 1O (0.0196 g) as a white solid following lyophilization. LCMS, [M+H]⁺=936.2.

Examples 1-1 and 1-2

(1R,6S,8R,9R,15R,17R,18R)-8,17-bis(6-amino-9H-purin-9-yl)-18-fluoro-12-hydroxy-3-sulfanyl-12-sulfanylidene-2,4,11,13,16-pentaoxa-3λ⁵,12λ⁵-diphosphatricyclo[13.3.0.0⁶,⁹]octadecan-3-one

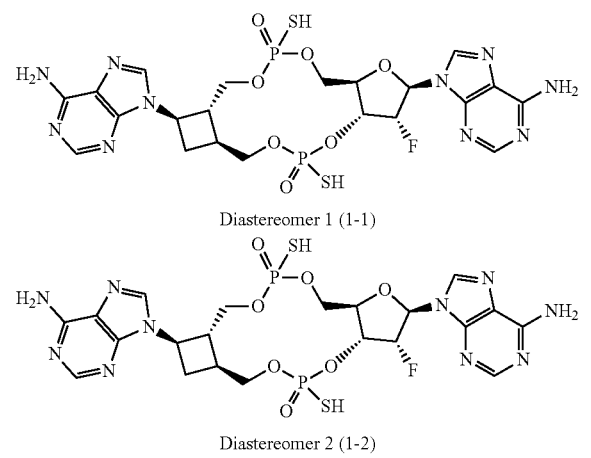

A mixture of Intermediate 1O (0.0196 g, 0.021 mmol) and ammonia (7 M in MeOH) (0.5 mL, 3.50 mmol) in acetonitrile (0.5 mL)/MeOH (0.5 mL) was stirred at 40° C. for 16 h. The crude material was purified via preparative LC/MS with the following conditions to afford two diastereomers: Column: Agilent Bonus RP 21.2×100 mm, 5-μm particles; Mobile Phase A: water with 20-mM ammonium acetate; Mobile Phase B: acetonitrile; Gradient: 0% B hold 0-6 minute. 0%-40% B over 20 minutes, then a 4-minute hold at 100% B; Flow: 20 mL/min. Fractions containing the desired product were combined and dried via centrifugal evaporation.

Example 1-1

1.9 mg. Retention Time: 2.14 min. (Column: Agilent Bonus RP, 2.1 mm×50 mm, 1.8 μm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm)). Observed Mass: 675.01.

Example 1-2

2.5 mg, Retention Time: 2.28 min (Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Observed Mass: 675.16.

Alternatively, Examples 1-1 and 1-2 may be prepared along with Examples 2-1 and 2-2 as described below.

Examples 2-1, 1-1, 2-2 and 1-2

(1R,6S,8R,9R,15R,17R,18R)-8,17-bis(6-amino-9H-purin-9-yl)-18-fluoro-3,12-disulfanyl-2,4,11,13,16-pentaoxa-3λ⁵,12λ⁵-diphosphatricyclo[13.3.0.0⁶,⁹]octadecane-3,12-dione

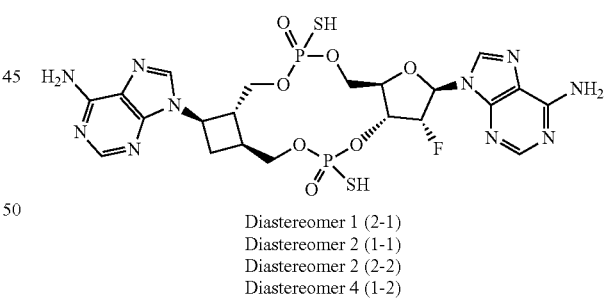

Diastereomer 1 (2-1)
Diastereomer 2 (1-1)
Diastereomer 2 (2-2)
Diastereomer 4 (1-2)

Preparation of Intermediate 2A:

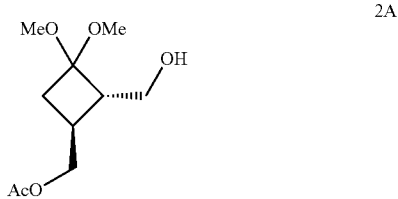 [SMILES: COC1(OC)C[C@H](COC(C)=O)[C@H]1CO]

To a solution of Intermediate 1B (24 g, 136 mmol) in toluene (1.3 L) at room temperature was added vinyl acetate (129 g, 1500 mmol). Then, lipase from porcine pancreas (Sigma, 36 g, 136 mmol) was added in one portion and the resulting light suspension was stirred at room temperature for 21.6 h. The mixture was then filtered through Celite and the filter cake was rinsed with EtOAc. The combined filtrates were then evaporated in vacuo and the residue was purified by column chromatography using a 330 g ISCO column eluting with 0-100% ethyl acetate in hexane to afford Intermediate 2A (30 g, 137 mmol) as an oil that was used as is in the next reaction. $^1$H NMR (400 MHz, CHLOROFORM-d) δ 4.27-3.99 (m, 2H), 3.88-3.61 (m, 2H), 3.33-3.05 (m, 6H), 2.46-2.32 (m, 2H), 2.32-2.17 (m, 1H), 2.12-2.00 (m, 3H), 1.88-1.73 (m, 1H).

Preparation of Intermediate 2B:

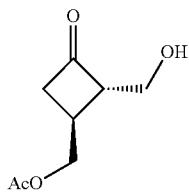

2B

Tosic acid (1.3 g, 6.9 mmol) was added in one portion to a solution of 2A (30 g, 137 mmol) in acetone (500 mL) at room temperature. The reaction was allowed to stir at room temperature for 3 h at which point the reaction was complete. Et$_3$N (1.92 ml, 13.8 mmol) was added and the mixture was evaporated in vacuo. The residue was then purified by ISCO using a hexane/ethyl acetate gradient-product eluted with neat ethyl acetate. The fractions containing product were then combined and evaporated. During evaporation, no heat was applied and 2B (22 g, 93%) was obtained as an oil. $^1$H NMR (400 MHz, CHLOROFORM-d) δ 4.44-4.22 (m, 2H), 4.02-3.88 (m, 1H), 3.85-3.69 (m, 1H), 3.41-3.25 (m, 1H), 3.17-3.02 (m, 1H), 2.97-2.85 (m, 1H), 2.85-2.66 (m, 1H), 2.20-2.09 (m, 3H), 1.86-1.72 (m, 1H).

Preparation of Intermediate 2C:

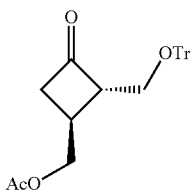

2C

A solution 2B (23.7 g, 140 mmol) in anhydrous DCM (920 mL) at room temperature under a nitrogen atmosphere was treated with Et$_3$N (30.7 mL, 220 mmol) followed by DMAP (1.68 g, 13.8 mmol). (Chloromethanetriyl)tribenzene (49.8 g, 179 mmol) was then added in one portion and the resulting mixture was allowed to stir at room temperature under a nitrogen atmosphere overnight. The reaction was quenched by the addition of saturated sodium bicarbonate solution (200 mL). The aqueous layer was then extracted with an additional portion of DCM (100 mL) and the combined organics were then dried (MgSO$_4$) and evaporated in vacuo. The resulting oil was then purified on a 330 g ISCO column eluting with 0-40% ethyl acetate in hexane to afford 2C (31.83 g) as a white solid. $^1$H NMR (400 MHz, CHLOROFORM-d) δ 7.57-7.39 (m, 6H), 7.39-7.18 (m, 9H), 4.41-4.21 (m, 2H), 3.57-3.42 (m, 1H), 3.34-3.24 (m, 1H), 3.24-3.11 (m, 2H), 2.95-2.78 (m, 2H), 2.07-1.93 (m, 3H).

Preparation of Intermediate 2D:

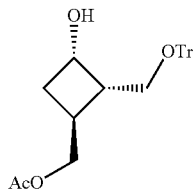

2D

LS-Selectride (36.2 mL, 36.2 mmol) was added dropwise via a pressure equalizing funnel to a stirred solution of 2C (12 g, 29.0 mmol) at −78° C. under a nitrogen atmosphere. The addition took a total of 30 min to complete. The reaction was then allowed to stir at −78° C. for 40 min. The reaction was quenched by the slow addition of sat'd aq. sodium bicarbonate solution (85 mL) and the cold bath was then removed and replaced with an ice-water bath. When the internal temperature had reached 0° C., hydrogen peroxide (59.1 mL, 580 mmol) was added dropwise via a glass pipette. The resulting mixture was allowed to stir at room temperature for ~4 h before diluting with water and extracting with ethyl acetate (3×). The combined organic layers were then washed with sat'd sodium bicarbonate solution, dried (MgSO$_4$) and evaporated in vacuo. This crude material was purified by column chromatography on an ISCO system eluting with a 0-40% ethyl acetate/hexane gradient. Fractions were collected and evaporated to give 2D (7.75 g, 18.61 mmol). $^1$H NMR (400 MHz, CHLOROFORM-d) δ 7.60-7.42 (m, 6H), 7.42-7.18 (m, 10H), 4.61-4.40 (m, 1H), 4.13-4.02 (m, 2H), 3.47-3.27 (m, 2H), 2.71-2.65 (m, 1H), 2.65-2.44 (m, 2H), 2.20-2.11 (m, 2H), 2.11-2.02 (m, 3H).

Preparation of Intermediate 2E:

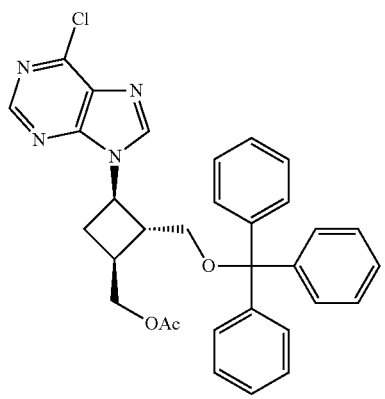

2E

To a 0° C. solution of Ph$_3$P (1.07 g, 4.1 mmol) in THF (20 mL)/toluene (4 mL) was added DIAD (0.70 ml, 3.6 mmol). The reaction was stirred at 0° C. for 30 min. To the reaction was added 6-chloro-9H-purine (0.557 g, 3.60 mmol) and 2D (1.0 g, 2.4 mmol). The reaction was stirred at 50° C. for 16 h and then concentrated in vacuo. The crude material was purified by flash chromatography over 40 g of silica gel (15 min gradient, with 0-100% ethyl acetate in hexanes) to give 2E (1.0 g, 1.8 mmol) as a white foam. [M+H]$^+$=553.2.

Preparation of Intermediate 2F:

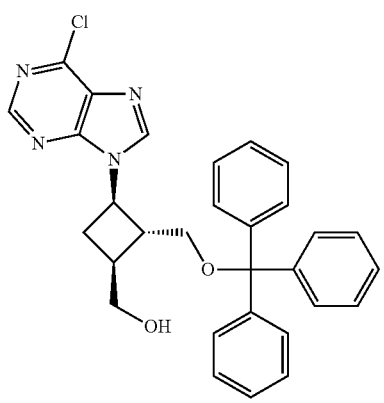

To a 0° C. solution of 2E (1.74 g, 3.15 mmol) in THF (16 mL) was added methylmagnesium chloride (3 M in THF) (2.1 mL, 6.3 mmol). The mixture was warmed to room temperature and the reaction was stirred for 2 h. The reaction was then quenched with saturated aqueous ammonium chloride and stirred at room temperature for 10 min. The mixture was then partitioned between EtOAc and water, the organic layer was separated, and the aqueous phase extracted with EtOAc. The combined organic layers were dried (sodium sulfate) and concentrated in vacuo. The crude material was purified by flash chromatography over 80 g of silica gel (15 minute gradient, with 0-100% EtOAc/DCM) to afford 2F (1.16 g, 2.27 mmol) as a white solid. LCMS, $[M+H]^+$=511.3.

Alternatively, 2F may be prepared from 1B as described below:

Preparation of Intermediate 2G:

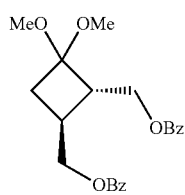

To a solution of Intermediate 1B (4.0 g, 22.70 mmol) in pyridine (60 mL) at 0° C. was added benzoyl chloride (6.59 mL, 56.7 mmol). The reaction mixture was allowed to warm to RT and stirred overnight. The reaction was quenched with water and then diluted with ethyl acetate, transferred to a separatory funnel, washed with 1M HCl (3×), brine (2×), saturated sodium bicarbonate (3×), brine (3×) and then dried (sodium sulfate). The mixture was filtered and the filtrate was concentrated to give crude product. The crude material was dissolved in a minimum of hexane and purified on an ISCO companion chromatography system (220 g silica cartridge, eluting with 0-25% ethyl acetate/hexanes, then 25-100% ethyl acetate/hexanes, 150 mL/min) to provide Intermediate 2G (8.06 g, 20.97 mmol). $^1$H NMR (499 MHz, CHLOROFORM-d) δ 8.21-7.91 (m, 4H), 7.64-7.51 (m, 2H), 7.42 (q, J=7.4 Hz, 4H), 4.74-4.53 (m, 1H), 4.49-4.32 (m, 3H), 3.25 (d, J=15.5 Hz, 6H), 2.93-2.66 (m, 1H), 2.58-2.44 (m, 1H), 2.42-2.28 (m, 1H), 2.04-1.82 (m, 1H).

Preparation of Intermediate 2H:

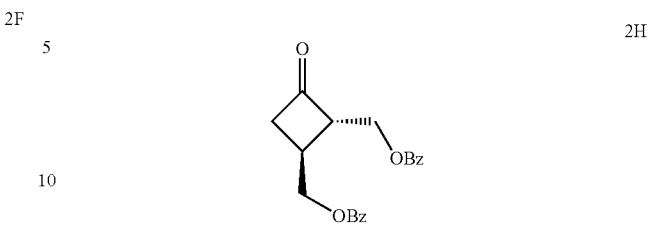

To a solution of Intermediate 2G (6.2 g, 16.1 mmol) in acetonitrile (100 mL) at 0° C. was added conc. sulfuric acid (1.63 mL, 29.0 mmol). The resulting mixture was allowed to warm to RT and stir overnight. The reaction mixture was then diluted with ethyl acetate, washed with water, saturated sodium bicarbonate (3×), and brine (3×). The organic layer was dried (sodium sulfate), filtered, and concentrated to give crude white solid. The solid was dissolved in a minimum amount of dichloromethane and purified by column chromatography using a 220 g ISCO column (2 min hold at 0% gradient then 19 min gradient, eluting with 0-75% ethyl acetate in hexanes) to provide Intermediate 2H (4.44 g, 13.12 mmol) as a white solid. $^1$H NMR (499 MHz, CHLOROFORM-d) δ 8.19-7.89 (m, 4H), 7.67-7.53 (m, 2H), 7.45 (dd, J=8.1, 3.1 Hz, 4H), 4.60 (d, J=6.4 Hz, 4H), 3.80-3.59 (m, 1H), 3.31-3.21 (m, 1H), 3.15-3.05 (m, 1H), 3.03-2.92 (m, 1H).

Preparation of Intermediate 2I:

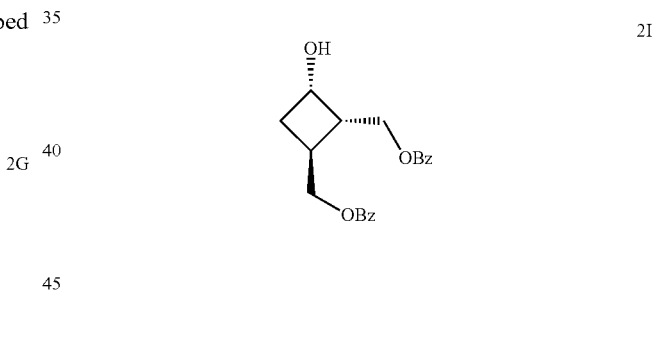

LS-Selectride (1 M THF) (21.0 mL, 21.0 mmol) was added dropwise over 15 min to a −78° C. solution of Intermediate 2H (5.93 g, 17.53 mmol) in THF (85 mL). The resulting mixture was stirred at −78° C. for 45 min. The reaction was quenched with water (6 mL) followed by the addition of hydrogen peroxide (30%) (2.15 mL, 21.0 mmol). The cooling bath was removed and the mixture was warmed to room temperature. The reaction was diluted with ethyl acetate, transferred to a separatory funnel, and partitioned with saturated sodium bicarbonate. The mixture was extracted with ethyl acetate. The organic layer was washed with brine (3×), dried (sodium sulfate), filtered and concentrated to provide a clear oil. The oil was dissolved in a minimum amount of dichloromethane and purified by column chromatography using a 330 g ISCO column (28 min gradient, eluting with 0-60% ethyl acetate/hexanes, 200 mL/min) to provide Intermediate 2I (3.66 g, 10.75 mmol) as a clear oil. LCMS, $[M+H]^+$=341.

Preparation of Intermediate 2J:

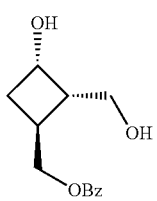

2J

To a solution of Intermediate 2I, (2.49 g, 7.32 mmol) in THF (35 mL) at 0° C. was added lithium borohydride (2 M in THF, 4.02 mL, 8.05 mmol). After 25 min, the cooling bath was removed and the reaction mixture was stirred at RT for 4 h. The reaction mixture was cooled to 0° C. and acetic acid (0.44 mL, 7.68 mmol) was slowly added, followed by water (30 mL). The reaction was diluted with ethyl acetate, transferred to a separatory funnel, washed with water and brine. The organic layer was dried with anhydrous sodium sulfate, filtered and concentrated to an oil. The oil was dissolved in a minimum amount of dichloromethane and purified by column chromatography using a 120 g ISCO column (19 min gradient, eluted with 0-8% methanol/dichloromethane, 80 mL/min) to provide Intermediate 2J (1.09 g, 4.61 mmol) as a white solid. LCMS, $[M+H]^+=237$. $^1$H NMR (499 MHz, CHLOROFORM-d) δ 8.06 (dd, J=8.3, 1.3 Hz, 2H), 7.59 (d, J=7.4 Hz, 1H), 7.51-7.41 (m, 2H), 4.91-4.57 (m, 1H), 4.37 (dd, J=9.5, 6.4 Hz, 2H), 3.96 (br s, 2H), 2.54 (br d, J=5.4 Hz, 3H), 2.39-2.07 (m, 3H).

Preparation of Intermediate 2K:

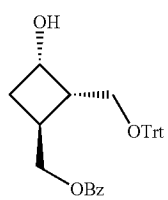

2K

To a 0° C. solution of Intermediate 2J (1.05 g, 4.44 mmol) in pyridine (25 mL) was added trityl chloride (1.86 g, 6.67 mmol). The reaction mixture was allowed to warm to RT and stirred overnight. The reaction was quenched with methanol (10 mL), stirred for 10 minutes and then concentrated in vacuo. The resulting residue was dissolved in dichloromethane, transferred to a separatory funnel, washed with water and brine. The organic layer was dried over anhydrous sodium sulfate, filtered and concentrated to provide a clear oil. The oil was dissolved in a minimum amount of dichloromethane and methanol and purified by column chromatography using a 80 g ISCO column (26 min gradient, eluted with 0-50% ethyl acetate/hexane, 60 mL/min) to yield Intermediate 2K (1.78 g, 3.72 mmol) as a thick, clear oil. $^1$H NMR (499 MHz, CHLOROFORM-d) δ 8.16-7.98 (m, 2H), 7.68-7.54 (m, 1H), 7.48 (dd, J=8.5, 1.3 Hz, 8H), 7.38-7.30 (m, 6H), 7.28 (s, 4H), 4.65-4.46 (m, 1H), 4.44-4.24 (m, 2H), 3.59-3.28 (m, 2H), 2.68 (d, J=6.3 Hz, 2H), 2.39-2.15 (m, 2H).

Preparation of Intermediate 2L:

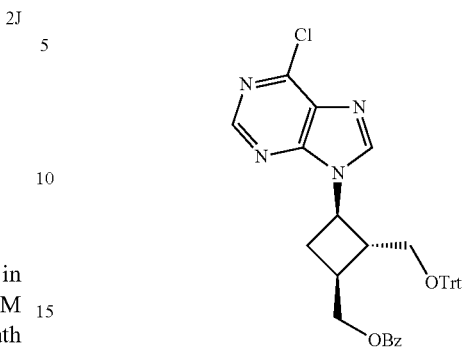

2L

Diisopropyl (E)-diazene-1,2-dicarboxylate (120 mg, 0.61 mmol) was dropwise added to a 0° C. solution of Intermediate 2K (145 mg, 0.30 mmol), 6-chloro-9H-purine (94 mg, 0.61 mmol) and triphenylphosphine (159 mg, 0.61 mmol) in THF (2 mL). The resulting mixture was stirred at 50° C. for 1 h, cooled to RT, then quenched with MeOH (0.2 mL), dichloromethane (2.5 mL) and triethylamine (0.1 mL). The mixture was stirred for 10 min and concentrated in vacuo. The residue was dissolved in a minimum amount of dichloromethane and purified by column chromatography using a 24 g ISCO column (eluted with 0-50% ethyl acetate/hexane, then flushed with 50-100% ethyl acetate/hexanes), 35 mL/min) to provide Intermediate 2L (169 mg, 0.275 mmol). LCMS, $[M+H]^+=615$.

Preparation of Intermediate 2F:

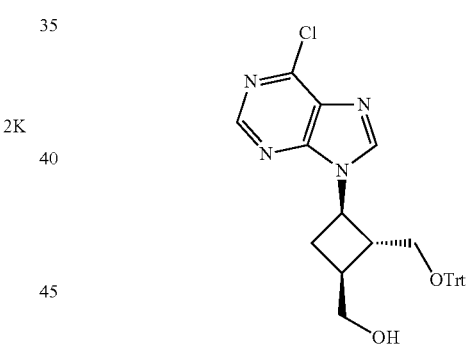

2F

Methylmagnesium chloride (1.008 mL, 3.02 mmol) was added to a 0° C. solution of Intermediate 2L (186 mg, 0.30 mmol) in THF (2 mL). The mixture was stirred at 0° C. for 30 min then at RT for 1 h. The reaction was quenched with methanol, diluted with saturated ammonium chloride solution and ethyl acetate and stirred to obtain clear layers. The mixture was transferred to a separatory funnel, diluted with ethyl acetate, washed with saturated ammonium chloride solution and then brine. The organic layer was dried over anhydrous sodium sulfate, filtered and concentrated in vacuo to give a yellow oil. The oil was dissolved in a minimum amount of dichloromethane and purified by column chromatography using a 24 g ISCO column (eluted with 0-100% ethyl acetate/hexanes, 35 mL/min) to yield 2F (60 mg, 0.117 mmol). LCMS, $[M+H]^+=511$. $^1$H NMR (499 MHz, CHLOROFORM-d) δ 9.07-8.57 (m, 1H), 8.29-7.89 (m, 1H), 7.42-7.34 (m, 6H), 7.28 (s, 9H), 4.86-4.61 (m, 1H), 3.88-3.65 (m, 2H), 3.51-3.28 (m, 2H), 3.04-2.84 (m, 1H), 2.72-2.60 (m, 1H), 2.54-2.42 (m, 1H), 2.40-2.26 (m, 2H).

Preparation of Intermediate 2M:

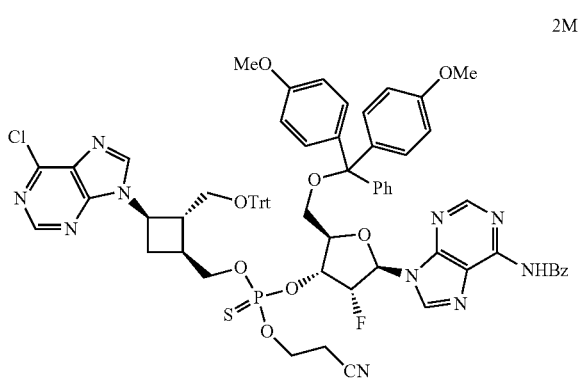

A mixture of 1H-tetrazole (33 mg, 0.470 mmol) and Intermediate 2F (200 mg, 0.39 mmol) was azeotroped with acetonitrile (3×5 mL) and then re-suspended in acetonitrile (2.5 mL) and left under a nitrogen atmosphere. Separately, (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (Sigma-Aldrich, 377 mg, 0.431 mmol) was azeotroped with acetonitrile (3×5 mL) and re-dissolved in acetonitrile (2.5 mL). This solution, under nitrogen, was added to the solution of Intermediate 2F and 1H-tetrazole prepared above. The reaction was allowed to stir for 1 h and then (E)-N,N-dimethyl-N'-(3-thioxo-3H-1,2,4-dithiazol-5-yl)formimidamide (96 mg, 0.47 mmol) was added and stirred for 30 min. The reaction mixture was then concentrated in vacuo, dissolved in MeOH and purified on reverse phase ISCO Gold 150 g C18 column, Mobile Phase A: 5:95 acetonitrile:water with 10 mM ammonium acetate; Mobile Phase B: 95:5 acetonitrile:water with 10 mM ammonium acetate; Gradient: 0-100% B over 15 column volumes to give Intermediate 2M (450 mg, 0.341 mmol) as a white solid following lyophilization. LCMS, [M+H]$^+$=1317/1318.

Preparation of Intermediate 2N:

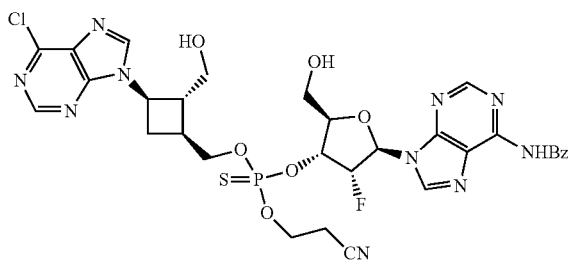

To a solution of Intermediate 2M in DCM (8 mL) was added triethylsilane (1 mL, 6.26 mmol) followed by the addition of TFA (0.15 mL, 1.9 mmol). The reaction was stirred for 1 h and then treated with pyridine (0.31 mL, 3.8 mmol) and concentrated to an oil. The residue was dissolved in MeOH and purified on reverse phase ISCO Gold 50 g C18 column, Mobile Phase A: 5:95 acetonitrile:water with 0.01M ammonium acetate; Mobile Phase B: 95:5 acetonitrile:water with 0.01M ammonium acetate; Gradient: hold at 0% B for 2 column volumes, 0-100% B over 20 column volumes to yielded Intermediate 2N (225 mg, 0.291 mmol) as a solid following lyophilization. LCMS, [M+H]$^+$=773.

Preparation of Intermediate 2O:

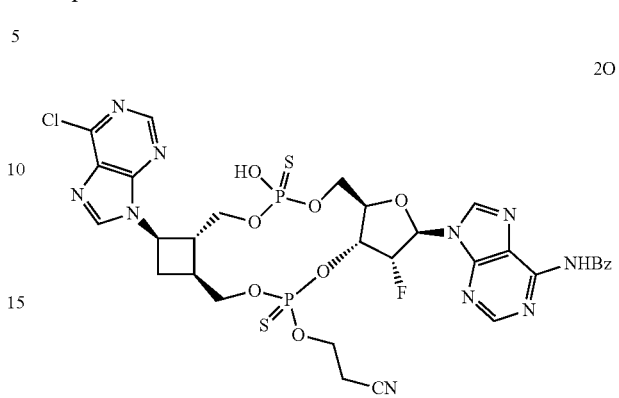

To a solution of Intermediate 2N (0.25 g, 0.323 mmol) in pyridine (16.2 ml) was added diphenyl phosphonate (0.09 ml, 0.45 mmol) dropwise over a period of 20 minutes at RT. To the reaction mixture was then added (E)-N,N-dimethyl-N'-(3-thioxo-3H-1,2,4-dithiazol-5-yl)formimidamide (0.11 g, 0.52 mmol) and stirred at room temperature for 2 h. Another portion of (E)-N,N-dimethyl-N'-(3-thioxo-3H-1,2, 4-dithiazol-5-yl)formimidamide (0.11 g, 0.52 mmol) was added and the reaction was stirred at RT for 5 h. The reaction was concentrated in vacuo, dissolved in methanol, filtered, and the filtrate was concentrated in vacuo to give crude product. The material was purified on reverse phase ISCO Gold 50 g C18 column, Mobile Phase A: 5:95 acetonitrile:water with 0.01 M ammonium acetate; Mobile Phase B: 95:5 acetonitrile:water with 0.01 M ammonium acetate; Gradient: 5-100%, 15 min gradient to give Intermediate 2O (230 mg, 0.270 mmol) as mixture of diastereomers following lyophilization. LCMS, [M+H]$^+$=851.

Examples 2-1, 1-1, 2-2 and 1-2

(1R,6S,8R,9R,15R,17R,18R)-8,17-bis(6-amino-9H-purin-9-yl)-18-fluoro-3,12-disulfanyl-2,4,11,13,16-pentaoxa-3λ$^5$,12λ$^5$-diphosphatricyclo[13.3.0.0$^{6,9}$]octadecane-3,12-dione

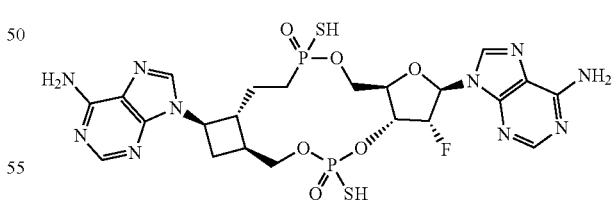

Diastereomer 1 (2-1)
Diastereomer 2 (1-1)
Diastereomer 2 (2-2)
Diastereomer 4 (1-2)

To the diastereomeric mixture, Intermediate 2O (0.23 g, 0.270 mmol) was added ammonium hydroxide (5.26 ml, 135 mmol) and the mixture was stirred at 40° C. for 16 h. The solvent was removed in vacuo and the diastereomers were separated on a Water Autopure with a Xselect RP Prep C18

OBD Column, 5 μm, 19×150 mm with water/acetonitrile (0.1% formic acid) as eluent to give Examples 2-1, 1-1, 2-2 and 1-2.

Example 2-1

7.5 mg. Analytical LCMS method A; $t_R$: 0.38 min; Observed Mass: 675.1;

Example 1-1

6 mg. Analytical LCMS method A; $t_R$: 0.40 min; Observed Mass: 675.0;

Example 2-2

11 mg. Analytical LCMS method A; $t_R$: 0.42 min; Observed Mass: 675.1;

Example 1-2

15.8 mg. Analytical LCMS method A; $t_R$: 0.46 min; Observed Mass: 675.1;

Examples 3

(1R,6S,8R,9R,15R,17R,18R)-17-(6-amino-9H-purin-9-yl)-18-fluoro-3,12-dihydroxy-8-{4-hydroxy-1H-imidazo[2,1-b]purin-1-yl}-2,4,11,13,16-pentaoxa-3λ⁵,12λ⁵-diphosphatricyclo[13.3.0.0⁶,⁹]octadecane-3,12-dithione

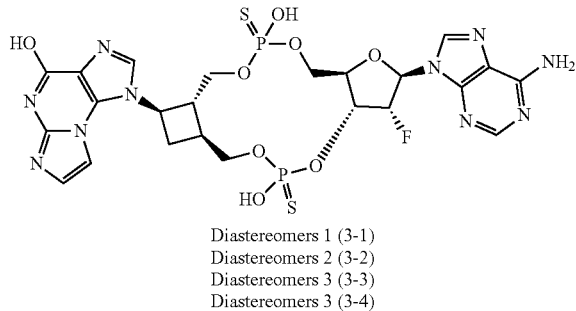 [SMILES: Nc1ncnc2c1ncn2[C@@H]1O[C@@H]2COP(O)(=S)OC[C@@H]3[C@@H](COP(O)(=S)O[C@H]2[C@H]1F)C[C@H]3n1cnc2c(O)nc3nccn3c21]

Diastereomers 1 (3-1)
Diastereomers 2 (3-2)
Diastereomers 3 (3-3)
Diastereomers 3 (3-4)

Preparation of Intermediate 3A

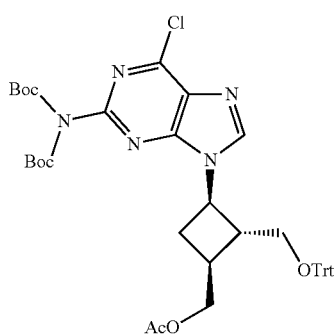

3A

A solution containing triphenylphosphine (732 mg, 2.79 mmol) in a mixture of THF (12 mL)/toluene (6 ml) was cooled in an ice bath and treated dropwise with DIAD (0.53 mL, 2.70 mmol). To the resulting slurry was added a solution containing Intermediate 2D (750 mg, 1.801 mmol) and ((1S,2R,3R)-3-(2-(bis(tert-butoxycarbonyl)amino)-6-chloro-9H-purin-9-yl)-2-(trityloxymethyl)cyclobutyl) methyl acetate (Prepared as in Journal of Organic Chemistry (2000), 65(22), 7697-7699; 999 mg, 2.70 mmol) in THF (5 mL). The ice bath was removed and the reaction was stirred at 35° C. for 20 h. The reaction mixture was cooled to RT and concentrated in vacuo. The residue was dissolved in a small amount of DCM and charged to an 80 g ISCO silica gel column and purified using the Teledyne ISCO system, eluting over a 20 min gradient with 0-100% DCM/EtOAc to give Intermediate 3A (900 mg, 1.171 mmol) LCMS, [M+H]⁺=768

Preparation of Intermediate 3B:

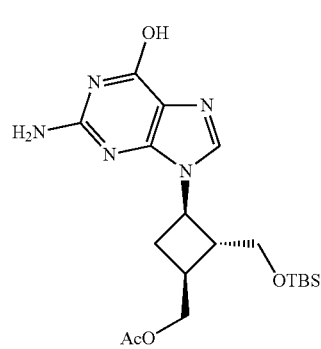

3B

To a solution of Intermediate 3A (1.9 g, 2.473 mmol) in dioxane (3 mL) was added formic acid (6 mL, 156 mmol) and H₂O (1 mL, 55.5 mmol)). The mixture was stirred at 75° C. for 3.5 h, then at 50° C. overnight. The reaction mixture was then concentrated, and the residue was co-evaporated with toluene twice and then with MeOH. The residue was dissolved in MeOH (70 mL), cooled to 0° C., and treated with ammonia in EtOH (2 M, 2.473 mL, 4.95 mmol), and the mixture was stirred for 1 h, and then another portion of ammonia in EtOH (2 M, 1.0 mL) was added and the mixture was stirred for 1 h. The reaction mixture was then concentrated to dryness and the residue was dissolved in DMF (8 mL). Imidazole (0.505 g, 7.42 mmol) and TBS-Cl (0.745 g, 4.95 mmol) were added and the mixture was stirred at RT for 1 h. Water was added and the mixture was extracted with EtOAc twice. The combined organic extracts were washed with 10% LiCl, brine, dried over MgSO₄ and concentrated. The residue was purified by silica column (40 g, 0-10% gradient MeOH/DCM) to give Intermediate 3B (0.57 g, 1.35 mmol).

Preparation of Intermediate 3C:

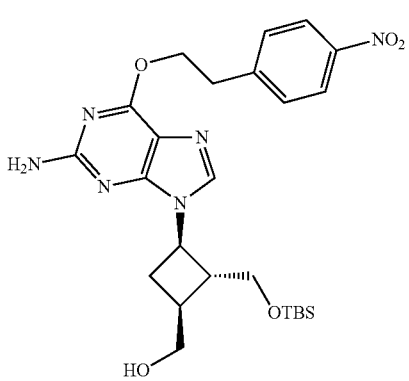

3C

To a solution of Intermediate 3B (0.57 g, 1.35 mmol), 2-(4-nitrophenyl)ethan-1-ol (0.34 g, 2.03 mmol) and Ph₃P (0.53 g, 2.03 mmol) in 1,4-dioxane (10 mL) was added DIAD (0.39 mL, 2.03 mmol). The mixture was stirred at RT overnight, and then concentrated. The residue was purified by silica gel column chromatography (24 g, 0-100% EtOAc/DCM), and the product obtained was further purified by reversed phase C18 ISCO column chromatography (50 g Gold, Mobile Phase A: 5:95 acetonitrile:water with 0.01 M ammonium acetate; Mobile Phase B: 95:5 acetonitrile:water with 0.01 M ammonium acetate; Gradient: 5-100% B). The resulting product was dissolved in MeOH (5 mL), NH₃ (7 N in MeOH, 1 mL) was added and the mixture was stirred at RT overnight. Another portion of NH₃ (7 N in MeOH, 9 mL) was added and the reaction was stirred at RT overnight. The reaction mixture was then concentrated to give Intermediate 3C (415 mg, 0.785 mmol). ¹H NMR (499 MHz, METHANOL-d₄) δ 8.23-8.14 (m, 2H), 8.04-8.00 (m, 1H), 7.66-7.58 (m, 2H), 4.84-4.72 (m, 2H), 4.63 (q, J=8.7 Hz, 1H), 3.90-3.77 (m, 1H), 3.76-3.69 (m, 3H), 3.30 (t, J=6.6 Hz, 2H), 3.06-2.90 (m, 1H), 2.63-2.47 (m, 1H), 2.35-2.12 (m, 2H), 0.79 (s, 9H), 0.02 (d, J=3.0 Hz, 6H). LCMS, [M+H]⁺=529.

Preparation of Intermediate 3D:

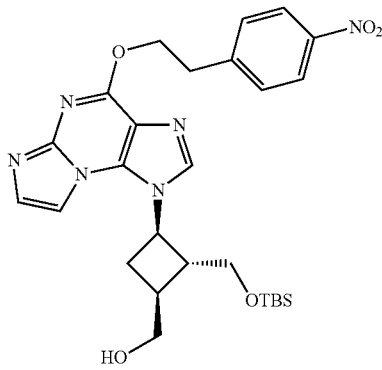

3D

To a solution of Intermediate 3C (415 mg, 0.79 mmol) in EtOH/pH=4.5 ammonium acetate buffer (12 mL/12 mL) was added 2-bromoacetaldehyde (1.3 M in ethanol/1 M HCl, 3.0 mL, 3.90 mmol). The mixture was stirred at RT overnight. Another portion of 2-bromoacetaldehyde (1.3 M in Ethanol/1 M HCl, 3.0 mL, 3.90 mmol) was then added and the reaction was stirred at RT overnight. The reaction mixture was then concentrated to remove most of the EtOH, and the aqueous layer was extracted with DCM twice. The combined extracts were washed with saturated aq. NaHCO₃, brine, dried (MgSO₄), filtered and concentrated in vacuo. The residue was purified by silica gel flash column chromatography (12 g, 0-10% gradient MeOH/DCM to give Intermediate 3D (154 mg, 0.279 mmol). LCMS, [M+H]⁺=553.

Preparation of Intermediate 3E:

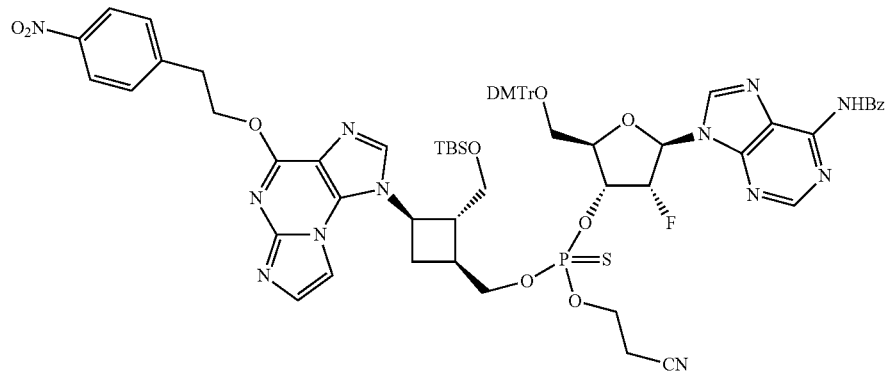

3E

A solution of Intermediate 3D (100 mg, 0.181 mmol) and 1H-tetrazole (63.4 mg, 0.905 mmol) in MeCN (6 mL) was concentrated to dryness on the rotary evaporator. This process was repeated twice, the last time concentrating to ~3 mL CH₃CN remaining. Activated MS 4 Å (8 pieces) was added and the mixture was stirred under a N₂ (g) atmosphere. Separately, (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (Sigma-Aldrich, 238 mg, 0.27 mmol) was azeotroped with MeCN twice, with the last azeotroped leaving ~3 mL CH₃CN remaining. Activated MS 4 Å (8 pieces) was added. This solution was transferred to the above solution by cannula, rinsing with dry MeCN (2×2 mL) for complete transfer. The reaction was stirred at RT for 1 h., and then (E)-N,N-dimethyl-N'-(3-thioxo-3H-1,2,4-dithiazol-5-yl)formimidamide (74 mg, 0.36 mmol) was added and the reaction was stirred at RT overnight. The reaction mixture was filtered and concentrated in vacuo. The residue was dissolved in DCM and washed with aq. NaHCO₃. The organic layer was concentrated to afford Intermediate 3E (246 mg) which was used as is in the next step.

Preparation of Intermediate 3F:

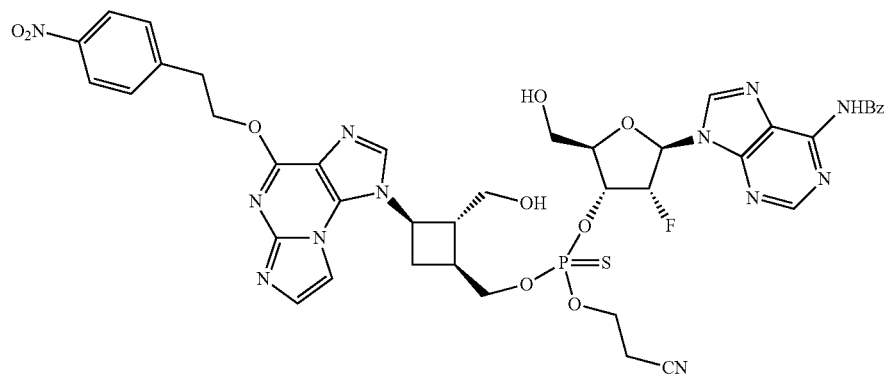

3F

To a solution of crude Intermediate 3E (246 mg, 0.18 mmol) in DCM (4 mL) was added MeOH (0.07 mL, 1.81 mmol) and dichloroacetic acid (0.06 mL, 0.72 mmol). The reaction was stirred for 20 min and more dichloroacetic acid (0.06 mL, 0.72 mmol) was added and the mixture was stirred for 1 h. To the reaction mixture was added pyridine (0.5 mL), and the mixture was then concentrated and the residue was coevaporated with toluene. The resulting residue was loaded on celite and purified on a reverse phase C18 column (50 g GOLD, Mobile Phase A: 5:95 acetonitrile:water with 0.01 M ammonium acetate; Mobile Phase B: 95:5 acetonitrile:water with 0.01 M ammonium acetate; Gradient: 0-100% B) to give O-((2R,3R,4R,5R)-5-(6-benzamido-9H-purin-9-yl)-4-fluoro-2-(hydroxymethyl)tetrahydrofuran-3-yl)O-(((1S,2R,3R)-2-(((tert-butyldimethylsilyl)oxy)methyl)-3-(4-(4-nitrophenethoxy)-1H-imidazo[2,1-b]purin-1-yl)cyclobutyl)methyl)O-(2-cyanoethyl) phosphorothioate (100 mg) and Intermediate 3F. The O-((2R,3R,4R,5R)-5-(6-benzamido-9H-purin-9-yl)-4-fluoro-2-(hydroxymethyl)tetrahydrofuran-3-yl)O-(((1S,2R,3R)-2-(((tert-butyldimethylsilyl)oxy)methyl)-3-(4-(4-nitrophenethoxy)-1H-imidazo[2,1-b]purin-1-yl)cyclobutyl)methyl)O-(2-cyanoethyl) phosphorothioate (100 mg) isolated above was treated with TFA/DCM (1.5 mL/1.5 mL) and stirred at RT for 3 h. The reaction mixture was then diluted with toluene and concentrated. The residue was dissolved in DCM and washed with saturated aq. NaHCO$_3$. The organic layer was combined with the Intermediate 3F from above, concentrated, and loaded onto celite and purified by silica gel column chromatography (12 g column, 0-10% gradient MeOH/DCM) to afford Intermediate 3F (119 mg, 0.126 mmol). LCMS, [M+H]$^+$=943.

Preparation of Intermediate 3G:

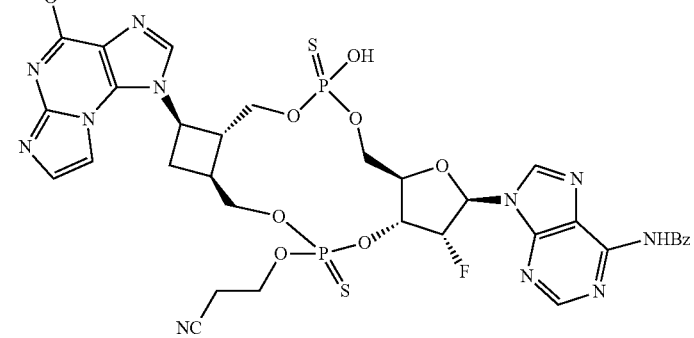

3G

Intermediate 3F (119 mg, 0.126 mmol) was azeotroped with pyridine (6 mL), dissolved in pyridine (25 mL) and then concentrated to about ~15 mL. At RT, a solution of diphenyl phosphite (59.1 mg, 0.252 mmol) in pyridine (1.5 mL) was added over 4 h. (E)-N,N-dimethyl-N'-(3-thioxo-3H-1,2,4-dithiazol-5-yl)formimidamide (78 mg, 0.38 mmol) was then added in one portion and the mixture was stirred at RT overnight. The reaction was quenched with water (0.1 mL) and concentrated in vacuo. The residue was dissolved in DCM/MeOH, loaded on celite and purified on reverse phase ISCO Gold 50 g C18 column, Mobile Phase A: 5:95 acetonitrile:water with 0.01M ammonium acetate; Mobile Phase B: 95:5 acetonitrile:water with 0.01M ammonium acetate; Gradient: 0-100% B over 25 min. Fractions containing desired product were concentrated to afford Intermediate 3G (113 mg). LCMS, [M+H]$^+$=1021.

Preparation of Intermediate 3H:

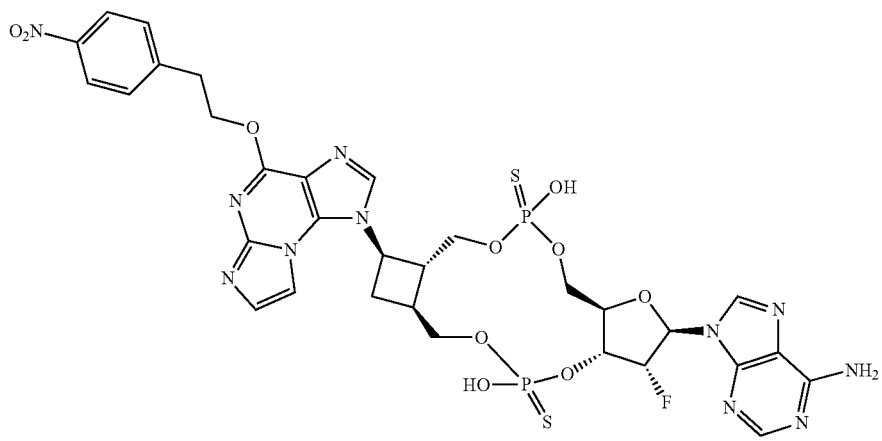

3H

To a solution of Intermediate 3G (110 mg, 0.11 mmol) in MeOH (4 mL) was added NH₄OH (27% aq., 7 mL). The mixture was sonicated and then stirred at RT for 3.5 h. The mixture was then stored in the freezer for three days and then warmed to RT and concentrated in vacuo. The residue was dissolved in a small amount of MeOH and water, loaded onto a solid loading cartridge and purified by reverse phase ISCO Gold 50 g C18Aq column for polar compounds; Mobile Phase A: 5:95 acetonitrile:water with 0.01M ammonium acetate; Mobile Phase B: 95:5 acetonitrile:water with 0.01M ammonium acetate; Gradient: 0-70% B. Fractions containing desired product were concentrated to give Intermediate 3H (120 mg, 0.139 mmol).

Examples 3-1, 3-2, 3-3, 3-4

(1R,6S,8R,9R,15R,17R,18R)-17-(6-amino-9H-purin-9-yl)-18-fluoro-3,12-dihydroxy-8-{4-hydroxy-1H-imidazo[2,1-b]purin-1-yl}-2,4,11,13,16-pentaoxa-3λ⁵,12λ⁵-diphosphatricyclo[13.3.0.0⁶,⁹]octadecane-3,12-dithione

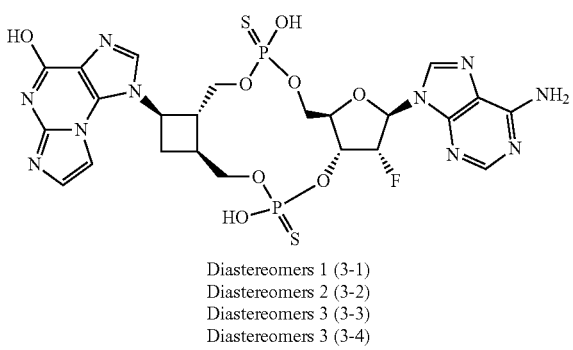 [SMILES: Nc1ncnc2c1ncn2[C@@H]1O[C@@H]2COP(O)(=S)OC[C@@H]3[C@@H](COP(O)(=S)O[C@H]2[C@H]1F)C[C@H]3n1cnc2c(O)nc3nccn3c21]

Diastereomers 1 (3-1)
Diastereomers 2 (3-2)
Diastereomers 3 (3-3)
Diastereomers 3 (3-4)

Intermediate 3H (110 mg, 0.127 mmol) was dissolved in pyridine (2 mL) and DBU (0.288 mL, 1.910 mmol) was added and the reaction mixture was stirred at 30° C. for two days. The reaction mixture was then diluted with acetonitrile, and AcOH was added (0.11 mL, 1.91 mmol). The mixture was concentrated and the residue was azeotroped with ACN two more times. The resulting residue was dissolved in H₂O/acetonitrile and purified by reverse phase ISCO Gold 50 g C18 column; Mobile Phase A: 5:95 acetonitrile:water with 0.01M ammonium acetate; Mobile Phase B: 95:5 acetonitrile:water with 0.01M ammonium acetate; Gradient: 0-30% B. Fractions containing desired product were combined, concentrated and lyophilized to give a mixture of diastereomers (87 mg) which were separated by Preparative HPLC Chromatographic Conditions: Instrument: Waters Autopure; Column: Xselect RP Prep C18 OBD Column, 5 µm, 19×150 mm; Flow rate: 20.0 mL/min; Mobile Phase: A: 100 mM NH₄OAc(pH 6.5); B: MeOH (% A=100–% B); Gradient: 5% B hold over 2 min, 5-26% B over 24.5 min, 29-95% B over 0.5 min, 95-5% B over 1 min. Detection: 260 nm. Fractions containing desired products were concentrated to afford Examples 3-1, 3-2, 3-3 and 3-4.

Example 3-1

6.4 mg; Analytical HPLC Chromatographic Conditions 7; Observed Mass: 715.2; $t_R$: 9.14 min. ¹H NMR (499 MHz, METHANOL-$d_4$) δ 9.02-8.97 (m, 1H), 8.31 (s, 1H), 8.23 (s, 1H), 8.00 (d, J=1.8 Hz, 1H), 7.29 (d, J=1.7 Hz, 1H), 6.41 (d, J=15.4 Hz, 1H), 5.52-5.36 (m, 1H), 5.35-5.20 (m, 1H), 5.07-4.97 (m, 1H), 4.54 (dt, J=11.4, 2.8 Hz, 1H), 4.48-4.37 (m, 2H), 4.31 (dd, J=11.4, 2.1 Hz, 1H), 4.22-4.14 (m, 1H), 4.12-3.98 (m, 2H), 3.13-3.01 (m, 1H), 2.75-2.59 (m, 2H), 2.32 (q, J=10.0 Hz, 1H).

Example 3-2

12.1 mg; Analytical HPLC Chromatographic Conditions 7; Observed Mass: 715.2; $t_R$: 10.05 min. ¹H NMR (499 MHz, METHANOL-$d_4$) δ 9.05-8.90 (m, 1H), 8.36 (s, 1H), 8.22 (s, 1H), 7.97 (d, J=1.8 Hz, 1H), 7.28 (br d, J=1.2 Hz, 1H), 6.41 (d, J=15.1 Hz, 1H), 5.53-5.30 (m, 1H), 5.24-5.07 (m, 1H), 5.05-4.96 (m, 1H), 4.61-4.52 (m, 1H), 4.50-4.41 (m, 2H), 4.24 (br d, J=9.4 Hz, 2H), 4.13-3.98 (m, 2H), 3.25-3.14 (m, 1H), 2.65 (br t, J=6.4 Hz, 2H), 2.40-2.27 (m, 1H).

Example 3-3

9.6 mg; Analytical HPLC Chromatographic Conditions 7; 715.2; $t_R$: 13.36 min. ¹H NMR (499 MHz, METHANOL-$d_4$) δ 8.72-8.61 (m, 1H), 8.29 (s, 1H), 8.22 (s, 1H), 8.09 (d, J=2.0 Hz, 1H), 7.30 (d, J=2.0 Hz, 1H), 6.39 (d, J=15.5 Hz, 1H), 5.66-5.45 (m, 1H), 5.39-5.23 (m, 1H), 5.15-5.02 (m, 1H), 4.60 (dt, J=11.7, 3.1 Hz, 1H), 4.50-4.37 (m, 2H), 4.28 (br dd, J=11.7, 3.0 Hz, 1H), 4.21-4.07 (m, 2H), 4.06-3.95 (m, 1H), 3.11-2.99 (m, 1H), 2.73-2.59 (m, 2H), 2.35-2.19 (m, 1H).

Example 3-4

9.5 mg; Analytical HPLC Chromatographic Conditions 7; 715.2; $t_R$: 14.78 min. $^1$H NMR (499 MHz, METHANOL-$d_4$) δ 8.72-8.59 (m, 1H), 8.30 (s, 1H), 8.22 (s, 1H), 8.07 (d, J=2.0 Hz, 1H), 7.27 (d, J=2.0 Hz, 1H), 6.40 (dd, J=15.1, 1.1 Hz, 1H), 5.61-5.41 (m, 1H), 5.10-5.04 (m, 2H), 4.56 (dt, J=11.8, 3.6 Hz, 1H), 4.49 (br d, J=8.1 Hz, 1H), 4.36-4.21 (m, 3H), 4.17-4.06 (m, 1H), 3.99 (dt, J=10.5, 7.0 Hz, 1H), 3.17-3.09 (m, 1H), 3.08-3.01 (m, 1H), 2.67-2.58 (m, 2H).

Analytical HPLC Chromatographic Conditions 7

Instrument: Agilent 1290; Column: Xselect CSH C18 Column, 3.5 µm, 2.0×150 mm; Flow rate: 0.3 mL/min; Mobile Phase: A: 20 mM NH$_4$OAc (pH 6.5); B: MeOH (% A=100−% B); Gradient: 0-50% B over 15 min, 50-95% B over 2 min.

Examples 4-1 and 4-2

(1R,6S,8R,9R,15R,17R,18R)-8,17-bis(6-amino-9H-purin-9-yl)-3,12,18-trihydroxy-2,4,11,13,16-pentaoxa-3λ$^5$,12λ$^5$-diphosphatricyclo[13.2.1.0$^{6,9}$]octadecane-3,12-dithione

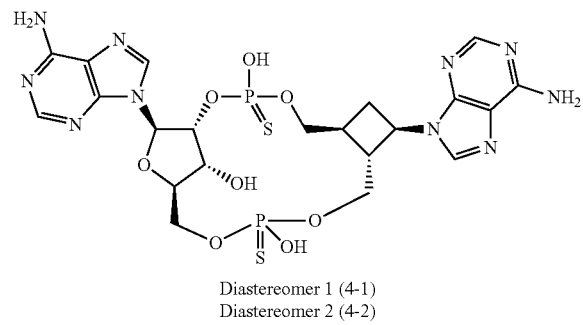 [SMILES: Nc1ncnc2c1ncn2[C@@H]1C[C@@H]2COP(O)(=S)O[C@@H]3[C@H](O)[C@@H](COP(O)(=S)OC[C@H]21)O[C@H]3n1cnc2c(N)ncnc21]

Diastereomer 1 (4-1)
Diastereomer 2 (4-2)

Preparation of intermediate 4A:

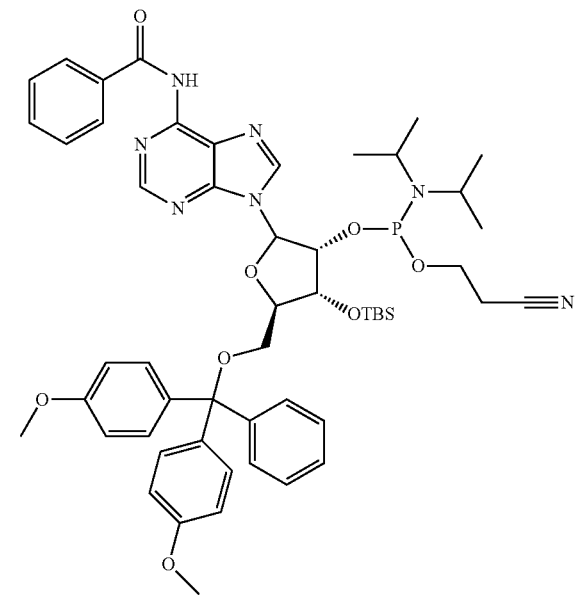

4A

To a solution of N-(9-((2R,3R,4S,5R)-5-((bis(4-methoxyphenyl)(phenyl)methoxy)methyl)-4-((tert-butyldimethylsilyl)oxy)-3-hydroxytetrahydrofuran-2-yl)-9H-purin-6-yl)benzamide (ArkPharm Inc, 10.3 g, 13.07 mmol) in anhydrous DCM (50 mL) was added 1H-imidazole-4,5-dicarbonitrile (1.0 M in acetonitrile, 9.15 mL, 9.15 mmol), followed by the dropwise addition of 3-((bis(diisopropylamino)phosphino)oxy)propanenitrile (4.73 g, 15.69 mmol). The reaction mixture was stirred at RT for 4 h and then additional 3-((bis(diisopropylamino) phosphino)oxy)propanenitrile (3 g, 9.89 mmol) was added and the reaction was stirred at RT overnight. The reaction was quenched with anhydrous MeOH (1.2 mL) and stirred for 10 min, then diluted with DCM, washed with sat'd NaHCO$_3$ and dried over MgSO$_4$. TEA (1 mL) was added, the mixture was filtered and the filtrate was concentrated in vacuo. The residue was purified by column chromatography using a 120 g ISCO column (the column was pretreated with 1% TEA/hexane, then run with EtOAc/hexane=0-100%) to give Intermediate 4A (12.8 g, 12.95 mmol). LCMS, [M+H]$^+$=905.

Preparation of Intermediate 4B:

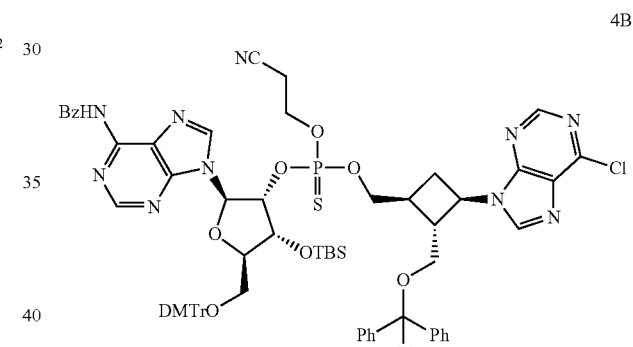

4B

A mixture of Intermediate 2F (0.32 g, 0.63 mmol) and 1H-tetrazole (0.05 g, 0.76 mmol) in anhydrous acetonitrile (5 mL) was concentrated to dryness on the rotary evaporator (2×5 mL) and then re-suspended in acetonitrile (2.5 mL) and left under a nitrogen atmosphere. Separately, Intermediate 4A (0.685 g, 0.693 mmol) in anhydrous ACN (2.5 mL) was concentrated to dryness in vacuo. The residue was dissolved in ACN (1 mL) and added dropwise to the stirred mixture from above at RT. The reaction mixture was stirred under nitrogen at room temperature for 16 h. Then (E)-N,N-dimethyl-N'-(3-thioxo-3H-1,2,4-dithiazol-5-yl)formimidamide (0.155 g, 0.76 mmol) was added and the mixture was stirred at RT for 2 h. The reaction mixture was then concentrated in vacuo and the crude material was purified by flash chromatography over 24 g of silica gel (15 min gradient, with 0-20% MeOH in DCM) to afford Intermediate 4B (0.9 g, 0.68 mmol) as a foam. LCMS, [M+H]$^+$=1429.9

Preparation of Intermediate 4C:

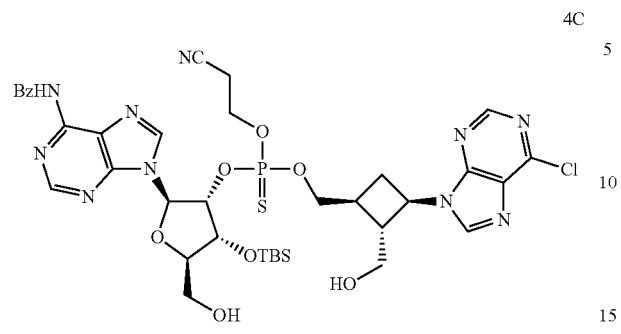

To a solution of Intermediate 4B (0.97 g, 0.68 mmol) and triethylsilane (1.08 ml, 6.8 mmol) in dichloromethane (14 mL) was added TFA (0.16 ml, 2.04 mmol) at room temperature. The reaction mixture was stirred at RT for 1 h and then water (5 mL) was added. The reaction was quenched with saturated aqueous sodium bicarbonate until evolution of gas ceased. The organic layer was separated and the aqueous layer was extracted with DCM (2×10 mL). The organic layers were combined, dried (magnesium sulfate), filtered and the filtrate was concentrated in vacuo. The crude material was suspended in diethyl ether, stirred at room temperature for 1 h to form a fine powder that was then collected by vacuum filtration, washing with hexanes and diethyl ether. The material was partitioned between hexanes and methanol. The methanol layer was separated and washed with hexanes (2×10 mL). The methanol layer was then concentrated in vacuo to give Intermediate 4C (0.48 g) as a pale-yellow solid. LCMS, [M+H]$^+$=885.

Preparation of Intermediate 4D:

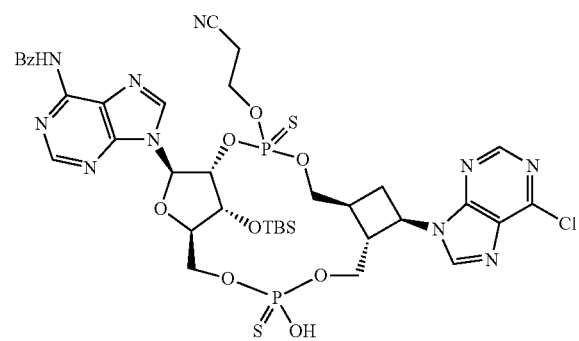

Intermediate 4D was prepared from Intermediate 4C following the procedure described for Intermediate 2O. The crude material was purified on a reverse phase ISCO Gold 50 g C18 column, Mobile Phase A: 5:95 acetonitrile:water with 0.01 M ammonium acetate; Mobile Phase B: 95:5 acetonitrile:water with 0.01 M ammonium acetate; Gradient: 0-100% over 15 min to give Intermediate 4D (0.2 g, 0.21 mmol) as a solid. LCMS, [M+H]$^+$=963.

Preparation of Intermediate 4E:

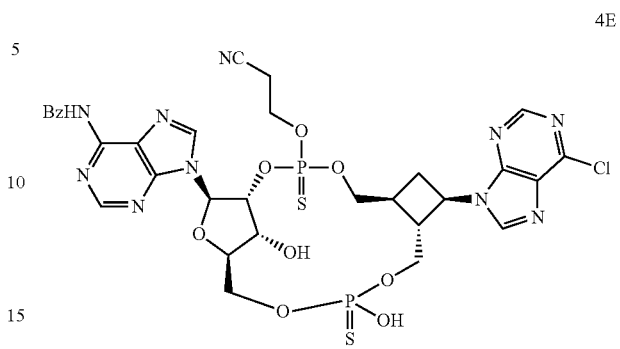

A mixture of Intermediate 4D (0.165 g, 0.171 mmol) and triethylamine trihydrofluoride (0.14 ml, 0.86 mmol) in pyridine (1.7 mL) was stirred at RT for 16 h. The reaction was quenched with calcium carbonate (0.86 g, 8.56 mmol), diluted with MeOH and filtered. The filtrate was concentrated in vacuo to give a mixture of two diastereomers of Intermediate 4E (0.145 g, 0.171 mmol) as an oil. LCMS, [M+H]$^+$=849.

Examples 4-1 and 4-2

(1R,6S,8R,9R,15R,17R,18R)-8,17-bis(6-amino-9H-purin-9-yl)-3,12,18-trihydroxy-2,4,11,13,16-pentaoxa-3λ$^5$,12λ$^5$-diphosphatricyclo[13.2.1.0$^{6,9}$]octadecane-3,12-dithione

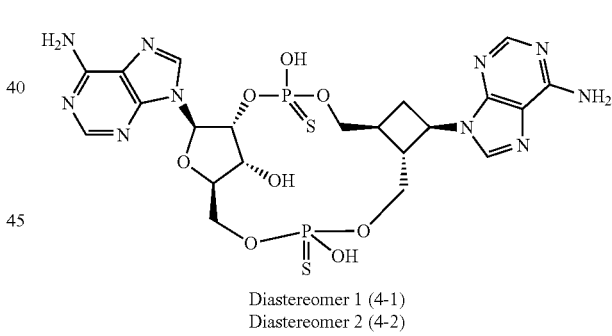

Diastereomer 1 (4-1)
Diastereomer 2 (4-2)

The diastereomeric mixture of Intermediate 4E (0.045 g, 0.053 mmol) and saturated ammonium hydroxide (2 mL, 51.4 mmol) was stirred at RT for 1 h and then heated to 50° C. for 16 h. The reaction mixture was concentrated in vacuo and then lyophilized to a solid crude product. The crude material was purified via preparative LC with the following conditions: Column: Agilent Bonus RP, 200 mm×19 mm, 5-μm particles; Mobile Phase A: 5:95 acetonitrile:water with 20-mM ammonium acetate; Mobile Phase B: 95:5 acetonitrile:water with 20-mM ammonium acetate; Gradient: a 6-minute hold at 0% B, 0-25% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation. Two diastereomers were isolated.

Example 4-1

1.4 mg; Analytical LCMS method B; $t_R$: 2.19 min; Observed Mass: 672.82.

Example 4-2

3.2 mg: Analytical LCMS method B; $t_R$: 2.28 min; Observed Mass: 672.95.

Examples 5-1, 5-2, 5-3 and 5-4

9-[(1R,6S,8R,9R,15R,17R,18R)-17-(6-amino-9H-purin-9-yl)-18-fluoro-3,12-dihydroxy-3,12-disulfanylidene-2,4,11,13,16-pentaoxa-3$\lambda^5$,12$\lambda^5$-diphosphatricyclo[13.3.0.0$^{6,9}$]octadecan-8-yl]-6,9-dihydro-1H-purin-6-one

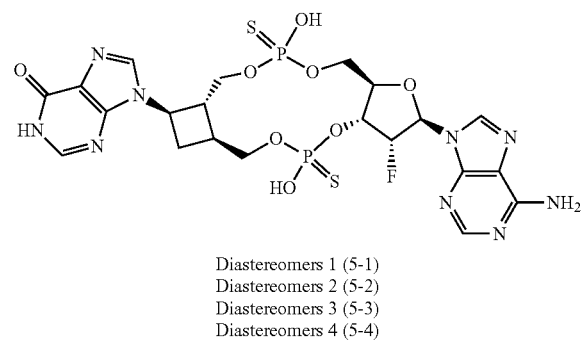 [SMILES: Nc1ncnc2c1ncn2[C@@H]1O[C@@H]2COP(O)(=S)OC[C@@H]3[C@@H](COP(O)(=S)O[C@H]2[C@H]1F)C[C@H]3n1cnc2c(=O)[nH]cnc21]

Diastereomers 1 (5-1)
Diastereomers 2 (5-2)
Diastereomers 3 (5-3)
Diastereomers 4 (5-4)

Preparation of Intermediate 5A:

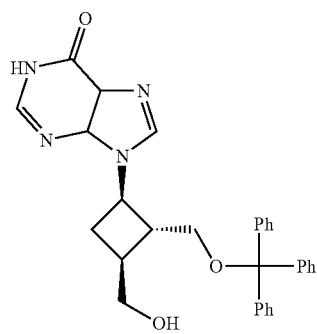

To a solution of Intermediate 2E (0.6 g, 1.085 mmol) in dioxane (9.04 ml) was added sodium hydroxide (0.121 g, 3.04 mmol). The reaction was stirred for 16 h, then at 60° C. for 3 days. Then, LiOH (1.0 M aq., 3.25 ml, 3.25 mmol) was added and the reaction was stirred at 60° C. for 16 h. The reaction mixture was then concentrated in vacuo to remove organic solvents. The remaining aqueous phase was extracted with EtOAc and the combined organic layer was dried (MgSO$_4$) and concentrated in vacuo. The crude material was purified by flash chromatography over 40 g of silica gel (15 min gradient, with 0-10% MeOH in DCM) to afford Intermediate 5A as a solid. LCMS, [M+H]$^+$=493.4

Preparation of Intermediate 5B:

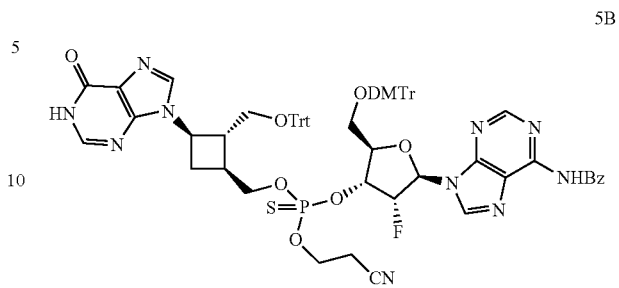

Intermediate 5B was prepared following the same procedure as described for Intermediate 4B. The crude material was purified by flash chromatography over 40 g of silica gel (15 min gradient, with 0-20% MeOH in DCM) to afford a mixture of Intermediate 5B and Intermediate 5C (1.0 g) as an oil.

Preparation of Intermediate 5C:

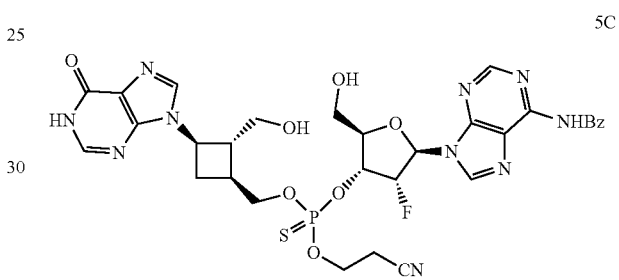

To the mixture of Intermediate 5B and Intermediate 5C (1.0 g, 0.77 mmol) from above and triethylsilane (0.62 ml, 3.9 mmol) in dichloromethane (15 mL) was added TFA (0.18 mL, 2.31 mmol) at room temperature. The reaction mixture was stirred at RT for 1 h. Water (5 mL) was added and the reaction mixture was quenched with saturated aqueous sodium bicarbonate until evolution of gas ceased. The organic layer was separated and the aqueous layer was extracted with DCM (2×10 mL) and with 2-Me-THF (2×10 mL). The organic layers were combined and dried (magnesium sulfate) and concentrated in vacuo. The residue was suspended in diethyl ether and stirred at room temperature for 1 h. A fine powder formed and was collected by vacuum filtration, washing with hexanes and diethyl ether. The material was partitioned between hexanes and methanol. Methanol layer separated and washed with hexanes (2×10 mL). The methanol layer was concentrated in vacuo to give Intermediate 5C (0.49 g, 0.65 mmol) as a pale-yellow solid. LCMS, [M+H]$^+$=755.

Preparation of Intermediate 5D:

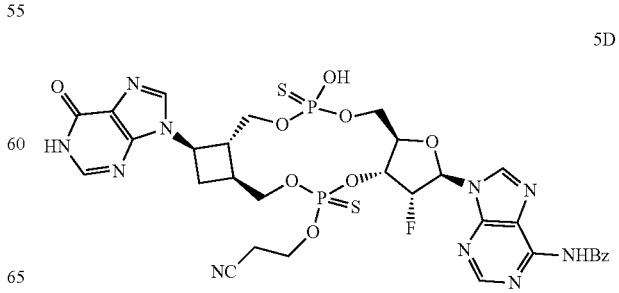

To a 0° C. solution of Intermediate 5C (0.44 g, 0.583 mmol) in pyridine (21.20 ml) was added a solution of diphenyl phosphonate (0.14 ml, 0.70 mmol) in pyridine (2.1 ml) dropwise over a period of 1 h. The reaction was stirred at room temperature for 16 h. The mixture was then treated with (E)-N,N-dimethyl-N'-(3-thioxo-3H-1,2,4-dithiazol-5-yl)formimidamide (0.180 g, 0.875 mmol) and the reaction was stirred at room temperature for 3 h. The reaction mixture was concentrated in vacuo. The residue was purified on reverse phase ISCO Gold 50 g C18 column, Mobile Phase A: 5:95 acetonitrile:water with 0.01M ammonium acetate; Mobile Phase B: 95:5 acetonitrile:water with 0.01M ammonium acetate; Gradient: 0-100% B over 15 min to give Intermediate 5D (0.081 g) as a solid mixture of diastereomers after lyophilization. LCMS, [M+H]$^+$=833.

Examples 5-1, 5-2, 5-3 and 5-4

9-[(1R,6S,8R,9R,15R,17R,18R)-17-(6-amino-9H-purin-9-yl)-18-fluoro-3,12-dihydroxy-3,12-disulfanylidene-2,4,11,13,16-pentaoxa-3λ$^5$,12λ$^5$-diphosphatricyclo[13.3.0.0$^{6,9}$]octadecan-8-yl]-6,9-dihydro-1H-purin-6-one

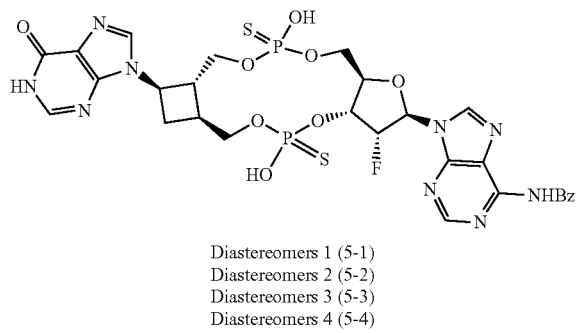

Diastereomers 1 (5-1)
Diastereomers 2 (5-2)
Diastereomers 3 (5-3)
Diastereomers 4 (5-4)

To the diastereomeric mixture of Intermediate 5D (0.08 g, 0.1 mmol) was added ammonia (7 N in MeOH, 6.95 mL, 48.6 mmol) and the mixture was stirred at RT for 1 h. The reaction was then heated to 50° C. for 3 h. The reaction mixture was then concentrated in vacuo and the residue was purified on a reverse phase ISCO Gold 50 g C18 column, Mobile Phase A: 5:95 acetonitrile:water with 0.01M ammonium acetate; Mobile Phase B: 95:5 acetonitrile:water with 0.01M ammonium acetate; Gradient: 0-100% B over 15 min to give a mixture of diastereomers that were separated by preparative LC/MS with the following conditions: Column: Agilent Bonus RP 21.2×100 mm, 5-μm particles; Mobile Phase A: water with 20-mM ammonium acetate; Mobile Phase B: acetonitrile; Gradient: 0% B hold 0-6 minute. 0%-25% B over 16 minutes, then a 4-minute hold at 100% B; Flow: 20 mL/min. Fractions containing the desired product were combined and dried via centrifugal evaporation.

Example 5-1

3.5 mg; Analytical LCMS method B; Observed Mass: 676.0; Retention Time: 2 min.

Example 5-2

3 mg; Analytical LCMS method B; Observed Mass: 676.0; Retention Time: 2.05 min.

Example 5-3

3.5 mg; Analytical LCMS method B; Observed Mass: 676.0; Retention Time: 2.14 min.

Example 5-4

3.1 mg; Analytical LCMS method B; Observed Mass: 676.0; Retention Time: 2.29 min.

Examples 6-1, 6-2, 6-3 and 6-4

(1S,6S,8R,9R,15R,17R)-8-(6-amino-9H-purin-9-yl)-17-{4-chloro-7H-pyrrolo[2,3-d]pyrimidin-7-yl}-3-hydroxy-12-sulfanyl-3-sulfanylidene-2,4,11,13,16-pentaoxa-3λ$^5$,12λ$^5$-diphosphatricyclo[13.3.0.0$^{6,9}$]octadecan-12-one

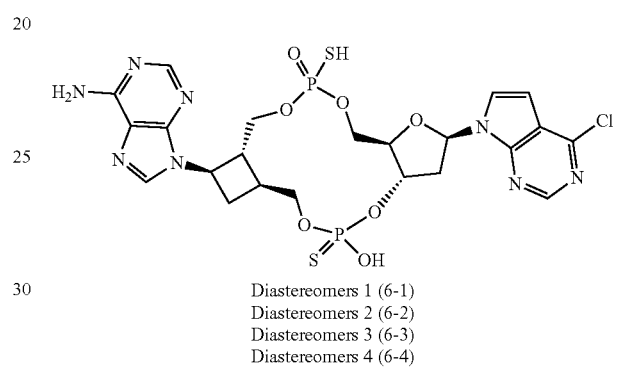

Diastereomers 1 (6-1)
Diastereomers 2 (6-2)
Diastereomers 3 (6-3)
Diastereomers 4 (6-4)

Preparation of Intermediate 6A:

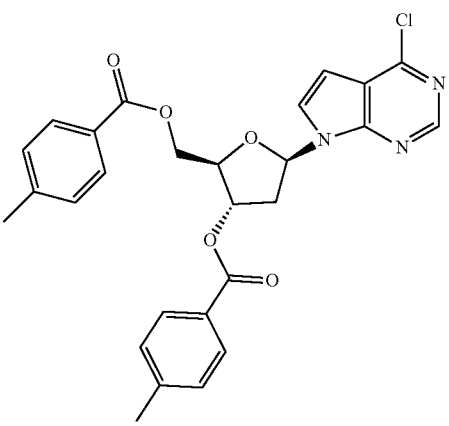

6A

To a round bottomed flask was added powdered KOH (1.28 g, 22.8 mmol), anhydrous acetonitrile (50 mL), tris (2-(2-methoxyethoxy)ethyl)amine (0.29 mL, 0.91 mmol) and the mixture was stirred at RT for 5 min. To the resulting suspension was added 4-chloro-7H-pyrrolo[2,3-d]pyrimidine (1 g, 6.5 mmol) and stirring continued at RT for 5 more minutes. To the resulting suspension was added (2R,3S,5R)-5-chloro-2-(((4-methylbenzoyl)oxy)methyl)tetrahydrofuran-3-yl 4-methylbenzoate (Carbosynth, 2.53 g, 6.51 mmol) portionwise over a 5 minute period and stirring continued at RT for 30 minutes. The reaction mixture was then filtered and the residue was washed with MeCN. The filtrate was concentrated and purified by silica gel chromatography using a 120 g ISCO column (27 min gradient, with 0-50% ethyl acetate in hexanes). The product containing fractions were combined and concentrated in vacuo to afford Intermediate 6A (1.95 g, 3.85 mmol) as a colorless solid. $^1$H NMR (499 MHz, DMSO-d$_6$) δ 8.65 (s, 1H), 7.99-7.94 (m, 3H), 7.85 (d, J=8.1 Hz, 2H), 7.38 (d, J=8.0 Hz, 2H), 7.31 (d, J=8.0 Hz, 2H), 6.80-6.74 (m, 2H), 5.76 (dt, J=6.3, 2.4 Hz, 1H), 4.66-4.50 (m, 3H), 3.21-3.13 (m, 1H), 2.77 (ddd, J=14.3, 6.1, 2.5 Hz, 1H), 2.41 (s, 3H), 2.38 (s, 3H). LCMS, [M+H]$^+$=506.2, t$_R$: 1.17 min, Analytical LCMS method A.

Preparation of Intermediate 6B:

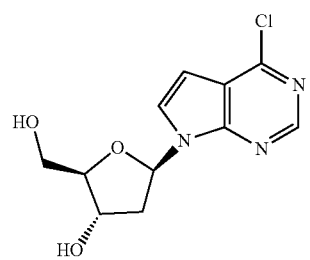

A suspension of Intermediate 6A (1.90 g, 3.76 mmol) in cold ammonia (7 N in methanol, 0.54 ml, 3.76 mmol) was warmed to RT and stirred under a nitrogen atmosphere for 24 h. The reaction mixture was then concentrated in vacuo. The resulting white residue was purified by flash chromatography over 80 g of silica gel (26 min gradient, eluted with 0-20% MeOH in DCM) to afford Intermediate 6B (0.83 g, 3.08 mmol) as a white solid. LCMS, [M+H]$^+$=270

Preparation of Intermediate 6C:

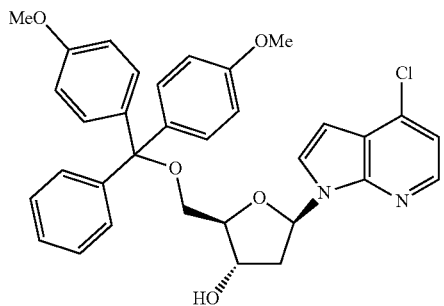

A solution of Intermediate 6B (0.83 g, 3.1 mmol) in pyridine (3 mL) was concentrated to dryness on a rotary evaporator. To the residue was added pyridine (20 mL), DMTr-Cl (1.1 g, 3.2 mmol), DMAP (0.02 g, 0.15 mmol) and the mixture was stirred at room temperature for 14 h. The reaction mixture was then quenched with methanol and concentrated in vacuo. The residue was dissolved in DCM and washed with saturated NaHCO$_3$ solution. The organic layer was dried over sodium sulfate, filtered and concentrated. The residue was purified by silica gel chromatography using a 80 g ISCO column (40 min gradient, eluted with 0-100% EtOAc in hexanes containing 0.5% TEA. Fractions containing product were combined and concentrated in vacuo to afford Intermediate 6C (1.66 g, 2.90 mmol). $^1$H NMR (499 MHz, DMSO-d$_6$) δ 8.63 (s, 1H), 7.80 (d, J=3.8 Hz, 1H), 7.40-7.29 (m, 2H), 7.27-7.16 (m, 7H), 6.90-6.76 (m, 4H), 6.69 (d, J=3.7 Hz, 1H), 6.63 (t, J=6.6 Hz, 1H), 5.40 (d, J=4.5 Hz, 1H), 4.49-4.39 (m, 1H), 3.98 (q, J=4.7 Hz, 1H), 3.75-3.69 (m, 6H), 3.17 (d, J=4.9 Hz, 2H), 2.68 (dt, J=13.3, 6.5 Hz, 1H), 2.35 (ddd, J=13.4, 6.6, 4.5 Hz, 1H). LCMS, [M+H]$^+$=571/572.

Preparation of Intermediate 6D:

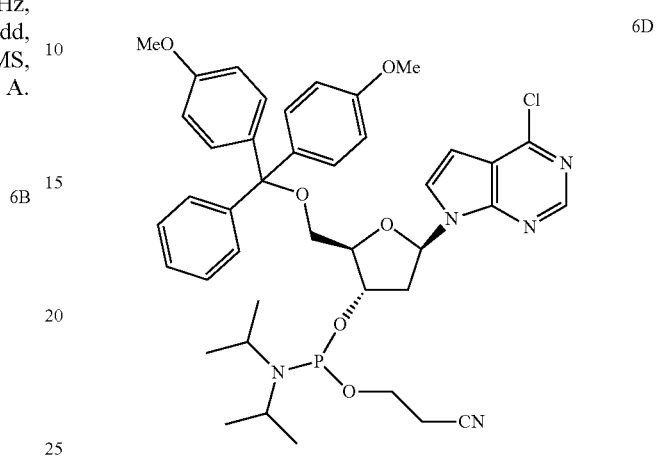

To a solution of Intermediate 6C (0.8 g, 1.40 mmol) in anhydrous DCM (15 mL) was added a solution of 4,5-dicyanoimidazole (0.17 g, 1.40 mmol) in acetonitrile (5.0 mL). 2-cyanoethyl N,N,N',N'-tetraisopropylphosphorodiamidite (0.70 mL, 2.2 mmol) was added and the reaction mixture was stirred for 3 h. The reaction mixture was then diluted with DCM and quenched with saturated NaHCO$_3$. The organic layer was separated and dried over sodium sulfate. The filtrate was then concentrated in vacuo and the crude residue was purified by column chromatography using a 40 g ISCO column (13 min gradient, eluted with 0-50% gradient DCM-EtOAc). Fractions containing product were concentrated to afford Intermediate 6D (0.8 g) as white foam. LCMS, [M+H]$^+$=689.3.

Preparation of Intermediate 6E:

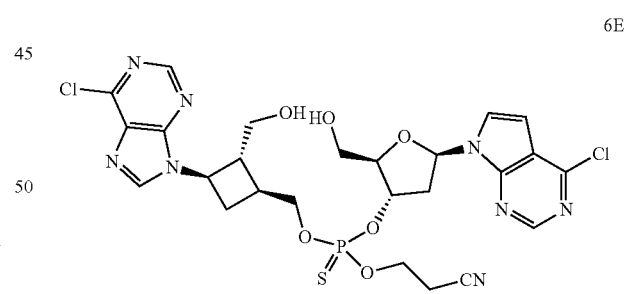

A solution of 1H-tetrazole (123 mg, 1.76 mmol) and Intermediate 2F (180 mg, 0.35 mmol) in MeCN (3 mL) was concentrated on a rotary evaporator and the azeotrope was repeated (2×3 mL). The resulting residue was dissolved in MeCN (3 mL) and activated MS 4 Å (150 mg) were added and the mixture was kept under a nitrogen atmosphere. Separately, Intermediate 6D (354 mg, 0.46 mmol) in MeCN (3 mL) was concentrated on a rotary evaporator and the process was repeated (3×1 mL). The resulting residue was dissolved in MeCN (3 mL) and added to the above stirring solution via syringe. The reaction mixture was stirred at RT overnight. The reaction mixture was then treated with DDTT (145 mg, 0.704 mmol) and stirred for 30 minutes, then concentrated in vacuo. The residue was dissolved in EtOAc, washed with saturated aq. NaHCO$_3$, then with brine. The organic layer was dried over sodium sulfate, filtered and concentrated in vacuo. The crude residue was suspended in DCM (6 mL) and 2,2-dichloroacetic acid (2.027 mL, 3.52 mmol) and triethylsilane (0.563 mL, 3.52 mmol) were added and the reaction mixture was stirred at RT for 0.5 h. The reaction was then quenched with pyridine (0.5 mL, 6.18 mmol) and concentrated on a rotary evaporator.

The residue was purified by column chromatography using a 12 g ISCO column (Solvent A: DCM, Solvent B: 20% DCM-MeOH). Fractions containing product were concentrated to afford Intermediate 6E (115 mg, 0.172 mmol). LCMS, [M+H]$^+$=669/671. An impure fraction (80 mg) was recovered and purified on a reverse phase ISCO Gold 15 g C18 column, Mobile Phase A: 5:95 acetonitrile:water with 0.01M ammonium acetate; Mobile Phase B: 95:5 acetonitrile:water with 0.01M ammonium acetate; Gradient: 0-100% B over 20 min. Fractions containing product were lyophilized to give an additional Intermediate 6E (20 mg, 0.030 mmol). LCMS, [M+H]$^+$=669/671.

Preparation of Intermediate 6F:

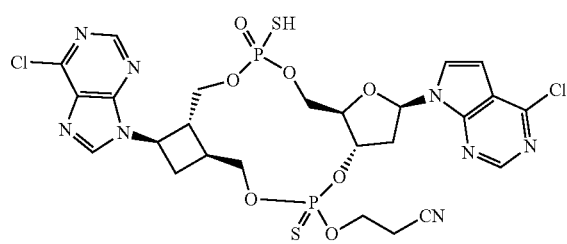

6F

A solution of Intermediate 6E (0.02 g, 0.030 mmol) in dry pyridine (6 mL) was concentrated on a rotary evaporator and the azeotrope was repeated (2×3 mL). The residue was re-dissolved in dry pyridine (6 mL) under a nitrogen atmosphere and a solution of diphenyl phosphite (0.012 ml, 0.060 mmol) in pyridine (1 mL) was added dropwise over 30 min. DDTT (0.025 g, 0.119 mmol) was then added and the reaction was stirred at RT overnight. The reaction mixture was concentrated in vacuo and the residue was suspended in EtOAc and washed with saturated aqueous sodium bicarbonate. The organic layer was washed with brine, dried over Na$_2$SO$_4$, filtered and concentrated in vacuo. The crude residue was dissolved in MeCN and concentrated on a rotary evaporator and the azeotrope was repeated a two times. A precipitate was formed in MeCN and was filtered. The filtrate was concentrated in vacuo to give Intermediate 6F that was taken to the next step without further purification. LCMS, [M+H]$^+$=747.

Examples 6-1, 6-2, 6-3 and 6-4

(1S,6S,8R,9R,15R,17R)-8-(6-amino-9H-purin-9-yl)-17-{4-chloro-7H-pyrrolo[2,3-d]pyrimidin-7-yl}-3-hydroxy-12-sulfanyl-3-sulfanylidene-2,4,11,13,16-pentaoxa-3λ$^5$,12λ$^5$-diphosphatricyclo[13.3.0.0$^{6,9}$]octadecan-12-one

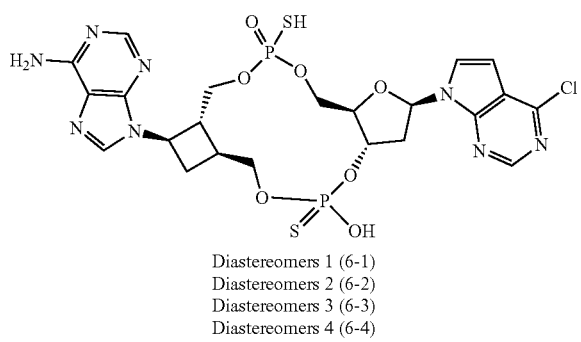 [SMILES: Nc1ncnc2c1ncn2[C@@H]1C[C@@H]2COP(O)(=S)O[C@H]3C[C@H](n4ccc5c(Cl)ncnc54)O[C@@H]3COP(=O)(S)OC[C@H]21]

Diastereomers 1 (6-1)
Diastereomers 2 (6-2)
Diastereomers 3 (6-3)
Diastereomers 4 (6-4)

To a solution of Intermediate 6F in MeCN (0.6 mL) was added 27% ammonium hydroxide (3 mL, 77 mmol) and the reaction mixture was stirred at 45° C. for 2 h. The reaction mixture was then dried under a gentle stream of nitrogen. The crude was purified under Preparative HPLC Chromatographic Conditions; Instrument: Waters Autopure; Column: Xselect RP Prep C18 OBD Column, 5 μm, 19×150 mm; Flow rate:20.0 mL/min; Mobile Phase: A: 20 mM TEAA (pH 6.5); B: 80:20 ACN:20 mM TEAA (pH6.5); Gradient: 5-35% B over 50 min, 35-95% B over 2 min, 95-5% B over 1 minute to afford Examples 6-1, 6-2, 6-3 and 6-4 after lyophilization.

Example 6-1

0.80 mg; Observed Mass: 676.0; $t_R$: 15.56 min.; Analytical HPLC Chromatographic Conditions 1

Example 6-2

0.92 mg; Observed Mass: 676.0; $t_R$: 16.15 min.; Analytical HPLC Chromatographic Conditions 1

Example 6-3

0.52 mg; Observed Mass: 676.0; $t_R$: 17.91 min.; Analytical HPLC Chromatographic Conditions 1

Example 6-4

1.14 mg; Observed Mass: 676.0; $t_R$: 18.64 min.; Analytical HPLC Chromatographic Conditions 1

Analytical HPLC Chromatographic Conditions 1:

Instrument: Agilent 1290 HPLC/MS; Column: Xselect CSH C18 Column, 3.5 μm, 3.0×150 mm; Flow rate: 0.5 mL/min; Mobile Phase: A: 10 mM TEAA (pH 6.5); B: 80:20 ACN:10 mM TEAA (pH 6.5); Gradient: 5-35% B over 30 min, 35-95% B over 2 min, 95-5% over 1 minute.

Examples 7-1, 7-2, 7-3 and 7-4

(1R,6S,8R,9R,15R,17R,18S)-8-(6-amino-9H-purin-9-yl)-17-{4-chloro-7H-pyrrolo[2,3-d]pyrimidin-7-yl}-18-fluoro-3,12-dihydroxy-2,4,11,13,16-pentaoxa-3$\lambda^5$,12$\lambda^5$-diphosphatricyclo[13.3.0.0$^{6,9}$]octadecane-3,12-dithione

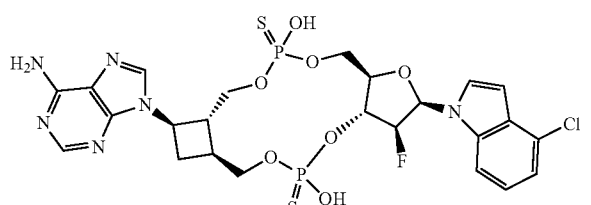

Diastereomers 1 (5-1)
Diastereomers 2 (5-2)
Diastereomers 3 (5-3)
Diastereomers 4 (5-4)

Preparation of Intermediate 7A:

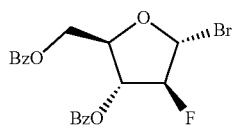

7A

To a solution of (2R,3S,4R,5R)-5-((benzoyloxy)methyl)-3-fluorotetrahydrofuran-2,4-diyl dibenzoate (Arkpharm Inc., 5 g, 10.8 mmol) in anhydrous DCM (20 mL) was added HBr (33% solution in acetic acid, 5.31 mL, 32.3 mmol). The reaction mixture was stirred at RT for 3 hours, then portionwise poured into an ice cold aqueous NaHCO$_3$ solution while stirring. Additional DCM was added and stirring was continued until the aqueous layer was pH ~7-8. The cold organic layer was separated and washed with saturated aq. NaHCO$_3$, dried over sodium sulfate and concentrated in vacuo to afford Intermediate 7A (~5 g) as a colorless gel that was immediately used in the next step. $^1$H NMR (499 MHz, Chloroform-D) δ 8.15-8.10 (m, 2H), 8.10-8.05 (m, 2H), 7.64 (tt, J=7.5, 1.3 Hz, 1H), 7.58 (tt, J=7.5, 1.3 Hz, 1H), 7.53-7.48 (m, 2H), 7.47-7.41 (m, 2H), 6.65 (d, J=12.2 Hz, 1H), 5.70-5.51 (m, 2H), 4.88-4.78 (m, 2H), 4.76-4.68 (m, 1H).

Preparation of Intermediate 7B:

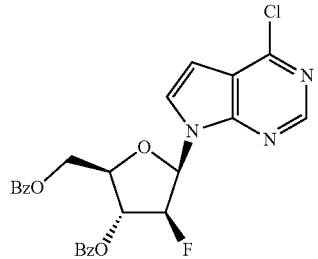

7B

A suspension of 4-chloro-7H-pyrrolo[2,3-d]pyrimidine (1.54 g, 10.0 mmol) and anhydrous acetonitrile (20 mL) was concentrated on a rotary evaporator and to the residue was added acetonitrile (20 mL) and the mixture was then concentrated again. The residue was then suspended in anhydrous acetonitrile (100 mL) and sodium hydride (60% dispersion in mineral oil, 0.40 g, 10.0 mmol) was added. The resulting suspension was stirred at RT for 15 minutes to form a cloudy mixture to which was added a freshly prepared solution of crude Intermediate 7A (4.23 g, 10 mmol) in anhydrous acetonitrile (25 mL). The reaction mixture was stirred at RT for 16 hours and then concentrated in vacuo. The residue was dissolved in DCM (400 mL) and washed with water (2×100 mL). The organic layer was dried over sodium sulfate, filtered and concentrated. The residue was chromatographed on silica gel using 0-50% EtOAc in hexanes to give Intermediate 7B (2.65 g, 5.34 mmol). LCMS, [M+H]$^+$=496.

Preparation of Intermediate 7C:

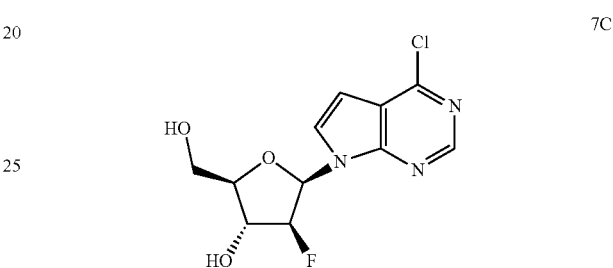

7C

To a stirring solution of Intermediate 7B (2.63 g, 5.30 mmol) in methanol (10 mL) was added sodium methoxide (0.5 M in methanol, 10.6 mL, 5.30 mmol). The reaction mixture was stirred at RT for 30 minutes, and then aqueous HCl (1 N, 5.30 mL, 5.30 mmol) was added and the mixture was concentrated in vacuo. The residue was purified by silica gel chromatography using a 40 g ISCO column; Gradient 0-30% MeOH in DCM. Fractions containing the desired product were combined and concentrated to afford Intermediate 7C (1.39 g, 4.83 mmol). $^1$H NMR (499 MHz, Chloroform-D) δ 8.65 (s, 1H), 7.49 (dd, J=3.8, 2.3 Hz, 1H), 6.74-6.65 (m, 2H), 5.26-5.09 (m, 1H), 4.78 (ddd, J=19.0, 5.0, 3.0 Hz, 1H), 4.09 (q, J=4.2 Hz, 1H), 4.01 (ddd, J=12.0, 3.7, 1.2 Hz, 1H), 3.98-3.89 (m, 1H), 2.81 (br s, 2H). LCMS: m/z 288.1 (M+H), t$_R$: 0.71 min, Analytical LCMS method A.

Preparation of Intermediate 7D

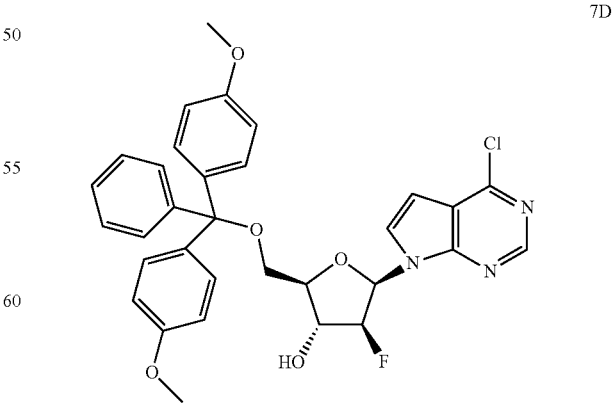

7D

A solution of Intermediate 7C (1.39 g, 4.83 mmol) in pyridine (3 mL) was concentrated on a rotary evaporator and to the residue was added pyridine (20 mL), DMTr-Cl (1.72 g, 5.1 mmol) and DMAP (0.030 g, 0.24 mmol) and the mixture was stirred at RT for 14 h. The reaction mixture was then quenched with methanol and concentrated. The residue was dissolved in DCM and washed with saturated NaHCO$_3$ solution. The organic layer was dried over sodium sulfate, concentrated and the residue was purified by silica gel chromatography using a 80 g ISCO column; Gradient: 0-100% EtOAc in hexanes containing 0.5% TEA. Fractions containing the desired product were combined and concentrated to afford Intermediate 7D (2.39 g, 4.05 mmol). $^1$H NMR (499 MHz, DMSO-d$_6$) δ 8.70 (s, 1H), 7.68 (dd, J=3.7, 2.3 Hz, 1H), 7.41 (d, J=7.3 Hz, 2H), 7.32-7.21 (m, 7H), 6.90-6.85 (m, 4H), 6.76-6.71 (m, 2H), 6.03 (d, J=5.0 Hz, 1H), 5.31-5.15 (m, 1H), 4.43 (dq, J=19.3, 4.6 Hz, 1H), 4.10-4.04 (m, 1H), 3.74 (s, 6H), 3.37-3.32 (m, 1H), 3.30-3.24 (m, 1H). LCMS: m/z 590.2 (M+H), t$_R$: 1.11 min, Analytical LCMS method A.

Preparation of Intermediate 7E

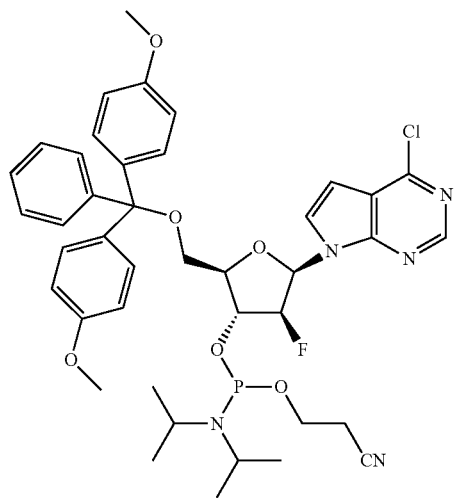

7E

To a solution of Intermediate 7D (2.38 g, 4.03 mmol) in anhydrous DCM (24 mL) was added a solution of 1H-imidazole-4,5-dicarbonitrile (0.48 g, 4.0 mmol) in anhydrous acetonitrile (8 mL), followed by neat 3-((bis(diisopropylamino) phosphanyl)oxy)propanenitrile (2.05 mL, 6.5 mmol). The reaction mixture was stirred at RT for 16 h. The reaction was then quenched with a few drops of methanol, diluted with DCM and washed with saturated aq. NaHCO$_3$ solution. The organic layer was dried over sodium sulfate, filtered and concentrated to a clear oil. The oil was dissolved in a minimal amount of DCM and chromatographed over silica gel using 0-50% EtOAc in Hexanes. Fractions containing the desired product were combined and concentrated, then re-concentrated twice on rotary evaporator from acetonitrile (2×5 mL) to afford Intermediate 7D (2.68 g) as a foam. $^1$H NMR (499 MHz, DMSO-d$_6$) δ 8.68 (d, J=5.0 Hz, 1H), 7.76 (ddd, J=5.5, 3.6, 2.2 Hz, 1H), 7.45-7.38 (m, 2H), 7.33-7.20 (m, 7H), 6.90-6.82 (m, 4H), 6.81-6.73 (m, 2H), 5.57-5.37 (m, 1H), 4.86-4.68 (m, 1H), 4.22-4.13 (m, 1H), 3.73 (d, J=3.0 Hz, 7H), 3.63-3.47 (m, 3H), 3.43-3.33 (m, 2H), 2.77-2.61 (m, 2H), 1.15-0.95 (m, 12H). LCMS: m/z 303.1 (DMTr+), 707.2, 709.2 (hydrolyzed product during analysis), t$_R$: 1.09 min, Analytical LCMS method A.

Preparation of Intermediate 7F:

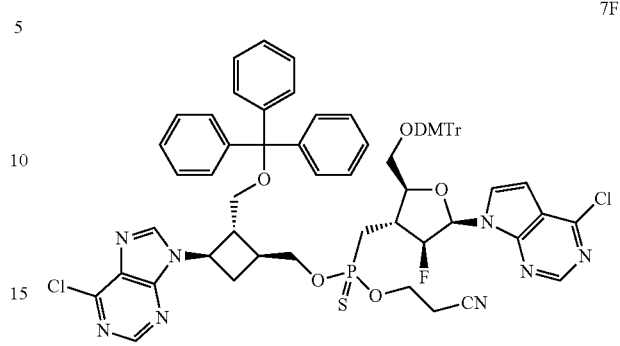

7F

A solution of 1H-tetrazole (68.5 mg, 0.98 mmol) and Intermediate 2F (100 mg, 0.20 mmol) in MeCN (3 mL) was concentrated on a rotary evaporator and the azeotrope was repeated (2×3 mL). The resulting residue was dissolved in MeCN (3 mL), activated MS 4 Å (150 mg) were added and the mixture was left under a nitrogen atmosphere. Separately, Intermediate 7E (186 mg, 235 mmol) in MeCN (3.00 mL) was concentrated on a rotary evaporator and the process was repeated (3×1 mL). The resulting residue was dissolved in MeCN (3.0 mL) and added to the above stirring mixture via syringe. The reaction mixture was stirred at RT overnight, then treated with DDTT (48.3 mg, 0.235 mmol), stirred for 30 min and concentrated in vacuo. The residue was dissolved in EtOAc, washed with saturated aq. NaHCO$_3$, then with brine. The organic layer was dried over sodium sulfate, filtered and concentrated in vacuo. The crude product, Intermediate 7F, was used as such in the next step. LCMS: m/z 1178.2 (M–H), t$_R$: 1.44 min, Analytical LCMS method C.

Preparation of Intermediate 7G:

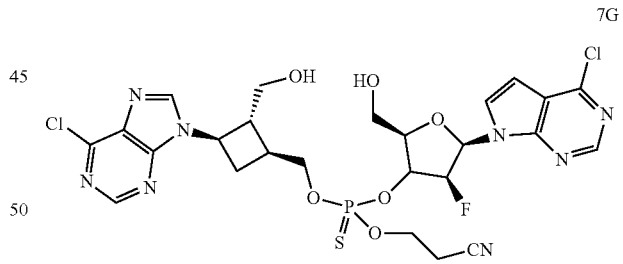

7G

To a solution of crude Intermediate 7F (172 mg, 0.14 mmol) in DCM (7 mL) was added water (1 drop), triethylsilane (0.22 mL, 1.4 mmol) and the mixture was stirred. A solution of dichloroacetic acid (0.092 mL, 1.12 mmol) in DCM (2 mL) was added over a 2 minute period. The reaction mixture was then diluted with DCM and extracted with saturated aq. NaHCO$_3$. The combined organic layer was dried over sodium sulfate, filtered and concentrated and then purified by silica gel chromatography using 0-20% methanol in DCM. Fractions containing product were combined and concentrated to afford Intermediate 7G (64 mg, 0.093 mmol) as a colorless gum. LCMS: m/z 686.8 (M+H), t$_R$ 0.80 min, Analytical LCMS method D.

Preparation of Intermediate 7H:

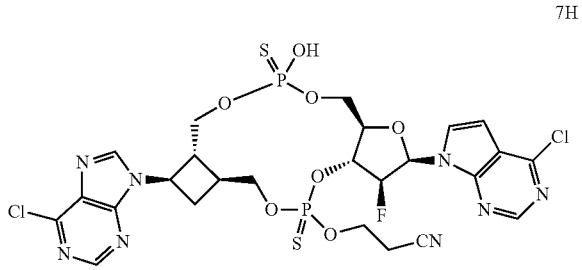 [SMILES: N#CCCOP1(=S)OC[C@H]2C[C@@H](n3cnc4c(Cl)ncnc43)[C@@H]2COP(O)(=S)OC[C@H]2O[C@@H](n3ccc4c(Cl)ncnc43)[C@@H](F)[C@@H]2O1]

7H

Intermediate 7G (64 mg, 0.09 mmol) was co-evaporated with anhydrous pyridine three times and the residue was then dissolved in anhydrous pyridine (25 mL). A solution of diphenyl phosphite (43.6 mg, 0.19 mmol) in pyridine (1 mL) was added dropwise and the reaction mixture was stirred at RT for 1 h. While monitoring the reaction by LCMS, the reaction mixture was titrated with diphenylphosphite in pyridine until complete disappearance of starting diol by LC (total, ~2.5 equivalents diphenylphosphite was need for reaction to go to completion). To the reaction mixture was added DDTT (115 mg, 0.56 mmol) and it was stirred at room temperature for 15 h. The reaction mixture was then concentrated to remove most of the pyridine. The resulting yellow solid was washed with methanol (3×5 mL), stirred and decanted via a fritted Bohdan tube. Celite was added to the filtrate and the suspension was concentrated on a rotary evaporator and kept under Hvac at RT for 1 h. The resulting powder was loaded onto a solid-load cartridge and purified by reverse phase ISCO using a Redisep 50 g C-18 column, eluting with 5-95% MeCN in water containing 0.01 M $NH_4OAc$, with a hold at ~50%. Fractions containing desired product were combined and concentrated under a gentle stream of nitrogen and left under Hvac to afford a diastereomeric mixture Intermediate 7H (46 mg, 0.060 mmol) as a white solid. LCMS: m/z 765 (M+H), $t_R$: 0.82 min, Analytical LCMS method D.

Examples 7-1, 7-2, 7-3 and 7-4

(1R,6S,8R,9R,15R,17R,18S)-8-(6-amino-9H-purin-9-yl)-17-{4-chloro-7H-pyrrolo[2,3-d]pyrimidin-7-yl}-18-fluoro-3,12-dihydroxy-2,4,11,13,16-pentaoxa-3λ$^5$,12λ$^5$-diphosphatricyclo[13.3.0.0$^{6,9}$]octadecane-3,12-dithione

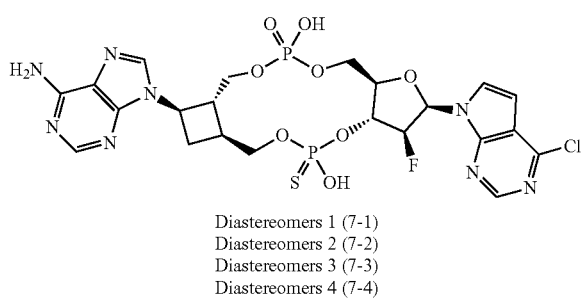 [SMILES: Nc1ncnc2c1ncn2[C@@H]1C[C@@H]2COP(O)(=S)O[C@H]3[C@H](F)[C@H](n4ccc5c(Cl)ncnc54)O[C@@H]3COP(=O)(O)OC[C@H]21]

Diastereomers 1 (7-1)
Diastereomers 2 (7-2)
Diastereomers 3 (7-3)
Diastereomers 4 (7-4)

To a 250 mL RB flask containing the diastereomeric mixture Intermediate 7H (46 mg, 0.060 mmol) was added 30% aq. $NH_4OH$ (10 mL). The flask was capped with a septum, vented with a fine bore needle and heated at 40° C. for 2 h. The reaction mixture was then cooled to room temperature and concentrated under a stream of nitrogen. The residue was dissolved in water (~5 mL) and purified by Preparative HPLC Chromatographic Conditions; Instrument: Waters Autopure; Column: Xselect RP Prep C18 OBD Column, 5 μm, 19×150 mm; Flow rate: 20.0 mL/min; Mobile Phase: A: 100 mM $NH_4OAc$(pH 6.5); B: Acetonitrile (% A=100-% B); 10-21% B over 10 min; 21-95% B over 1 min; hold at 95% B for 1 min; Detection: 260 nm to afford Examples 7-1, 7-2, 7-3 and 7-4 as white solids.

Example 7-1

2.2 mg; Analytical LCMS method D; Observed Mass: 693; $t_R$: 0.44 min.

Example 2-2

4.3 mg; Analytical LCMS method D; Observed Mass: 693; $t_R$: 0.48 min.

Example 7-3

3.2 mg; Analytical LCMS method D; Observed Mass: 693; $t_R$: 0.53 min.

Example 7-4

6.7 mg; Analytical LCMS method D; Observed Mass: 693; $t_R$: 0.58 min.

Examples 8-1, 8-2, 8-3 and 8-4

(1R,6S,8R,9R,15R,17R,18S)-17-{4-amino-7H-pyrrolo[2,3-d]pyrimidin-7-yl}-8-(6-amino-9H-purin-9-yl)-18-fluoro-3,12-dihydroxy-2,4,11,13,16-pentaoxa-3λ$^5$,12λ$^5$-diphosphatricyclo[13.3.0.0$^{6,9}$]octadecane-3,12-dithione

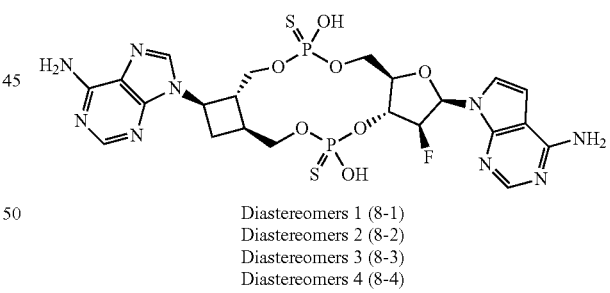

Diastereomers 1 (8-1)
Diastereomers 2 (8-2)
Diastereomers 3 (8-3)
Diastereomers 4 (8-4)

In a separate 2 dram pressure vial containing each diastereomer of Examples 7-1, 7-2, 7-3 and 7-4 was added 28% aqueous ammonium hydroxide (500 uL). The vials were capped with a pressure-safe septum cap and heated at 50° C. for 16 h and then cooled. Products made from diastereomer Examples 7-1, 7-2 and 7-3 were purified by Preparative HPLC Chromatographic Conditions; Instrument: Waters Autopure; Column: Xselect RP Prep C18 OBD Column, 5 μm, 19×150 mm; Flow rate: 20.0 mL/min; Mobile Phase: A: 100 mM $NH_4OAc$(pH 6.5); B: Acetonitrile (% A=100-% B); 10-13.3% B over 6 min; 13.3-95% B over 0.5 min; hold at 95% B for 1.5 min; Detection: 260 nm, to afford Examples 8-1, 8-2 and 8-3, respectively.

Product made from diastereomer Examples 7-4 was purified by Preparative HPLC Chromatographic Conditions; Instrument: Waters Autopure; Column: Xselect RP Prep C18 OBD Column, 5 μm, 19×150 mm; Flow rate: 20.0 mL/min; Mobile Phase: A: 100 mM NH$_4$OAc(pH 6.5); B: Acetonitrile (% A=100–% B); 10-15.5% B over 10 min; 15.5-95% B over 0.5 min; hold at 95% B for 1.5 min; Detection: 260 nm, to afford Examples 8-4.

Example 8-1

2.2 mg; t$_R$: 6.33 min; M+1 obs=674.2; Analytical HPLC Chromatographic Conditions 2

Example 8-2

4.3 mg; t$_R$: 6.58 min; M+1 obs=674.2; Analytical HPLC Chromatographic Conditions 2

Example 8-3

3.2 mg; t$_R$: 6.65 min; M+1 obs=674.2; Analytical HPLC Chromatographic Conditions 2

Example 8-4

6.7 mg; t$_R$: 8.67 min; M+1 obs=674.2; Analytical HPLC Chromatographic Conditions 2

Analytical HPLC Chromatographic Conditions 2:

Instrument: Agilent 1290 (LVL-L4021 Lab); Column: Xselect CSH C18 Column, 3.5 μm, 3.0×150 mm; Flow rate: 0.5 mL/min; Mobile Phase: A: 20 mM NH$_4$OA (pH 6.5); B: ACN (% A=100–% B); Gradient: 5-30% B over 20 min; 95% B for 1 min. Detection: 260 nm.

Examples 9-1, 9-2, 9-3 and 9-4

1-[(1R,6S,8R,9R,15R,17R,18R)-8-(6-amino-9H-purin-9-yl)-18-fluoro-3,12-dihydroxy-3,12-disulfanylidene-2,4,11,13,16-pentaoxa-3λ$^5$,12λ$^5$-diphosphatricyclo[13.3.0.0$^{6,9}$]octadecan-17-yl]-1H,4H,5H-imidazo[2,1-b]purin-4-on

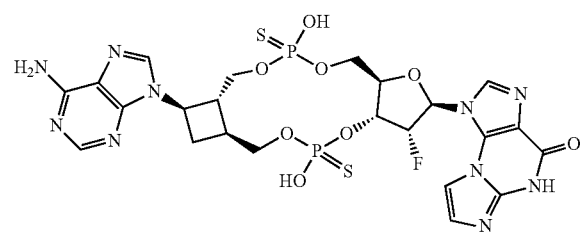

Diastereomers 1 (9-1)
Diastereomers 2 (9-2)
Diastereomers 3 (9-3)
Diastereomers 4 (9-4)

Preparation of Intermediate 9A:

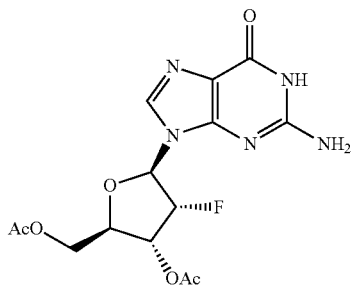

2-Amino-9-((2R,3R,4R,5R)-3-fluoro-4-hydroxy-5-(hydroxymethyl)tetrahydrofuran-2-yl)-1,9-dihydro-6H-purin-6-one (Astatech, 5 g, 17.53 mmol) was dissolved in pyridine (100 mL) and concentrated on a rotary evaporator. This procedure was repeated and the residue was re-dissolved in pyridine (125 mL), and then treated dropwise with acetic anhydride (4.96 mL, 52.6 mmol) and stirred at RT overnight. The reaction mixture was then treated with MeOH (20 mL), stirred for 5 min and then concentrated to dryness. The resulting residue was suspended in water (100 mL), sonicated and stirred until a fine precipitation was formed. The solids were filtered, rinsed with water and diethyl ether and dried to give Intermediate 9A (5 g, 13.54 mmol). $^1$HNMR (400 MHz, DMSO-d$_6$) δ 10.75 (s, 1H), 7.91 (s, 1H), 6.57-6.50 (bm, 2H), 6.16-6.07 (m, 1H), 5.83-5.64 (m, 1H), 5.59-5.49 (m, 1H), 4.41-4.32 (m, 2H), 4.27-4.17 (m, 1H), 2.18-2.12 (m, 3H), 2.09-2.01 (m, 3H); LCMS, [M+H]$^+$=370.

Preparation of Intermediate 9B:

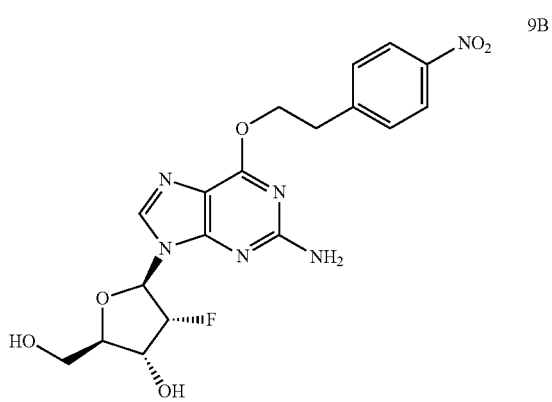 [SMILES: Nc1nc(OCCc2ccc([N+](=O)[O-])cc2)c2ncn([C@@H]3O[C@H](CO)[C@@H](O)[C@H]3F)c2n1]

To a solution of Intermediate 9A (5 g, 13.54 mmol), 2-(4-nitrophenyl)ethan-1-ol (3.39 g, 20.3 mmol) and triphenylphosphine (5.33 g, 20.3 mmol) in 1,4-dioxane (100 mL) was added dropwise DIAD (3.95 mL, 20.3 mmol). The reaction mixture was stirred overnight and then concentrated. The residue was dissolved in a small amount of DCM and charged onto a 120 g ISCO silica gel column and purified using the Teledyne ISCO system, eluting over a 20 min gradient with 5-100% DCM/EtOAc to give product with residual triphenylphospine oxide. The material was dissolved in MeOH (10 mL) and treated with ammonia (7 N in MeOH, 0.293 mL, 13.54 mmol), stirred for 8 h, and then concentrated to ~½ volume. The mixture was then treated with diethyl ether and allowed to stir for 5 h. The precipitated product was filtered and washed with diethyl ether to give Intermediate 9B (4 g, 9.21 mmol), LCMS, [M+H]⁺=435. ¹H NMR (400 MHz, DMSO-d₆) δ 8.22-8.17 (m, 2H), 8.12-8.09 (m, 1H), 7.67-7.61 (m, 2H), 6.60-6.52 (m, 2H), 6.14-6.05 (m, 1H), 5.69-5.64 (m, 1H), 5.40-5.21 (m, 1H), 5.17-5.11 (m, 1H), 4.71-4.64 (m, 2H), 4.46-4.34 (m, 1H), 3.98-3.91 (m, 1H), 3.78-3.70 (m, 1H), 3.64-3.54 (m, 1H), 3.29-3.22 (m, 2H).

Preparation of Intermediate 9C:

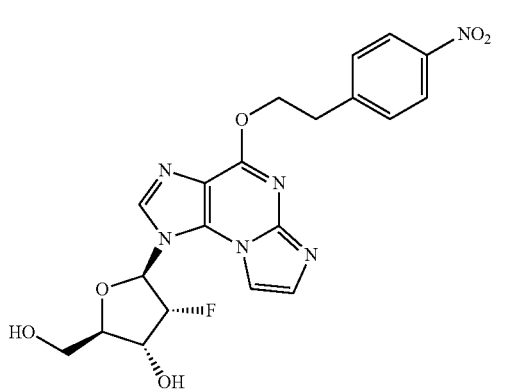

A solution Intermediate 9B (4 g, 9.21 mmol) in EtOH (50 mL) and ammonium acetate buffer (pH 4.5, 50 mL, 9.2 mmol) was treated with 2-bromoacetaldehyde (~1.3 M, in EtOH/1 N HCl 1:1, 29.5 mL, 36.8 mmol). The reaction mixture was stirred at 35° C. for 48 h. The reaction was cooled to RT and then concentrated to ~½ volume and brought to pH ~8 with solid ammonium bicarbonate. The precipitated product was filtered, washed with ice water and diethyl ether to afford Intermediate 9C (2 g, 4.36 mmol), m/z (459, M+H). ¹H NMR (400 MHz, DMSO-d₆) δ 8.39 (s, 1H), 8.22-8.17 (m, 2H), 7.87-7.84 (m, 1H), 7.67 (d, J=8.7 Hz, 2H), 7.52-7.49 (m, 1H), 6.71 (d, J=14.2 Hz, 1H), 5.78 (d, J=6.7 Hz, 1H), 5.64-5.47 (m, 1H), 5.13 (t, J=5.1 Hz, 1H), 4.79 (t, J=6.4 Hz, 2H), 4.46-4.33 (m, 1H), 4.08 (br d, J=7.6 Hz, 1H), 3.80-3.67 (m, 1H), 3.58 (ddd, J=12.5, 5.1, 2.8 Hz, 1H), 3.34 (br m, 2H).

Preparation of Intermediate 9D:

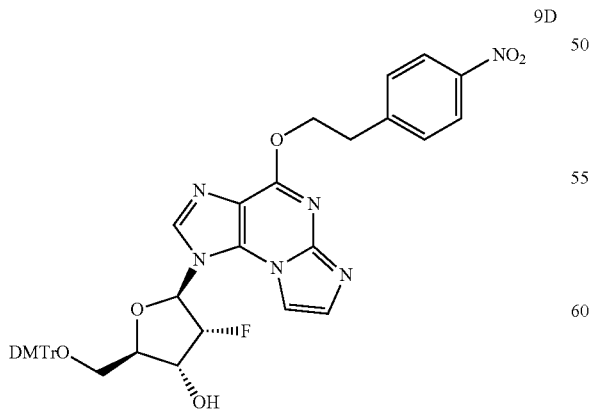

Intermediate 9C (2 g, 4.36 mmol) was dissolved in anhydrous pyridine (25 mL) and concentrated on a rotary evaporator. The procedure was repeated and the residue was then re-dissolved in pyridine (25 mL) under nitrogen and DMTr-Cl (1.478 g, 4.36 mmol) was added in one portion. The reaction mixture was stirred for 22 hours and then treated with methanol (~2 mL) and concentrated in vacuo. The residue was dissolved in DCM (200 mL), washed with water, saturated aq. sodium bicarbonate, dried over sodium sulfate, filtered and concentrated. The crude product was dissolved in a small amount of DCM and charged to 80 g ISCO silica gel column and purified using the Teledyne ISCO system, eluting over 20 minutes, 0-50% gradient; solvent A: DCM with 0.25% TEA; Solvent B: EtOAc. Fractions containing the desired product were combined and concentrated to give Intermediate 9D (2.2 g, 2.89 mmol). LCMS, [M+H]⁺=761.

Preparation of Intermediate 9E:

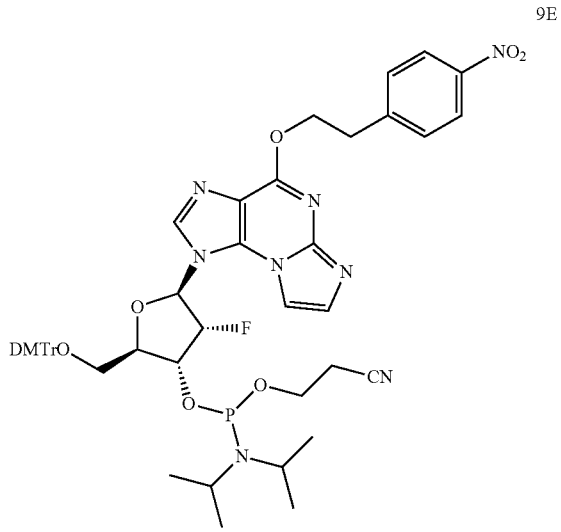

To a solution of Intermediate 9D (0.5 g, 0.657 mmol) and 1H-imidazole-4,5-dicarbonitrile (0.085 g, 0.72 mmol) in DCM (5 mL) was added 3-((bis(diisopropylamino)phosphanyl)oxy) propanenitrile (0.43 mL, 1.31 mmol). The reaction mixture was stirred overnight, then quenched with saturated aq. sodium bicarbonate (10 mL) and diluted with DCM (50 mL). The organic layer was dried (Na₂SO₄), filtered and concentrated. The crude product was dissolved in a small amount of DCM, charged onto a 24 g ISCO silica gel column and purified using the Teledyne ISCO system, eluting over a 10 minutes, 0-50% gradient; Solvent A: DCM with 0.25% TEA; Solvent B: EtOAc to give Intermediate 9D (625 mg, 0.65 mmol) as a mixture of diastereomers.

Preparation of Intermediate 9F:

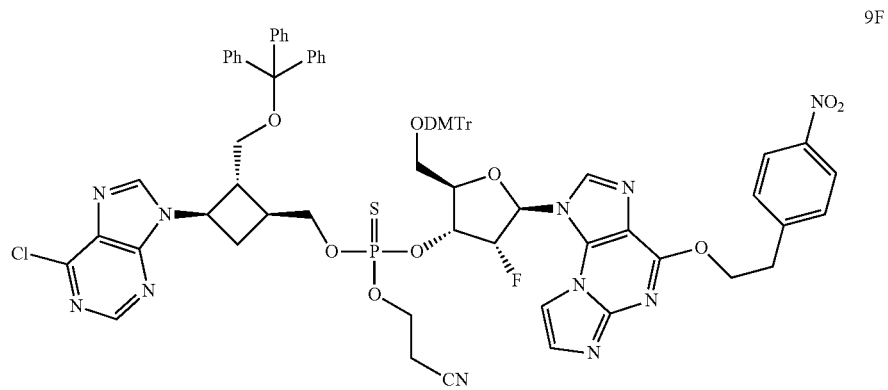

9F

A solution of Intermediate 2F (0.26 g, 0.509 mmol) and 1H-tetrazole (0.043 g, 0.611 mmol) in anhydrous acetonitrile (5 mL) was concentrated on a rotary evaporator and then the residue was dissolved in anhydrous acetonitrile (2.5 mL). Intermediate 9E (0.54 g, 0.56 mmol) in anhydrous acetonitrile (2.5 mL) was azeotroped, and then dissolved in acetonitrile (1 mL) and added dropwise to the stirred mixture from above.

The reaction mixture was stirred under nitrogen at room temperature for 16 h. (E)-N,N-dimethyl-N'-(3-thioxo-3H-1,2,4-dithiazol-5-yl)formimidamide (0.125 g, 0.61 mmol) was then added and the reaction was stirred at room temperature for 2 h. The reaction mixture was then concentrated in vacuo and the residue was purified by flash chromatography over 12 g of silica gel (15 min gradient, with 0-100% DCM/EtOAc) to afford Intermediate 9F (0.3 g, 0.273 mmol) as an oil. LCMS, [M+H]$^+$=1402/1403.

Preparation of Intermediate 9G:

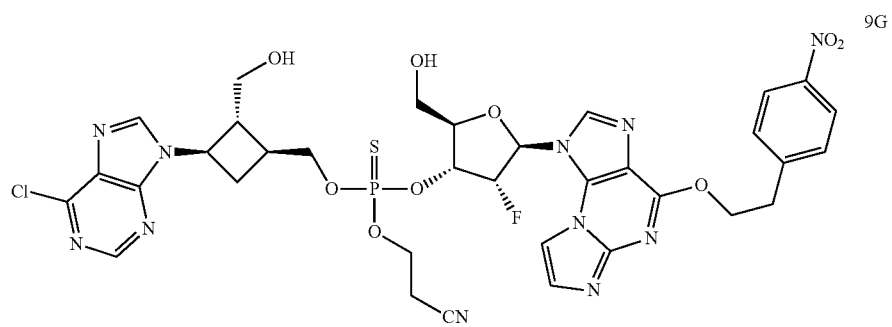 [SMILES: N#CCCOP(=S)(OC[C@H]1C[C@@H](n2cnc3c(Cl)ncnc32)[C@@H]1CO)O[C@H]1[C@@H](F)[C@H](n2cnc3c(OCCc4ccc([N+](=O)[O-])cc4)nc4nccn4c32)O[C@@H]1CO]

9G

To a solution of Intermediate 9F (0.28 g, 0.20 mmol) in DCM (2 mL) was added triethylsilane (0.32 mL, 1.99 mmol) and TFA (0.05 ml, 0.6 mmol) at room temperature. The reaction mixture was stirred for 2 h. and then quenched with 50% aqueous sodium bicarbonate. The organic layer was separated and the aqueous layer extracted with THF (2×5 mL). The organic layers were combined, dried over sodium sulfate, filtered and concentrated in vacuo. The crude material was triturated with diethyl ether (3×10 mL) to form a precipitate that was filtered and dried to afford Intermediate 9G (0.250 g, 0.29 mmol) as an off-white solid. LCMS, [M+H]$^+$=858.

Preparation of Intermediate 9H:

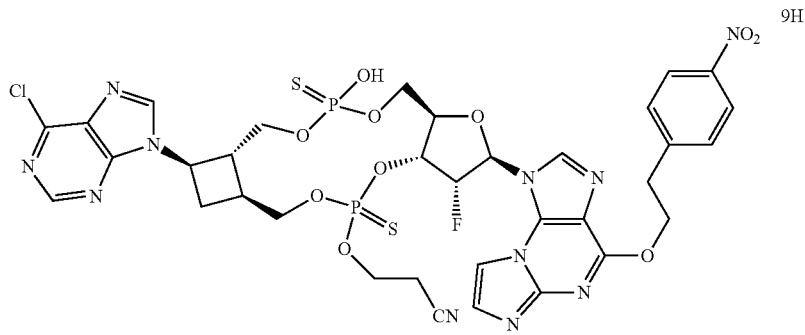 [SMILES: N#CCCOP1(=S)OC[C@H]2C[C@@H](n3cnc4c(Cl)ncnc43)[C@@H]2COP(O)(=S)OC[C@H]2O[C@@H](n3cnc4c(OCCc5ccc([N+](=O)[O-])cc5)nc5nccn5c43)[C@H](F)[C@@H]2O1]

To a solution of Intermediate 9G (0.25 g, 0.29 mmol) in dry pyridine (47.7 mL) was added dropwise a solution of diphenyl phosphite (0.09 ml, 0.47 mmol) in pyridine (5.3 mL) over a period of 4 hours. The reaction was stirred under nitrogen for 16 h., and then DDTT (0.120 g, 0.583 mmol) was added and the mixture was stirred at room temperature for 2 h. The reaction mixture was then concentrated in vacuo and the crude material was purified by reverse phase ISCO over 50 g of C18 with 0-100%, over 15 min gradient, Mobile Phase A: 5:95 acetonitrile:water with 0.01M ammonium acetate; Mobile Phase B: 95:5 acetonitrile:water with 0.01M ammonium acetate, to give a mixture of diastereomers of Intermediate 9H (0.168 g, 0.179 mmol) as a solid after lyophilization. LCMS, $[M+H]^+=936$ Preparation of Intermediate 9I:

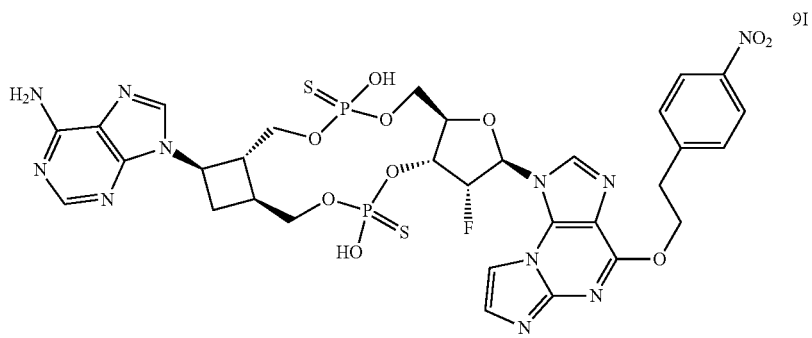 [SMILES: Nc1ncnc2c1ncn2[C@@H]1C[C@@H]2COP(O)(=S)O[C@H]3[C@@H](F)[C@H](n4cnc5c(OCCc6ccc([N+](=O)[O-])cc6)nc6nccn6c54)O[C@@H]3COP(O)(=S)OC[C@H]21]

A mixture of Intermediate 9H (0.168 g, 0.179 mmol) and ammonia (2 M in isopropy alcohol, 5 ml, 10.00 mmol) was stirred at 50° C. for 8 h. The solvent was then reduced under a gentle stream of nitrogen and the residue was dissolved in ammonium hydroxide (2 mL, 51.4 mmol) and heated at 50° C. for 3 h. The reaction mixture was reduced with a gentle stream of nitrogen and lyophilized overnight to afford diastereomeric mixtures of Intermediate 9I (0.155 g, 0.179 mmol) as a solid.

Examples 9-1, 9-2, 9-3 and 9-4

1-[(1R,6S,8R,9R,15R,17R,18R)-8-(6-amino-9H-purin-9-yl)-18-fluoro-3,12-dihydroxy-3,12-disulfanylidene-2,4,11,13,16-pentaoxa-3λ⁵,12λ⁵-diphosphatricyclo[13.3.0.0⁶,⁹]octadecan-17-yl]-1H,4H,5H-imidazo[2,1-b]purin-4-on

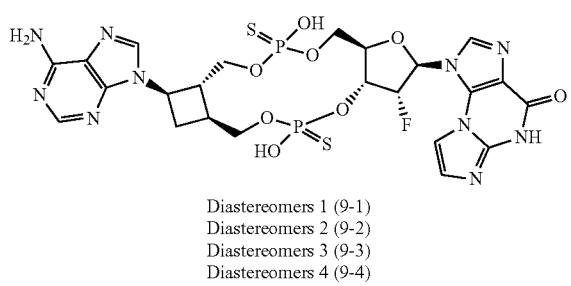 [SMILES: Nc1ncnc2c1ncn2[C@@H]1C[C@@H]2COP(O)(=S)O[C@H]3[C@@H](F)[C@H](n4cnc5c(=O)[nH]c6nccn6c54)O[C@@H]3COP(O)(=S)OC[C@H]21]

Diastereomers 1 (9-1)
Diastereomers 2 (9-2)
Diastereomers 3 (9-3)
Diastereomers 4 (9-4)

A mixture of Intermediate 9I (0.155 g, 0.179 mmol) and DBU (0.27 mL, 1.795 mmol) in pyridine (1.8 mL) was stirred at RT for 1 h. Ammonium acetate/AcOH buffer (pH 4.5, 2 mL) was added and the reaction mixture was concentrated in vacuo. The residue was purified by reverse phase ISCO over 50 g of C18 with 0-100%, over 15 min gradient, Mobile Phase A: 5:95 acetonitrile:water with 0.01M ammonium acetate; Mobile Phase B: 95:5 acetonitrile:water with 0.01M ammonium acetate to give a mixture of diastereomers (0.08 g, 0.112 mmol) after lyophilization. Diastereomers were separated by Preparative HPLC Chromatographic Conditions: Instrument: Waters Autopure Column: Xselect RP Prep C18 OBD Column, 5 µm, 19×150 mm; Flow rate: 20.0 mL/min; Mobile Phase: A: 20 mM TEAA (pH 6.5); B: 80:20 ACN:20 mM TEAA (pH6.5); Gradient; 7-14% B over 14 min, 14-95% B over 0.5 min, 95% B hold over 0.5 min and 95-5% B over 0.5 min. to afford Examples 9-1, 9-2, 9-3 and 9-4 as white solids after lyophilization.

Example 9-1

5.0 mg; $t_R$: 0.36 min; M+1 obs=714.9; Analytical LCMS method A

Example 9-2

3.1 mg; $t_R$: 0.39 min; M+1 obs=715.0; Analytical LCMS method A

Example 9-3

6.3 mg; $t_R$: 0.41 min; M+1 obs=715.4; Analytical LCMS method A

Example 9-4

1.8 mg; $t_R$: 0.46 min; M+1 obs=715.1; Analytical LCMS method A

Examples 10

(1R,6S,8R,9R,15R,17R,18R)-8,17-bis(6-amino-9H-purin-9-yl)-18-fluoro-3,12-dihydroxy-2,4,11,13,16-pentaoxa-3λ⁵,12λ⁵-diphosphatricyclo[13.3.0.0⁶,⁹]octadecane-3,12-dione

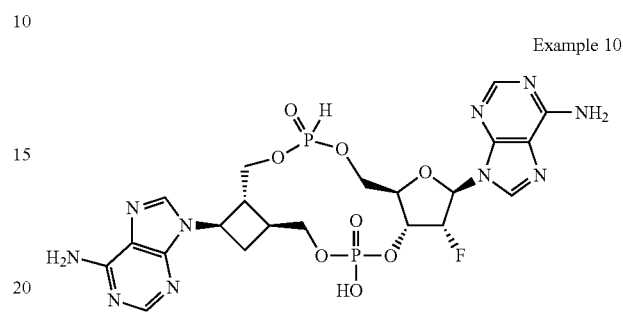

Example 10

Preparation of Intermediate 10A:

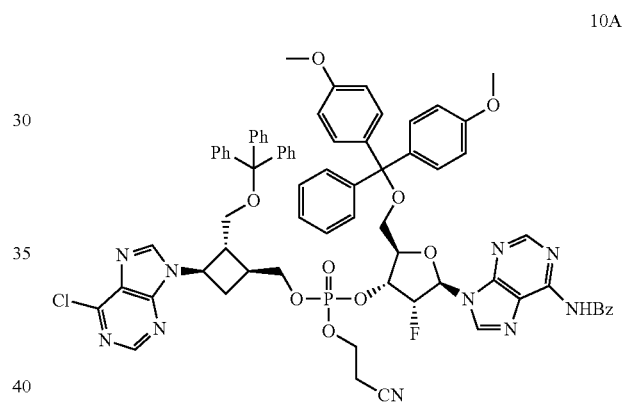

10A

A solution of Intermediate 2F (0.100 g, 0.20 mmol) and 1H-tetrazole (0.016 g, 0.24 mmol) in anhydrous MeCN (1 mL) was concentrated on a rotary evaporator and the resulting residue was dissolved in anhydrous MeCN (1 mL). A solution of (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (Sigma-Aldrich, 0.19 g, 0.22 mmol) in anhydrous MeCN (2.5 mL) was concentrated on a rotary evaporator, re-dissolved in MeCN (1 mL) and added dropwise to the stirred mixture from above at RT. The reaction mixture was stirred under nitrogen at RT for 16 h. tert-Butyl hydroperoxide (0.089 mL, 0.49 mmol) was added and the reaction mixture was stirred at room temperature for 2 h. The reaction was then quenched with saturated aqueous potassium thiosulfate and stirred for 20 min. The mixture was extracted with EtOAc, dried over sodium sulfate, filtered and concentrated in vacuo. The crude material was purified by flash chromatography over 12 g of silica gel (15 min gradient, with 0-100% DCM/EtOAc) to afford Intermediate 10A (0.22 g, 0.169 mmol) as a white solid. LCMS, [M+H]⁺=1301.

Preparation of Intermediate 10B:

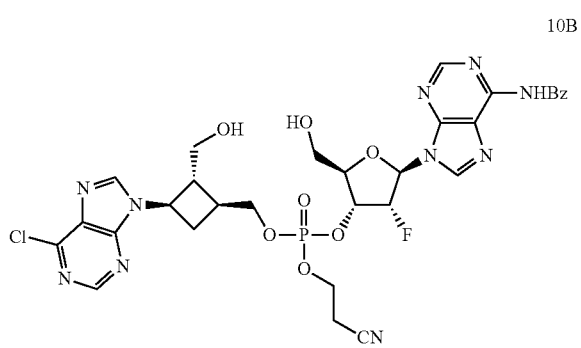

10B

To a solution of Intermediate 10A (0.22 g, 0.17 mmol) and triethylsilane (0.27 mL, 1.69 mmol) in DCM (1.69 mL) was added TFA (0.04 mL, 0.51 mmol) at room temperature. The reaction mixture was stirred at RT for 2 h, diluted with DCM (5 mL), water (5 mL) and treated with saturated sodium bicarbonate until evolution of gas ceased. The mixture was stirred for 30 minutes, and the organic layer was separated and the aqueous layer was extracted with DCM (2×5 mL). The organic layers were combined, dried over sodium sulfate, filtered and concentrated in vacuo. The residue was triturated with diethyl ether (3×10 mL) then with hexanes (2×10 mL) to afford Intermediate 10B (0.089 g, 0.118 mmol) as a white solid. LCMS, [M+H]$^+$=757.4

Preparation of Intermediate 10C:

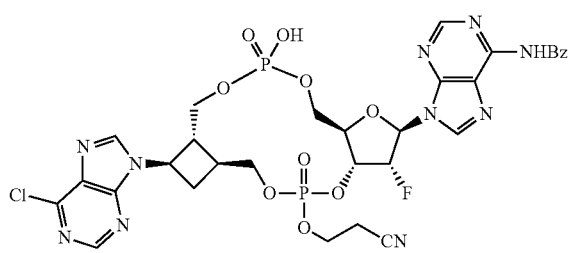

10C

To a solution of Intermediate 10B (0.09 g, 0.11 mmol) in dry pyridine (20 mL) was added dropwise a solution of diphenyl phosphite (0.04 mL, 0.18 mmol) in pyridine (2.2 mL) over 4 hours. The reaction mixture was stirred under nitrogen for 16 h, and then water (0.04 mL, 2.25 mmol) was added, followed by iodine (0.043 g, 0.17 mmol) and the mixture was stirred at RT for 15 min. The reaction was quenched with saturated sodium thiosulfate until the color disappeared and the mixture was then concentrated in vacuo. The residue was triturated three times with 10:1 diethyl ether:acetonitrile to give Intermediate 10C (0.05 g, 0.061 mmol) as a yellow solid. LCMS, [M+H]$^+$=819

Examples 10

(1R,6S,8R,9R,15R,17R,18R)-8,17-bis(6-amino-9H-purin-9-yl)-18-fluoro-3,12-dihydroxy-2,4,11,13,16-pentaoxa-3λ$^5$,12λ$^5$-diphosphatricyclo[13.3.0.0$^{6,9}$]octadecane-3,12-dione

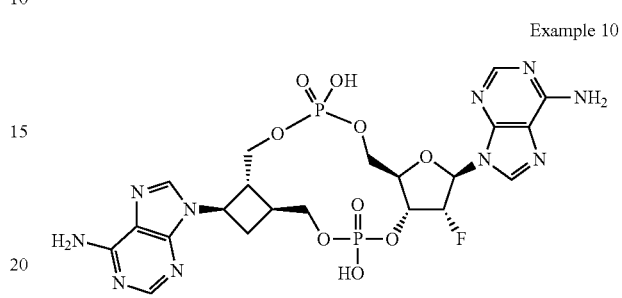

Example 10

A mixture of Intermediate 10C (0.05 g, 0.061 mmol) and ammonia (2 M in isopropanol, 6.10 mL, 12.21 mmol) was stirred at 50° C. for 8 h. The product was isolated by preparative LC/MS with the following conditions: Column: Agilent Bonus RP 21.2×100 mm, 5-μm particles; Mobile Phase A: water with 20-mM ammonium acetate; Mobile Phase B: acetonitrile; Gradient: 0% B hold 0-6 minute. 0%-25% B over 16 minutes, then a 4-minute hold at 100% B; Flow: 20 mL/min. Fractions containing the desired product were combined and dried via centrifugal evaporation to afford Examples 10 (9.2 mg); Observed Mass: 643.1; Retention Time: 2.14 min.

Analytical LCMS Method B.

Examples 11-1, 11-2, 11-3, 11-4

1-[(1S,6S,8R,9R,15R,17R,18R)-8-(6-amino-9H-purin-9-yl)-18-fluoro-3,12-dihydroxy-3,12-disulfa-nylidene-2,4,11,13,16-pentaoxa-3λ$^5$,12λ$^5$-diphos-phatricyclo[13.2.1.0$^{6,9}$]octadecan-17-yl]-1H-1,2,3-benzotriazole-4-carboxamide

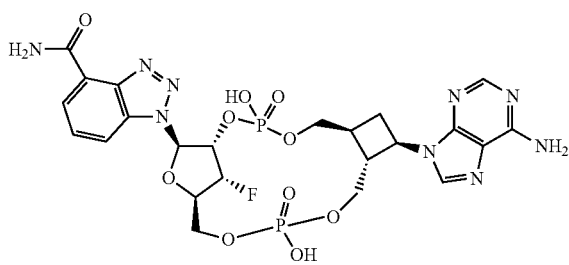

Diastereomers 1 (11-1)
Diastereomers 2 (11-2)
Diastereomers 3 (11-3)
Diastereomers 4 (11-4)

Preparation of Intermediate 11A:

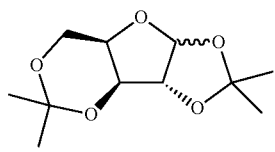

11A

To a dark brown solution of iodine (1.69 g, 6.7 mmol) in acetone (250 mL) was added D-(+)-xylose (10.0 g, 66.6 mmol) as a solid. The resulting heterogeneous mixture was stirred at room temperature. After 2.5 hours, a second portion of iodine (1.30 g, 5.13 mmol) in acetone (150 mL) was added to the reaction mixture. After 4.5 hours, the reaction was quenched with 10% aqueous sodium thiosulfate (200 mL), resulting in a colorless mixture, which was concentrated in vacuo. The aqueous phase was then extracted with DCM (4×100 mL) and the combined organic layers were dried over sodium sulfate, filtered, and concentrated in vacuo to afford Intermediate 11A (13.03 g, 56.6 mmol) as a clear, colorless oil. $^1$H NMR (500 MHz, CHLOROFORM-d) δ 6.01 (d, J=3.7 Hz, 1H), 4.52 (d, J=3.7 Hz, 1H), 4.29 (d, J=2.1 Hz, 1H), 4.14-4.04 (m, 2H), 4.04-4.01 (m, 1H), 1.49 (s, 3H), 1.44 (s, 3H), 1.39 (s, 3H), 1.33 (s, 3H).

Preparation of Intermediate 11B:

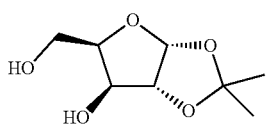

11B

To a stirred solution of Intermediate 11A (4.61 g, 20.0 mmol) in acetonitrile (17.4 mL) and water (18.5 mL) was added CAN (0.33 g, 0.60 mmol) as a solid. The resulting mixture was stirred at room temperature. After 6 hours, the reaction was quenched with ammonium hydroxide (1.4 mL, 10.00 mmol) and the resulting suspension was filtered over a pad of Celigel (9:1 w/w Celite/silica gel), rinsing with MeOH (3×10 mL). The filtrate was concentrated in vacuo and the residue was co-evaporated with MeOH several times then dried overnight under high vacuum to afford Intermediate 11B (3.83 g, 20.14 mmol) as a clear yellow oil. $^1$H NMR (499 MHz, CHLOROFORM-d) δ 5.99 (d, J=3.7 Hz, 1H), 4.53 (d, J=3.7 Hz, 1H), 4.33 (d, J=2.7 Hz, 1H), 4.20-4.11 (m, 2H), 4.08-4.03 (m, 1H), 3.86 (br s, 1H), 2.51 (br s, 1H), 1.49 (s, 3H), 1.33 (s, 3H).

Preparation of Intermediate 11C:

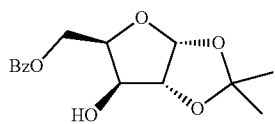

11C

To a cooled (0° C.) suspension of Intermediate 11B (3.80 g, 20.0 mmol) in CH$_2$Cl$_2$ (32 mL) and pyridine (8 mL) under a nitrogen atmosphere was added a solution of benzoyl chloride (2.3 mL, 20.0 mmol) in CH$_2$Cl$_2$ (3 mL) via addition funnel over 2 hours. The reaction was allowed to stir overnight at room temperature. The reaction was cooled again to 0° C. and another portion of benzoyl chloride (0.46 ml, 4.0 mmol) in CH$_2$Cl$_2$ (0.60 mL) was added via addition funnel over 40 min. The mixture was stirred at 0° C. for another hour, then the reaction was quenched with H$_2$O (10 mL) and concentrated in vacuo. The residue was partitioned between CH$_2$Cl$_2$ (100 mL) and water (50 mL). The organic phase was washed with saturated aq. sodium bicarbonate (50 mL) and water (3×50 mL), dried over sodium sulfate, filtered, and concentrated in vacuo. Residual pyridine was removed by co-evaporating a few times with toluene to afford Intermediate 11C (5.46 g, 18.55 mmol) as a clear yellow oil. LCMS, [M+H]$^+$=295.

Preparation of Intermediate 11D:

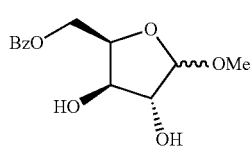

11D

To a solution of Intermediate 11C (10.6 g, 35.8 mmol) in MeOH (90 mL) was added iodine (0.90 g, 3.6 mmol) as a solid. The resulting mixture was stirred at reflux for 2 h., then allowed to stir at room temperature over the weekend. The reaction was quenched with 10% aqueous sodium thiosulfate (100 mL), resulting in a colorless mixture, which was concentrated in vacuo to remove methanol and then extracted with CH$_2$Cl$_2$ (3×100 mL). The combined organic layers were washed with brine (200 mL), dried (Na$_2$SO$_4$), filtered and concentrated in vacuo. The crude product was dissolved in a small amount of CH$_2$Cl$_2$, adsorbed onto a plug of SiO$_2$, and purified by flash chromatography (SiO$_2$, 0-10% MeOH in CH$_2$Cl$_2$, 120 g column, 27.1 min gradient) to afford Intermediate 11D (7.64 g, 28.5 mmol) as a clear colorless oil.

Preparation of Intermediate 11E:

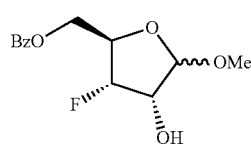

11E

A solution of Intermediate 11D (7.64 g, 28.5 mmol) in CH$_2$Cl$_2$ (142 mL) was treated with DAST (18.81 mL, 142 mmol) via syringe. The resulting mixture was stirred at room temperature under a nitrogen atmosphere. After 8 hours, the reaction was cooled to 0° C. and carefully poured into a large beaker containing a 2:1 mixture of saturated aqueous NaHCO$_3$ and ice (600 mL). Solid NaHCO$_3$ was added to the mixture in small amounts until the pH was ~8-9. The layers were then separated and the aqueous phase was extracted with CH$_2$Cl$_2$ (3×200 mL). The combined organic layers were dried (Na$_2$SO$_4$), filtered and concentrated in vacuo. The crude product was dissolved in a small amount of CH$_2$Cl$_2$, adsorbed onto a plug of SiO$_2$ and purified by flash chromatography (SiO$_2$, 0-75% EtOAc in hexanes, 220 g column, 26.7 min gradient) to afford Intermediate 11E (4.14 g, 15.32 mmol) as a clear colorless oil.

Preparation of Intermediate 11F:

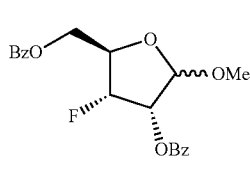

11F

To a solution of Intermediate 11E (4.14 g, 15.32 mmol) in pyridine (30.6 mL) was added benzoyl chloride (2.67 ml, 22.98 mmol) dropwise via syringe. The reaction was stirred at room temperature under a nitrogen atmosphere. After 16 hours, the reaction was poured into saturated aqueous sodium bicarbonate (150 mL) at 0° C. and extracted with Et$_2$O (3×150 mL). The combined organic layers were washed with 1 M aq. HCl (2×100 mL), water (100 mL), brine (100 mL), dried (MgSO$_4$), filtered and concentrated in vacuo. The residue was co-evaporated twice with toluene and dried under high vacuum. The crude product was dissolved in a small amount of CH$_2$Cl$_2$, adsorbed onto a plug of SiO$_2$ and purified by flash chromatography (SiO$_2$, 0-50% EtOAc in hexanes, 120 g column, 27.1 min gradient) to afford the β-anomer: (3.34 g, 8.92 mmol) $^1$H NMR (500 MHz, CHLOROFORM-d) δ 8.12-8.07 (m, 4H), 7.63-7.56 (m, 2H), 7.50-7.44 (m, 4H), 5.45 (td, J=4.9, 1.7 Hz, 1H), 5.44 (dt, J=53.1, 4.9 Hz, 1H), 5.14 (t, J=1.6 Hz, 1H), 4.71-4.64 (m, 1H), 4.63-4.58 (m, 1H), 4.49 (dd, J=11.7, 4.7 Hz, 1H), 3.40 (s, 3H) as a clear colorless oil and the α-anomer: (1.66 g, 4.43 mmol). $^1$H NMR (500 MHz, CHLOROFORM-d) δ 8.15-8.11 (m, 2H), 8.08-8.03 (m, 2H), 7.63-7.57 (m, 2H), 7.51-7.44 (m, 4H), 5.32 (d, J=4.4 Hz, 1H), 5.27 (ddd, J=55.8, 5.8, 1.8 Hz, 1H), 5.12 (ddd, J=22.6, 5.8, 4.6 Hz, 1H), 4.70 (dtd, J=25.8, 3.7, 1.8 Hz, 1H), 4.60 (dd, J=11.9, 4.0 Hz, 1H), 4.53 (dd, J=12.1, 3.7 Hz, 1H), 3.51 (s, 3H) as a clear colorless oil. (Combined anomeric mixtures, Intermediate 11F)

Preparation of Intermediate 11G:

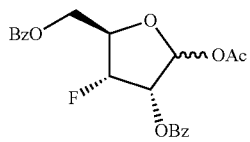

11G

To a solution of anomeric mixtures of Intermediate 11F (5.00 g, 13.36 mmol) in acetic acid (40.0 mL) was added acetic anhydride (4.79 mL, 50.8 mmol) followed by sulfuric acid (2.78 mL, 52.1 mmol). The resulting clear yellow solution was stirred at room temperature. After 4.5 hours, the reaction was carefully poured into a large beaker containing a stirred 2:1 (v/v) mixture of saturated aqueous NaHCO$_3$ and ice (600 mL). Solid NaHCO$_3$ was added until the pH was ~7-8 and the resulting mixture was extracted with CH$_2$Cl$_2$ (4×200 mL), washed with water (300 mL), brine (300 mL), dried over sodium sulfate, filtered and concentrated in vacuo. The crude product was dissolved in a small amount of CH$_2$Cl$_2$, adsorbed onto a plug of SiO$_2$ and purified by flash chromatography (SiO$_2$, 0-50% EtOAc in hexanes, 120 g column, 27.1 min gradient) to afford Intermediate 11G (4.43 g, 11.01 mmol) as a clear colorless oil.

Preparation of Intermediate 11H:

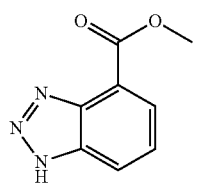

11H

To a solution of methyl 2,3-diaminobenzoate (Combi-block, 10 g, 60.2 mmol) in AcOH (250 mL) was added sodium nitrite (4.15 g, 60.2 mmol) in small portions over 40 minutes and the reaction was stirred overnight at RT. To the reaction mixture was added water (200 mL) and the product precipitated as a solid. The solid was filtered, washed with water (3×20 mL) and dried under vacuum to afford Intermediate 11H (8.0 g). The filtrate was concentrated with silica (10 g) and then purified on a silica gel column (0-10% MeOH in DCM, 24 g column, 18 min gradient, to give additional product (1.96 g); total recovery of Intermediate 11H (9.96 g, 56.2 mmol). $^1$H NMR (499 MHz, CHLOROFORM-d) δ 8.38 (d, J=8.4 Hz, 1H), 8.21 (d, J=7.3 Hz, 1H), 7.51 (t, J=7.9 Hz, 1H), 4.11 (s, 3H).

Preparation of Intermediate 11I:

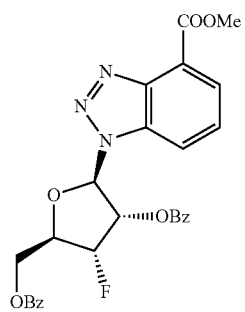

11I

To a suspension of Intermediate 11H (2 g, 11.29 mmol) and Intermediate 11G (4.54 g, 11.29 mmol) in anhydrous CH$_3$CN (30 mL) at RT was added dropwise tin(IV) chloride (1.33 mL, 11.29 mmol). The reaction mixture was stirred for 5 h at RT, then made basic with sat'd aq. sodium bicarbonate and extracted with EtOAc (3×50 mL). The organic layers were combined, washed with water, brine, dried over Na$_2$SO$_4$, filtered and concentrated in vacuo. The residue was purified on an ISCO column (80 g, 0-60% EtOAc in Hexane) to give Intermediate 11I (5.5 g, 9.53 mmol). LCMS, [M+H]$^+$=520. $^1$H NMR (499 MHz, CHLOROFORM-d) δ 8.12 (dd, J=7.4, 0.8 Hz, 1H), 8.10-8.05 (m, 2H), 8.02-7.96 (m, 2H), 7.91 (dd, J=8.3, 1.0 Hz, 1H), 7.63-7.60 (m, 1H), 7.55-7.43 (m, 6H), 6.75 (dd, J=4.9, 1.1 Hz, 1H), 6.54-6.38 (m, 1H), 6.01-5.76 (m, 1H), 5.06-4.86 (m, 1H), 4.73 (dd, J=12.4, 3.8 Hz, 1H), 4.58 (dd, J=12.4, 3.9 Hz, 1H), 4.11 (s, 3H).

Preparation of Intermediate 11J:

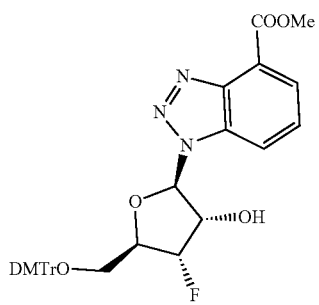

To a solution of Intermediate 11I (5.5 g, 10.6 mmol) in anhydrous MeOH (30 mL) was added sodium methanolate (4.23 ml, 2.117 mmol) and the reaction mixture was stirred at RT for 2 h. To the reaction was added DOEW 200 H+ resin (2 g). The mixture was stirred for 20 minutes, filtered and then the filtrate was concentrated to dryness. The residue was co-evaporated on a rotary evaporator with pyridine (5 mL). The residue was dissolved in pyridine (20 mL) and DMTr-Cl (3.95 g, 11.65 mmol) was added. After stirring the reaction mixture at RT for 5 hours, MeOH (5 mL) was added and the mixture was stirred at RT for 10 min. The reaction mixture was then concentrated in vacuo and the residue was purified on a silica gel column (80 g), 33 min gradient 0-60% EtOAc in Hex to give Intermediate 11J (4.7 g, 7.66 mmol). LCMS, $[M+H]^+=614$. $^1$H NMR (499 MHz, CHLOROFORM-d) δ 8.12 (dd, J=7.3, 0.9 Hz, 1H), 8.00 (dd, J=8.3, 0.8 Hz, 1H), 7.75-7.67 (m, 1H), 77.37-7.30 (m, 4H), 7.25-7.19 (m, 5H), 6.76 (d, J=8.8 Hz, 4H), 6.38 (dd, J=6.0, 0.8 Hz, 1H), 5.57-5.44 (m, 1H), 5.43-5.27 (m, 1H), 4.69-4.51 (m, 1H), 4.13 (s, 3H), 3.79 (d, J=1.1 Hz, 6H), 3.45 (dd, J=10.7, 3.9 Hz, 1H), 3.31 (dd, J=10.7, 4.1 Hz, 1H), 2.96 (br d, J=3.9 Hz, 1H))

Preparation of Intermediate 11H:

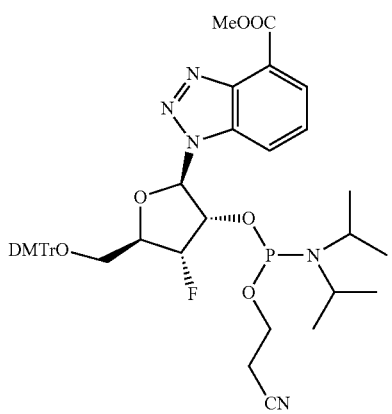

To a solution of Intermediate 11J (3.2 g, 5.21 mmol) in anhydrous DCM (50 mL) was added 1H-imidazole-4,5-dicarbonitrile (1.0 M in acetonitrile, 3.65 mL, 3.65 mmol), followed by the dropwise addition of 3-((bis(diisopropylamino)phosphanyl) oxy)propanenitrile (1.886 g, 6.26 mmol) and the reaction was stirred at RT for 16 h. The reaction mixture was then diluted with DCM, washed with saturated aq. NaHCO₃, and dried over MgSO₄, and TEA (1 mL) was added. The mixture was filtered and the filtrate was concentrated in vacuo. The residue was purified by silica gel chromatography (40 g column, 0-60% gradient eluted with EtOAc in hexane with 0.5% v/v triethylamine, over 21 minutes) to afford Intermediate 11K (3.98 g, 4.89 mmol).

Preparation of Intermediate 11L:

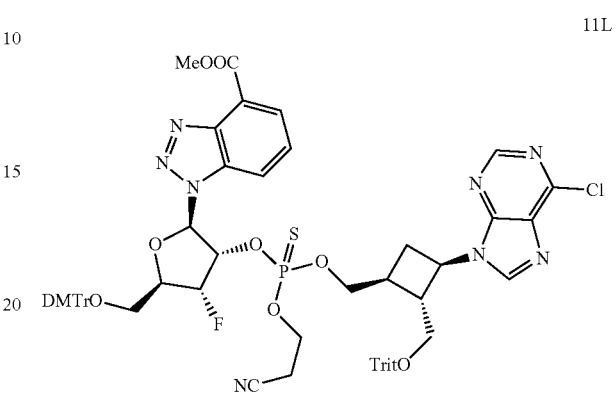

Intermediate 11L was prepared from 1H-tetrazole (54.8 mg, 0.78 mmol), Intermediate 2F (200 mg, 0.391 mmol), Intermediate 11K (350 mg, 0.431 mmol) and DDTT (88 mg, 0.431 mmol) following the procedure described for Intermediate 7F. The crude product was purified on silica gel (4 g column, eluted with 0-50% gradient EtOAc in Hexanes over 15 minutes) to give Intermediate 1L (350 mg, 0.279 mmol).

Preparation of Intermediate 11M:

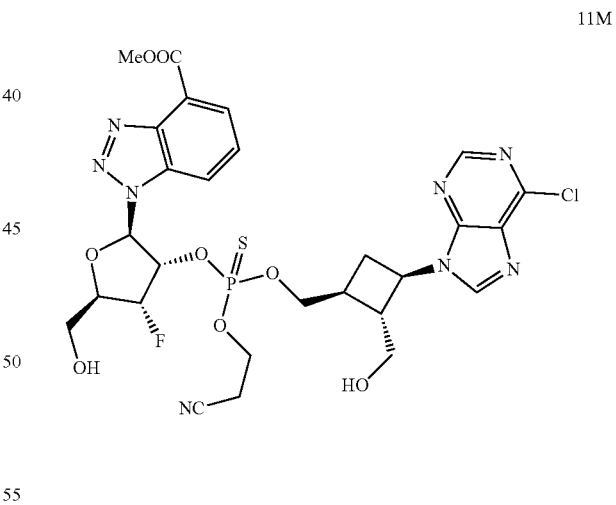

Intermediate 11L (350 mg, 0.279 mmol) was dissolved in dichloromethane (10 mL), and triethylsilane (445 µl, 2.79 mmol) and 2,2-dichloroacetic acid (230 µl, 2.79 mmol) were added. The reaction was stirred for three hours at RT. The reaction mixture was then diluted with DCM (30 mL), washed with saturated aq. NaHCO₃, dried over Na₂SO₄, was filtered and concentrated in vacuo. The residue was purified on a silica gel column (12 g, eluted with 0-20% MeOH in DCM) to give Intermediate 11M (153 mg, 0.215 mmol). LCMS, $[M+H]^+=711$.

Preparation of Intermediate 11N:

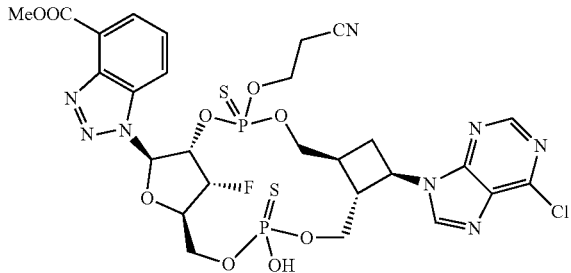

11N

Intermediate 11M (153 mg, 0.215 mmol) was azeotroped with pyridine (2 mL), and the residue was redissolved in pyridine (10 mL) and to the solution was added diphenyl phosphonate (83 µL, 0.43 mmol) dropwise over 20 minutes. (E)-N,N-dimethyl-N'-(3-thioxo-3H-1,2,4-dithiazol-5-yl) formimidamide (133 mg, 0.646 mmol) was then added and the reaction mixture was stirred at room temperature for 16 hours and then concentrated in vacuo. The residue was suspended in methanol to form a yellow precipitate that was filtered and the filtrate was concentrated in vacuo. The resulting residue was taken in DCM and co-evaporated with celite (5 g), loaded onto a column and purified on a reverse phase ISCO Gold 50 g C18 column, Mobile Phase A: 5:95 acetonitrile:water with 0.01M ammonium acetate; Mobile Phase B: 95:5 acetonitrile:water with 0.01M ammonium acetate; Gradient: 0-50% B over 14, hold at 50% gradient for 5 min. to give a mixture of four diastereomers of Intermediate 11N (80 mg, 0.101 mmol). LCMS, $[M+H]^+=789$.

Example 11

1-[(1S,6S,8R,9R,15R,17R,18R)-8-(6-amino-9H-purin-9-yl)-18-fluoro-3,12-dihydroxy-3,12-disulfanylidene-2,4,11,13,16-pentaoxa-3$\lambda^5$,12$\lambda^5$-diphosphatricyclo[13.2.1.0$^{6,9}$]octadecan-17-yl]-1H-1,2,3-benzotriazole-4-carboxamide

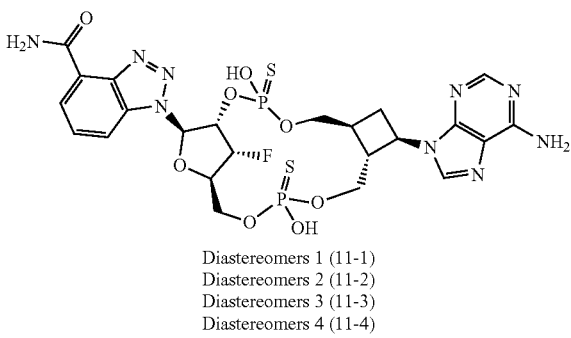 [SMILES: NC(=O)c1cccc2c1nnn2[C@@H]1O[C@@H]2COP(O)(=S)OC[C@@H]3[C@@H](COP(O)(=S)O[C@@H]1[C@@H]2F)C[C@H]3n1cnc2c(N)ncnc21]

Diastereomers 1 (11-1)
Diastereomers 2 (11-2)
Diastereomers 3 (11-3)
Diastereomers 4 (11-4)

Intermediate 11N (80 mg, 0.101 mmol) in 27% ammonium hydroxide (3 mL) was heated at 50° C. for 3 hours and then concentrated in vacuo. The residue was dissolved in water (2 mL), filtered and purified by Preparative HPLC Chromatographic Conditions; Instrument: Agilent 1260 Bionert Quat LC/FLD; Column: Luna Phenyl-Hex 5 um 4.6×250; Flow rate: 1 mL/min; Mobile Phase: A: 100 mM NH4OAc(pH 6.5); B: Methanol (% A=100−% B); Gradient: 20% hold over 10 min, 20-95% over 1 min, 95-20% over 2 min and 20% hold over 3 min. to afford Examples 11-1, 11-2, 11-3 and 11-4.

Example 11-1

4.7 mg; $t_R$: 8.73 min; M+1 obs=701.9; Analytical HPLC Chromatographic Conditions 3; $^1$H NMR (499 MHz, METHANOL-d$_4$) δ 8.60 (s, 1H), 8.34 (d, J=8.5 Hz, 1H), 8.21 (s, 1H), 8.12 (d, J=7.0 Hz, 1H), 7.64 (dd, J=8.2, 7.4 Hz, 1H), 6.67 (d, J=8.2 Hz, 1H), 5.99-5.67 (m, 2H), 4.82-4.62 (m, 2H), 4.59-4.45 (m, 2H), 4.21-4.10 (m, 2H), 4.04 (br d, J=10.1 Hz, 1H), 3.83-3.73 (m, 1H), 3.72-3.63 (m, 1H), 2.73-2.61 (m, 1H), 2.55-2.44 (m, 1H), 2.38-2.24 (m, 1H).

Example 11-2

3.2 mg; $t_R$: 10.13 min; M+1 obs=702.0; Analytical HPLC Chromatographic Conditions 3; $^1$H NMR (499 MHz, METHANOL-d$_4$) δ 8.43 (s, 2H), 8.21 (s, 1H), 8.07 (dd, J=7.3, 0.7 Hz, 1H), 7.66 (dd, J=8.3, 7.3 Hz, 1H), 6.68 (d, J=8.3 Hz, 1H), 5.96-5.71 (m, 2H), 4.85-4.66 (m, 3H), 4.44-4.32 (m, 1H), 4.27-4.21 (m, 3H), 4.20-4.13 (m, 1H), 3.93-3.82 (m, 1H), 3.44-3.36 (m, 1H), 2.69-2.47 (m, 2H), 2.30 (d, J=9.5 Hz, 1H).

Example 11-3

3.7 mg; $t_R$: 11.10 min; M+1 obs=702.0; Analytical HPLC Chromatographic Conditions 3; $^1$H NMR (499 MHz, METHANOL-d$_4$) δ 8.55 (s, 1H), 8.42 (d, J=8.5 Hz, 1H), 8.20 (s, 1H), 8.15-8.05 (m, 1H), 7.71-7.64 (m, 1H), 6.68 (d, J=8.3 Hz, 1H), 5.91-5.70 (m, 1H), 5.65-5.43 (m, 1H), 4.87-4.80 (m, 1H), 4.77-4.67 (m, 1H), 4.66-4.57 (m, 1H), 4.43-4.31 (m, 1H), 4.21-4.11 (m, 1H), 4.10-4.04 (m, 1H), 4.03-3.90 (m, 2H), 3.71-3.57 (m, 1H), 2.80-2.65 (m, 1H), 2.48-2.33 (m, 1H), 2.23-2.11 (m, 1H).

Example 11-4

4.2 mg; $t_R$: 11.72 min; M+1 obs=701.9; Analytical HPLC Chromatographic Conditions 3; $^1$H NMR (499 MHz, METHANOL-d$_4$) δ 8.58 (d, J=8.3 Hz, 1H), 8.38 (s, 1H), 8.20 (s, 1H), 8.09 (d, J=7.3 Hz, 1H), 7.72 (dd, J=8.3, 7.4 Hz, 1H), 6.67 (d, J=8.5 Hz, 1H), 5.74-5.39 (m, 2H), 4.85-4.81 (m, 1H), 4.80-4.63 (m, 1H), 4.41-4.34 (m, 1H), 4.32-4.22 (m, 2H), 4.21-4.05 (m, 2H), 4.01-3.89 (m, 1H), 3.45-3.37 (m, 1H), 2.64-2.48 (m, 2H), 2.26-2.12 (m, 1H).

Analytical HPLC Chromatographic Conditions 3:

Instrument: Agilent 1200 HPLC/MS; Column: Luna Phenyl-Hex 3 um 3×150; Flow rate: 0.5 mL/min; Mobile Phase: A: 20 mM NH$_4$OAc(pH 6.5); B: Methanol (% A=100−% B); Gradient: 0-15% over 20 min, 15-95% over 1 min. Detection at 260 nm.

Examples 12

1-[(1R,6S,8R,9R,15R,17R,18R)-8-(6-amino-9H-purin-9-yl)-18-fluoro-3,12-dihydroxy-3,12-disulfanylidene-2,4,11,13,16-pentaoxa-3λ⁵,12λ-diphosphatricyclo[13.3.0.0⁶,⁹]octadecan-17-yl]-1H-1,2,3-benzotriazole-4-carboxamide

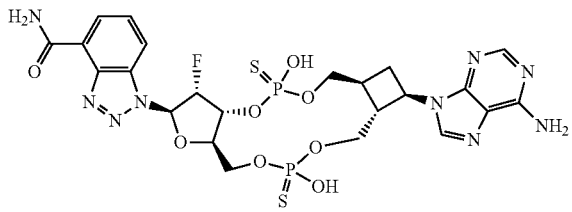

Diastereomers 1 (12-1)
Diastereomers 2 (12-2)
Diastereomers 3 (12-3)
Diastereomers 4 (12-4)

Preparation of Intermediate 12A

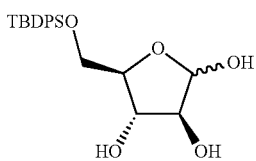

2A

A suspension of D-(−)Arabinose (10 g, 66.6 mmol) in DMF (150 mL) was heated to 95° C. under a nitrogen atmosphere until homogeneous and then cooled to 55° C. 4H-imidazole (9.07 g, 133 mmol) was added followed by the dropwise addition of tert-butylchlorodiphenylsilane (17.11 mL, 66.6 mmol) over 10 min. The reaction mixture was then stirred at 55° C. for 3 h and then cooled to RT. The mixture was then diluted with $CH_2Cl_2$ (300 mL) and washed with aq. HCl (0.2 M, 100 mL), followed by $NaHCO_3$ (150 mL). The organic layer was dried over $MgSO_4$, filtered and the filtrate was concentrated in vacuo. The residue was co-evaporated on a rotary evaporator with toluene (3×100 mL) and the resulting yellow oil was dried under high vacuum for 15 min. The crude material was purified by flash chromatography over 750 g of silica gel (eluted with 0-15% gradient over 13 min., 10% B hold for 5 min; Solvent A: DCM, solvent B: 20% MeOH in DCM) to afford Intermediate 12A (14.8 g, 57.2%). LCMS, [M+H]⁺=389.

Preparation of Intermediate 12B:

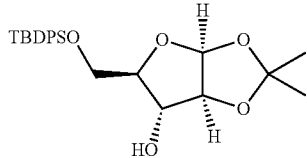

12B

To a solution of Intermediate 12A (14.8 g, 38.1 mmol) in dry acetone[1] (190 mL) at RT was added concentrated sulfuric acid (0.77 mL, 13.71 mmol) and anhydrous copper(II) sulfate[2] (14.6 g, 91 mmol). The resulting suspension was stirred at RT under an argon atmosphere for 8 h. The reaction mixture was filtered through a medium fritted funnel and the solids in the funnel were rinsed with acetone. $NH_4OH$ (27%, 3.0 mL) was added to the filtrate and the precipitated (ammonium sulfate) was removed by filtration through a medium fritted funnel. The filtrate was concentrated in vacuo and the residue was dried under vacuum to give the crude product which was purified by flash chromatography over 220 g of silica gel (35-65% EtOAc/Hexanes) to afford Intermediate 12B (13.8 g, 32.2 mmol) as a colorless oil.

[1]Acetone was dried by stirring it with $MgSO_4$ for 15.5 h and then filtration through a medium sintered funnel.
[2]Anhydrous $CuSO_4$ was further dried by heating at 120° C. in a vacuum oven for 14.0 h.

Preparation of Intermediate 12C

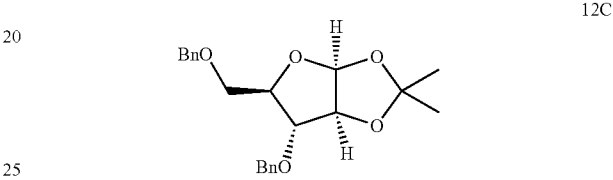

12C

To a solution of Intermediate 12B (13.2 g, 30.8 mmol) in THF (130 mL) at RT was added benzyl chloride (20.0 ml, 170 mmol) and powdered potassium hydroxide (18.0 g, 273 mmol, freshly ground with a mortar and pestle). The mixture was stirred at 62° C. for 19 h, then cooled to RT and filtered through celite. The filter cake was rinsed with THF and the filtrate was concentrated in vacuo. The residue was dried under vacuum overnight and was purified by flash chromatography (ISCO 330 g $SiO_2$, eluted with 0-10% EtOAc/$CH_2Cl_2$) to afford Intermediate 12C (5.44 g, 14.69 mmol) as a colorless oil. An additional impure fraction was further purified by chromatography (ISCO 120 g $SiO_2$, 0-30% EtOAc/Hexanes) to afford additional Intermediate 12C (4.41 g, 11.90 mmol) as a colorless oil. ¹H NMR (500 MHz, Chloroform-d) δ 7.34 (m, 10H), 5.92 (d, J=4.5 Hz, 1H), 4.67 (d, J=4.0 Hz, 1H), 4.60 (m, 4H), 4.29 (m, 1H), 4.06 (d, J=3.0 Hz, 1H), 3.67 (d, J=6.0 Hz, 2H), 1.47 (s, 3H), 1.35 (s, 3H). LCMS, [M+H]⁺=393.

Preparation of Intermediate 12D:

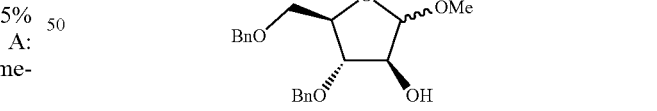

12D

Acetyl chloride (34 mL) was added to MeOH (131 mL) at 0° C. and stirred at RT for 30 min. Intermediate 12C (9.85 g, 26.6 mmol) was then added. The resulting solution was stirred at RT for 3.1 hours, cooled to 0° C. and quenched with $NaHCO_3$ (16.7 g), added in portions. The resulting suspension was filtered through a medium fritted funnel and the solids were rinsed with MeCN. The filtrate was concentrated almost to dryness, dissolved in EtOAc (170 mL), washed with saturated $NaHCO_3$ twice (1×150 mL and 1×75 mL) then washed with saturated NaCl (100 mL). The organic layer was dried over sodium sulfate, filtered and concentrated in vacuo to give the crude product, which was chromatographed (ISCO 120 g, $SiO_2$, flash column, 0-40%

EtOAc/Hexanes) to afford Intermediate 12D (8.93 g, 25.7 mmol) as a colorless oil. LCMS, [M+H]$^+$=367.

Preparation of Intermediate 12E

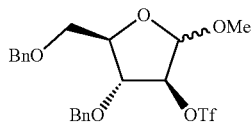

12E

To a stirred solution of Intermediate 12D (8.26 g, 23.74 mmol), was added pyridine (15.5 ml, 191 mmol) in dichloromethane (250 ml) at 0° C. under an argon atmosphere. Trifluoromethanesulfonic anhydride (4.9 ml, 28.8 mmol) was then added dropwise. After stirring at 0° C. for 30 min, the reaction mixture was diluted with EtOAc (300 mL), washed with aqueous 1 M HCl (3×200 mL) and saturated NaHCO$_3$ (200 mL).

The organic layer was dried (Na$_2$SO$_4$), filtered and concentrated in vacuo. The residue was dried under vacuum for 1 h to give the crude Intermediate 12E (11.15 g, 23.40 mmol) as a pale yellow oil that was immediately used as is in the next step. LCMS, [M+Na]$^+$=499.

Preparation of Intermediate 12F:

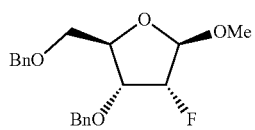

12F

To a solution of freshly prepared Intermediate 12E (11.15 g, 23.40 mmol) in THF (150 mL) at 0° C. under an argon atmosphere was added tetrabutylammonium fluoride (1 M in THF, 117 mL, 117 mmol). The reaction mixture was stirred at RT for 66 h and then concentrated in vacuo. The residue was dissolved in diethyl ether/dichloromethane (6:1, 50 mL), washed with saturated NH$_4$C$_1$ (3×200 mL), 5% aq. NaHCO$_3$ (200 mL) and water/saturated aq. NaCl (1:1, 150 mL). The organic layer was dried over sodium sulfate and concentrated and the residue was purified by flash chromatography over 120 g of silica gel eluted with 0-50% ethyl acetate/Hexane to give Intermediate 12F (2.1 g, 6.06 mmol) as a colorless oil. LCMS, [M+Na]$^+$=369.

Preparation of Intermediate 12G:

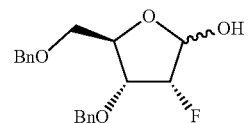

12G

To a stirring solution of Intermediate 12F (2.1 g, 6.06 mmol) in AcOH (61.0 ml) was added aq. HCl (1 M, 12.5 ml, 12.50 mmol) at RT. The reaction mixture was stirred at 65° C. for 3 hours, cooled to RT and then evaporated under reduced pressure to remove most of the AcOH. The remaining aqueous mixture was cooled to 0° C. and made basic by slow addition of saturated NaHCO$_3$ (40 mL). The mixture was partitioned between EtOAc (100 mL) and water (25 mL) and the aqueous layer was extracted with EtOAc (2×40 mL). The organic layers were combined, washed with water (40 mL) and saturated NaCl (40 mL), dried over sodium sulfate, filtered and concentrated in vacuo. The residue was dried under vacuum to give Intermediate 12G (2.0 g, 6.02 mmol) as a yellowish oil. LCMS, [M+Na]$^+$=355.

Preparation of Intermediate 12H:

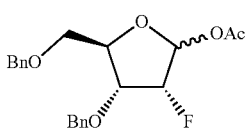

12H

To a stirred solution of Intermediate 12G (2.0 g, 6.02 mmol) in dichloromethane (16.0 mL) at 0° C. under an argon atmosphere was added triethylamine (2.6 ml, 18.56 mmol). After stirring for 5 min at 0° C., acetic anhydride (0.70 ml, 7.26 mmol) was added followed by 4-dimethylaminopyridine (0.074 g, 0.602 mmol). The reaction mixture was stirred at RT for 15 minutes, cooled to 0° C. and quenched by slow addition of saturated aq. NH$_4$C$_1$ (4.0 mL). The mixture was partitioned between water (20 mL) and EtOAc (100 mL) and the aqueous layer was extracted with EtOAc (2×30 mL). The organic layers were combined, washed with water (40 mL) and saturated NaCl (40 mL), dried (Na$_2$SO$_4$), filtered and concentrated in vacuo. The residue was purified by flash chromatography over 80 g of silica gel eluted with 0-30% ethyl acetate/Hexanes to afford Intermediate 12H (1.9 g, 5.07 mmol) as a colorless oil. LCMS, [M+Na]$^+$=397 as an anomeric mixture.

Preparation of Intermediate 12I:

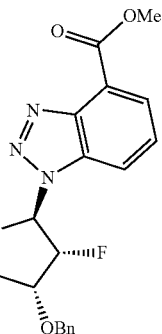

12I

To a suspension of Intermediate 12H (2 g, 5.34 mmol) and Intermediate 11H (0.946 g, 5.34 mmol) in acetonitrile (30 mL) under a nitrogen atmosphere at RT was added perchlorostannane (0.625 mL, 5.34 mmol), dropwise. The reaction mixture was stirred for 5 h, and then quenched with saturated aq. NaHCO$_3$ and extracted with EtOAc (3×30 mL). The combined organic layers were dried over sodium sulfate, filtered and concentrated in vacuo. The residue was purified on an ISCO column (40 g, 0-60% EtOAc/hexanes) to give Intermediate 12I (1.6 g, 3.26 mmol). LCMS, [M+H]$^+$=492.

Preparation of Intermediate 12J:

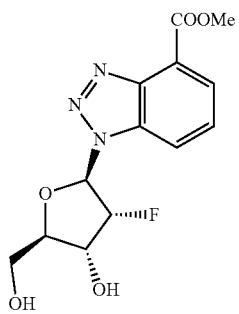

Intermediate 12I (1.2 g, 2.441 mmol) in DCM (100 mL) was cooled to −78° C.

Trichloroborane (19.53 ml, 19.53 mmol) was added dropwise and the reaction mixture was stirred at −78° C. for 4 h. The reaction was quenched carefully with saturated aq. NaHCO$_3$ to form a precipitate, which was collected and washed with DCM (5×1 mL) and dried to afford Intermediate 12J (522 mg). LCMS, [M+H]$^+$=312.

Preparation of Intermediate 12K:

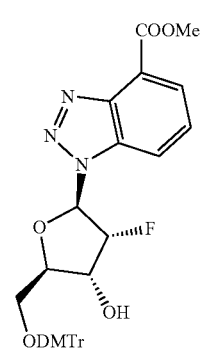

To Intermediate 12J (522 mg, 1.677 mmol) in 5 mL of pyridine was added DMTr-Cl (682 mg, 2.012 mmol). The reaction mixture was stirred at RT overnight, and then quenched with MeOH (1 mL), stirred for 10 min. and concentrated on a rotary evaporator. The residue was purified on an ISCO column (40 g, 0-60% EtOAc/hexanes over 27 min.) to give Intermediate 12K (500 mg, 0.815 mmol). LCMS, [M+Na]$^+$=636.

Preparation of Intermediate 12L:

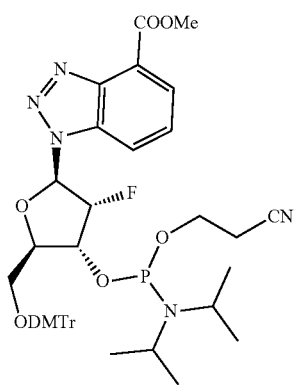

To a solution of Intermediate 12K (500 mg, 0.815 mmol) in anhydrous DCM (10 mL) at 0° C. was added 1H-imidazole-4,5-dicarbonitrile (0.815 mL, 0.815 mmol) followed by 3-((bis(diisopropylamino)phosphanyl)oxy)propanenitrile (295 mg, 0.978 mmol). The reaction was stirred at RT for 4 h, and then diluted with DCM (20 mL), washed with saturated aq. NaHCO$_3$, dried over sodium sulfate and concentrated in vacuo. The residue was purified on an ISCO column (24 g, 24 min gradient: 0-100% EtOAc/Hex with 0.5% NEt$_3$) to give Intermediate 12L (570 mg, 0.700 mmol). LCMS, [M+H]$^+$=814.

Preparation of Intermediate 12M:

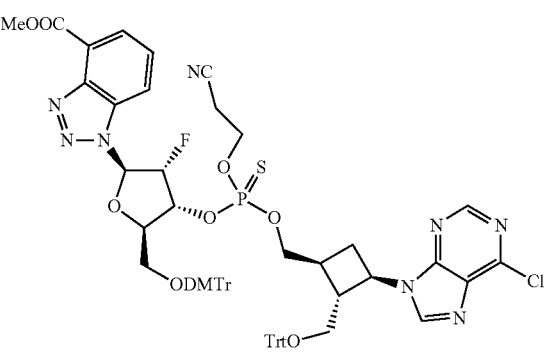

Intermediate 12M was prepared from 1H-tetrazole (68.5 mg, 0.978 mmol), Intermediate 2F (250 mg, 0.489 mmol), Intermediate 12L (397 mg, 0.489 mmol) and DDTT (110 mg, 0.538 mmol) following the procedure described for Intermediate 7F. The crude product was purified on an ISCO column (24 g, eluted with 0-100% EtOAc/Hexanes over 18 min.) to give Intermediate 12M (617 mg, 0.491 mmol). LCMS, [M+H]$^+$=1255.

Preparation of Intermediate 12N:

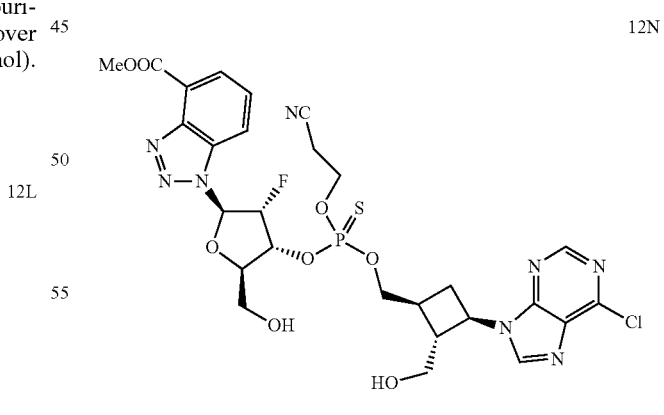

Intermediate 12N was prepared from Intermediate 12M (617 mg, 0.491 mmol), triethylsilane (785 μl, 4.91 mmol) and 2,2-dichloroacetic acid (405 μl, 4.91 mmol) following the procedure described for Intermediate 11N. The crude material was purified on an ISCO column (24 g, 0-10% MeOH/DCM over 18 minutes) to provide Intermediate 12N (211 mg, 0.297 mmol).

Preparation of Intermediate 12O:

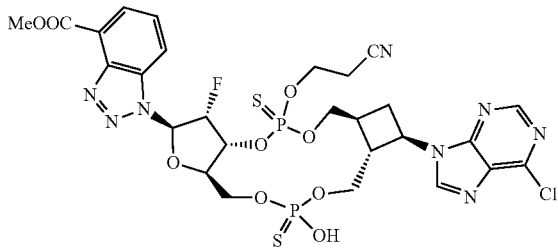

To a solution of Intermediate 12N (211 mg, 0.297 mmol) in pyridine (15 mL)) was added a solution of diphenyl phosphonate (0.115 mL, 0.593 mmol) in pyridine (5 mL) dropwise over a period of 40 minutes. (E)-N,N-dimethyl-N'-(3-thioxo-3H-1,2,4-dithiazol-5-yl)formimidamide (183 mg, 0.890 mmol) was added and the reaction was stirred at room temperature for 16 h and then concentrated in vacuo. The residue was dissolved in methanol, filtered and the filtrate was concentrated to a residue that was purified on a reverse phase ISCO Gold 50 g C18 column, Mobile Phase A: 5:95 acetonitrile:water with 0.01M ammonium acetate; Mobile Phase B: 95:5 acetonitrile:water with 0.01M ammonium acetate; Gradient: 0-50% B over 13 min; 50% hold for 3 min to afford Intermediate 12O (74 mg, 0.094 mmol) as a mixture of diastereomers.

Example 12

1-[(1R,6S,8R,9R,15R,17R,18R)-8-(6-amino-9H-purin-9-yl)-18-fluoro-3,12-dihydroxy-3,12-disulfa-nylidene-2,4,11,13,16-pentaoxa-3λ$^5$,12λ$^5$-diphos-phatricyclo[13.3.0.0$^{6,9}$]octadecan-17-yl]-1H-1,2,3-benzotriazole-4-carboxamide

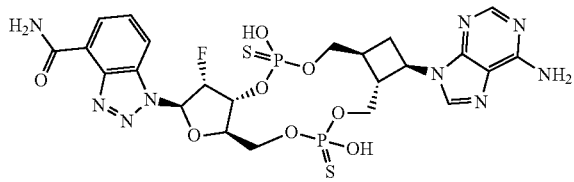

Diastereomers 1 (12-1)
Diastereomers 2 (12-2)
Diastereomers 3 (12-3)
Diastereomers 4 (12-4)

Intermediate 12O (74 mg, 0.094 mmol) in 27% ammonium hydroxide (2 mL) was heated at 50° C. for 3 hours and then concentrated in vacuo. The residue was dissolved in water (2 mL), filtered and purified by Preparative HPLC Chromatographic Conditions: Instrument: Waters Autopure; Column: Agilent Zorbax Eclipse Plus C18 Prep column, 5 µm, 21.2×250 mm; Flow rate: 20.0 mL/min Mobile Phase: A: 100 mM NH$_4$OAc (pH 4.7); B: ACN (% A=100–% B); Gradient; 5-21% B over 20 min; 21-95% B over 1 min; 95-5% B over 1 min; detection at 260 nm to afford Examples 12-1, 12-2, 12-3 and 12-4

Example 12-1

4.2 mg; t$_R$: 11.95 min; M+1 obs=702.3; Analytical HPLC Chromatographic Conditions 4: $^1$H NMR (499 MHz, METHANOL-d$_4$) δ 8.57 (s, 1H), 8.31 (d, J=8.2 Hz, 1H), 8.23 (s, 1H), 8.12 (d, J=7.2 Hz, 1H), 7.77-7.64 (m, 1H), 6.90-6.79 (m, 1H), 6.15-5.82 (m, 1H), 5.54-5.36 (m, 1H), 4.87-4.81 (m, 1H), 4.73 (br d, J=7.5 Hz, 1H), 4.63-4.54 (m, 1H), 4.51-4.38 (m, 1H), 4.23-4.10 (m, 3H), 4.09-4.03 (m, 1H), 4.02-3.91 (m, 1H), 2.65-2.54 (m, 2H), 2.53-2.45 (m, 1H).

Example 12-2

2.6 mg; t$_R$: 13.62 min; M+1 obs=702.2; Analytical HPLC Chromatographic Conditions 4: $^1$H NMR (499 MHz, METHANOL-d$_4$) δ 8.51 (s, 1H), 8.27 (d, J=7.9 Hz, 1H), 8.22 (s, 1H), 8.12 (d, J=7.3 Hz, 1H), 7.73 (dd, J=8.3, 7.4 Hz, 1H), 6.82 (dd, J=16.1, 1.7 Hz, 1H), 6.15-5.91 (m, 1H), 5.70-5.55 (m, 1H), 4.85-4.70 (m, 1H), 4.59-4.49 (m, 1H), 4.44-4.33 (m, 1H), 4.32-4.16 (m, 2H), 4.13-4.02 (m, 2H), 4.00-3.89 (m, 1H), 3.28-3.14 (m, 1H), 2.64-2.51 (m, 2H), 2.47-2.34 (m, 1H).

Example 12-3

5.3 mg; t$_R$: 14.58 min; M+1 obs=702.1; Analytical HPLC Chromatographic Conditions 4: $^1$H NMR (499 MHz, METHANOL-d$_4$) δ 8.47 (s, 1H), 8.27-8.18 (m, 2H), 8.11 (d, J=7.2 Hz, 1H), 7.80-7.54 (m, 1H), 6.81 (br d, J=16.5 Hz, 1H), 6.20-5.95 (m, 1H), 5.71-5.52 (m, 1H), 4.86-4.74 (m, 2H), 4.53 (br d, J=6.7 Hz, 1H), 4.33-4.22 (m, 3H), 4.14 (br d, J=4.2 Hz, 3H), 2.63-2.51 (m, 2H), 2.46-2.35 (m, 1H)

Example 12-4

5.7 mg; t$_R$: 17.49 min; M+1 obs=702.1; Analytical HPLC Chromatographic Conditions 4: $^1$H NMR (499 MHz, METHANOL-d$_4$) δ 8.52 (s, 1H), 8.32-8.17 (m, 2H), 8.11 (d, J=6.9 Hz, 1H), 7.74-7.62 (m, 1H), 6.82 (dd, J=16.3, 1.9 Hz, 1H), 6.10-5.86 (m, 1H), 5.64-5.40 (m, 1H), 4.85-4.70 (m, 1H), 4.58 (br d, J=5.1 Hz, 1H), 4.34-4.01 (m, 7H), 2.64-2.45 (m, 3H).

Analytical HPLC Chromatographic Conditions 4:
Instrument: Agilent 1200 HPLC/MS; Column: Agilent Eclipse Plus C18 Column 3.5 µm, 4.6×100 mm; Flow rate: 1 mL/min; Mobile Phase: A: 100 mM NH$_4$OAc (pH 4.7); B: ACN (% A=100–% B); Gradient; 10-50% B over 15 min; 50-95% B over 1 min.

Examples 13

1-[(1R,6S,8R,9R,15R,17R,18R)-17-(6-amino-9H-purin-9-yl)-18-fluoro-3,12-dihydroxy-3,12-disulfa-nylidene-2,4,11,13,16-pentaoxa-3λ$^5$,12λ$^5$-diphos-phatricyclo[13.3.0.0$^{6,9}$]octadecan-8-yl]-1H-1,2,3-benzotriazole-4-carboxamide

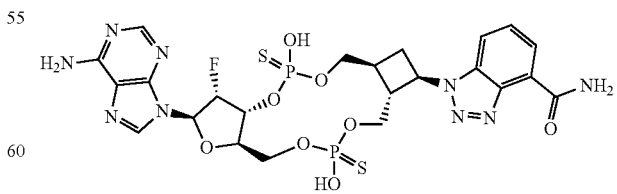

Diastereomers 1 (13-1)
Diastereomers 2 (13-2)
Diastereomers 3 (13-3)
Diastereomers 4 (13-4)

Preparation of Intermediate 13A:

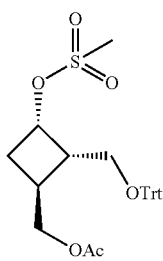

13A

A solution of Intermediate 2D (500 mg, 1.2 mmol) and triethylamine (491 µl, 3.60 mmol) in DCM (20 mL) was cooled to 0° C. and methanesulfonyl chloride (189 µl, 2.4 mmol) was added dropwise. The reaction mixture was slowly warmed to RT, stirred for 1 hour, washed with saturated aq. NaHCO$_3$, brine, dried over Na$_2$SO$_4$ filtered and concentrated in vacuo to afford crude Intermediate 13A. $^1$H NMR (499 MHz, CHLOROFORM-d) δ 7.54-7.29 (m, 9H), 7.28-7.16 (m, 6H), 5.25-5.17 (m, 1H), 3.50-3.36 (m, 2H), 3.31 (dd, J=9.7, 6.8 Hz, 1H), 2.85 (s, 3H), 2.80-2.72 (m, 1H), 2.66-2.55 (m, 2H), 2.50-2.39 (m, 1H), 2.33-2.23 (m, 1H), 2.07 (s, 3H).

Preparation of Intermediate 13B:

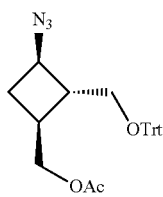

13B

The crude Intermediate 13A was dissolved in DMF (5 mL), sodium azide (234 mg, 3.60 mmol) was added and the reaction was stirred at 60° C. for two days. The reaction mixture was diluted with water (10 mL) and extracted with EtOAc (3×15 mL).

The combined organic layers were washed with brine, dried over Na$_2$SO$_4$, filtered and concentrated in vacuo to afford Intermediate 13B. $^1$H NMR (499 MHz, CHLOROFORM-d) δ 7.50-7.39 (m, 9H), 7.38-7.31 (m, 6H), 4.07 (d, J=5.7 Hz, 2H), 3.69 (d, J=8.3 Hz, 1H), 3.22-3.08 (m, 2H), 2.65-2.52 (m, 1H), 2.42-2.31 (m, 2H), 2.29-2.20 (m, 1H), 1.99 (s, 3H).

Preparation of Intermediate 13C:

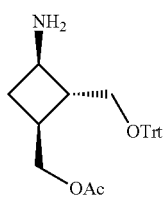

13C

Intermediate 13B was dissolved in MeOH (30 mL) and 10% Pd on Carbon (0.4 eq) was added under 25 psi H2 (g). The reaction mixture was stirred at RT for 3 hours, then filtered through celite and the filter cake was washed with MeOH (3×5 mL). The filtrate was concentrated in vacuo to afford Intermediate 13C.

Preparation of Intermediate 13D:

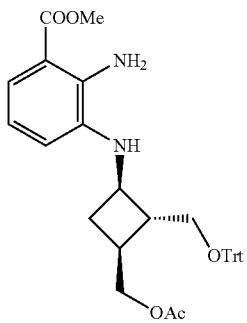

13D

To a solution of Intermediate 13C in DMF (5 mL) was added methyl 3-fluoro-2-nitrobenzoate (239 mg, 1.2 mmol) and N-ethyl-N-isopropylpropan-2-amine (418 µl, 2.4 mmol). The reaction was stirred at 50° C. for 16 hours, diluted with water (10 mL) and extracted with EtOAc (2×15 mL). The organic layer was washed with brine, dried over Na$_2$SO$_4$ filtered and concentrated. The crude material was dissolved in MeOH (30 mL), and treated with 10% Pd on carbon (0.4 eq.) and stirred under 25 psi H2 (g) for 4 h. The reaction mixture was filtered through celite and the filter cake was washed with MeOH (3×5 mL). The combined filtrates were concentrated to give Intermediate 13D.

Preparation of Intermediate 13G:

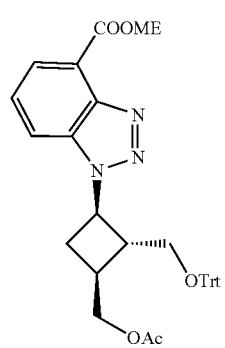

13G

Crude Intermediate 13D was dissolved in AcOH (10 mL), sodium nitrite (83 mg, 1.20 mmol) was added and the reaction was stirred at RT for 16 h. The reaction mixture was concentrated and the residue was dissolved in EtOAc (20 mL), washed with saturated aq. NaHCO$_3$, brine, dried over Na$_2$SO$_4$ and concentrated to dryness. This mixture was azeotroped with pyridine (2 mL), then dissolved in pyridine (5 mL) and trityl chloride (502 mg, 1.80 mmol) was added. The reaction mixture was stirred at RT overnight. MeOH (1 mL) was added and the mixture was stirred for 10 min and the reaction mixture was concentrated in vacuo. The resulting residue was purified on silica 0-100% EtOAc/hex to give Intermediate 13G (230 mg). LCMS, [M+H]$^+$=576.

Preparation of Intermediate 13H:

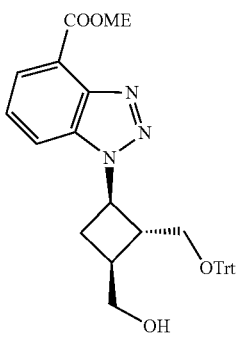

13H

To a solution of Intermediate 13G (230 mg, 0.400 mmol) in dry MeOH (5 mL) was added sodium methanolate (160 µl, 0.080 mmol). The reaction was stirred at RT for 4 h, quenched with AcOH (0.1 mL) and then concentrated in vacuo. The resulting residue was dissolved in EtOAc (20 mL), washed with saturated aq. NaHCO$_3$, brine, dried over Na$_2$SO$_4$, filtered and concentrated. The crude material was purified on silica (ISCO 12 g, 0-100% EtOAc/hexanes over 18 min) to afford Intermediate 13H. $^1$H NMR (499 MHz, CHLOROFORM-d) δ 8.10 (d, J=7.3 Hz, 1H), 7.69 (d, J=8.3 Hz, 1H), 7.46 (br d, J=7.2 Hz, 1H), 7.37 (br d, J=8.0 Hz, 6H), 7.28 (s, 9H), 5.06 (d, J=8.6 Hz, 1H), 4.20-4.09 (s, 3H), 3.88-3.76 (m, 2H), 3.48-3.35 (m, 1H), 3.29-3.21 (m, 1H), 3.20-3.10 (m, 1H), 2.80-2.65 (m, 2H), 2.48 (br d, J=4.4 Hz, 1H). LCMS, [M+H]$^+$=534.

Preparation of Intermediate 13I:

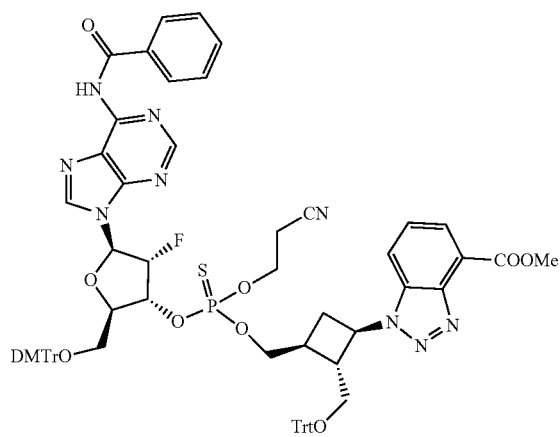

13I

Intermediate 13I was prepared from 1H-tetrazole (55.9 mg, 0.798 mmol), Intermediate 13H (213 mg, 0.399 mmol), (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (Sigma-Aldrich, 524 mg, 0.599 mmol) and DDTT (90 mg, 0.439 mmol) following the procedure described for Intermediate 7F. The crude product was purified on silica (ISCO 24 g; Gradient: 0-100% EtOAc/hexanes over 27 min) to give Intermediate 13I (490 mg, 0.366 mmol). LCMS, [M+H]$^+$=1340

Preparation of Intermediate 13J:

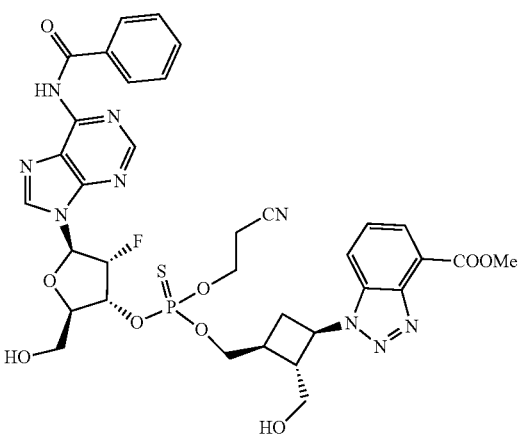

13J

To a solution of Intermediate 13I (490 mg, 0.366 mmol) in DCM (10 mL) was added triethylsilane (584 µl, 3.66 mmol) and 2,2-dichloroacetic acid (302 µl, 3.66 mmol). After 2 h, the reaction mixture was diluted with DCM (20 mL), washed with saturated aq. NaHCO$_3$, dried over Na$_2$SO$_4$, and concentrated. The residue was purified on silica (12 g; 0-10% MeOH/DCM) to give Intermediate 13J (290 mg, 0.364 mmol) as a pair of diastereomers. LCMS, [M+H]$^+$=796.

Preparation of Intermediate 13K:

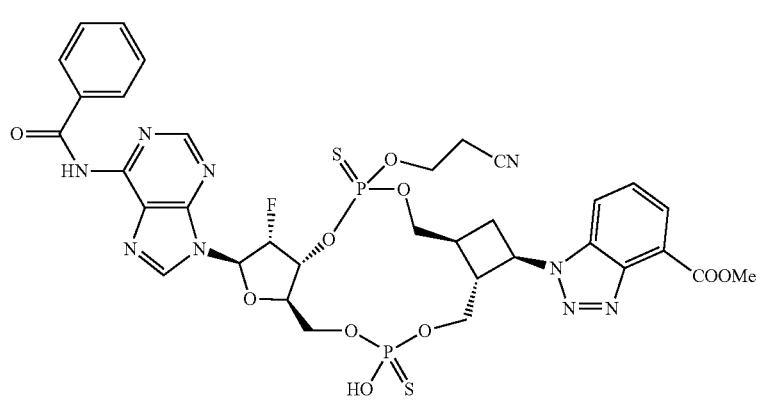

13K

To Intermediate 13J (290 mg, 0.364 mmol) in pyridine (15 mL) at RT under nitrogen atmosphere was added dropwise a solution of diphenyl phosphonate (141 μl, 0.729 mmol) in pyridine (4 mL) over 2 h. (E)-N,N-dimethyl-N'-(3-thioxo-3H-1,2,4-dithiazol-5-yl)formimidamide (224 mg, 1.093 mmol) was then added and the reaction mixture was stirred overnight. The reaction mixture was concentrated on a rotary evaporator. The residue was stirred in MeOH (10 mL) for 10 min and the resulting yellow precipitate was filtered. To the filtrate was added celite (3 g), and the mixture was concentrated in vacuo, loaded onto a column and purified on a reverse phase ISCO Gold 150 g C18 column, Mobile Phase A: 5:95 acetonitrile:water with 0.01M ammonium acetate; Mobile Phase B: 95:5 acetonitrile:water with 0.01M ammonium acetate; Gradient: 0-60% B over 20 min; 60% B hold for 5 min to afford a mixture of two fast eluting diastereomers of Intermediate 13K (80 mg, 25.1%) and another mixture of two slower eluting diastereomers of Intermediate 13K (87 mg, 27.3%). LCMS, [M+H]+=874.

Examples 13

1-[(1R,6S,8R,9R,15R,17R,18R)-17-(6-amino-9H-purin-9-yl)-18-fluoro-3,12-dihydroxy-3,12-disulfa-nylidene-2,4,11,13,16-pentaoxa-3λ$^5$,12λ$^5$-diphos-phatricyclo[13.3.0.0$^{6,9}$]octadecan-8-yl]-1H-1,2,3-benzotriazole-4-carboxamide

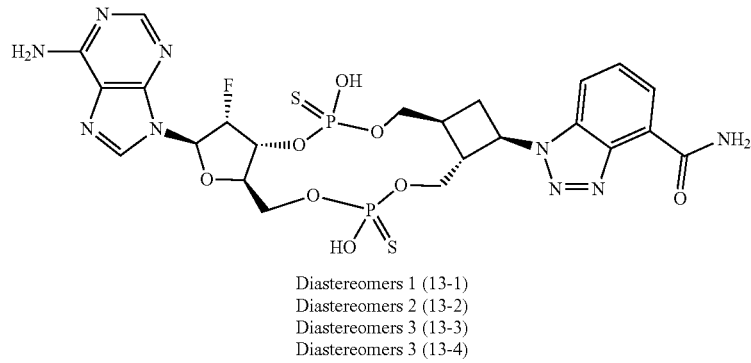 [SMILES: NC(=O)c1cccc2c1nnn2[C@@H]1C[C@@H]2COP(O)(=S)O[C@H]3[C@@H](F)[C@H](n4cnc5c(N)ncnc54)O[C@@H]3COP(O)(=S)OC[C@H]21]

Diastereomers 1 (13-1)
Diastereomers 2 (13-2)
Diastereomers 3 (13-3)
Diastereomers 3 (13-4)

The mixture of two fast eluting diastereomers of Intermediate 13K (80 mg, 0.092 mmol) in NH$_3$ (7N in MeOH, 5 mL) was heated at 50° C. for 3 h. The reaction was concentrated, dissolved in water (2 mL), filtered and purified by Preparative HPLC Chromatographic Conditions: Instrument: Waters Autopure; Column: Agilent Zorbax Eclipse Plus C18 Prep column, 5 μm, 21.2×250 mm; Flow rate: 20.0 mL/min; Mobile Phase: A: 0.1% TFA in H2O; B: ACN (% A=100−% B); Gradient; 5-20% B over 15 min, 20-95% B over 1 min, 95-5% B over 1 min; Detection: 260 nm to afford Examples 13-1 and 13-2

Example 13-1

1.2 mg; t$_R$: 10.00 min; M+1 obs=702.3; Analytical HPLC Chromatographic Conditions 5: $^1$H NMR (499 MHz, DEUTERIUM OXIDE) δ 8.43 (s, 1H), 8.31 (d, J=8.3 Hz, 1H), 8.10 (s, 1H), 7.46 (d, J=7.4 Hz, 1H), 7.25-7.11 (m, 1H), 6.27 (d, J=14.2 Hz, 1H), 6.06-5.84 (m, 1H), 5.30 (br d, J=8.3 Hz, 2H), 5.01-4.85 (m, 5H), 4.63-4.53 (m, 2H), 4.52-4.45 (m, 2H), 4.19-4.12 (m, 2H), 4.07 (s, 3H), 3.25 (s, 1H), 3.11 (d, J=7.4 Hz, 1H), 2.97-2.86 (m, 1H), 2.65-2.49 (m, 2H).

Example 13-2

2.3 mg; t$_R$: 11.58 min; M+1 obs=702.3; Analytical HPLC Chromatographic Conditions 5: $^1$H NMR (499 MHz, DEUTERIUM OXIDE) δ 8.41 (s, 1H), 8.27 (d, J=8.7 Hz, 1H), 8.10 (s, 1H), 7.44 (d, J=6.8 Hz, 1H), 7.13-7.00 (m, 1H), 6.26 (d, J=13.9 Hz, 1H), 5.57-5.38 (m, 1H), 5.30 (br d, J=8.8 Hz, 1H), 5.06-4.92 (m, 1H), 4.54-4.42 (m, 2H), 4.20-4.09 (m, 2H), 4.09-4.03 (m, 1H), 4.02-3.93 (m, 1H), 3.38-3.28 (m, 1H), 3.11 (d, J=7.2 Hz, 1H), 2.97-2.86 (m, 1H), 2.66-2.49 (m, 2H)

Analytical HPLC Chromatographic Conditions 5:

Instrument: Agilent 1200 HPLC/MS; Column: Agilent Eclipse Plus C18 Column 3.5 μm, 3.0×100 mm; Flow rate: 0.5 mL/min; Mobile Phase: A: 0.05% TFA in H$_2$O; B: ACN (% A=100−% B); Gradient; 10-41% B over 20 min, 41-95% B over 1 min, 95-10% B over 1 min.

The mixture of two slower eluting diastereomers of Intermediate 13K (87 mg, 0.092 mmol) in NH$_3$ (7N in MeOH, 5 mL) was heated 50° C. for 3 h. The reaction was concentrated, dissolved in water (2 mL), filtered and purified by Preparative HPLC Chromatographic Conditions: Instrument: Waters Autopure Column: Agilent Zorbax Eclipse Plus C18 Prep column, 5 μm, 21.2×250 mm; Flow rate: 20.0 mL/min; Mobile Phase: A: 100 mM NH$_4$OAc (pH 4.7); B: ACN (% A=100−% B); gradient 10-25% B over 20 min, 25-95% B over 1 min, 95-10% B over 1 min.; Detection: 260 nm to afford Examples 13-3 and 13-4.

Example 13-3

1.0 mg; t$_R$: 8.60 min; M+1 obs=702.0; Analytical HPLC Chromatographic Conditions 6: $^1$H NMR (499 MHz, METHANOL-d$_4$) δ 8.70-8.51 (m, 1H), 8.39-8.27 (m, 1H), 8.22 (s, 1H), 8.11-8.02 (m, 1H), 7.67-7.51 (m, 1H), 6.46-6.25 (m, 1H), 5.77-5.58 (m, 1H), 5.43-5.33 (m, 1H), 5.30-5.18 (m, 1H), 4.65-4.52 (m, 1H), 4.46 (br d, J=7.6 Hz, 1H), 4.42-4.33 (m, 1H), 4.27 (br d, J=11.6 Hz, 1H), 4.23-4.12 (m, 2H), 4.11-3.99 (m, 1H), 3.74-3.61 (m, 1H), 2.81-2.52 (m, 3H).

Example 13-4

2.2 mg; t$_R$: 12.98 min; M+1 obs=702.0; Analytical HPLC Chromatographic Conditions 6: $^1$H NMR (499 MHz, METHANOL-d$_4$) δ 8.70-8.47 (m, 1H), 8.34-8.12 (m, 2H), 8.07-7.97 (m, 2H), 7.55 (t, J=7.7 Hz, 1H), 6.38 (br d, J=15.0

Hz, 1H), 5.65-5.43 (m, 1H), 5.37 (br d, J=8.0 Hz, 1H), 5.20-5.04 (m, 1H), 4.61-4.45 (m, 2H), 4.40-4.22 (m, 3H), 4.18 (br s, 1H), 4.09-4.00 (m, 1H), 3.80-3.65 (m, 1H), 3.23 (d, J=7.5 Hz, 2H), 2.80-2.55 (m, 3H).

Analytical HPLC Chromatographic Conditions 6:

Instrument: Agilent 1200 HPLC/MS; Column: Agilent Eclipse Plus C18 Column 3.5 µm, 4.6×100 mm; Flow rate: 1 mL/min; Mobile Phase: A: 100 mM NH4OAc (pH 4.7); B: ACN (% A=100% B); Gradient; 5% B hold over 2 min; 5-25% B over 15 min; 25-95% B over 1 min.

Examples 14

(1R,6S,8R,9R,15R,17R,18R)-18-hydroxy-8-(6-hydroxy-9H-purin-9-yl)-17-{4-oxo-1H,4H,5H-imidazo[2,1-b]purin-1-yl}-3,12-disulfanyl-2,4,11,13,16-pentaoxa-3$\lambda^5$,12$\lambda^5$-diphosphatricyclo[13.2.1.0$^{6,9}$]octadecane-3,12-dione

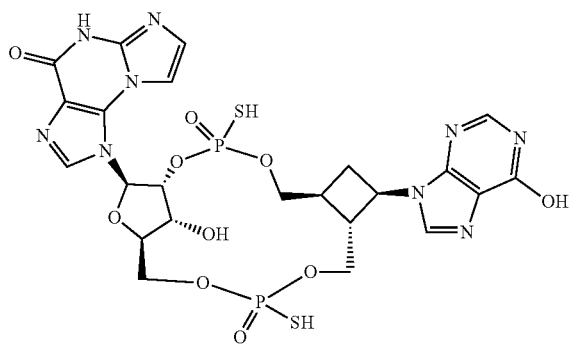

Diastereomers 1 (14-1)
Diastereomers 2 (14-2)
Diastereomers 3 (14-3)
Diastereomers 3 (14-4)

Preparation of Intermediate 14A

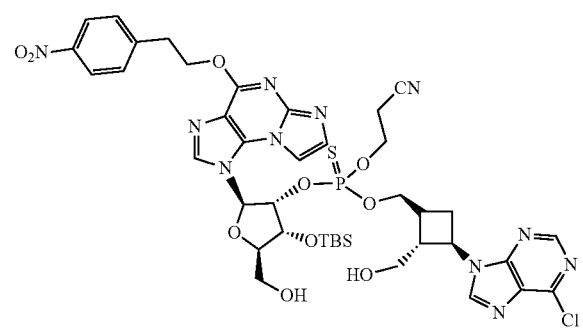

14A

A solution of Intermediate 2F (250 mg, 0.489 mmol) and 1H-tetrazole (171 mg, 2.446 mmol) in MeCN (10 mL) was concentrated on a rotary evaporator and the azeotroped was repeated twice. To the residue was added CH₃CN (6 mL) and activated MS 4 Å (180 mg) and the mixture was left stirring under a nitrogen atmosphere. Separately, Intermediate 15G (735 mg, 0.685 mmol) was azeotroped with MeCN three times, the residue was dissolved in CH₃CN (6 mL) and activated MS 4 Å (180 mg) was added. This mixture was transferred to the above solution via cannula and rinsed with dry MeCN (2×2 mL) for complete transfer. The reaction was stirred at RT for 4 h, and then DDTT (201 mg, 0.978 mmol) was added and the mixture was stirred for 30 min. The reaction mixture was then filtered, concentrated, and the residue was dissolved in EtOAc and washed with saturated aq. NaHCO₃. The organic layer was concentrated to dryness and the residue was dissolved in DCM (8 mL). Triethylsilane (0.391 mL, 2.45 mmol) and dichloroacetic acid (0.404 mL, 4.89 mmol) and a couple drops of water were added and the mixture was stirred at RT for 1.5 h. TFA (0.113 mL, 3 eq., 1.47 mmol) was added and the mixture was stirred for 4 h. Pyridine (4 mL) was added and the mixture was concentrated. To the residue was added saturated aq. NaHCO₃ and the aqueous layer was extracted with DCM 3 times. The combined organic layers were dried (sodium sulfate), filtered and concentrated. The residue was purified on a silica column (12 g, elute with 0-100% gradient EtOAc/hexane). A second purification by flash chromatography on silica (12 g, 0-20% gradient MeOH/DCM) afforded Intermediate 14A (250 mg). LCMS, [M+H]⁺=970.

Preparation of Intermediate 14B:

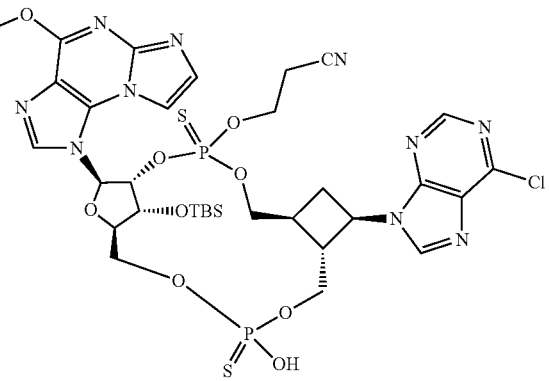

14B

Intermediate 14A (250 mg, 0.258 mmol) was azeotroped with pyridine 3 times and the residue was taken up in pyridine (30 mL). A solution of diphenyl phosphonate (0.10 mL, 0.52 mmol) in pyridine (1.5 mL) was added over 30 minutes and the resulting mixture was stirred at RT overnight. (E)-N,N-dimethyl-N'-(3-thioxo-3H-1,2,4-dithiazol-5-yl)formimidamide (212 mg, 1.03 mmol) was added and the mixture was stirred for two days. The reaction mixture was then concentrated and the residue was azeotroped with ACN (2×5 mL). The residue was then suspended in ACN, the solid was filtered, and the filtrate was concentrated. The residue was dissolved in DCM, loaded onto celite and purified on a reverse phase ISCO Gold 50 g C18 column (Mobile Phase A: 5:95 acetonitrile:water with 0.01M ammonium acetate; Mobile Phase B: 95:5 acetonitrile:water with 0.01M ammonium acetate; Gradient: 5-70% B, the desired product eluted around 40-50% B). The fractions containing desired product were combined and concentrated to remove most of the acetonitrile. The remaining aqueous solution was extracted with DCM and concentrated to give Intermediate 14B (110 mg, 0.105 mmol). LCMS, [M+H]$^+$=1048.

Preparation of Intermediate 14C

14C

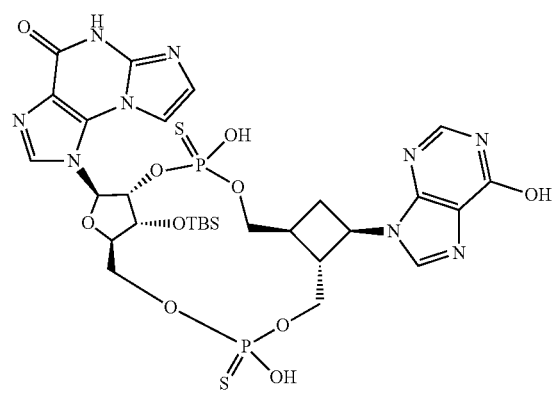

A solution of DBU (0.24 mL, 1.6 mmol) and nitromethane (0.085 mL, 1.6 mmol) in pyridine (1.0 mL) was stirred for 20 min. This solution was added to a solution of Intermediate 14B (110 mg, 0.105 mmol) in pyridine (0.5 mL) over 10 min. The resulting mixture was stirred at RT overnight, concentrated and azeotroped with ACN three times. The residue was dissolved in conc. NH$_4$OH (27% aq.) and heated in a sealed pressure vessel at 50° C. overnight. The reaction mixture was then concentrated, loaded onto celite and purified on a reverse phase ISCO Gold 15.5 g C18 column (Mobile Phase A: 5:95 acetonitrile:water with 0.01M ammonium acetate; Mobile Phase B: 95:5 acetonitrile:water with 0.01M ammonium acetate; Gradient:0-50% B). Fractions containing the desired product were combined and concentrated to give Intermediate 14C (100 mg, 0.121 mmol).

Example 14

(1R,6S,8R,9R,15R,17R,18R)-18-hydroxy-8-(6-hydroxy-9H-purin-9-yl)-17-{4-oxo-1H,4H,5H-imidazo[2,1-b]purin-1-yl}-3,12-disulfanyl-2,4,11,13,16-pentaoxa-3λ$^5$,12λ$^5$-diphosphatricyclo[13.2.1.0$^{6,9}$]octadecane-3,12-dione

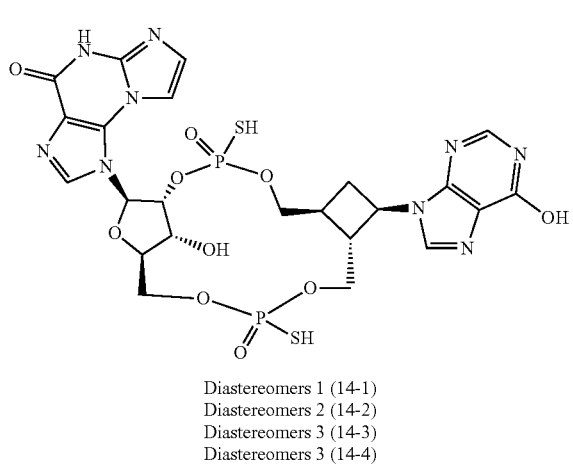 [SMILES: O=c1[nH]c2nccn2c2c1ncn2[C@@H]1O[C@@H]2COP(=O)(S)OC[C@@H]3[C@@H](COP(=O)(S)O[C@@H]1[C@@H]2O)C[C@H]3n1cnc2c(O)ncnc21]

Diastereomers 1 (14-1)
Diastereomers 2 (14-2)
Diastereomers 3 (14-3)
Diastereomers 3 (14-4)

Intermediate 14C (100 mg, 0.121 mmol) was treated with pyridine (0.2 mL) and TEA.3HF (0.8 mL), sonicated to a homogeneous solution and heated at 50° C. for 5 h. Triethylammonium acetate (1 M, 2 mL) was added, the mixture was concentrated and the residue was dissolved in water. The crude products were purified via preparative LC/MS with the following conditions: Column: Agilent Bonus RP, 200 mm×21.2 mm, 5-μm particles; Mobile Phase A: 5:95 acetonitrile:water with 20 mM ammonium acetate; Mobile Phase B: 95:5 acetonitrile:water with 20-mM ammonium acetate; Gradient: a 6-minute hold at 0% B, 0-100% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation to afford Examples 14-1, 14-2, 14-3 and 14-4.

Example 14-1

2.0 mg; Analytical LCMS method E; Observed Mass: 714.0; $t_R$: 0.22 min.

Example 14-2

2.6 mg; Analytical LCMS method E; Observed Mass: 714.2; $t_R$: 0.25 min.

Example 14-3

3.7 mg; Analytical LCMS method E; Observed Mass: 714.2; $t_R$: 0.27 min.

Example 14-4

2.2 mg; Analytical LCMS method E; Observed Mass: 714.2; $t_R$: 0.44 min.

Analytical LCMS Method E:

Injection 1 conditions: Column: Waters XBridge BEH C18 XP(50×2.1 mm) 2.5 μm; Mobile Phase A: 5:95 acetonitrile:water with 10 mM NH₄OAc; Mobile Phase B: 95:5 acetonitrile:water with 10 mM NH₄OAc; Temperature: 50° C.; Gradient: 0-100% B over 3 minutes; Flow: 1.1 ml/min.

Examples 15

(1R,6S,8R,9R,15R,17R,18R)-8-(6-amino-9H-purin-9-yl)-3,12,18-trihydroxy-17-{4-hydroxy-1H-imidazo[2,1-b]purin-1-yl}-2,4,11,13,16-pentaoxa-3λ⁵,12λ⁵-diphosphatricyclo[13.2.1.0⁶,⁹]octadecane-3,12-dithione

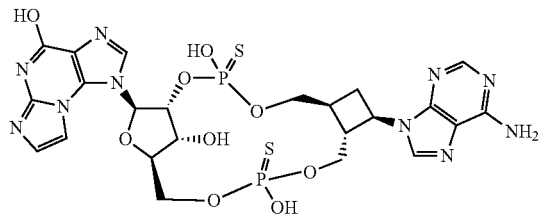

Diastereomers 1 (15-1)
Diastereomers 2 (15-2)
Diastereomers 3 (15-3)
Diastereomers 4 (15-4)

Preparation of Intermediate 15A:

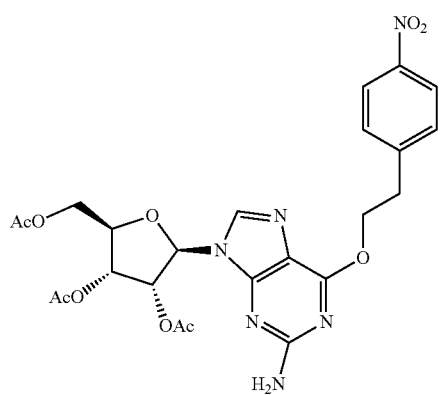

To a suspension of (2R,3R,4R,5R)-2-(acetoxymethyl)-5-(2-amino-6-oxo-1,6-dihydro-9H-purin-9-yl)tetrahydrofuran-3,4-diyl diacetate (20 g, 48.9 mmol), 2-(4-nitrophenyl)ethan-1-ol (12.25 g, 73.3 mmol) and triphenylphosphine (19.22 g, 73.3 mmol) in THF (100 mL) under nitrogen was added DIAD (14.25 mL, 73.3 mmol) dropwise. The reaction mixture slowly became a clear yellow solution after 2 h. The reaction mixture was concentrated and the residue was dissolved in EtOAc (500 mL). The resulting solution was washed with sat. NaHCO₃ aq., brine, dried over Na₂SO₄, filtered and then concentrated to give crude Intermediate 15A as a thick brown oil. LCMS, [M+H]⁺=559.

Preparation of Intermediate 15B:

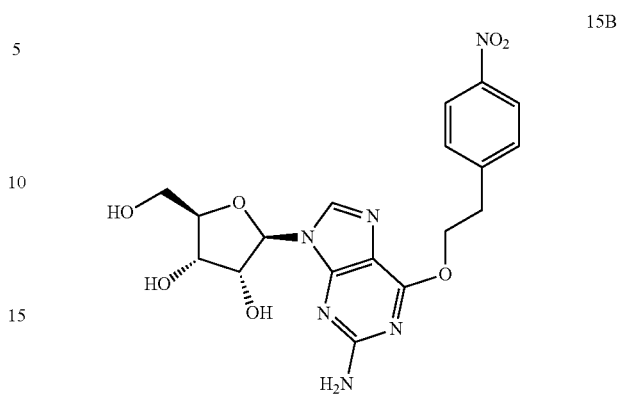

To the crude Intermediate 15A in MeOH (50 mL), was added NH₃ (7 N in MeOH, 50 mL). The resulting mixture was stirred at RT for 8 h, and then concentrated. The residue was washed with water (20 mL×3), which was decanted each time. The resulting sticky residue was washed with Et₂O (20 mL×3), then treated with 50 mL of EtOAc and allowed to stir for 5 h. The product precipitated out as a solid. The solid was collected and washed with diethyl ether to give Intermediate 15B (17.5 g, 40.5 mmol). LCMS, [M+H]⁺=432. ¹H NMR (499 MHz, DMSO-d₆) δ 8.19 (d, J=8.8 Hz, 2H), 8.10 (s, 1H), 7.65 (d, J=8.7 Hz, 2H), 6.46 (s, 2H), 5.78 (d, J=6.0 Hz, 1H), 5.39 (br d, J=6.1 Hz, 1H), 5.13 (d, J=4.6 Hz, 1H), 5.09 (s, 1H), 4.68 (t, J=6.8 Hz, 2H), 4.46 (br d, J=5.4 Hz, 1H), 4.15-4.08 (m, 1H), 3.89 (br d, J=3.7 Hz, 1H), 3.69-3.59 (m, 1H), 3.57-3.47 (m, 1H), 3.26 (t, J=6.9 Hz, 2H).

Preparation of Intermediate 15C:

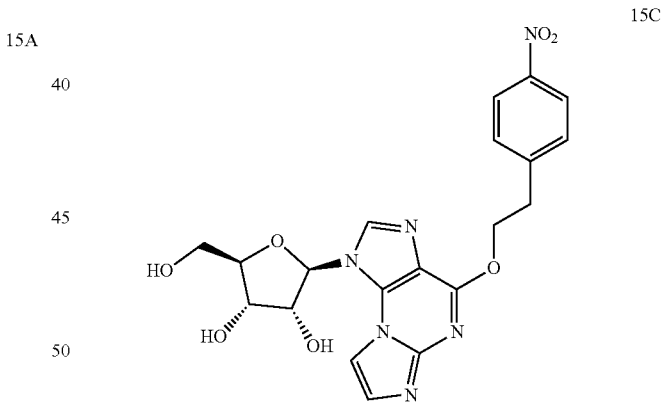

To a solution of Intermediate 15B (17.5 g, 40.5 mmol) in 50 mL of EtOH was added 150 mL of NH₄OAc/AcOH buffer (pH 4.5) and 2-bromoacetaldehyde (~1.3 M in ethanol/1 M HCl, 93 mL, 121 mmol). The mixture was stirred for 24 h at 35° C. then the volume was reduced in vacuo to about 50 mL. The remaining mixture was neutralized with solid ammonium bicarbonate to pH 7 and treated with acetonitrile (~200 mL). The product Intermediate 15C precipitated as a while solid. The solid was filtered and rinsed with acetonitrile and dried to give ~6 g of product. The filtrate was concentrated to give a slurry. The slurry was diluted with acetonitrile (100 mL) and MeOH (10 mL) and the solid was filtered and rinsed with acetonitrile. The solids were combined to give Intermediate 15C (9.5 g), LCMS, [M+H]⁺=457.

Preparation of Intermediate 15D:

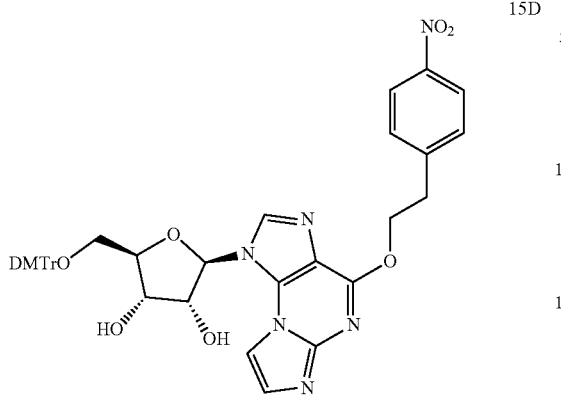

Intermediate 15C (3.75 g, 8.22 mmol) was co-evaporated on a rotary evaporator with pyridine (10 mL×2). Then it was dissolved in pyridine (60 mL) and 4,4'-dimethoxytrityl chloride (2.92 g, 8.63 mmol) was added. After stirring at room temperature for 20 hours, the reaction mixture was quenched with MeOH (3 mL) and stirred for 10 min. Then it was concentrated in vacuo and the residue was taken up in DCM (100 mL), washed with 1.5 M KHPO$_4$ and then concentrated. The crude material was purified on a 220 g silica column that was treated with DCM (with 0.25% TEA) and eluted with 0% to 10% MeOH/DCM (with 0.25% TEA) to give Intermediate 15D (4 g, 5.27 mmol, 64.2%). LCMS, [M+H]$^+$=759. $^1$H NMR (499 MHz, DMSO-d$_6$) δ 8.32 (s, 1H), 8.14 (d, J=8.7 Hz, 2H), 8.05 (d, J=1.7 Hz, 1H), 7.62 (d, J=8.7 Hz, 2H), 7.53 (d, J=1.7 Hz, 1H), 7.17-7.05 (m, 5H), 7.03-6.92 (m, 4H), 6.69 (d, J=8.9 Hz, 2H), 6.68-6.57 (m, 2H), 6.29 (d, J=2.1 Hz, 1H), 5.96 (d, J=5.1 Hz, 1H), 5.28 (d, J=7.2 Hz, 1H), 4.83 (td, J=4.8, 2.2 Hz, 1H), 4.78-4.66 (m, 2H), 4.38 (td, J=7.1, 4.8 Hz, 1H), 4.20 (dd, J=6.8, 3.5 Hz, 1H), 3.69 (d, J=4.9 Hz, 6H), 3.34-3.30 (m, 2H), 3.24 (dd, J=10.8, 2.3 Hz, 1H), 2.96 (dd, J=10.9, 3.9 Hz, 1H).

Preparation of Intermediate 15E:

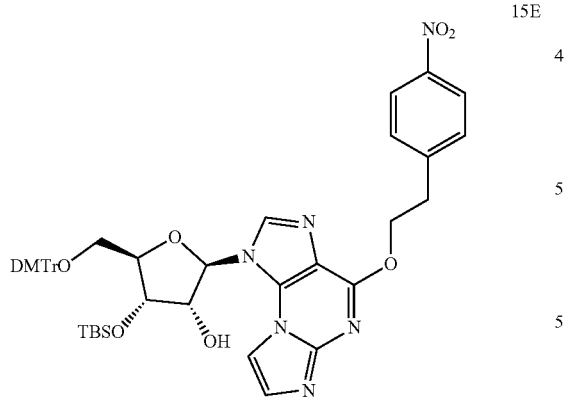

Intermediate 15D (3.4 g, 4.48 mmol) in 5 mL of DMF and 5 mL of DCM was treated with 1H-imidazole (1.22 g, 17.92 mmol), followed by addition of tert-butylchlorodimethylsilane (0.743 g, 4.93 mmol). The reaction was stirred at RT for 16 h, and an additional 1 eq. of tert-butylchlorodimethylsilane was added and the reaction was stirred for 16 h. The reaction was then quenched with 2 mL of MeOH and stirred for 10 min. Then it was diluted with 200 mL of EtOAc, washed with sat.NaHCO$_3$ aq., brine, dried over Na$_2$SO$_4$, filtered and concentrated. The residue was purified on an ISCO 330 g Gold column with 0-30% EtOAc/DCM over 60 min to give Intermediate 15E (1.9 g, 2.176 mmol). LCMS, [M+H]$^+$=873. $^1$H NMR (499 MHz, DMSO-d$_6$) δ 8.41-8.28 (m, 1H), 8.14 (d, J=8.8 Hz, 2H), 8.04 (d, J=1.7 Hz, 1H), 7.62 (d, J=8.8 Hz, 2H), 7.55 (d, J=1.5 Hz, 1H), 7.16-7.03 (m, 5H), 7.00-6.93 (m, 4H), 6.77-6.60 (m, 4H), 6.32 (d, J=2.0 Hz, 1H), 5.81 (d, J=5.6 Hz, 1H), 4.89-4.80 (m, 1H), 4.78-4.67 (m, 2H), 4.51 (dd, J=7.3, 4.6 Hz, 1H), 4.27-4.17 (m, 1H), 3.74-3.60 (m, 6H), 3.42-3.22 (m, 3H), 2.89 (dd, J=11.0, 3.1 Hz, 1H), 0.75 (s, 9H), 0.14-0.21 (m, 6H).

Preparation of Intermediate 15G:

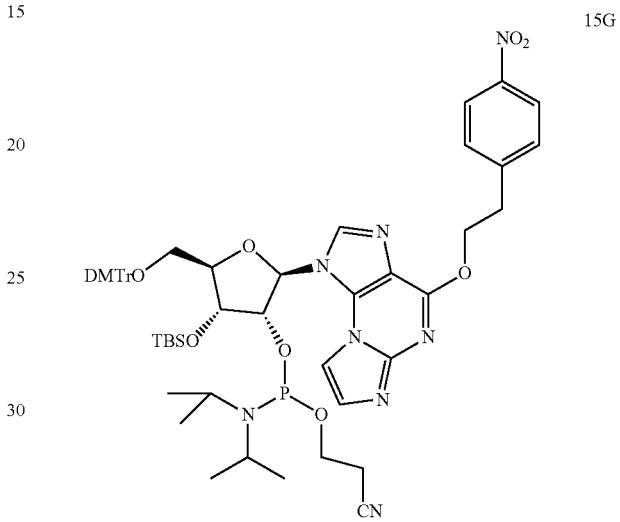

To a solution of Intermediate 15E (0.52 g, 0.596 mmol) in DCM (10 mL) at RT under N$_2$, was added 1H-imidazole-4,5-dicarbonitrile (0.596 ml, 0.596 mmol) (1 M in ACN), followed by the dropwise addition of 3-((bis(diisopropylamino)phosphaneyl) oxy)propanenitrile (0.359 g, 1.191 mmol). The mixture was stirred at RT overnight, and then diluted with DCM (60 mL), and washed with 10% NaHCO$_3$ aq. The aqueous layer was extracted with additional DCM (30 mL). The combined DCM layers were dried over Na$_2$SO$_4$ filtered and concentrated. The residue was purified on an ISCO system (12 g column, 0-100% EtOAc/DCM with 0.25% TEA eluted over 18 min) to give a pair of diastereomers of Intermediate 15G (0.52 g, 0.484 mmol) as a white solid. LCMS, [M+H]$^+$=1073.

Preparation of Intermediate 15I:

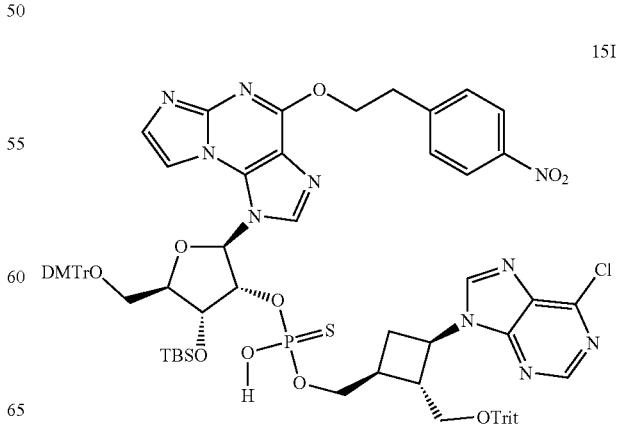

Intermediate 15I was prepared from 1H-tetrazole (53.5 mg, 0.764 mmol), Intermediate 2F (195 mg, 0.382 mmol), Intermediate 15G (410 mg, 0.382 mmol) and DDTT (86 mg, 0.420 mmol) following the procedure described for Intermediate 7F. The crude was purified on silica (4 g column, eluted with 0-10% MeOH/DCM with 0.25% TEA over 15 min) to give Intermediate 15I (500 mg, 0.274 mmol). LCMS, $[M+H]^+=1463$.

Preparation of Intermediate 15J:

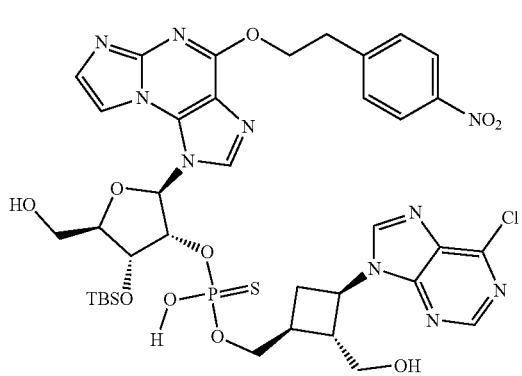

15J

Intermediate 15I (0.5 g, 0.342 mmol) in 20 mL of DCM was treated with triethylsilane (0.546 ml, 3.42 mmol) and 2,2-dichloroacetic acid (0.282 ml, 3.42 mmol).

The solution turned from bright pink to colorless over ~3 hours indicating completion of the reaction. The reaction mixture was diluted with DCM (30 mL), washed with sat'd NaHCO₃ aq., dried over Na₂SO₄, filtered and then concentrated in vacuo. The residue was purified on silica (12 g column, eluted with 0-20% MeOH/DCM over 18 min) to give Intermediate 15J (233 mg, 0.254 mmol). LCMS, $[M+H]^+=917$.

Preparation of Intermediate 15K

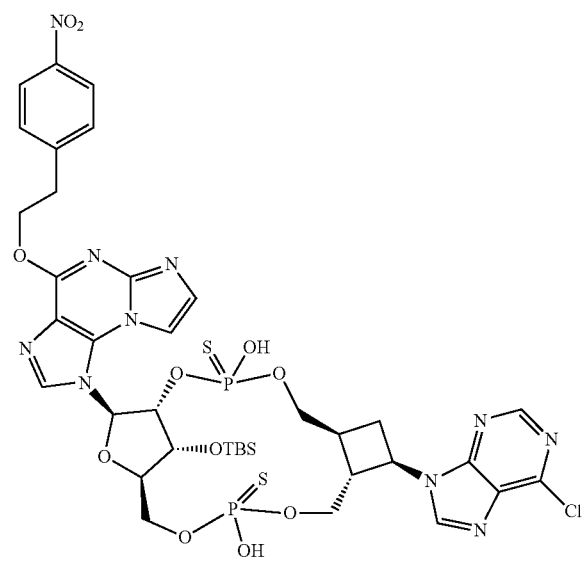

15K

Intermediate 15J (233 mg, 0.254 mmol) was co-evaporated with pyridine (2 mL), then dissolved in pyridine (10 mL). To this pyridine solution was added diphenyl phosphonate (0.098 mL, 0.508 mmol) dropwise over 20 minutes. (E)-N,N-dimethyl-N'-(3-thioxo-3H-1,2,4-dithiazol-5-yl)formimidamide (156 mg, 0.762 mmol) was then added and the reaction mixture was stirred at room temperature for 16 hours. The mixture was then concentrated in vacuo and the residue was suspended in methanol to form a yellow precipitate that was removed by filtration. The filtrate was concentrated in vacuo and the resulting residue, in MeOH (10 mL), was co-evaporated with celite (5 g), loaded onto a column and purified on a reverse phase ISCO Gold 50 g C18 column (Mobile Phase A: 5:95 acetonitrile:water with 0.01M ammonium acetate; Mobile Phase B: 95:5 acetonitrile:water with 0.01M ammonium acetate; Gradient: 0-50% B over 14 min, hold at 50% gradient for 5 min.) to give a mixture of four diastereomers of Intermediate 15K (110 mg, 0.111 mmol) LCMS, $[M+H]^+=995$.

Preparation of Intermediate 15L:

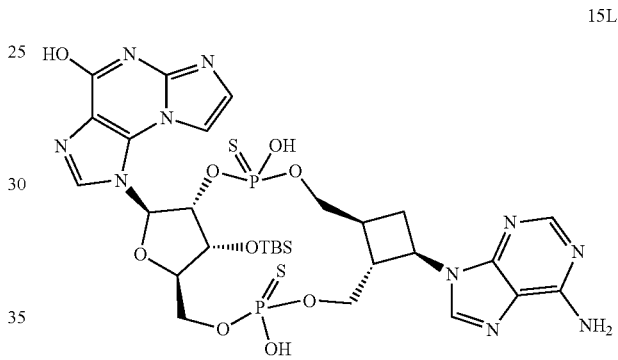

15L

Intermediate 15K (110 mg, 0.111 mmol) in 4 mL of 27% ammonium hydroxide was heated at 50° C. for 3 hours, then concentrated in vacuo. The residue was dissolved in 5 mL of pyridine and DBU (218 μl, 0.884 mmol) was added. The reaction was stirred at RT overnight for 18 h. To the reaction mixture was added 3 g of celite and then the mixture was concentrated in vacuo. The resulting solid was loaded onto a column and purified on a reverse phase ISCO Gold 50 g C18 column (Mobile Phase A: 5:95 acetonitrile:water with 0.01M ammonium acetate; Mobile Phase B: 95:5 acetonitrile:water with 0.01M ammonium acetate; Gradient: 0-40% B over 20 min, hold at 40% gradient for 10 min.) to give 4 isolates containing diastereomers of Intermediate 15L (Isolate 1: 17 mg, 0.021 mmol); (Isolate 2: 20 mg, 0.024 mmol); (Isolate 3: 15 mg, 0.018 mmol), (Isolate 4: 20 mg, 0.024 mmol), LCMS, $[M+H]^+=827$.

Example 15

(1R,6S,8R,9R,15R,17R,18R)-8-(6-amino-9H-purin-9-yl)-3,12,18-trihydroxy-17-{4-hydroxy-1H-imidazo[2,1-b]purin-1-yl}-2,4,11,13,16-pentaoxa-3λ$^5$,12λ$^5$-diphosphatricyclo[13.2.1.0$^{6,9}$]octadecane-3,12-dithione

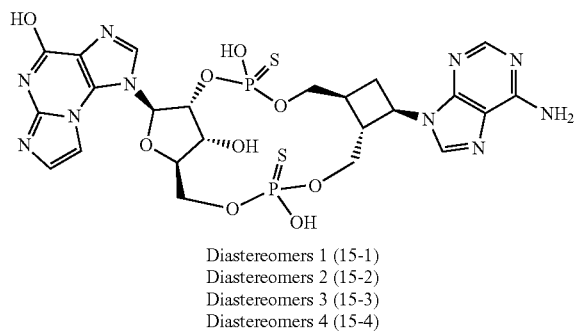 [SMILES: Nc1ncnc2c1ncn2[C@@H]1C[C@@H]2COP(O)(=S)O[C@@H]3[C@H](O)[C@@H](COP(O)(=S)OC[C@H]21)O[C@H]3n1cnc2c(O)nc3nccn3c21]

Diastereomers 1 (15-1)
Diastereomers 2 (15-2)
Diastereomers 3 (15-3)
Diastereomers 4 (15-4)

Separately, Isolates 1-4 of Intermediate 15L were dissolved in 0.4 mL of trihydrofluoride triethylamine complex and stirred at 37° C. for 2 h. To each reaction mixture, 2 M NH$_4$OAc aq. (2 mL) was added and stirred for 10 min. Then each reaction was filtered and purified by Preparative HPLC.

Isolate 1:
Chromatographic Conditions: Instrument: Waters Autopure; Column: Xselect RP Prep C18 OBD column, 5 µm, 19×150 mm; Flow rate: 20.0 mL/min; Mobile Phase: A: 100 mM NH$_4$OAc in H2O (PH 6.5); B: MeOH (% A=100−% B); Gradient; 5-26% B over 26.5 min, 26-95% B over 0.5 min, 95-5% B over 1 min; Detection: 260 nm; to afford Example 15-1

Example 15-1

1.2 mg; $t_R$: 8.42 min; M+1 obs=713.2; Analytical HPLC Chromatographic Conditions A: $^1$H NMR (499 MHz, METHANOL-d$_4$) δ 8.72 (s, 1H), 8.31 (s, 1H), 8.19 (s, 1H), 7.88 (d, J=2.0 Hz, 1H), 7.22 (d, J=1.9 Hz, 1H), 6.38 (d, J=8.0 Hz, 1H), 5.12 (br d, J=4.1 Hz, 1H), 4.61 (d, J=4.4 Hz, 1H), 4.47 (br d, J=2.3 Hz, 1H), 4.28 (br dd, J=5.6, 1.9 Hz, 1H), 4.26-4.13 (m, 4H), 4.08 (dt, J=11.1, 3.5 Hz, 1H), 4.03-3.93 (m, 1H), 2.64-2.50 (m, 2H), 2.21 (br d, J=9.3 Hz, 2H).

Isolate 2:
Chromatographic Conditions: Instrument: Waters Autopure; Column: Xselect RP Prep C18 OBD column, 5 µm, 19×150 mm; Flow rate: 20.0 mL/min; Mobile Phase: A: 100 mM NH$_4$OAc in H2O (PH 6.5); B: MeOH (% A=100−% B); Gradient; 5-16.8% B over 17 min, 16.8-95% B over 0.5 min, 95-5% B over 1 min; Detection: 260 nm; to afford Example 15-2.

Example 15-2

2.6 mg; $t_R$: 9.57 min; M+1 obs=712.3; Analytical HPLC Chromatographic Conditions A: $^1$H NMR (499 MHz, METHANOL-d$_4$) δ 8.44 (s, 1H), 8.37 (s, 1H), 8.19 (s, 1H), 7.96 (d, J=1.4 Hz, 1H), 7.21 (d, J=1.5 Hz, 1H), 6.35 (d, J=7.9 Hz, 1H), 5.20-5.08 (m, 1H), 4.83-4.73 (m, 1H), 4.67-4.54 (m, 2H), 4.46 (d, J=1.5 Hz, 1H), 4.24-4.12 (m, 2H), 4.11-3.95 (m, 3H), 3.27-3.17 (m, 1H), 2.65 (dt, J=10.7, 8.0 Hz, 1H), 2.40 (td, J=8.7, 4.2 Hz, 1H), 2.22-2.13 (m, 1H).

Isolate 3:
Chromatographic Conditions: Instrument: Waters Autopure; Column: Xselect RP Prep C18 OBD column, 5 µm, 19×150 mm; Flow rate: 20.0 mL/min; Mobile Phase: A: 100 mM NH$_4$OAc in H2O (PH 6.5); B: MeOH (% A=100−% B); Gradient; 5-16.8% B over 17 min, 16.8-95% B over 0.5 min, 95-5% B over 1 min; Detection: 260 nm; to afford Example 15-3.

Example 15-3

2.6 mg; $t_R$: 9.22 min; M+1 obs=712.3; Analytical HPLC Chromatographic Conditions A: $^1$H NMR (499 MHz, METHANOL-d$_4$) δ 8.67 (s, 1H), 8.32 (s, 1H), 8.19 (s, 1H), 7.87 (d, J=2.1 Hz, 1H), 7.22 (d, J=2.0 Hz, 1H), 6.35 (d, J=8.0 Hz, 1H), 5.15 (td, J=8.0, 4.2 Hz, 1H), 4.97 (d, J=4.2 Hz, 1H), 4.90-4.87 (m, 1H), 4.51 (d, J=2.6 Hz, 1H), 4.39-4.22 (m, 2H), 4.20-4.00 (m, 3H), 3.94 (dt, J=10.1, 8.2 Hz, 1H), 3.27-3.16 (m, 1H), 2.70 (td, J=9.2, 2.7 Hz, 1H), 2.55 (dt, J=10.6, 8.2 Hz, 1H), 2.36-2.20 (m, 1H).

Isolate 4:
Chromatographic Conditions: Instrument: Waters Autopure; Column: Xselect RP Prep C18 OBD column, 5 µm, 19×150 mm; Flow rate: 20.0 mL/min; Mobile Phase: A: 100 mM NH$_4$OAc in H2O (PH 6.5); B: MeOH (% A=100−% B); Gradient; 5-26% B over 26.5 min, 26-95% B over 0.5 min, 95-5% B over 1 min; Detection: 260 nm; to afford Example 15-4

Example 15-4

1.0 mg; $t_R$:11.64 min; M+1 obs=712.3; Analytical HPLC Chromatographic Conditions A: $^1$H NMR (499 MHz, METHANOL-d$_4$) δ 8.43 (s, 1H), 8.38 (s, 1H), 8.19 (s, 1H), 7.89 (d, J=2.1 Hz, 1H), 7.21 (d, J=2.0 Hz, 1H), 6.33 (d, J=7.6 Hz, 1H), 5.24-5.15 (m, 1H), 4.78 (d, J=8.7 Hz, 1H), 4.50 (br d, J=2.1 Hz, 2H), 4.42-4.27 (m, 2H), 4.23 (ddd, J=10.3, 5.8, 3.9 Hz, 1H), 4.15-4.08 (m, 1H), 4.07-4.03 (m, 1H), 3.96-3.86 (m, 1H), 3.24-3.14 (m, 1H), 2.63 (dt, J=10.4, 8.1 Hz, 1H), 2.59-2.48 (m, 1H), 2.30-2.19 (m, 1H).

Analytical HPLC Chromatographic Conditions A:
Instrument: Agilent 1290 HPLC/MS; Column: Xselect CSH C18 Column 3.5 µm, 3.0×150 mm; Flow rate: 0.5 mL/min; Mobile Phase: A: 20 mM NH4OAc (pH 6.5); B: MeOH (% A=100−% B); Gradient: 0-40% B in 23 min, 40% B-95% B in 1 min

Example 16

(1S,6S,8R,9R,15R,17R,18R)-8-(6-amino-9H-purin-9-yl)-3,12,18-trihydroxy-17-(6-hydroxy-9H-purin-9-yl)-2,4,11,13,16-pentaoxa-3λ$^5$,12λ$^5$-diphosphatricyclo[13.3.0.0$^{6,9}$]octadecane-3,12-dithione

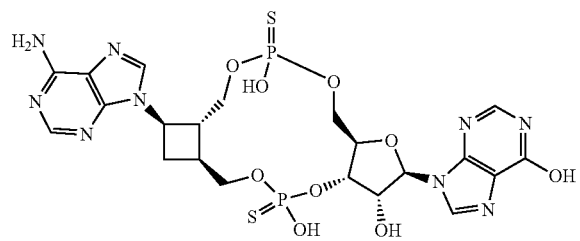

Preparation of Intermediate 16A:

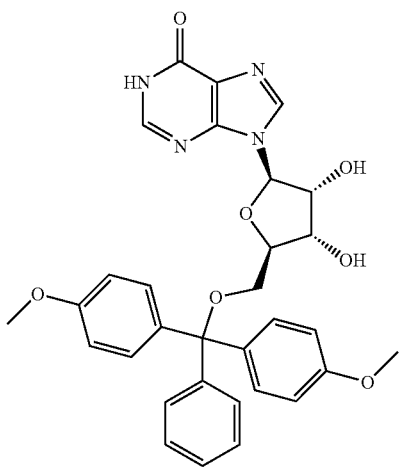

16A

DMTr-Cl (60.6 g, 179 mmol) was added in one portion to a suspension of 9-((2R,3R,4S,5R)-3,4-dihydroxy-5-(hydroxymethyl)tetrahydrofuran-2-yl)-1H-purin-6(9H)-one (Sigma, 40 g, 149 mmol) in anhydrous pyridine (1.5 L). The reaction mixture was stirred at RT over the weekend. The reaction was then quenched by the addition of methanol and the mixture was evaporated in vacuo. The residue was taken up in DCM and washed with sat'd aqueous sodium bicarbonate solution. The organic layer was dried (Na$_2$SO$_4$), filtered and evaporated in vacuo to give crude product, which was purified by flash chromatography over 1.5 kg of silica gel: mobile phase A; DCM, mobile phase B: 20% MeOH in DCM; Gradient 0-25% B over 10.5 min, 25-75% B over 2.5 min, 75% B hold for 2 min to afford Intermediate 16A (25.3 g). LCMS, [M+H]$^+$=571.

Preparation of Intermediate 16B:

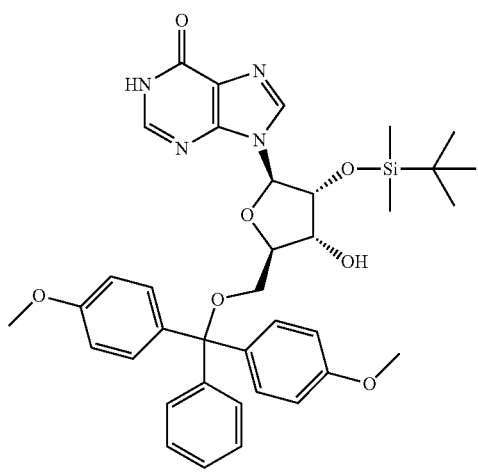

16B

TBDMS-Cl (10.02 g, 66.5 mmol) was added in one portion to a solution of Intermediate 16A (25.3 g, 44.3 mmol) and imidazole (9.06 g, 133 mmol) in anhydrous pyridine (296 ml). The reaction mixture was stirred at RT overnight. Additional imidazole (4.53 g, 66.5 mmol) and TBDMS-Cl (5.01 g, 33.3 mmol) were added and reaction was stirred overnight. The reaction mixture was then concentrated to dryness and the crude material was purified by flash chromatography over 1.5 kg of silica gel: Mobile phase A; DCM; Mobile phase B; EtOAc: Gradient: 0-50% B over 8 min, 50% B hold for 2 min to afford Intermediate 16B (25.3 g). LCMS, [M+H]$^+$=685.

Preparation of Intermediate 16C

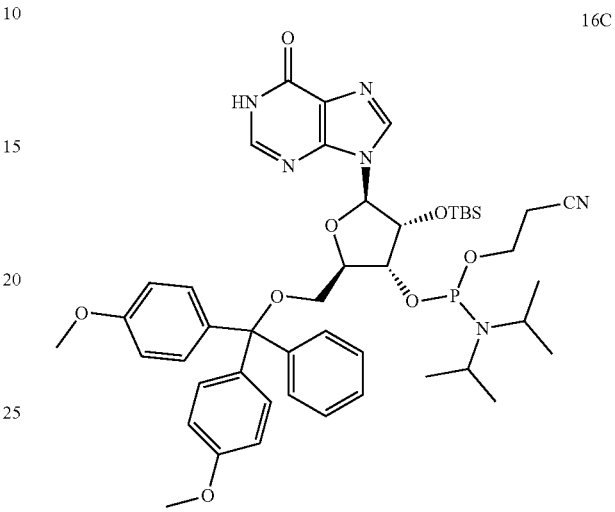

16C

To a solution of Intermediate 16B (10 g, 14.60 mmol) in anhydrous DCM (60 mL) was added 1H-imidazole-4,5-dicarbonitrile (1 M in MeCN, 10.22 mL, 10.22 mmol) followed by dropwise addition of 3-((bis(diisopropylamino)phosphino)oxy)propanenitrile (5.72 g, 18.98 mmol). The mixture was stirred at RT overnight. The reaction was then quenched with anhydrous MeOH (2 mL) and stirred for 10 min. The mixture was diluted with DCM, washed with saturated aq. NaHCO$_3$, dried over MgSO$_4$, TEA (1 mL) was added, filtered and the filtrate was concentrated. The residue was purified by silica gel chromatography (40 g column was equilibrated with 0.5% TEA/DCM, eluted with gradient 0-50% EtOAc/DCM) to afford Intermediate 16C (8 g, 9.04 mmol).

Preparation of Intermediate 16D:

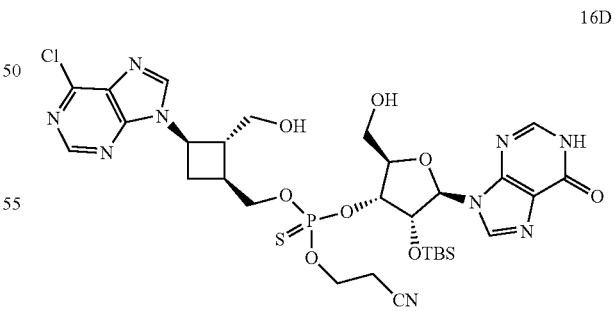

16D

A solution of Intermediate 2F (0.150 g, 0.294 mmol) and 1H-tetrazole (0.062 g, 0.881 mmol) in anhydrous acetonitrile (5 mL) was concentrated on rotary evaporator and the residue was dissolved anhydrous acetonitrile (5 mL). Separately, Intermediate 16C (0.403 g, 0.455 mmol) in anhydrous acetonitrile (5 mL) was concentrated on a rotary evaporator, then dissolved in anhydrous acetonitrile (2.5 mL) and added dropwise to the stirred mixture above at room temperature. After 3.5 h, (E)-N,N-dimethyl-N'-(3-thioxo-3H-1,2,4-dithiazol-5-yl)formimidamide (0.090 g, 0.440 mmol) was added and the mixture was stirred for 30 min. The reaction mixture was then concentrated in vacuo and the residue was purified by flash chromatography over silica gel (12 g column, eluted 0-100% gradient EtOAc/Hexane over 25 min) to give a white foam following concentration in vacuo. The resulting material was dissolved in DCM (5 mL) and triethylsilane (0.469 ml, 2.94 mmol), and dichloroacetic acid (0.114 g, 0.881 mmol) were added. The mixture was stirred for 3 h. Additional dichloroacetic acid was added, and the mixture was stirred another 3 hours. TFA (300 uL) was then added and the reaction mixture was stirred overnight. The reaction mixture was then quenched with MeOH and concentrated. The residue was dissolved in MeOH, neutralized with pyridine and concentrated. The residue was purified by flash chromatography over silica gel (0-50% MeOH/DCM, 12 g column, 25 min gradient) to afford Intermediate 16D (230 mg, 0.294 mmol). LCMS, [M+H]$^+$=782.

Preparation of Intermediate 16E:

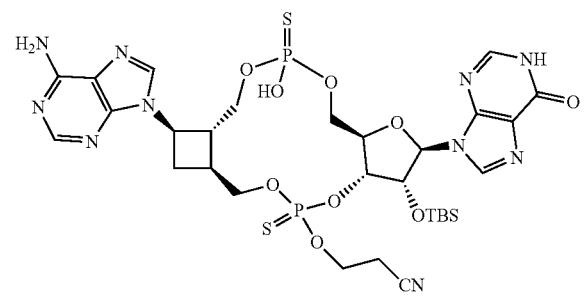

16E

To solution of Intermediate 16D (0.176 g, 0.228 mmol) in pyridine (11.38 mL) at room temperature was added diphenyl phosphonate (0.062 mL, 0.319 mmol) dropwise over 20 min. The reaction was quenched with (E)-N,N-dimethyl-N'-(3-thioxo-3H-1,2,4-dithiazol-5-yl)formimidamide (0.093 g, 0.455 mmol), stirred at RT for 16 hours and concentrated in vacuo. The residue was suspended in methanol, filtered and the filtrate was concentrated in vacuo. The resulting residue was purified by reverse phase ISCO (50 g of C18 with 0-100% gradient over 15 minutes; Mobile Phase A: 5:95 acetonitrile:water with 0.01M ammonium acetate; Mobile Phase B: 95:5 acetonitrile:water with 0.01M ammonium acetate) to give Intermediate 16E (50 mg, 0.058 mmol) as a mixture of diastereomers. LCMS, [M+H]$^+$=860.

Example 16

(1S,6S,8R,9R,15R,17R,18R)-8-(6-amino-9H-purin-9-yl)-3,12,18-trihydroxy-17-(6-hydroxy-9H-purin-9-yl)-2,4,11,13,16-pentaoxa-3λ$^5$,12λ$^5$-diphosphatricyclo[13.3.0.0$^{6,9}$]octadecane-3,12-dithione

16

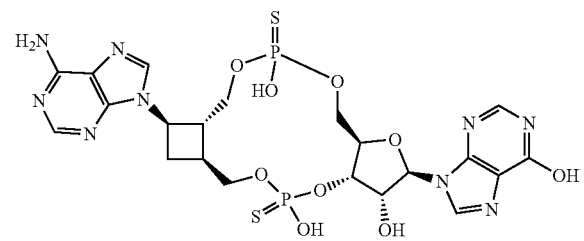 [SMILES: Nc1ncnc2c1ncn2[C@@H]1C[C@@H]2COP(O)(=S)O[C@H]3[C@@H](O)[C@H](n4cnc5c(O)ncnc54)O[C@@H]3COP(O)(=S)OC[C@H]21]

To Intermediate 16E (50 mg, 0.058 mmol) was added ammonium hydroxide (2 mL, 51.4 mmol) and the reaction was stirred at 50° C. for 10 h. The reaction mixture was concentrated, azeotroped in pyridine, and triethylamine trihydrofluoride (0.8 mL, 4.91 mmol) was added. The mixture was stirred at 37° C. for 2 h and then quenched with NH$_4$Ac (1 M, 2 mL) and purified by preparative LC/MS with the following conditions: Column: Agilent Bonus RP 21.2×100 mm, 5-μm particles; Mobile Phase A: water with 20-mM ammonium acetate; Mobile Phase B: acetonitrile; Gradient: 0% B hold 0-6 minute. 0%-100% B over 20 minutes, then a 4-minute hold at 100% B; Flow: 20 mL/min. Fractions containing the desired product were combined and dried via centrifugal evaporation to afford a mixture of all four diastereomers. Observed Mass: 674; Retention Time: 2.11 min. Analytical LC/MS method: Column: Agilent Poroshell 120 Bonus-RP, 2.1 mm×100 mm, 2.7 μm particles; Mobile Phase A: water with 20-mM ammonium acetate; Mobile Phase B: acetonitrile; Gradient: 0% B hold 0-1 minute. 0%-100% B over 4 minutes, then a 0.5-minute hold at 100% B; Flow:1 mL/min; Detection: MS and UV (220 nm).

Preparation of Phosphorus (V) Reagents

Reagent 1

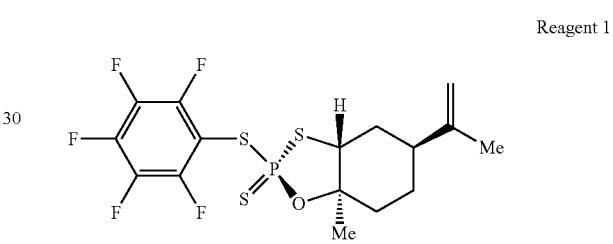

Reagent 2

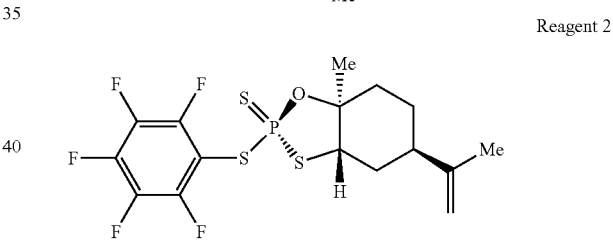

Reagent 3

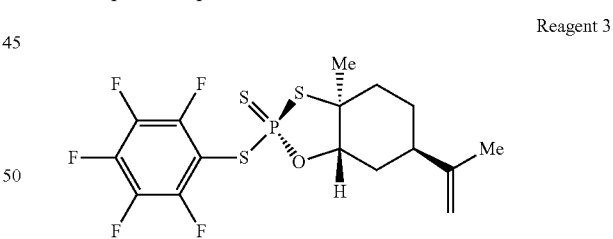

Reagent 4

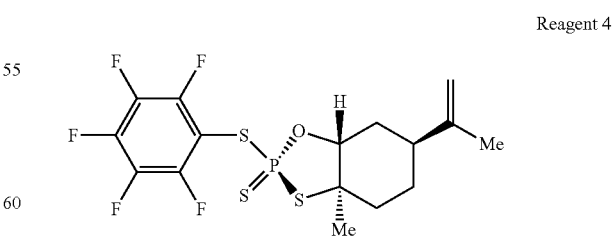

The phosphorus (V) reagents (Reagents 1-4) used in the preparation of Examples 17 and 18 were prepared according to the procedures provided in U.S. Ser. No. 62/657,551 filed Apr. 13, 2018.

Examples 17-1 and 17-2

(1R,6S,8R,9R,15R,17R,18S)-8,17-bis(6-amino-9H-purin-9-yl)-18-fluoro-3,12-dihydroxy-2,4,11,13,16-pentaoxa-3λ⁵,12λ⁵-diphosphatricyclo[13.3.0.0⁶,⁹]octadecane-3,12-dithione

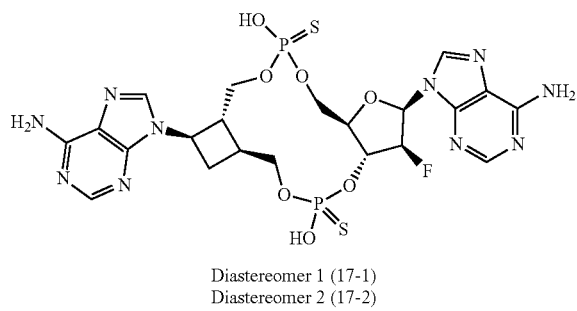 [SMILES: Nc1ncnc2c1ncn2[C@@H]1C[C@@H]2COP(O)(=S)O[C@H]3[C@H](F)[C@H](n4cnc5c(N)ncnc54)O[C@@H]3COP(O)(=S)OC[C@H]21]

Diastereomer 1 (17-1)
Diastereomer 2 (17-2)

Preparation of Intermediate 17A:

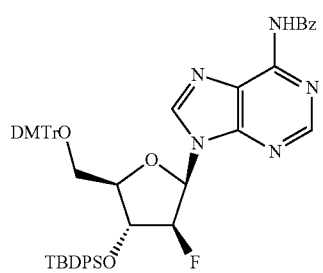

To a 50 mL flask was added N-(9-((2R,3S,4R,5R)-5-((bis(4-methoxyphenyl)(phenyl)methoxy)methyl)-3-fluoro-4-hydroxytetrahydrofuran-2-yl)-9H-purin-6-yl)benzamide (WO2004097049, 1 g, 1.480 mmol), imidazole (0.302 g, 4.44 mmol) and anhydrous DMF (3 mL). To the resulting pale brown solution was dropwise added TBDPS-Cl (0.570 mL, 2.22 mmol) over a 5 minute period. The resulting reaction mixture was stirred under a nitrogen atmosphere at room temperature for 40 h. The reaction mixture was quenched with methanol, stirred for 10 minutes, diluted with EtOAc (100 mL), and washed with water (2×100 mL) followed by brine (1×100 mL). The organic layer was dried over sodium sulfate, filtered and concentrated. The resulting pale yellow gum was dissolved in minimal DCM (containing 0.5% TEA) and purified by silica gel chromatography using 0-100% EtOAc in hexanes (containing 0.5% triethylamine). The product containing fractions were combined and concentrated to afford Intermediate 17A (1.13 g, 1.236 mmol). LCMS: m/z 914.0 (M+H), $t_R$:1.44 min, Analytical LCMS method A. ¹H NMR (499 MHz, DMSO-d₆) δ 11.21 (br s, 1H), 8.51 (s, 1H), 8.29 (d, J=1.5 Hz, 1H), 8.03 (d, J=7.3 Hz, 2H), 7.69-7.58 (m, 1H), 7.58-7.46 (m, 8H), 7.37 (td, J=7.5, 4.4 Hz, 4H), 7.25-7.14 (m, 5H), 7.12-7.04 (m, 4H), 6.78-6.72 (m, 4H), 6.66 (dd, J=12.0, 5.2 Hz, 1H), 5.69-5.45 (m, 1H), 4.86-4.69 (m, 1H), 4.37-4.22 (m, 1H), 3.70 (d, J=3.6 Hz, 6H), 3.23-3.03 (m, 2H), 0.97 (s, 9H).

Preparation of Intermediate 17B:

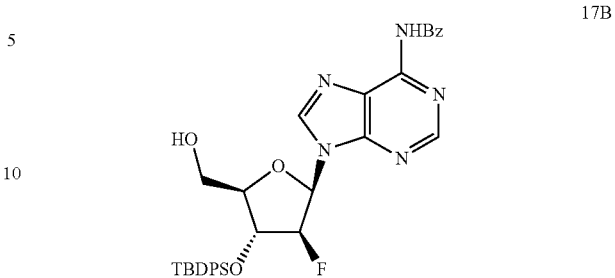

To a flask containing Intermediate 17A (1.12 g, 1.225 mmol) was added reagent grade DCM (20 mL), triethylsilane (1.566 mL, 9.80 mmol) and water (2 drops). To the resulting solution was dropwise added a solution of dichloroacetic acid (0.203 mL, 2.450 mmol) in DCM (1 mL). The resulting tan colored solution was stirred at room temperature for 5 h. To the reaction mixture was added saturated aqueous NaHCO₃ solution. The resulting mixture was extracted with DCM (3×25 mL). The combined organics were dried over sodium sulfate, filtered and concentrated. The gummy residue was dissolved in minimal DCM and purified by silica gel chromatography using a 80 g silica gel column and 0-10% MeOH in DCM over 25 min. The product containing fractions were combined and concentrated to afford Intermediate 17B (711 mg, 1.162 mmol). LCMS: m/z 612.5 (M+H), $t_R$: 1.04 min Analytical LCMS method A. ¹H NMR (499 MHz, DMSO-d₆) without F decoupling: δ 11.21 (br s, 1H), 8.72 (s, 1H), 8.45 (d, J=1.5 Hz, 1H), 8.11-7.99 (m, 2H), 7.71-7.61 (m, 5H), 7.59-7.42 (m, 8H), 6.63 (dd, J=14.7, 4.4 Hz, 1H), 5.53-5.34 (m, 1H), 5.00 (t, J=5.7 Hz, 1H), 4.71 (dt, J=17.8, 4.2 Hz, 1H), 4.09 (q, J=4.6 Hz, 1H), 3.54-3.36 (m, 2H), 1.08 (s, 9H).

Preparation of Intermediate 17C:

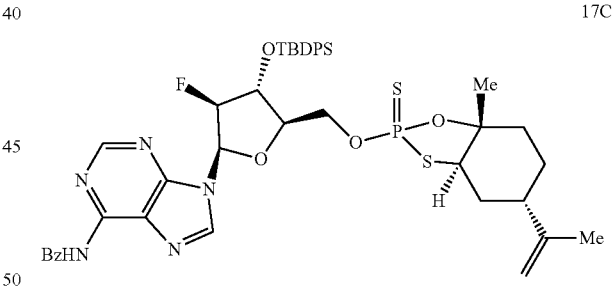

A 50 mL flask was charged with Intermediate 17B (100 mg, 0.163 mmol), Reagent 1 (146 mg, 0.327 mmol) and anhydrous acetonitrile (1.6 mL). To the resulting colorless clear solution was dropwise added DBU (0.074 mL, 0.490 mmol). The reaction mixture was stirred at RT for 15 min. The reaction mixture was then diluted with ether (20 mL) and washed with aq. NaHCO₃ (1 g NaHCO₃ in 20 mL water). The pale yellow organic layer was separated. The aq. layer was extracted with ether (1×10 mL). The combined organics was dried over sodium sulfate, filtered and concentrated. The residue was dissolved in minimal DCM and purified by silica gel chromatography (24 g silica column) using hexanes for 2 min, 0-60% EtOAc in hexanes over 7 min, hold at 60% EtOAc for 2 min, 60-100% EtOAc over 6 minutes. The product containing fractions were combined and concentrated to afford Intermediate 17C (132 mg, 0.154 mmol) as a colorless gum that was coevaporated with MeCN (3×) to obtain a white solid. This white powder was used in the next step. LCMS: m/z 858.6 (M+H), $t_R$: 1.25 min, Analytical LCMS method A.

Preparation of Intermediate 17G:

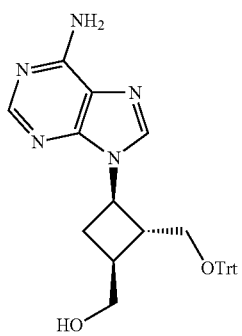

17G

To a steel bomb was added Intermediate 2E (1.94 g, 3.51 mmol) and dioxane (10 mL). To the resulting colorless solution was added 30% aqueous ammonium hydroxide (20 mL, 154 mmol). The resulting cloudy reaction mixture was heated at 70° C. for 2 d. The reaction mixture was then concentrated to dryness. The crude product was adsorbed onto Celite and was purified by silica gel chromatography using an 80 g column and eluting with 0-20% MeOH in DCM to afford Intermediate 17G (1.59 g, 3.23 mmol) as a white solid. LCMS: m/z 492.5 (M+H), $t_R$: 0.82 min Analytical LCMS method A. $^1$H NMR (499 MHz, CHLOROFORM-d) δ 8.32 (s, 1H), 7.72 (s, 1H), 7.42-7.33 (m, 6H), 7.31-7.18 (m, 9H), 5.61 (br s, 2H), 4.61 (q, J=8.6 Hz, 1H), 3.81-3.66 (m, 2H), 3.39 (dd, J=9.9, 5.5 Hz, 1H), 3.30 (dd, J=10.0, 6.5 Hz, 1H), 3.23 (br s, 1H), 3.08-2.98 (m, 1H), 2.63-2.48 (m, 2H), 2.36-2.25 (m, 1H).

Preparation of Intermediate 17H:

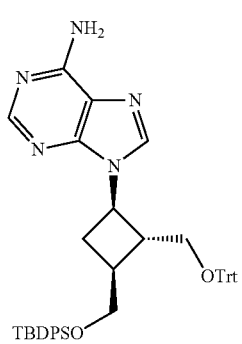

17H

To a flask containing Intermediate 17G (1.91 g, 3.89 mmol) was added imidazole (1.058 g, 15.54 mmol) and anhydrous DMF (6 mL). To the resulting solution was dropwise added TBDPSCl (1.497 mL, 5.83 mmol). The resulting reaction mixture was stirred under a nitrogen atmosphere for 40 h. To the reaction mixture was added additional imidazole (350 mg) and TBDPSCl (0.5 mL) and it was stirred at RT for an additional 1 h. The reaction was then quenched with methanol and stirred for 10 min.

The resulting mixture was diluted with EtOAc and washed with water (2×100 mL) and brine (1×100 mL). The organic layer was dried over sodium sulfate, filtered and concentrated. The resulting gum was purified by silica gel chromatography using 0-20% MeOH in DCM. The product containing fractions were combined and concentrated to afford Intermediate 17H (2.51 g, 3.44 mmol). LCMS: m/z 730.6 (M+H), $t_R$: 1.20 min, Analytical LCMS method A.

Preparation of Intermediate 17I:

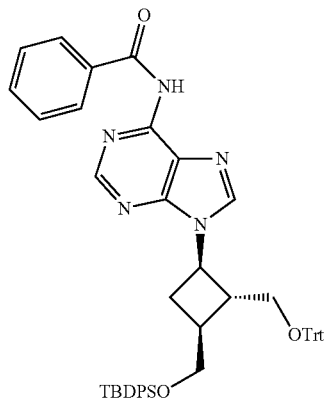

17I

A solution of Intermediate 17H (2.50 g, 3.42 mmol) in anhydrous pyridine (5 mL) was cooled in an ice water bath and then benzoyl chloride (0.48 mL, 4.11 mmol) was added dropwise. After 10 minutes at 0° C., the ice water bath was removed and the reaction was stirred at RT overnight. Water (~20 mL) was added and the product formed a solid gum. The water was decanted and the gum was dissolved in THF (~10 mL), 28-30% aq. NH$_4$OH (~6 mL) was added and the mixture was stirred vigorously at RT for 2 h. The reaction mixture then was concentrated in vacuo and the residue was diluted with EtOAc and washed with water (1×) and brine (1×). The organic phase was dried over sodium sulfate, filtered and concentrated. The residue was dissolved in minimal DCM and purified by silica gel flash chromatography on a 220 g column, using 0-100% EtOAc in hexanes. The product containing fractions were combined and concentrated to afford Intermediate 17I (2.56 g, 3.07 mmol) as a white foam. $^1$H NMR (499 MHz, CHLOROFORM-d) δ 8.94 (s, 1H), 8.76 (s, 1H), 8.10 (s, 1H), 8.07-8.00 (m, 2H), 7.70-7.60 (m, 5H), 7.58-7.51 (m, 2H), 7.47-7.30 (m, 12H), 7.25-7.17 (m, 9H), 4.86 (q, J=8.8 Hz, 1H), 3.75 (d, J=4.5 Hz, 2H), 3.34 (dd, J=9.8, 4.7 Hz, 1H), 3.27-3.18 (m, 1H), 3.17-3.06 (m, 1H), 2.64-2.54 (m, 1H), 2.53-2.41 (m, 1H), 2.39-2.25 (m, 1H), 1.06 (s, 9H).

Preparation of Intermediate 17J:

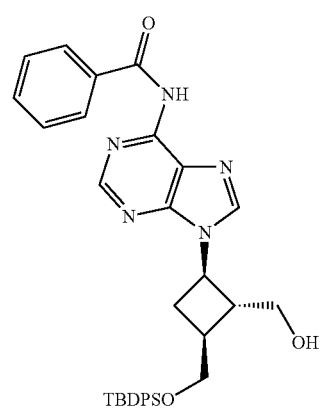

17J

To a solution of Intermediate 17I (300 mg, 0.360 mmol) in DCM (5 mL), triethylsilane (0.574 mL, 3.60 mmol) and water (2 drops) was added a solution of dichloroacetic acid (0.21 mL, 2.52 mmol) in DCM (1 mL) and the reaction was stirred at RT for 5 h. To the reaction mixture was added saturated aqueous NaHCO₃ and the aqueous layer was extracted with DCM (3×15 mL). The combined organics were dried over sodium sulfate and concentrated in vacuo. The residue was dissolved in minimal DCM and purified by flash chromatography using a 40 g silica gel column eluted 0-10% MeOH/DCM over 10 min. Fractions containing desired product were combined and concentrated to afford Intermediate 17J (188 mg, 0.318 mmol) as a white foam. $^1$H NMR (499 MHz, DMSO-$d_6$) δ 11.12 (br s, 1H), 8.68 (s, 1H), 8.54 (s, 1H), 8.10-8.00 (m, 2H), 7.70-7.61 (m, 5H), 7.59-7.52 (m, 2H), 7.51-7.41 (m, 6H), 4.82 (q, J=8.7 Hz, 1H), 4.70 (t, J=5.1 Hz, 1H), 3.88-3.75 (m, 2H), 3.65-3.48 (m, 2H), 3.08-2.98 (m, 1H), 2.52-2.24 (m, 3H, overlapping with DMSO peak), 1.02 (s, 9H). LCMS: m/z 592.5 (M+H), $t_R$: 1.04 min, Analytical LCMS method A.

Preparation of Intermediate 17D:

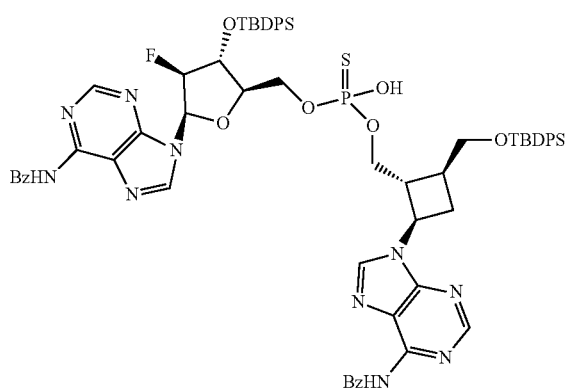

17D

To a 50 mL flask was added Intermediate 17J (45.5 mg, 0.077 mmol) and anhydrous acetonitrile (1 mL). The resulting suspension was co-evaporated with MeCN (3×1 mL). To the resulting white powder was added anhydrous acetonitrile (1 mL). To the resulting white suspension was added DBU (0.023 mL, 0.154 mmol) to obtain a clear solution. To this solution was added a sonicated fine suspension of Intermediate 17C (132 mg, 0.154 mmol, co-evaporated with MeCN three times) in anhydrous acetonitrile (3 mL) dropwise over 5 minutes. The resulting cloudy reaction mixture was stirred at room temperature for 1 h. The reaction mixture was then concentrated. To the residue was added MeCN (1 mL). The resulting solution was stirred at room temperature for 2 h. The reaction mixture was concentrated to <100 μL, acidified with acetic acid (0.026 mL, 0.461 mmol) and purified by silica gel chromatography using 0-30% MeOH in DCM to obtain Intermediate 17D (68 mg, 0.042 mmol).

Preparation of Intermediate 17E:

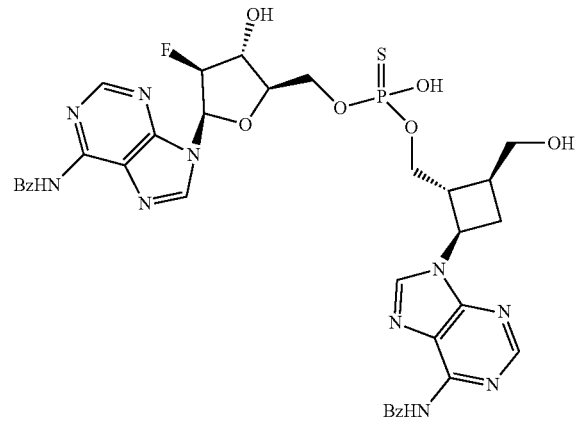

17E

To a flask containing Intermediate 17D (68 mg, 0.042 mmol) was added triethylamine trihydrofluoride (1 g, 6.20 mmol). The resulting suspension was stirred under nitrogen atmosphere at room temperature for 5 h. The reaction mixture was then diluted with MeCN (~3 mL) and the excess HF was quenched with triethylamine (1.8 mL, 12.73 mmol). The excess fluoride was then quenched with iso-propoxytrimethylsilane (2.8 mL, 21.22 mmol). The resulting reaction mixture was stirred for 10 min at room temperature and then concentrated to dryness. The residue was dissolved in MeCN, adsorbed onto Celite and purified by reverse phase silica gel chromatography.

Conditions: Column: 15.5 g HP C18; C18 RediSep High Performance GOLD; CV 13.5 mL, Recommended flow rate 30 mL/min. Teledyne ISCO cat #69-2203-334; Lot #281127806W; Solvent A: 95% water, 5% MeCN, NH₄Oac; Solvent B: 5% water, 95% MeCN, NH₄Oac; Gradient (in A): 0% B for 5 min, 0-50% B over 20 min. The desired product eluted at ~20% B. The product containing fractions were combined and concentrated to obtained Intermediate 17E (22 mg, 0.027 mmol). LCMS: m/z 805.5 (M+H), $t_R$: 0.63 min, Analytical LCMS method A.

Preparation of Intermediate 17F:

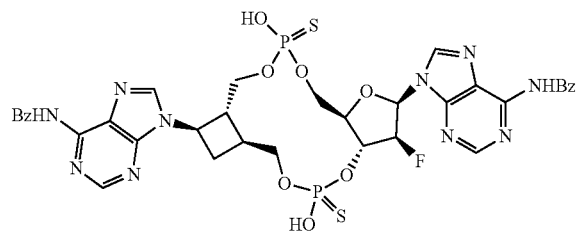

17F

To a flask containing Intermediate 17E (22 mg, 0.027 mmol), was added anhydrous DMF (3 mL) and DBU (0.062 mL, 0.410 mmol). To the resulting solution was portion wise added Reagent 4 (16.99 mg, 0.041 mmol) over a 10 minute period while stirring vigorously. After 20 min at room temperature, additional Reagent 4 (16.99 mg, 0.041 mmol) was added and the mixture was stirred at room temperature for an additional 30 min. The reaction mixture was quenched with methanol and concentrated. The resulting oil containing Intermediate 17F was used as such in the next step. LCMS: m/z 883.0 (M–H), $t_R$: 0.46 min, Analytical LCMS method A.

Examples 17-1 and 17-2

(1R,6S,8R,9R,15R,17R,18S)-8,17-bis(6-amino-9H-purin-9-yl)-18-fluoro-3,12-dihydroxy-2,4,11,13,16-pentaoxa-3$\lambda^5$,12$\lambda^5$-diphosphatricyclo[13.3.0.0$^{6,9}$]octadecane-3,12-dithione

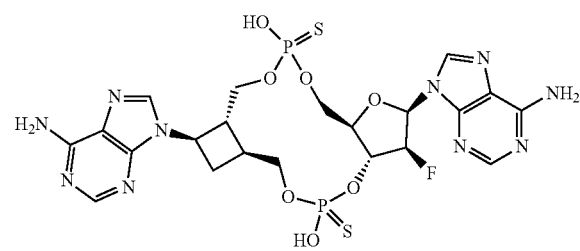

Diastereomer 1 (17-1)
Diastereomer 2 (17-2)

To the crude Intermediate 17F was added a methanolic solution of 7.0 N ammonia (4 mL, 28.0 mmol). The resulting solution was transferred to a 40 mL pressure vial and heated at 50° C. for 2 h. The reaction mixture was cooled to room temperature and concentrated. To the residue was added water followed by acetic acid until pH<5 was achieved. The sample was then diluted to ~2 mL, and filtered through a syringe filter. The filtrate was purified by preparative HPLC Chromatography. Conditions; Instrument: Waters Autopure; Column: Xselect RP Prep C18 OBD Column, 5 μm, 19×150 mm; Flow rate: 20 mL/min; Mobile Phase: A: 100 mM NH$_4$OAc (pH 6.5); B: ACN (% A=100–% B); Gradient: 5% B for 8 min; 5-26.5% B over 14 min, 26.5-95% B over 0.5 min, 95-5% B over 1.5 min to afford Examples 17-1 and 17-2 after lyophilization.

Example 17-1

1.5 mg; Observed Mass: 675.2; $t_R$: 14.32 min.; Analytical HPLC Chromatographic Conditions 8

Example 17-2

4.5 mg; Observed Mass: 675.2; $t_R$: 14.62 min.; Analytical HPLC Chromatographic Conditions 8
Analytical HPLC Chromatographic Conditions 8:

Instrument: Agilent 1290 HPLC/MS; Column: Xselect CSH C18 Column, 3.5 μm, 3.0×150 mm; Flow rate: 0.5 mL/min; Mobile Phase: A: 20 mM NH$_4$OAc (pH 6.5); B: ACN (% A=100–% B); Gradient: 5% B for 10 min; 5-50% B over 15 min, 50-95% B over 1 min.

Examples 18-1, 18-2

2-amino-9-[(1R,6S,8R,9R,15R,17R,18R)-17-(6-amino-9H-purin-9-yl)-18-fluoro-3,12-dihydroxy-3,12-disulfanylidene-2,4,11,13,16-pentaoxa-3$\lambda^5$,12$\lambda^5$-diphosphatricyclo[13.3.0.0$^{6,9}$]octadecan-8-yl]-6,9-dihydro-1H-purin-6-one Diastereomer 1 (18-1)
Diastereomer 2 (18-2)

Preparation of Intermediate 18A:

18A

A mixture of N-(9-((2R,3R,4R,5R)-5-((bis(4-methoxyphenyl) (phenyl)methoxy)methyl)-3-fluoro-4-hydroxytetrahydrofuran-2-yl)-9H-purin-6-yl)benzamide (AstraTech, 503 mg, 0.744 mmol) and Reagent 4 (499 mg, 1.117 mmol) was azeotropically dried with ACN (3×3 mL) with sonication between each azeotrope to free solids from the vessel walls. The resulting white solid was suspended in acetonitrile (5 mL). DBU (0.223 mL, 1.489 mmol) was dropwise added. After 20 minutes the reaction was quenched with acetic acid (0.224 mL, 3.72 mmol), stirred for a few minutes, diluted with ethyl acetate, transferred to a separatory funnel, washed with sat NaHCO$_3$, dried over anhydrous sodium sulfate, filtered and concentrated. The residue was dissolved in a minimum of dichloromethane and purified on an ISCO companion chromatography system (40 g silica cartridge, eluting with 0-100% ethyl acetate/hexanes, 40 ml/min). Fractions containing desired product were combined and concentrated to provide Intermediate 18A (654 mg, 0.709 mmol) as a white foam. LCMS, [M+H]$^+$=922. 1H NMR (499 MHz, CHLOROFORM-d) δ 9.13-8.95 (m, 1H), 8.77 (s, 1H), 8.24 (s, 1H), 8.12-7.97 (m, 2H), 7.69-7.61 (m, 1H), 7.59-7.53 (m, 2H), 7.46-7.39 (m, 2H), 7.36-7.19 (m, 7H), 6.82 (d, J=8.9 Hz, 4H), 6.44-6.32 (m, 1H), 6.02-5.84 (m, 1H), 5.83-5.74 (m, 1H), 5.09-4.97 (m, 1H), 4.92-4.82 (m, 1H), 4.60-4.42 (m, 2H), 3.80 (s, 6H), 3.67-3.55 (m, 1H), 3.52-3.38 (m, 1H), 2.65-2.53 (m, 1H), 2.29-2.21 (m, 1H), 2.21-2.10 (m, 1H), 2.03-1.84 (m, 3H), 1.81-1.77 (m, 4H), 1.76-1.73 (m, 3H).

Preparation of Intermediate 18B:

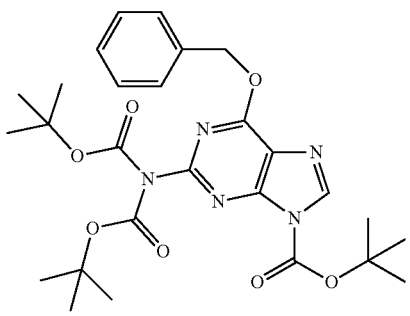

Di-tert-butyl dicarbonate (9.77 g, 44.8 mmol) was added to a suspension of 6-(benzyloxy)-9H-purin-2-amine (Accela, 3 g, 12.44 mmol) and N,N-dimethylpyridin-4-amine (0.152 g, 1.244 mmol) in THF (100 mL). The resulting clear light green solution was stirred overnight at room temperature. The THF was then removed in vacuo. The resulting residue was dissolved in dichloromethane, washed with 1M HCl and brine, dried over anhydrous sodium sulfate, filtered and concentrated. The resulting residue was dissolved in a minimum of dichloromethane and purified on an ISCO companion chromatography system (220 g silica cartridge, eluting with 0-100% ethyl acetate/hexanes, 150 ml/min). Fractions containing desired product were combined and concentrated to give the Intermediate 18B (5.3 g, 9.79 mmol) as a white solid. LCMS, [M+H]$^+$=542. $^1$H NMR (499 MHz, DMSO-$d_6$) δ 8.74 (s, 1H), 7.59-7.48 (m, 2H), 7.46-7.33 (m, 3H), 5.70-5.52 (m, 2H), 1.62 (s, 9H), 1.42 (s, 18H)

Preparation of Intermediate 18C.

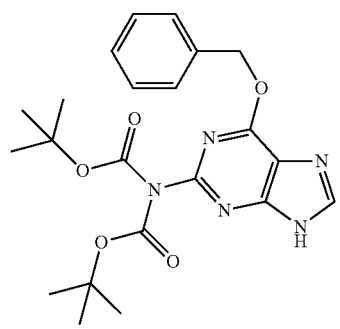

Saturated sodium bicarbonate (50 mL, 9.73 mmol) was added to a solution of Intermediate 18B (5.27 g, 9.73 mmol) in MeOH (100 mL). The reaction mixture was warmed to 50° C. for 2 hours, then cooled to room temperature and then most of the methanol was removed on a rotovap. Water (50 mL) was added, and the resulting mixture was extracted with dichloromethane (3×50 mL). The combined dichloromethane extracts were dried over anhydrous sodium sulfate, filtered and concentrated to provide a white foam. The foam was dissolved in a minimum of dichloromethane and purified on an ISCO companion chromatography system (220 g silica cartridge, eluting with 0-5% methanol/dichloromethane, 150 ml/min). Fractions containing desired product were combined and concentrated to afford Intermediate 18C (3.74 g, 8.47 mmol). LCMS, [M+H]$^+$=442. $^1$H NMR (499 MHz, DMSO-$d_6$) δ 13.73-13.49 (m, 1H), 8.64-8.27 (m, 1H), 7.57-7.48 (m, 2H), 7.45-7.27 (m, 3H), 5.70-5.53 (m, 2H), 1.39 (s, 18H)

Preparation of Intermediate 18D.

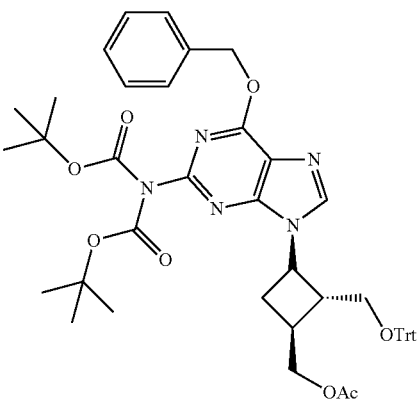

Diisopropyl (E)-diazene-1,2-dicarboxylate (1.242 mL, 5.99 mmol) was dropwise added to a 0° C. solution of triphenylphosphine (1.572 g, 5.99 mmol) in THF (20 mL) and toluene (10 mL). After 20 min at 0° C., a solution of Intermediate 2D (1.248 g, 3.00 mmol), Intermediate 18C (1.984 g, 4.49 mmol) in THF (20 mL) and toluene (10 mL) was added to the DEAD/Ph$_3$P mixture via cannula. The flask was rinsed with THF (10 mL) and toluene (5 mL) and transferred via cannula to the reaction mixture. After 1 h., the cooling bath was removed and the reaction was stirred at room temperature overnight. The reaction was then concentrated on a rotovap. The residue was dissolved in a minimum of dichloromethane and purified on an ISCO companion chromatography system (220 g silica cartridge, eluting with 0-25% ethyl acetate/dichloromethane, followed by 25-100% ethyl acetate/dichloromethane 150 ml/min). Fractions containing desired product were combined and concentrated to provide Intermediate 18D (2.32 g, 2.76 mmol) as a white foam. LCMS, [M+H]$^+$=840; $^1$H NMR (499 MHz, CHLOROFORM-d) δ 7.99-7.79 (m, 1H), 7.57-7.51 (m, 2H), 7.28 (s, 18H), 5.75-5.50 (m, 2H), 5.15-4.95 (m, 1H), 4.26-4.16 (m, 2H), 3.36-3.20 (m, 2H), 3.13-2.97 (m, 1H), 2.72-2.59 (m, 1H), 2.54-2.35 (m, 2H), 2.05-2.00 (m, 3H), 1.45-1.38 (m, 18H).

Preparation of Intermediate 18E.

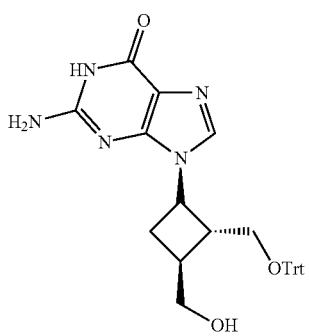

Potassium hydroxide (1.46 g, 26.0 mmol) was added to a room temperature solution of Intermediate 18D (2.18 g, 2.60 mmol) in MeOH (50 mL) and water (20 mL). The resulting solution was refluxed (80° C.) for 10 days. On day 1 after 5 h, water (10 mL) was added. Additional KOH (0.8 g) dissolved in water (6 mL) was added on both days 2 and 3. On day 10 the reaction was cooled to RT. Most of the methanol was removed on a rotovap. The residue was diluted with water and adjusted to pH 4 with 1M HCl. The resulting white precipitate was collected by vacuum filtration and washed with water to provide a white solid that was dried under high vacuum overnight at 50° C. The solid was further dried on a lyophilizer for 2 days to provide Intermediate 18E (1.84 g, 3.62 mmol) as a white solid. Intermediate 18E was used without further purification. LCMS, [M+H]$^+$=508.

Preparation of Intermediate 18F:

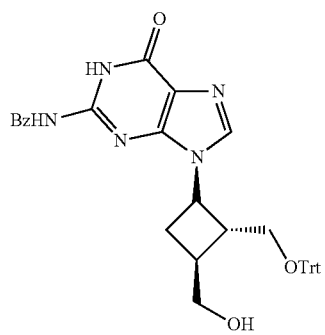

Chlorotrimethylsilane (1.570 mL, 12.37 mmol) was dropwise added to a 0° C. solution of Intermediate 18E in a mixture of dichloromethane (8 mL) and pyridine (2 mL). After 5 min., the cooling bath was removed and the mixture was allowed to stir at room temperature for 30 min. The mixture was cooled to 0° C. and benzoyl chloride (0.197 mL, 1.701 mmol) was added. After 1.5 h, the reaction mixture was concentrated to dryness and the residue was dissolved in THF (10 mL), then treated with 1M LiOH (2.1 mL). The reaction mixture was placed in a freezer for two days. Additional LiOH (1 M) and THF were added until the reaction was complete. The reaction was quenched with HOAc and then concentrated on a rotovap to remove most of the THF. The resulting residue was diluted with water and extracted with dichloromethane. The extracts were combined, washed with brine, dried over anhydrous sodium sulfate, filtered, and concentrated to provide an oil. The oil was dissolved in a minimum of dichloromethane and purified on an ISCO companion chromatography system (80 g silica cartridge, eluting with 0-15% methanol/dichloromethane, 60 ml/min). Fractions containing desired product were combined to provide Intermediate 18F (355 mg, 0.580 mmol) as a white solid. LCMS, [M+H]$^+$=612. $^1$H NMR (499 MHz, DMSO-d$_6$) δ 12.57-12.12 (m, 1H), 11.86 (s, 1H), 8.41-8.27 (m, 1H), 8.06-7.95 (m, 2H), 7.75-7.64 (m, 1H), 7.62-7.50 (m, 2H), 7.31-7.23 (m, 6H), 7.21 (s, 9H), 4.73-4.63 (m, 1H), 4.62-4.55 (m, 1H), 3.57-3.45 (m, 2H), 3.19-3.15 (m, 1H), 3.11-3.04 (m, 1H), 3.02-2.93 (m, 1H), 2.49-2.42 (m, 1H), 2.23-2.11 (m, 1H), 2.08-1.97 (m, 1H).

Preparation of Intermediate 18G:

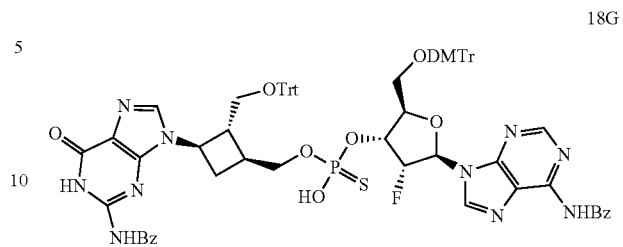

A mixture of Intermediate 18F (100 mg, 0.164 mmol) and Intermediate 18A (126 mg, 0.137 mmol) was azeotroped with acetonitrile (3×3 mL) then dried under high vacuum for 20 min. The residue was placed under a nitrogen atmosphere and dissolved in DMF (2 mL). DBU (0.061 mL, 0.410 mmol) was dropwise added and the resulting mixture was stirred at room temperature for 1 h. The reaction was quenched by the addition of MeOH followed by HOAc. The resulting mixture was concentrated to dryness. The residue was dissolved in a minimum of dichloromethane and purified on an ISCO companion chromatography system (24 g silica cartridge, eluting with 0-15% methanol/dichloromethane, followed by 15-100% methanol/dichloromethane, 35 ml/min). Fractions containing the desired material were combined and concentrated to provide Intermediate 18G (64 mg, 0.047 mmol). LCMS, [M+H]$^+$=1365.

Preparation of Intermediate 18H:

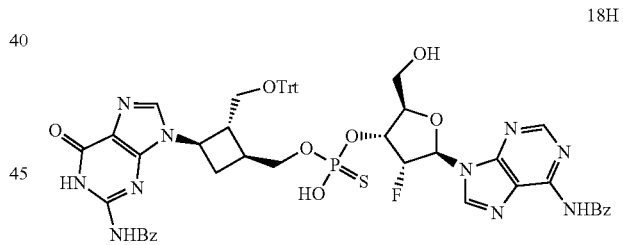

2,2-Dichloroacetic acid (0.015 mL, 0.187 mmol) was added to a room temperature solution of methanol (0.019 mL, 0.469 mmol) and Intermediate 18G (64 mg, 0.047 mmol) in dichloromethane (1.0 mL). After 35 minutes, the reaction was quenched with triethylamine (0.026 mL, 0.187 mmol) and then concentrated to dryness. The resulting clear oil was dissolved in a minimum of dichloromethane and purified on an ISCO companion chromatography system (24 g silica cartridge, eluting with 0-100% methanol/dichloromethane, 35 ml/min). Fractions containing desired product were combined and concentrated to provide Intermediate 18H (50 mg, 0.047 mmol) as a white solid. LCMS, [M+H]$^+$=1063

Preparation of Intermediate 18I:

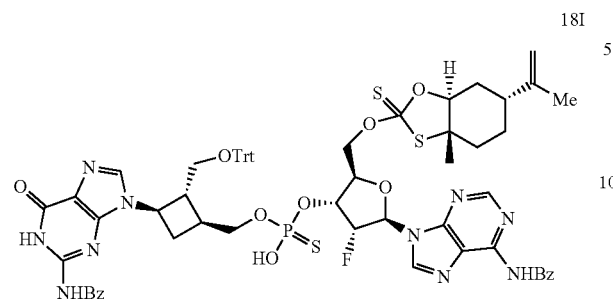

A mixture Intermediate 18H (10.2 mg, 9.59 µmol) and Reagent 3 (12.85 mg, 0.029 mmol) was azeotroped with acetonitrile (3×3 mL), sonicating after every addition of acetonitrile. The resulting residue was placed under a nitrogen atmosphere and suspended in DCM (1 mL), sonicated and cooled to 0° C. to provide a cloudy suspension. After 5 min at 0° C., DBU (8.61 µl, 0.058 mmol) was added. The reaction became clear. After 20 minutes, the reaction was quenched with isopropoxytrimethylsilane (8.52 µl, 0.048 mmol) followed by acetic acid (5.49 µl, 0.096 mmol). The reaction mixture was directly purified on an ISCO companion chromatography system (12 g silica cartridge, eluting with 0-100% methanol/dichloromethane, 35 ml/min). Fractions containing desired products were combined to provide Intermediate 18I (10.7 mg, 8.17 µmol). LCMS, [M+H]+ =1309.

Preparation of Intermediate 18J:

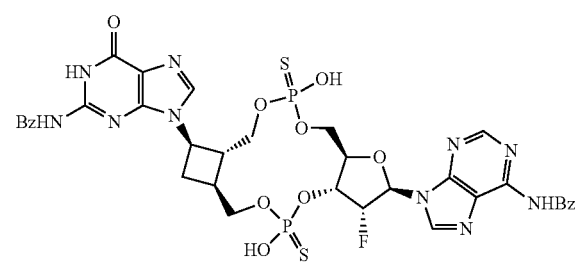

2,2-Dichloroacetic acid (6.05 µl, 0.073 mmol) was added to a room temperature solution of triisopropylsilane (0.018 mL, 0.088 mmol) and Intermediate 18I (9.60 mg, 7.33 µmol) in dichloromethane (2.0 mL). After 35 min, the reaction mixture was added to a room temperature solution of DBU (0.033 mL, 0.220 mmol) in dichloromethane (2 mL). After 15 min, the reaction was concentrated to dryness. The residue was washed with ether (3×3 mL), and the ether washings were carefully decanted and discarded. The resulting residue was dissolved in a mixture of MeOH/DCM and concentrated onto enough celite to provide a free flowing powder. The powder was loaded into an ISCO solid load cartridge and purified on an ISCO companion chromatography system (15.5 g ISCO GOLD C-18 column that had been equilibrated with mobile Phase A: 5:95 acetonitrile/water with 0.01M ammonium acetate. Mobile Phase B: 95:5 acetonitrile/water with 0.01M ammonium acetate. Eluting with 0-100% B, 30 mL/min). Fractions containing the desired material were lyophilized to provide Intermediate 18J (7.7 mg, 8.57 µmol), which was used without further purification. LCMS, [M+H]+=899 (m+1).

Example 18-1

2-amino-9-[(1R,6S,8R,9R,15R,17R,18R)-17-(6-amino-9H-purin-9-yl)-18-fluoro-3,12-dihydroxy-3,12-disulfanylidene-2,4,11,13,16-pentaoxa-3λ⁵,12λ⁵-diphosphatricyclo[13.3.0.0⁶,⁹]octadecan-8-yl]-6,9-dihydro-1H-purin-6-one

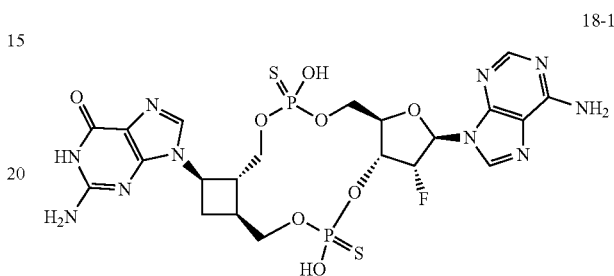

A solution of Intermediate 18J (6.6 mg, 7.34 µmol) and ammonia (7N in MeOH, 2 mL, 14.69 mmol) was stirred at 40° C. for 4.5 h, then cooled to room temperature. The reaction was concentrated to dryness under a stream of nitrogen to provide 10 mg of a clear oil. The oil was purified by preparative reverse phase HPLC. Instrument: Agilent Bionert 1260, Column: Xselect RP Prep C18 OBD Column, 5 µm, 10×250 mm. Flow rate: 5.0 mL/min. Mobile Phase: A: 100 mM NH₄OAc (pH 6.5); B: ACN (% A=100–% B). 0-20% B from 0-10 min. 20-100% B 10-111 min. Detection: 260 nm. Injection Volume: 500 µL. Rentention time of target 5.713 min. Sample Preparation: 10 mg of the sample dissolved in ~2.5 mL MeOH/DMSO/DMF. Fractions containing product were pooled and lyophilized to provide Example 18-1 (1.3 mg, 1.610 µmol) as a white solid. Observed Mass: 691.1; $t_R$: 3.65 min.; Analytical HPLC Chromatographic Conditions 9

Analytical HPLC Chromatographic Conditions 9:

Instrument: Agilent 1290 HPLC/MS; Column: Xselect CSH C18 Column, 3.5 µm, 2.1×150 mm; Flow rate: 0.35 mL/min; Mobile Phase: A: 20 mM NH₄OAc (pH 6.5); B: ACN (% A=100–% B); Gradient: 5-95% B over 15 min.

Preparation of Intermediate 18K:

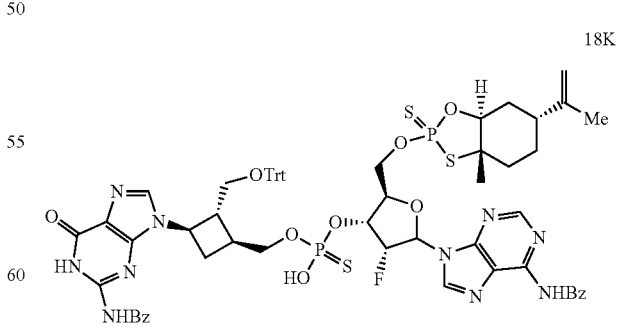

A mixture of Intermediate 18H (15.2 mg, 0.014 mmol) and Reagent 4 (19.15 mg, 0.043 mmol) was azeotroped with acetonitrile (3×3 mL), sonicating after every addition of acetonitrile. The resulting residue was purged with nitrogen, suspended in DCM (1 mL), sonicated and cooled to 0° C. to provide a cloudy suspension. After 10 min, DBU (0.013 mL, 0.086 mmol) was added. The reaction became clear. After 20 min., the reaction was quenched with isopropoxytrimethylsilane (0.013 mL, 0.071 mmol), followed by acetic acid (8.19 µl, 0.143 mmol). The reaction mixture was directly purified on an ISCO companion chromatography system (12 g silica cartridge, eluting with 0-100% methanol/dichloromethane, 35 ml/min). Fractions containing the desired material were combined to provide Intermediate 18K (25 mg, 0.019 mmol) as a white solid. Which was used without further purification. LCMS, [M+H]+=1309 (m+1).

Preparation of Intermediate 18L:

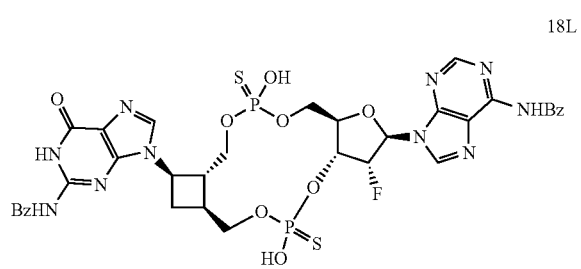

18L 2,2-Dichloroacetic acid (0.012 mL, 0.143 mmol) was added to a room temperature solution of triisopropylsilane (0.035 mL, 0.172 mmol) and Intermediate 18K (18.72 mg, 0.014 mmol) in dichloromethane (2.0 mL). After 25 min, more 2,2-dichloroacetic acid (0.012 mL, 0.143 mmol) was added. After an additional 10 min, the reaction mixture was added to a room temperature solution of DBU (0.064 mL, 0.429 mmol) in dichloromethane (2 mL). After 15 min, the reaction was concentrated to dryness. The residue was treated with ether (3×3 mL), the ether washings were carefully decanted and discarded. The resulting residue was dissolved in MeOH/DCM and concentrated onto enough celite to provide a free flowing powder. The powder was loaded into an ISCO solid load cartridge and purified on a reverse phase ISCO companion chromatography system (15.5 g ISCO GOLD C-18 column that had been equilibrated with mobile Phase A: 5:95 acetonitrile/water with 0.01M ammonium acetate. Mobile Phase B: 95:5 acetonitrile/water with 0.01M ammonium acetate. Eluting with 0-100% B, 30 mL/min). Fractions containing desired product were lyophilized to provide Intermediate 18L (7 mg, 7.79 µmol) as a white solid. LCMS, [M+H]+=899.

Example 18-2

2-amino-9-[(1R,6S,8R,9R,15R,17R,18R)-17-(6-amino-9H-purin-9-yl)-18-fluoro-3,12-dihydroxy-3,12-disulfanylidene-2,4,11,13,16-pentaoxa-3$\lambda^5$,12$\lambda^5$-diphosphatricyclo[13.3.0.0$^{6,9}$]octadecan-8-yl]-6,9-dihydro-1H-purin-6-one

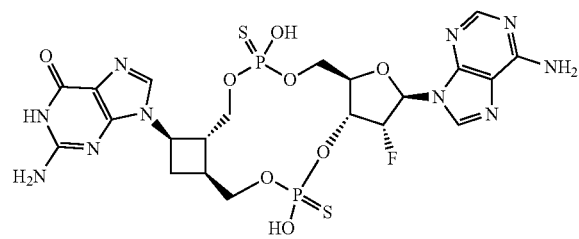 [SMILES: Nc1nc2c(ncn2[C@@H]2C[C@@H]3COP(O)(=S)O[C@H]4[C@@H](F)[C@H](n5cnc6c(N)ncnc65)O[C@@H]4COP(O)(=S)OC[C@H]32)c(=O)[nH]1]

A solution of Intermediate 18L (7 mg, 7.79 µmol) and ammonia (7 N in MeOH, 2 mL, 15.58 mmol) was warmed to 40° C. After 3 h, the reaction was cooled to room temperature. The reaction was concentrated to dryness under a stream of nitrogen, then further dried under vacuum to provide 8.7 mg of a residue. The residue was purified by reverse phase HPLC: Instrument: Waters Autopure, Column: Luna Omega Polar C18 Column 5 µm, 21.2×250 mm. Flow rate: 20.0 mL/min Mobile Phase: A: 100 mM NH$_4$OAc (pH 4.7); B: ACN (% A=100–% B). Gradient 0-18% B over 13 min, 18-95% B from 13-13.5 min. Desired compound retention time 11.56 min. Detection: 260 nm, Injection Volume: 100 µL. Sample Preparation: 8.7 mg of the sample dissolved in ~1.5 mL DMSO/DMF/MeOH. The fractions containing product were lyophilized to provide Example 18-2 (2.5 mg, 3.44 µmol) as a white solid. Observed Mass: 691.1; t$_R$: 3.08 min.; Analytical HPLC Chromatographic Conditions 10

Analytical HPLC Chromatographic Conditions 10:

Instrument: Agilent 1290 HPLC/MS; Column: Luna Omega Polar C18 Column, 3 µm, 2.1×150 mm; Flow rate: 0.35 mL/min; Mobile Phase: A: 20 mM NH$_4$OAc (pH 4.7); B: ACN (% A=100–% B); Gradient: 5-100% B over 15 min.

Examples 18-3, 18-4

2-amino-9-[(1R,6S,8R,9R,15R,17R,18R)-17-(6-amino-9H-purin-9-yl)-18-fluoro-3,12-dihydroxy-3,12-disulfanylidene-2,4,11,13,16-pentaoxa-3$\lambda^5$,12$\lambda^5$-diphosphatricyclo[13.3.0.0$^{6,9}$]octadecan-8-yl]-6,9-dihydro-1H-purin-6-one

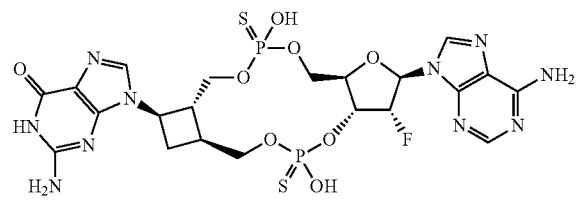

Diastereomer 3 (18-3)
Diastereomer 4 (18-4)

Preparation of Intermediate 18M:

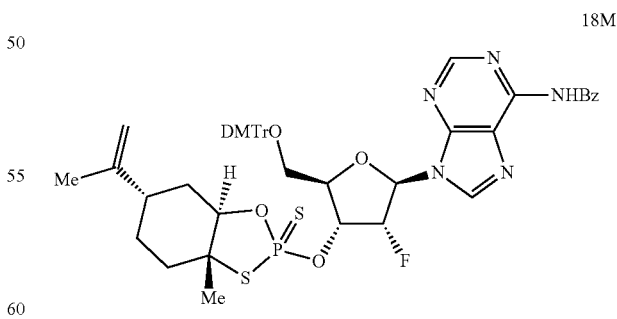

18M

Intermediate 18M was prepared by a similar method as 18A from N-(9-((2R,3R,4R,5R)-5-((bis(4-methoxyphenyl)(phenyl)methoxy)methyl)-3-fluoro-4-hydroxytetrahydrofuran-2-yl)-9H-purin-6-yl)benzamide (AstraTech) and Reagent 3 LCMS, [M+H]+=922. t$_R$: 1.29 min. Analytical Method C.

Preparation of Intermediate 18N.

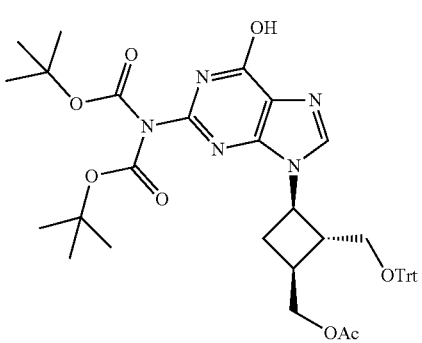

18N

A suspension of 18D (75 mg, 0.089 mmol) and 10% Pd/C (12 mg, 0.089 mmol) in MeOH (2 mL) was vacuum purged with hydrogen, and then stirred under a balloon of hydrogen overnight. The reaction was purged with nitrogen and then diluted with DCM (2 mL), filtered through a 0.35 μm frit, and concentrated in vacuo to provide 18N (67 mg, 100%). LCMS: $[M+H]^+=750$, $t_R$: 1.15 min. Analytical Method A.

Preparation of Intermediate 18O and 18P.

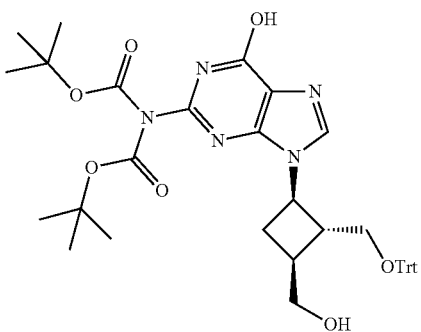

18O

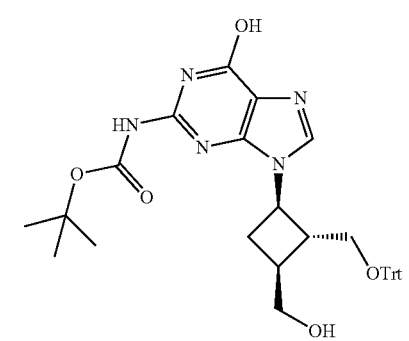

18P

Intermediate 18N (67 mg, 0.089 mmol) was treated with ammonia (7 M in MeOH) (2.7 ml, 18.76 mmol). The resulting clear solution was stirred at room temperature for two days. The resulting mixture was concentrated and purified by silica gel chromatography (4 g column, MeOH/DCM=0-10%) to give a mixture of Intermediates 18O and 18P (49 mg). 18O: LCMS: $[M+H]^+=708$, $t_R$: 1.08 min; 18P: LCMS: $[M+H]^+=608$, $t_R$: 1.00 min. Analytical Method A

Preparation of Intermediates 18Q and 18R:

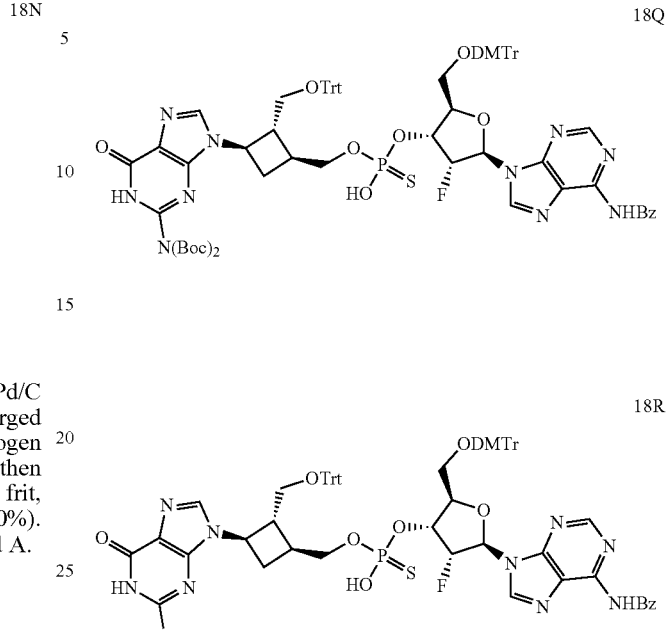

18Q

18R

A mixture of 18O and 18P (49 mg) and 18M (128 mg, 0.138 mmol) was azetropped with ACN (2×5 mL). The residue was dissolved in DCM (3 mL), and the clear solution was cooled to 0° C. DBU (0.063 mL, 0.415 mmol) was added in one portion. After 30 min, additional 18M (55 mg) was added and stirring was continued for 30 min. The reaction was quenched with MeOH (0.5 mL) and then concentrated. The residue was dissolved in a small amount of MeOH and purified by reverse phase C18 column chromatography (50 g GOLD, ACN/H₂O=5-90% with 10 mM NH₄OAc) to give a mixture of 18Q an 18R (120 mg). 18Q: LCMS: $[M+H]^+=1462$, $t_R$: 1.14 min; 18R: LCMS: $[M+H]^+=1362$, $t_R$: 1.09 min. Analytical Method C.

Preparation of Intermediates 18S:

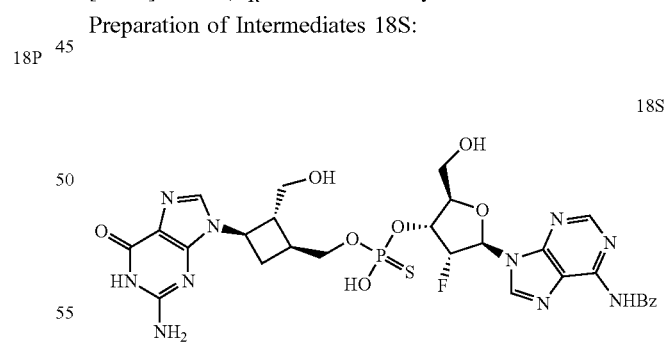

18S

A mixture of 18Q and 18R (115 mg) was dissolved in DCM (1.5 mL), and triethylsilane (0.101 mL, 0.629 mmol) and TFA (1.5 mL) were added. The mixture was stirred at RT for 3 h, and then diluted with MeOH and concentrated. The residue was dissolved in 7N NH₃/MeOH and then concentrated. The residue was loaded onto celite and purified on a C18 reverse phase ISCO column (15.5 g, GOLD, ACN/H₂O=5-40% with 10 mM NH₄OAc) to give 18S (38 mg). LCMS: $[M+H]^+=717$, $t_R$: 0.43 min. Analytical Method C.

Preparation of Intermediates 18T:

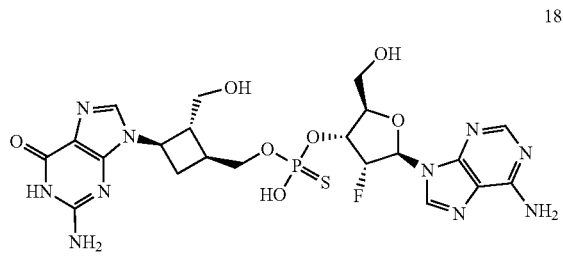

A solution of 18S (36 mg, 0.050 mmol) in 7N NH$_3$/MeOH (6 mL) was stirred at RT for 4.5 h and then concentrated to give crude Intermediate 18T (36 mg). LCMS: [M+H]$^+$=613, t$_R$: 0.28 min. Analytical Method C.

Examples 18-3 and 18-4

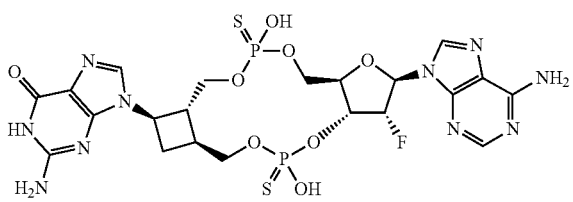

Diastereomer 3 (18-3)
Diastereomer 4 (18-4)

Intermediate 18T (31 mg, 0.051 mmol) was azetroped with pyridine (5 mL) two times, then dissolved in pyridine (8 mL), and DBU (114 µl, 0.759 mmol) was added. The mixture was azeotroped again to remove about 3 mL of pyridine, and the remaining solution was stirred for 10 min. A solution of Reagent 4 (56.5 mg, 0.127 mmol) in ACN (1 mL) was added very slowly over 30 min. The reaction was then concentrated, and azeotropped with toluene two times. The residue was then treated with ether, sonicated, and the clear ether solution was decanted (×3). The remaining solid residue was then dissolved in MeOH/H$_2$O (3 mL) and purified by reverse phase HPLC (Instrument: Waters Autopure, Column: Xselect RP Prep C18 OBD Column, 5 µm, 19×150 mm, Flow rate: 20.0 mL/min Mobile Phase: A: 100 mM NH$_4$OAc (pH 6.5); B: ACN (% A=100–% B). Gradient 0-16% B over 16 min, 16-95% B from 16-16.5 min.) to afford the desired compounds:

Example 18-3

(2.8 mg). LCMS: [M+H]$^+$=691. t$_R$: 5.48 min, Analytical HPLC Chromatographic Conditions 11.

Example 18-4

(4.6 mg), LCMS: [M+H]$^+$=691, t$_R$: 6.80 min, Analytical HPLC Chromatographic Conditions 11.

Analytical HPLC Chromatographic Conditions 11:
Instrument: Agilent 1290 HPLC/MS; Column: Xselect CSH C18 Column, 3.5 µm, 2.1×150 mm; Flow rate: 0.35 mL/min; Mobile Phase: A: 20 mM NH$_4$OAc (pH 6.5); B: ACN (% A=100–% B); Gradient: 5-100% B over 15 min.).

Analytical LCMS Method A:
Waters Acquity UPLC BEH C18 (2.1×50 mm), 1.7 micron; Solvent A=100% water with 0.05% TFA; Solvent B=100% acetonitrile with 0.05% TFA; Gradient=2-98% B over 1 minute, then a 0.5-minute hold at 98% B; Flow rate: 0.8 mL/min; Detection: UV at 220 nm).

Analytical LCMS Method B:
Injection 1 conditions: Column: Agilent Bonus RP, 2.1 mm×50 mm, 1.8 µm particles; Mobile Phase A: water with 20 mM ammonium acetate; Mobile Phase B: acetonitrile.
Temperature: 50° C.; Gradient: 0% B hold 1 min, then 0% B to 100% B over 4 min, then a 0.75 min hold at 100% B; Flow: 1 mL/min; Detection: MS and UV (220 nm). Injection 1 results.

Analytical LCMS Method C:
Waters Acquity UPLC BEH C18 (2.1×50 mm), 1.7 micron; Solvent A=95% water/5% acetonitrile with ammonium acetate; Solvent B=95% acetonitrile/5% water with ammonium acetate; Gradient=5-95% B over 1 minute, then a 0.5-minute hold at 100% B; Flow rate: 0.8 mL/min; Detection: UV at 220 nm); (NH4OAc+/− mode).

Analytical LCMS Method D:
Waters Acquity UPLC BEH C18 BEH C18 (2.1×50 mm), 1.7 micron; Solvent A=100% water with 0.05% TFA; Solvent B=100% acetonitrile with 0.05% TFA; Gradient=15-98% B over 5 minute, then a 0.5-minute hold at 98% B; Flow rate: 0.8 mL/min; Detection: UV at 220 nm).

Analytical LCMS Method E:
Injection 1 conditions: Column: Waters XBridge BEH C18 XP(50×2.1 mm) 2.5 µm; Mobile Phase A: 5:95 acetonitrile:water with 10 mM NH$_4$OAc; Mobile Phase B: 95:5 acetonitrile:water with 10 mM NH$_4$OAc; Temperature: 50° C.; Gradient: 0-100% B over 3 minutes; Flow: 1.1 ml/min.

Evaluation of Biological Activity

STING THP1 Reporter Assay Protocol

THP1-Dual™ cells were derived from the human THP-1 monocyte cell line by stable integration of two inducible reporter constructs. To this end, THP1-Dual™ cells allow the simultaneous study of the NF-κB pathway, by monitoring the activity of SEAP, and the IRF pathway by assessing the activity of a secreted luciferase (Lucia). Both reporter proteins are readily measurable in the cell culture supernatant when using QUANTI-Blue™, a SEAP detection reagent, and QUANTI-Luc™, a luciferase detection reagent.
THP1-Dual™ cells induce the activation of NF-κB in response to STING agonists. They also trigger the IRF pathway upon stimulation with STING agonists, such as cGAMP. Here, the THP-1-Dual cells were used to assess STING binders for function on the cellular level.
Serial dilutions of compounds in DMSO were added to low volume 384 well plates at 100 nl/well using an ECHO acoustic dispenser (Labcyte, model 550) to achieve final starting concentration of 100 µM in cell suspension. THP-1 Dual™ STING reporter cells (Invivogen, Dual cells cat # THPD-nfis) were added to the plates with compounds at 15,000 cells in 10 µL per well in RPMI media (Gibco, cat #11875) containing 10% human plasma in a low volume 384-well black wall clear bottom tissue culture plate (Corning, cat #3542) for SEAP assay and low volume solid white plate (Corning, cat #3826) for luciferase assay. One column of the plate was reserved for treatment with cGAMP at 100 µM for 100% activation calculation and one column for no treatment (DMSO only) for baseline activation. Plates were then incubated in 37° C. incubator at 5% CO$_2$ for 20 hours.
In the SEAP assay, 5 µl of 2× QuantiBlue (Invivogen, cat # Rep-qb2) is added to 384 well black plates seeded with THP1 cells and incubated at 37° C. for 2 hours. Plates were read on the Envision (Perkin Elmer) at 620 nm wavelength (OD620). In the luciferase assay, 5 μl of Quantiluc (Invivogen, Rep-qlc2) is added to white 384 well plates seeded with THP1 cells and read at 5 minutes on the Envision (Perkin Elmer) using a luminescence protocol (RLU). For both cell lines, 100% activation was determined by value (RLU) of THP-1 Dual STING cells stimulated with 100 μM cGAMP (Invivogen, cat # TLRL-NACGA23-5).

STING HTRF Binding Assays

A time resolved FRET-based competition binding assay was used to assess test article binding to STING WT and STING AQ. His-tagged STING cytoplasmic domain (WT or AQ) at a concentration of 20 nM was incubated with 2.5 nM Tb-labeled anti-His antibody, test compound, and fluorescein-labeled cGAMP analog probe (BioLog cat. no. C195) at a concentration of 200 nM (STING WT) or 40 nM (STING AQ) in PBS containing 0.005% Tween-20 and 0.1% BSA for one hour. Fluorescence at 495 nm and 520 nm was measured using an EnVision microplate reader to quantify FRET between Tb-labeled anti-His antibody and fluorescein-labeled probe. Background was defined as the signal obtained in the absence of STING protein, and background subtracted FRET ratios were normalized to the maximum signal obtained in the absence of test compound. These values were converted to a percent inhibition. Percent inhibition was determined for test compounds at 11 concentrations. The $IC_{50}$, defined as the concentration of competing test compound needed to reduce specific binding of the probe by 50%, was calculated using the 4 parameter logistic equation to fit the data

```
STING WT: His-TVMV-S-hSTING(155-341)-H232R
                                         (SEQ ID NO: 1)
MGSSHHHHHHSSGETVRFQGHMSVAHGLAWSYYIGYLRLILPELQARIRT

YNQHYNNLLRGAVSQRLYILLPLDCGVPDNLSMADPNIRFLDKLPQQTGD

RAGIKDRVYSNSIYELLENGQRAGTCVLEYATPLQTLFAMSQYSQAGFSR

EDRLEQAKLFCRTLEDILADAPESQNNCRLIAYQEPADDSSFSLSQEVLRH

LRQEEKEEV

STING AQ: His-TVMV-S-hSTING(155-341)-G230A-R293Q
                                         (SEQ ID NO: 2)
MGSSHHHHHHSSGETVRFQGHMSVAHGLAWSYYIGYLRLILPELQARIRT

YNQHYNNLLRGAVSQRLYILLPLDCGVPDNLSMADPNIRFLDKLPQQTAD

RAGIKDRVYSNSIYELLENGQRAGTCVLEYATPLQTLFAMSQYSQAGFSR

EDRLEQAKLFCQTLEDILADAPESQNNCRLIAYQEPADDSSFSLSQEVLRH

LRQEEKEEV
```

| | THP1 Reporter Assays $EC_{50}$ (μM) | | HTRF Binding Assays $IC_{50}$ (μM) | |
|---|---|---|---|---|
| Example # | IRF3 | NFkB | STING WT | STING AQ |
| Example 1-1 | >100 | >100 | 1.60 | 0.06 |
| Example 1-2 | 3.0 | 6.0 | 0.09 | 0.01 |
| Example 2-1 | >100 | >100 | 24.0 | 0.21 |
| Example 2-2 | 85.0 | >100 | 0.88 | 0.01 |
| Example 3-1 | >100 | >100 | 15.0 | 0.43 |
| Example 3-2 | >100 | >100 | 4.0 | 0.46 |
| Example 3-3 | 33.0 | 58.0 | 0.18 | 0.14 |
| Example 3-4 | 31.0 | 40.0 | 1.0 | 0.09 |
| Example 4-1 | >100 | >100 | >100 | 2.8 |
| Example 4-2 | 72.0 | 87.0 | 3.7 | 0.05 |
| Example 5-1 | >100 | >100 | 5.7 | 0.10 |
| Example 5-2 | >100 | >100 | 0.44 | 0.02 |
| Example 5-3 | >100 | >100 | 2.7 | 0.04 |
| Example 5-4 | 12.0 | 91.0 | 0.12 | 0.01 |
| Example 6-1 | >100 | >100 | >100 | 38.9 |
| Example 6-2 | >100 | >100 | >100 | 82.6 |
| Example 6-3 | >100 | >100 | >100 | 31.9 |
| Example 6-4 | >100 | >100 | >100 | 14.8 |
| Example 7-1 | >100 | >100 | >100 | 32.7 |
| Example 7-2 | >100 | >100 | >100 | |
| Example 7-3 | >100 | >100 | >100 | 61.1 |
| Example 7-4 | >100 | >100 | 49.1 | 6.3 |
| Example 8-1 | >100 | 23.0 | >100 | 113.5 |
| Example 8-2 | >100 | 97.0 | 33.0 | >100 |
| Example 8-3 | >100 | >100 | >100 | >100 |
| Example 8-4 | >100 | >100 | >100 | 15.8 |
| Example 9-1 | >100 | >100 | >100 | 20.0 |
| Example 9-2 | >100 | >100 | 4.3 | 0.92 |
| Example 9-3 | >100 | >100 | 9.1 | 0.35 |
| Example 9-4 | >100 | >100 | 1.4 | 0.08 |
| Example 10 | >100 | >100 | 5.2 | 0.04 |
| Example 11-1 | >100 | >100 | 20.5 | 3.1 |
| Example 11-2 | >100 | >100 | 19.4 | 1.4 |
| Example 11-3 | 70.0 | 51.0 | 0.82 | 0.11 |
| Example 11-4 | >100 | >100 | 66.2 | 23.1 |
| Example 12-1 | >100 | >100 | 52.8 | 19.9 |
| Example 12-2 | >100 | >100 | >100 | 88.7 |
| Example 12-3 | >100 | >100 | >100 | 64.4 |
| Example 12-4 | >100 | >100 | 22.0 | 0.40 |
| Example 13-1 | >100 | >100 | >100 | 85.1 |
| Example 13-2 | >100 | >100 | >100 | 3.0 |
| Example 13-3 | >100 | >100 | >100 | 3.8 |
| Example 13-4 | 86.0 | >100 | 3.0 | 0.05 |
| Example 14-1 | >100 | >100 | 83.0 | 4.5 |
| Example 14-2 | >100 | >100 | 25.5 | 5.1 |
| Example 14-3 | >100 | >100 | 14.3 | 1.7 |
| Example 14-4 | >100 | >100 | 4.3 | 0.92 |
| Example 15-1 | >100 | >100 | 33.5 | 4.4 |
| Example 15-2 | >100 | >100 | 26.9 | 1.8 |
| Example 15-3 | >100 | >100 | 32.6 | 1.2 |
| Example 15-4 | >100 | >100 | 3.9 | 0.47 |
| Example 16 | >100 | 31 | 17.9 | 0.23 |
| Example 17-1 | >100 | 2 | >100 | >100 |
| Example 17-2 | >100 | >100 | >100 | 1.9 |
| Example 18-1 | 0.6 | 2.6 | 0.004 | 0.002 |
| Example 18-2 | >100 | >100 | 0.15 | 0.02 |
| Example 18-3 | >100 | >100 | 0.52 | 0.02 |
| Example 18-4 | >100 | 74.5 | 0.05 | 0.004 |

We claim:

1. A compound of formula I

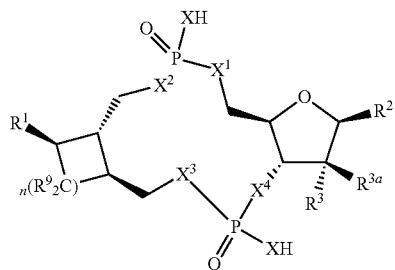

wherein
X is O or S;
$X^1$, $X^2$, $X^3$ and $X^4$ are each independently O or NH;
$R^1$ and $R^2$ are independently

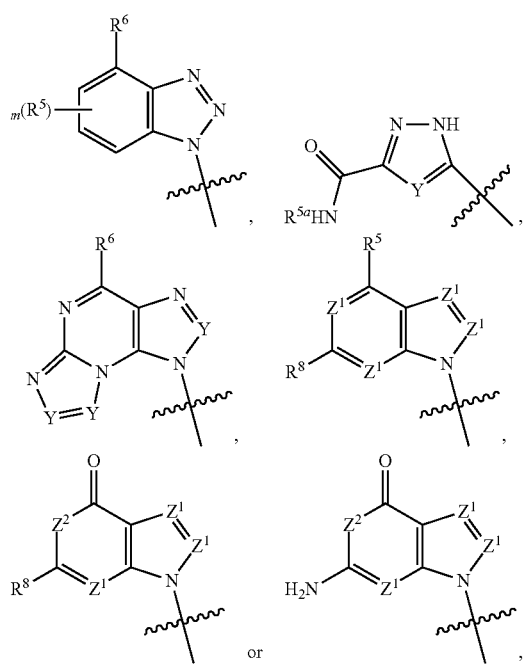

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$ C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H or $C_{1-3}$ alkyl;

$R^3$ is H, $CH_3$, halogen, $NH_2$ or OH;

$R^{3a}$ is H, $CH_3$, halogen, $NH_2$ or OH; or $R^3$ and $R^{3a}$ may be taken together to form a 3-4 membered carbocycle; or $R^3$ and $R^{3a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^5$ or N;

m is 0, 1, 2 or 3;

n is 0 or 1;

or a pharmaceutically acceptable salt, tautomer or stereoisomer thereof.

2. The compound according to claim 1 of formula I

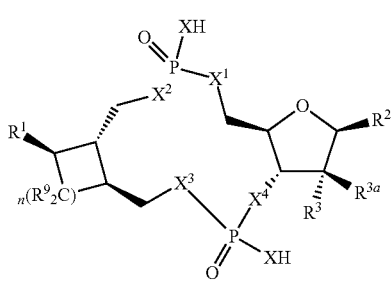

(I)

wherein
X is S;
$X^1$, $X^2$, $X^3$ and $X^4$ are each independently O or NH;
$R^1$ and $R^2$ are independently

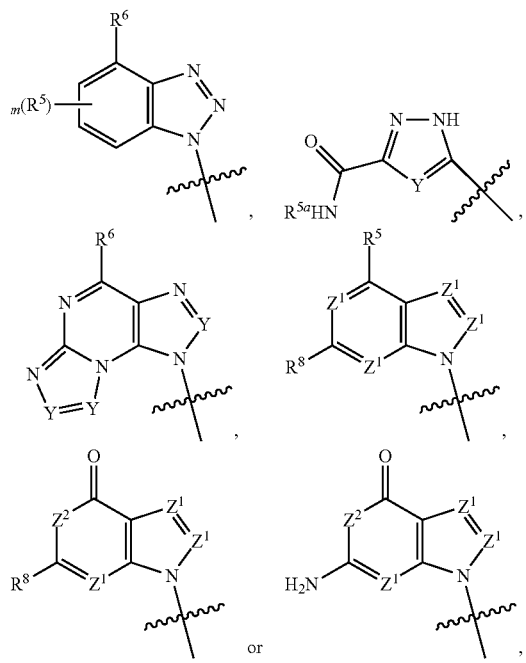

or $Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O) $R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl;
$R^3$ is H, $CH_3$, halogen, $NH_2$ or OH;
$R^{3a}$ is H, $CH_3$, halogen, $NH_2$ or OH; or
$R^3$ and $R^{3a}$ may be taken together to form a 3-4 membered carbocycle; or
$R^3$ and $R^{3a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, halogen or methyl;
Y is $CR^5$ or N;
m is 0, 1, 2 or 3;
n is 0 or 1;
or a pharmaceutically acceptable salt, tautomer or stereoisomer thereof.

3. The compound according to claim 1 of formula I

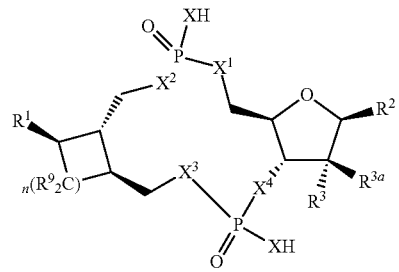

(I)

wherein
X is O;
$X^1$, $X^2$, $X^3$ and $X^4$ are each independently O or NH;
$R^1$ and $R^2$ are independently

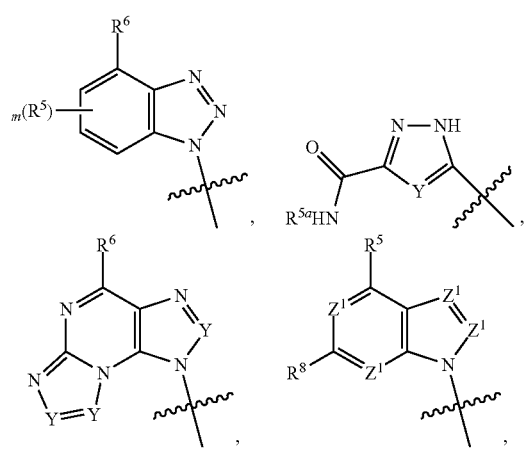

-continued

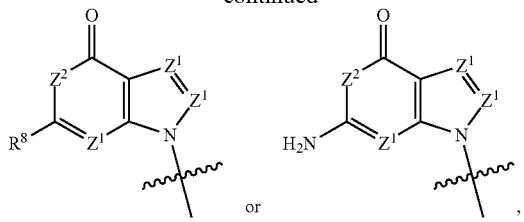

Z¹ is N or CR$^a$;

Z² is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^3$ is H, CH$_3$, halogen, NH$_2$ or OH;

R$^{3a}$ is H, CH$_3$, halogen, NH$_2$ or OH; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1;

or a pharmaceutically acceptable salt, tautomer or stereoisomer thereof.

4. The compound according to claim 1 of the formula

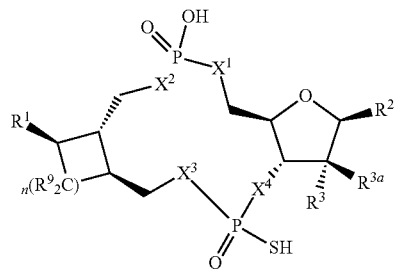

wherein

X¹, X², X³ and X⁴ are each independently O or NH;

R¹ and R² are independently

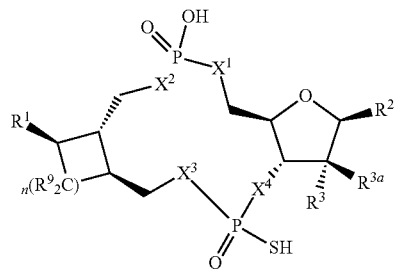

Z¹ is N or CR$^a$;

Z² is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^3$ is H, CH$_3$, halogen, NH$_2$ or OH;

R$^{3a}$ is H, CH$_3$, halogen, NH$_2$ or OH; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)

NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1;

or a pharmaceutically acceptable salt, tautomer or stereoisomer thereof.

5. The compound according to claim 1 of the formula wherein

X$^1$, X$^2$, X$^3$ and X$^4$ are each independently O or NH;

R$^1$ and R$^2$ are independently

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^3$ is H, CH$_3$, halogen, NH$_2$ or OH;

R$^{3a}$ is H, CH$_3$, halogen, NH$_2$ or OH; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1;

or a pharmaceutically acceptable salt, tautomer or stereoisomer thereof.

6. The compound according to claim 1 of the formula

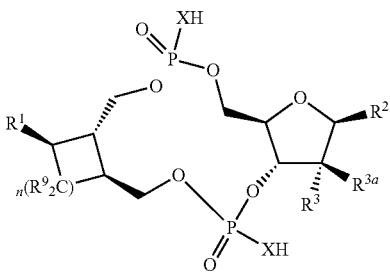

wherein

X is O or S;

R$^1$ and R$^2$ are independently

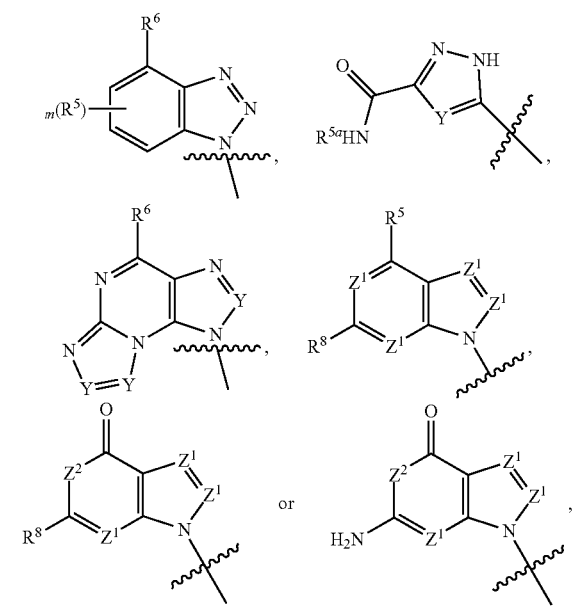

Z$^1$ is N or CR$^a$;
Z$^2$ is NR$^b$;
R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;
R$^{a1}$ is H or C$_{1-3}$ alkyl;
R$^3$ is H, CH$_3$, halogen, NH$_2$ or OH;
R$^{3a}$ is H, CH$_3$, halogen, NH$_2$ or OH; or
R$^3$ and R$^{3a}$ may be taken together to form a 3-4 membered carbocycle; or
R$^3$ and R$^{3a}$ may be taken together to form a C=CH$_2$ substituent;
R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^{5a}$ is H or C$_{1-3}$ alkyl;
R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^9$ is H, halogen or methyl;
Y is CR$^5$ or N;
m is 0, 1, 2 or 3;
n is 0 or 1;
or a pharmaceutically acceptable salt, tautomer or stereoisomer thereof.

7. The compound according to claim 1 of the formula

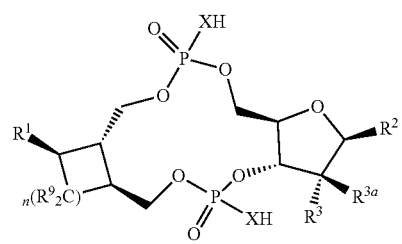

wherein

X is O or S;

R$^1$ and R$^2$ are independently

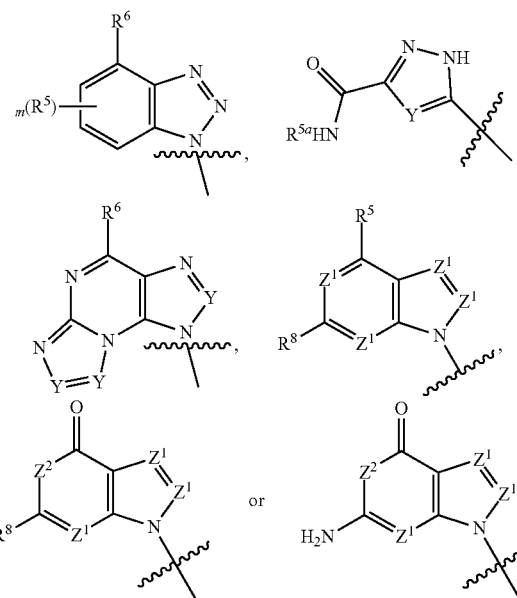

Z$^1$ is N or CR$^a$;
Z$^2$ is NR$^b$;
R$^a$ is H, halogen, C$_{1-6}$ alkyl substituted with 0-6 R$^5$, C$_{3-6}$ cycloalkyl substituted with 0-6 R$^5$, CN, NO$_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H or $C_{1-3}$ alkyl;

$R^3$ is H, $CH_3$, halogen, $NH_2$ or OH;

$R^{3a}$ is H, $CH_3$, halogen, $NH_2$ or OH; or $R^3$ and $R^{3a}$ may be taken together to form a 3-4 membered carbocycle; or $R^3$ and $R^{3a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^5$ or N;

m is 0, 1, 2 or 3;

n is 0 or 1;

or a pharmaceutically acceptable salt, tautomer or stereoisomer thereof.

8. The compound according to claim 1 of the formula

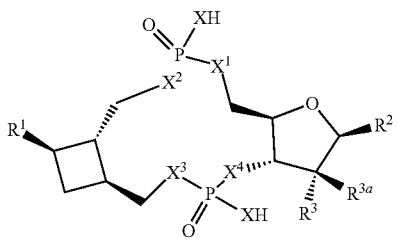

wherein

X is O or S;

$X^1$, $X^2$, $X^3$ and $X^4$ are each independently O or NH;

$R^1$ and $R^2$ are independently

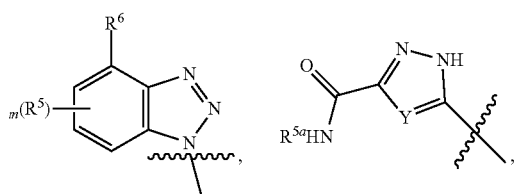

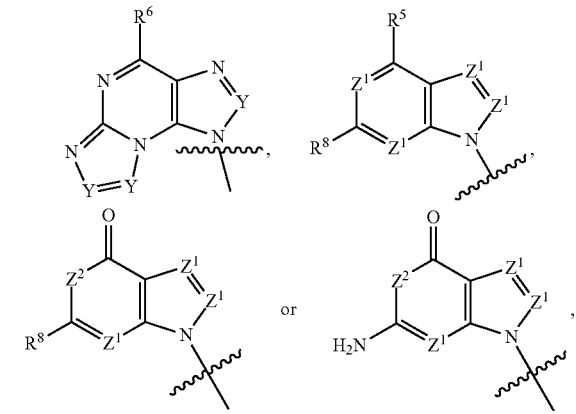

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H or $C_{1-3}$ alkyl;

$R^3$ is H, $CH_3$, halogen, $NH_2$ or OH;

$R^{3a}$ is H, $CH_3$, halogen, $NH_2$ or OH; or $R^3$ and $R^{3a}$ may be taken together to form a 3-4 membered carbocycle; or $R^3$ and $R^{3a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

Y is $CR^5$ or N;

m is 0, 1, 2 or 3;

or a pharmaceutically acceptable salt, tautomer or stereoisomer thereof.

9. The compound according to claim 1 of the formula

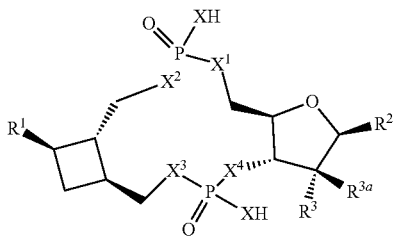

wherein
X is S;
X$^1$, X$^2$, X$^3$ and X$^4$ are each independently O or NH;
R$^1$ and R$^2$ are independently

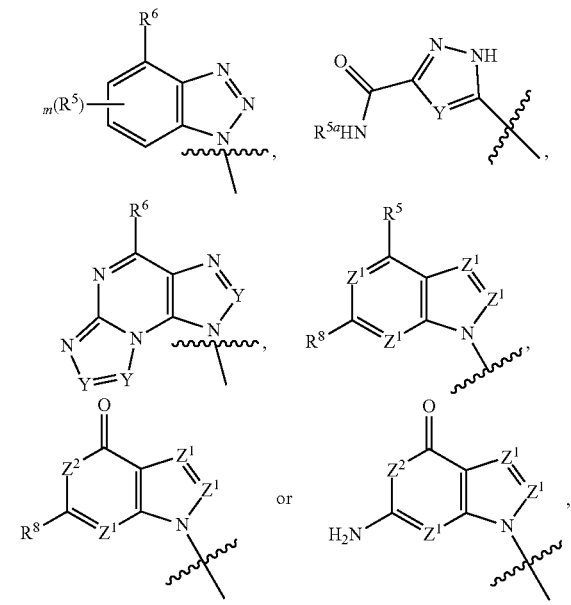

Z$^1$ is N or CR$^a$;
Z$^2$ is NR$^b$;
R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;
R$^{a1}$ is H or C$_{1-3}$ alkyl;
R$^3$ is H, CH$_3$, halogen, NH$_2$ or OH;
R$^{3a}$ is H, CH$_3$, halogen, NH$_2$ or OH; or
R$^3$ and R$^{3a}$ may be taken together to form a 3-4 membered carbocycle; or
R$^3$ and R$^{3a}$ may be taken together to form a C=CH$_2$ substituent;
R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^{5a}$ is H or C$_{1-3}$ alkyl;
R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
Y is CR$^5$ or N;
m is 0, 1, 2 or 3;
or a pharmaceutically acceptable salt, tautomer or stereoisomer thereof.

10. The compound according to claim 1 of the formula

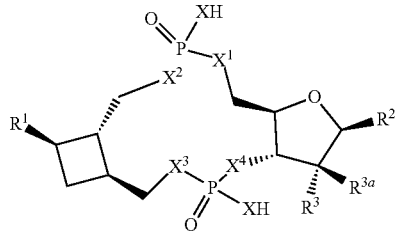

wherein
X is O;
X$^1$, X$^2$, X$^3$ and X$^4$ are each independently O or NH;
R$^1$ and R$^2$ are independently

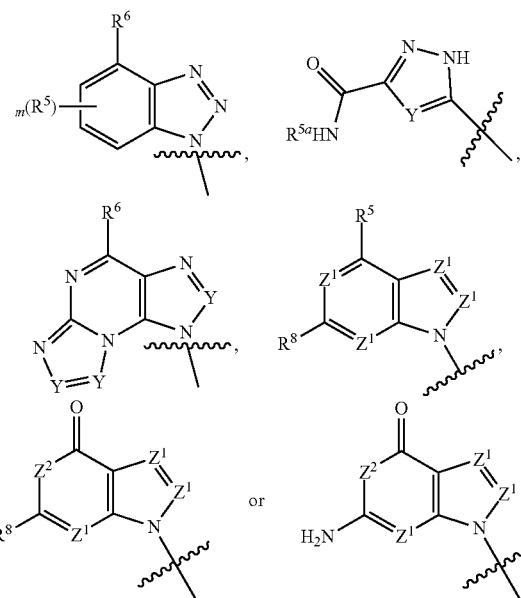

Z$^1$ is N or CR$^a$;
Z$^2$ is NR$^b$;
R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$ C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^3$ is H, CH$_3$, halogen, NH$_2$ or OH;

R$^{3a}$ is H, CH$_3$, halogen, NH$_2$ or OH; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

11. The compound according to claim 1 of the formula

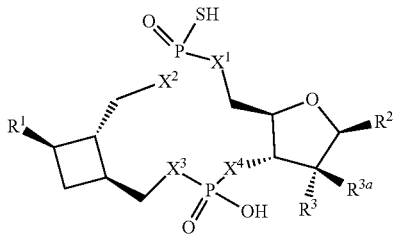

wherein

X$^1$, X$^2$, X$^3$ and X$^4$ are each independently O or NH;

R$^1$ and R$^2$ are each independently

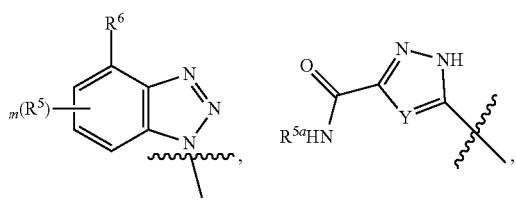

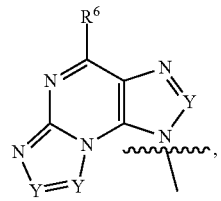, 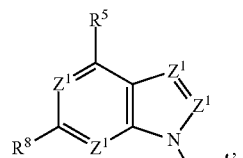

-continued

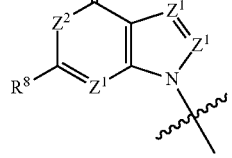 or 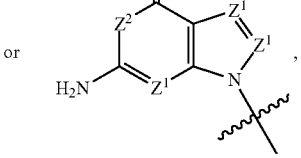,

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$ C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^3$ is H, CH$_3$, halogen, NH$_2$ or OH;

R$^{3a}$ is H, CH$_3$, halogen, NH$_2$ or OH; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

12. The compound according to claim 1 of the formula

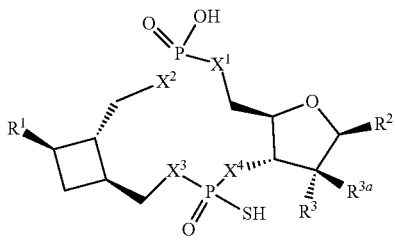

wherein
$X^1$, $X^2$, $X^3$ and $X^4$ are each independently O or NH;
$R^1$ and $R^2$ are each independently

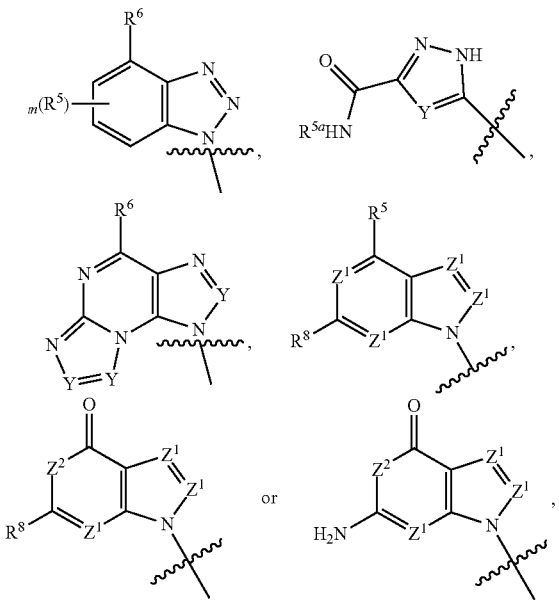

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$ C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl;
$R^3$ is H, $CH_3$, halogen, $NH_2$ or OH;
$R^{3a}$ is H, $CH_3$, halogen, $NH_2$ or OH; or
$R^3$ and $R^{3a}$ may be taken together to form a 3-4 membered carbocycle; or
$R^3$ and $R^{3a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
Y is $CR^5$ or N;
m is 0, 1, 2 or 3;
or a pharmaceutically acceptable salt, tautomer or stereoisomer thereof.

13. The compound according to claim 1 of the formula

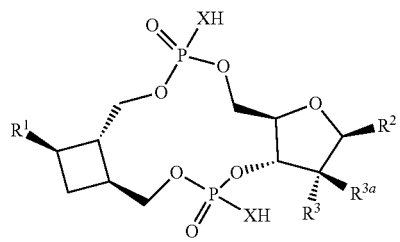

wherein
X is O or S;
$R^1$ and $R^2$ are each independently

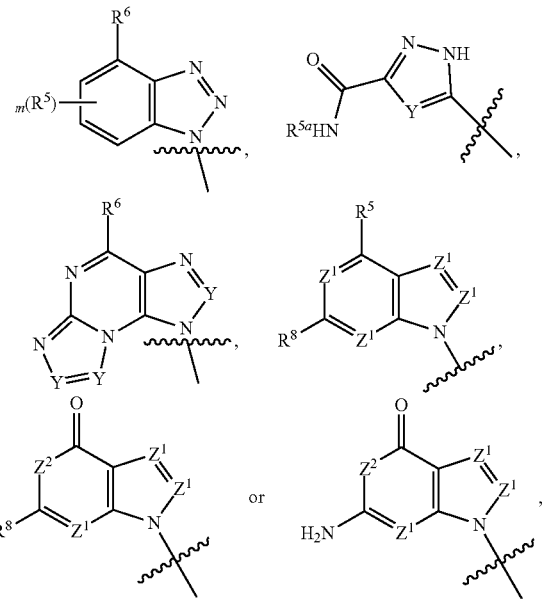

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$ C(O)$R^{a1}$, —$NR^{a1}$COO$R^{a1}$, —$NR^{a1}$C(O)$NR^{a1}R^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^3$ is H, CH$_3$, halogen, NH$_2$ or OH;

R$^{3a}$ is H, CH$_3$, halogen, NH$_2$ or OH; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

14. The compound according to claim 1 of the formula

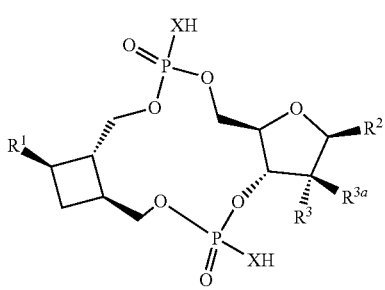

wherein

X is S;

R$^1$ and R$^2$ are each independently

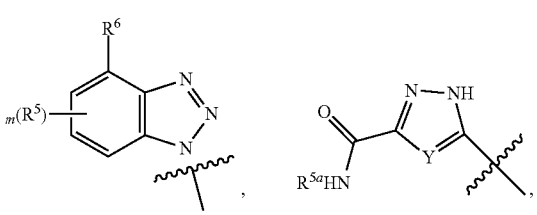

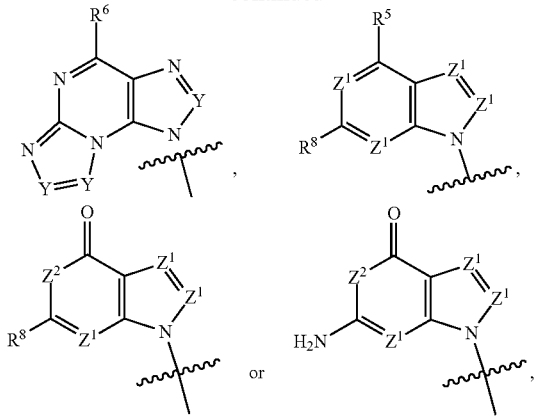

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^3$ is H, CH$_3$, halogen, NH$_2$ or OH;

R$^{3a}$ is H, CH$_3$, halogen, NH$_2$ or OH; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

15. The compound according to claim 1 of the formula

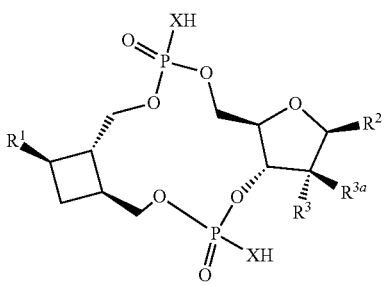

wherein
X is O;
R¹ and R² are each independently

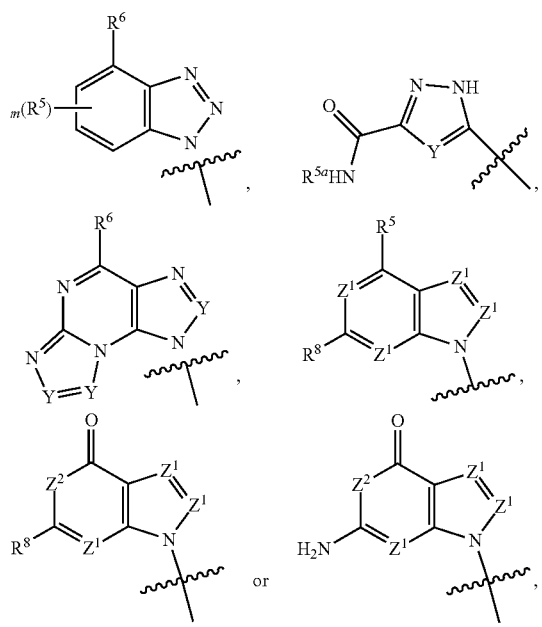

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, NO₂, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —$NR^{a1}R^{a1}$, —$NR^{a1}$ C(O)$R^{a1}$, —$NR^{a1}$COOR$^{a1}$, —$NR^{a1}$C(O)$NR^{a1}R^{a1}$, —$NR^{a1}$S(O)₂$R^{a1}$, —$NR^{a1}$S(O)₂$NR^{a1}R^{a1}$, —S(O)$R^{a1}$, —S(O)$NR^{a1}R^{a1}$, —S(O)₂$R^{a1}$ or S(O)₂$NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)₂$R^{a1}$ or S(O)₂$NR^{a1}R^{a1}$;
$R^{a1}$ is H or $C_{1-3}$ alkyl;
$R^3$ is H, CH₃, halogen, NH₂ or OH;
$R^{3a}$ is H, CH₃, halogen, NH₂ or OH; or
$R^3$ and $R^{3a}$ may be taken together to form a 3-4 membered carbocycle; or
$R^3$ and $R^{3a}$ may be taken together to form a C=CH₂ substituent;
$R^5$ is H, halogen, $C_{1-3}$ alkyl, CN, NO₂, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COOR$^{a1}$, —$NR^{a1}$C(O)$NR^{a1}R^{a1}$, —$NR^{a1}$S(O)₂$R^{a1}$, —$NR^{a1}$S(O)₂$NR^{a1}R^{a1}$, —S(O)$R^{a1}$, —S(O)$NR^{a1}R^{a1}$, —S(O)₂$R^{a1}$ or S(O)₂$NR^{a1}R^{a1}$;
$R^{5a}$ is H or $C_{1-3}$ alkyl;
$R^6$ is H, halogen, $C_{1-3}$ alkyl, CN, NO₂, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COOR$^{a1}$, —$NR^{a1}$C(O)$NR^{a1}R^{a1}$, —$NR^{a1}$S(O)₂$R^{a1}$, —$NR^{a1}$S(O)₂$NR^{a1}R^{a1}$, —S(O)$R^{a1}$, —S(O)$NR^{a1}R^{a1}$, —S(O)₂$R^{a1}$ or S(O)₂$NR^{a1}R^{a1}$;
$R^8$ is H, halogen, $C_{1-3}$ alkyl, CN, NO₂, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COOR$^{a1}$, —$NR^{a1}$C(O)$NR^{a1}R^{a1}$, —$NR^{a1}$S(O)₂$R^{a1}$, —$NR^{a1}$S(O)₂$NR^{a1}R^{a1}$, —S(O)$R^{a1}$, —S(O)$NR^{a1}R^{a1}$, —S(O)₂$R^{a1}$ or S(O)₂$NR^{a1}R^{a1}$;
Y is $CR^5$ or N;
m is 0, 1, 2 or 3;
or a pharmaceutically acceptable salt, tautomer or stereoisomer thereof.

16. The compound according to claim 1 of the formula

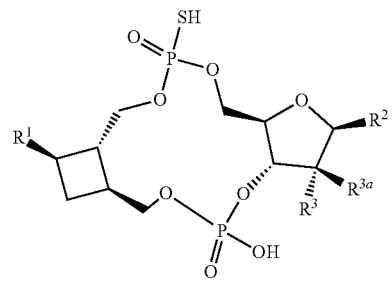

wherein
R¹ and R² are each independently

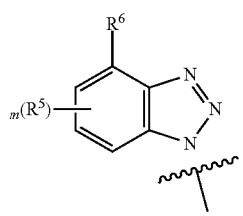

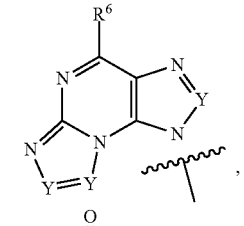

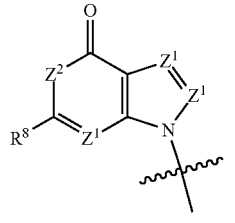

$Z^1$ is N or $CR^a$;
$Z^2$ is $NR^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^3$ is H, CH$_3$, halogen, NH$_2$ or OH;

R$^{3a}$ is H, CH$_3$, halogen, NH$_2$ or OH; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

17. The compound according to claim 1 of the formula

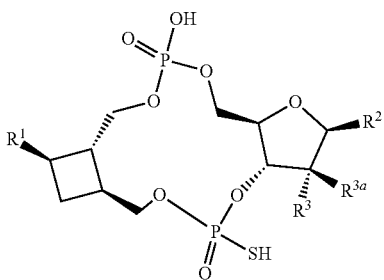

wherein

R$^1$ and R$^2$ are each independently

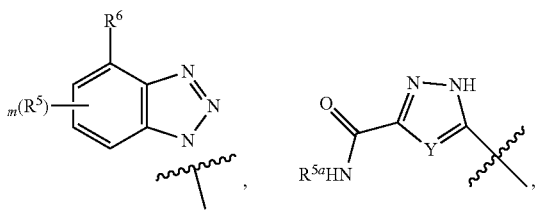

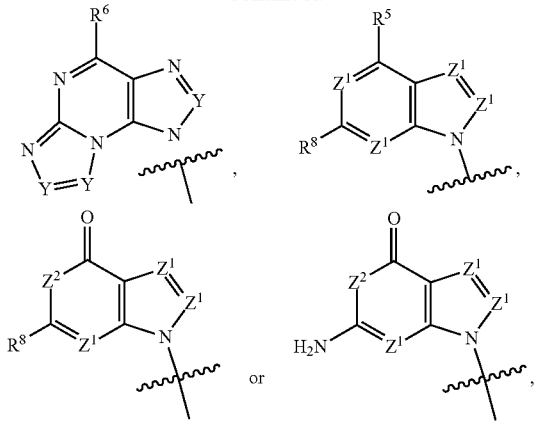

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^3$ is H, CH$_3$, halogen, NH$_2$ or OH;

R$^{3a}$ is H, CH$_3$, halogen, NH$_2$ or OH; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

18. The compound according to claim 1 of the formula
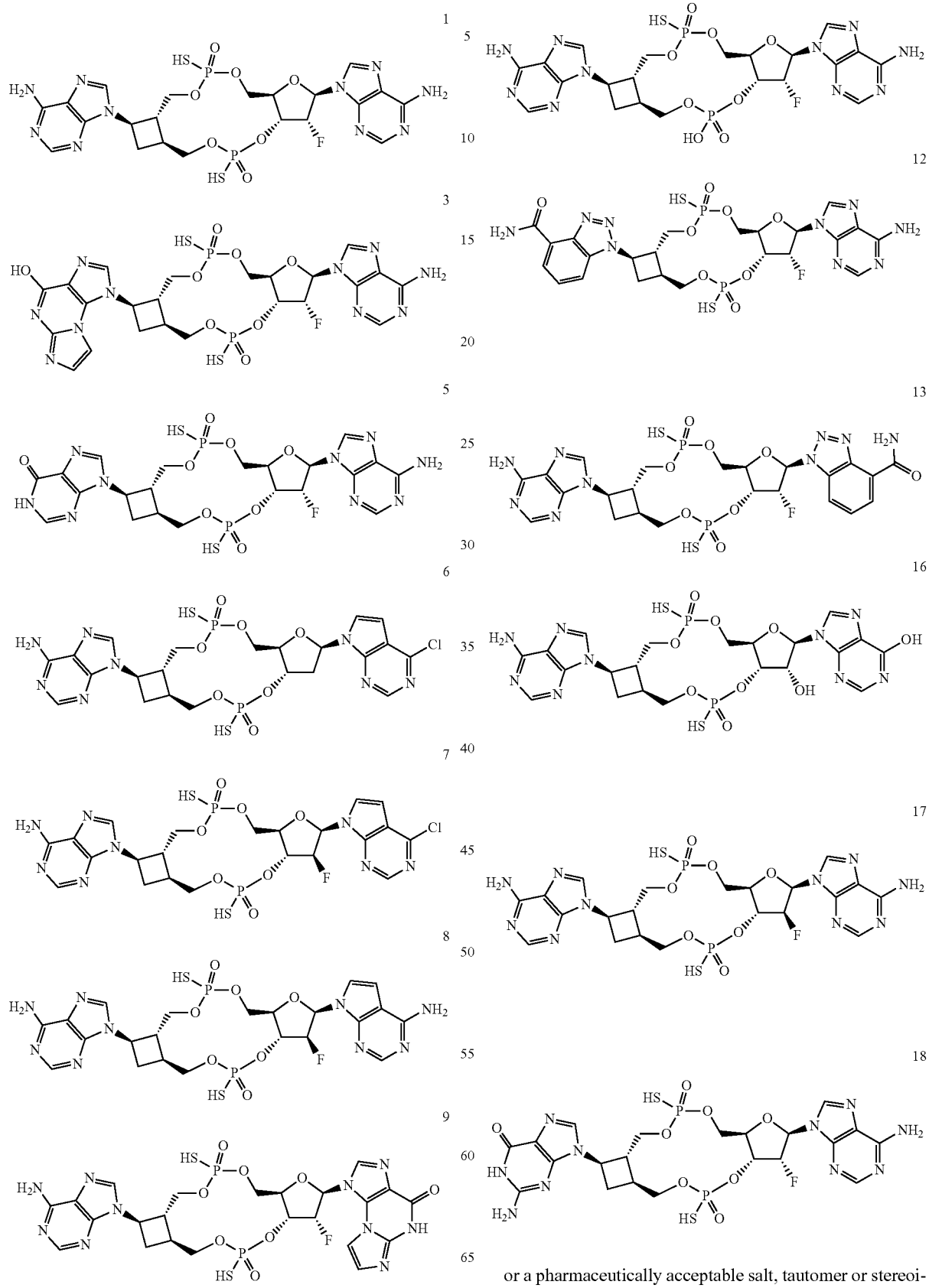
or a pharmaceutically acceptable salt, tautomer or stereoisomer thereof.

19. The compound according to claim 1 of the formula
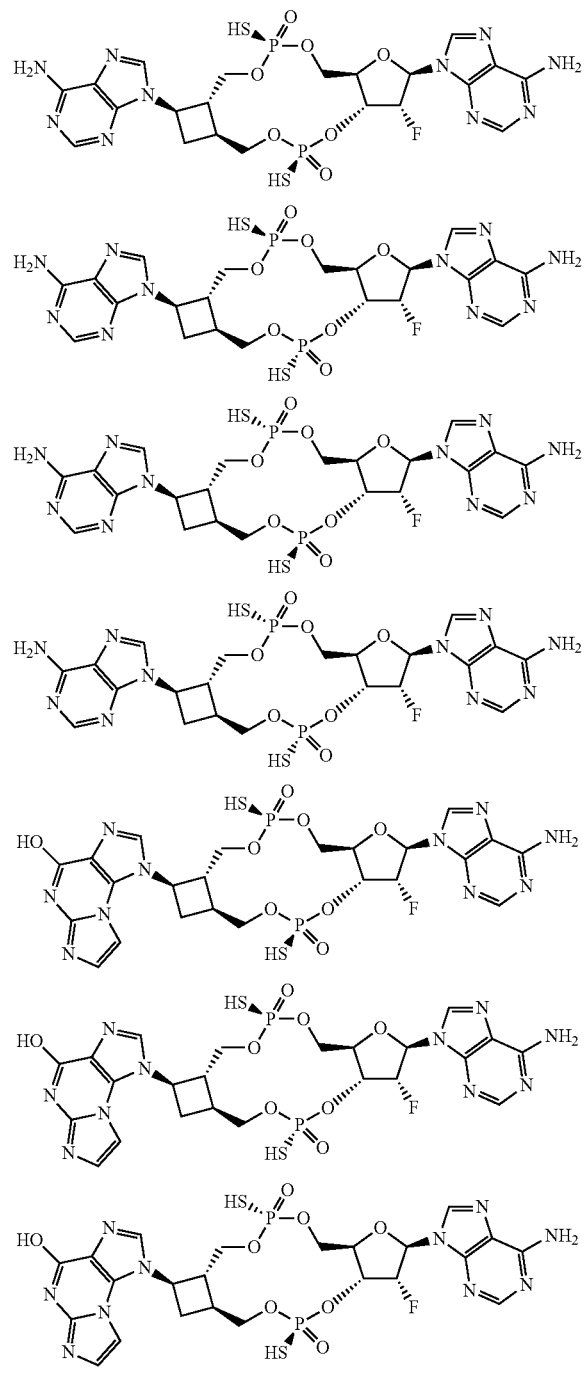
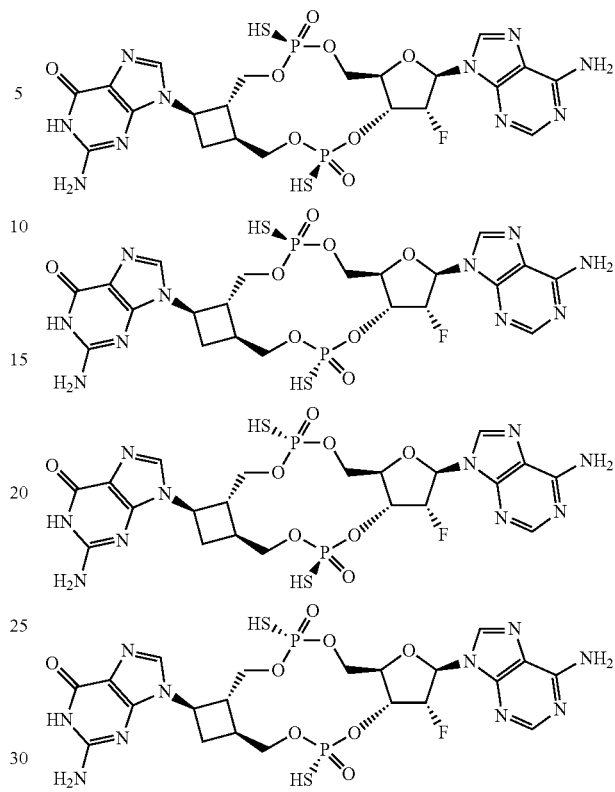
or a pharmaceutically acceptable salt, tautomer or stereoisomer thereof.
20. A compound of formula II
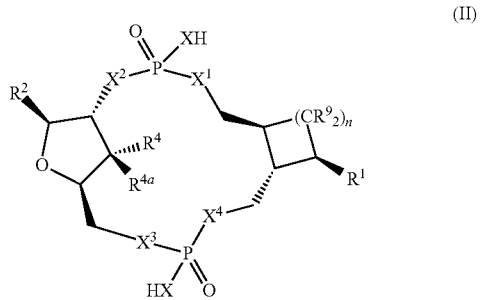
wherein
X is O or S;
$X^1$, $X^2$, $X^3$ and $X^4$ are each independently O or NH;
$R^1$ and $R^2$ are each independently
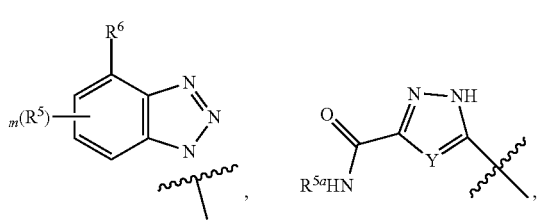

-continued

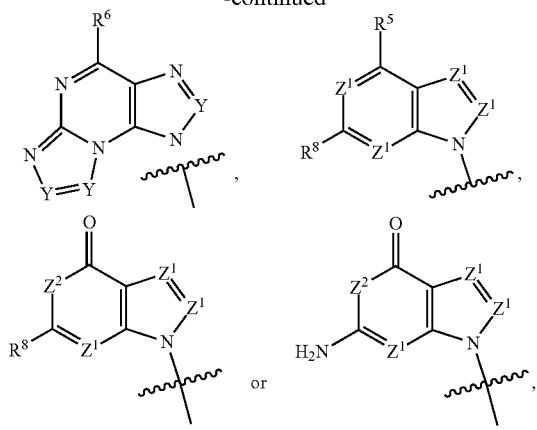

or

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^4$ is H, CH$_3$, halogen, NH$_2$ or OH;

R$^{4a}$ is H, CH$_3$, halogen, NH$_2$ or OH; or

R$^4$ and R$^{4a}$ may be taken together to form a 3-4 membered carbocycle; or

R$^4$ and R$^{4a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1;

or a pharmaceutically acceptable salt, tautomer or stereoisomer thereof.

21. The compound according to claim 20 of formula II

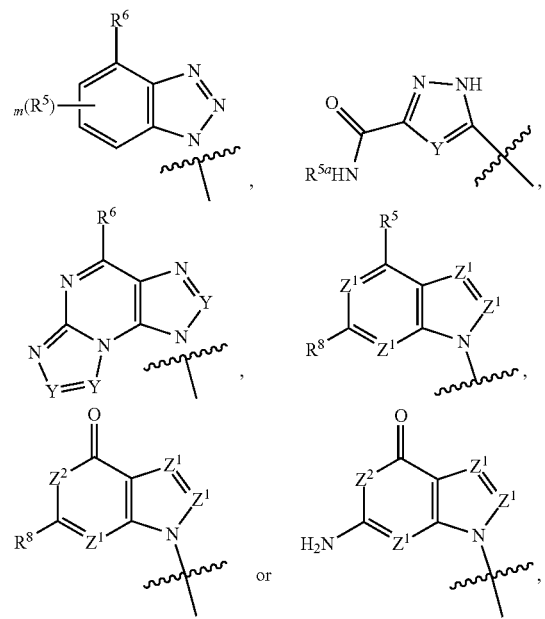

wherein

X is S;

X$^1$, X$^2$, X$^3$ and X$^4$ are each independently O or NH;

R$^1$ and R$^2$ are each independently

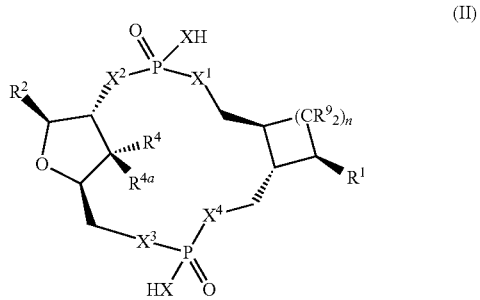

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^4$ is H, CH$_3$, halogen, NH$_2$ or OH;

R$^{4a}$ is H, CH$_3$, halogen, NH$_2$ or OH; or

R$^4$ and R$^{4a}$ may be taken together to form a 3-4 membered carbocycle; or

R$^4$ and R$^{4a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1;

or a pharmaceutically acceptable salt, tautomer or stereoisomer thereof.

22. The compound according to claim 20 of formula II

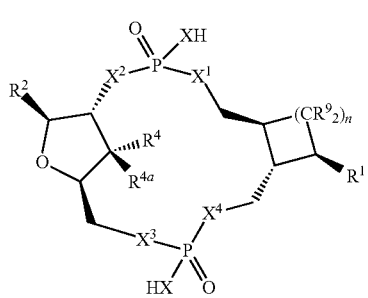
(II)

wherein

X is O,

X$^1$, X$^2$, X$^3$ and X$^4$ are each independently O or NH;

R$^1$ and R$^2$ are each independently

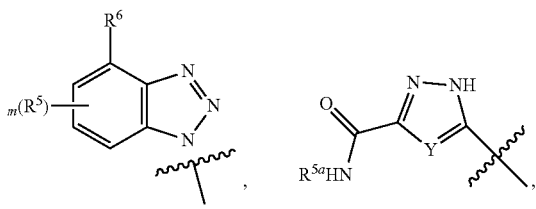

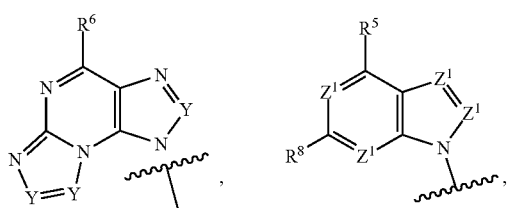

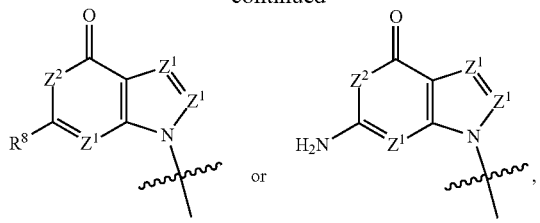

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^4$ is H, CH$_3$, halogen, NH$_2$ or OH;

R$^{4a}$ is H, CH$_3$, halogen, NH$_2$ or OH; or

R$^4$ and R$^{4a}$ may be taken together to form a 3-4 membered carbocycle; or

R$^4$ and R$^{4a}$ may be taken together to form a C═CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1;

or a pharmaceutically acceptable salt, tautomer or stereoisomer thereof.

23. The compound according to claim 20 of the formula

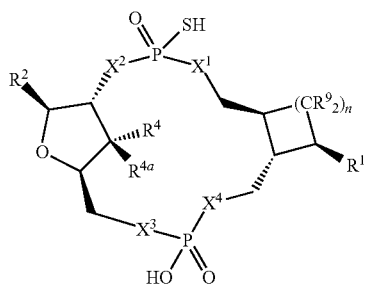

wherein
$X^1$, $X^2$, $X^3$ and $X^4$ are each independently O or NH;
$R^1$ and $R^2$ are each independently

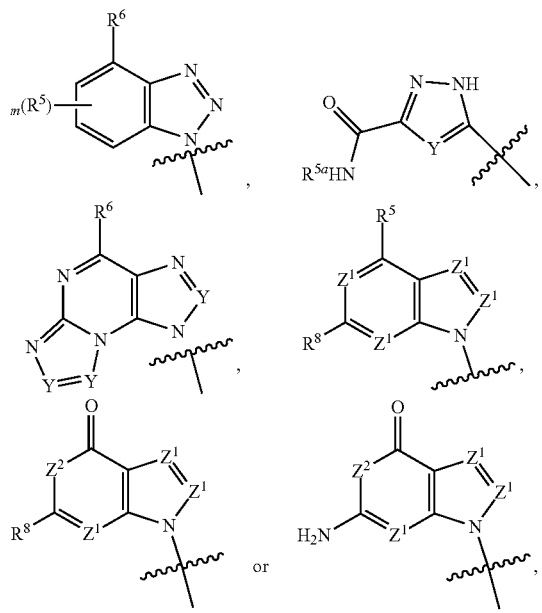

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H or $C_{1-3}$ alkyl;
$R^4$ is H, $CH_3$, halogen, $NH_2$ or OH;
$R^{4a}$ is H, $CH_3$, halogen, $NH_2$ or OH; or
$R^4$ and $R^{3a}$ may be taken together to form a 3-4 membered carbocycle; or
$R^4$ and $R^{3a}$ may be taken together to form a $C=CH_2$ substituent;
$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^9$ is H, halogen or methyl;
Y is $CR^5$ or N;
m is 0, 1, 2 or 3;
n is 0 or 1;
or a pharmaceutically acceptable salt, tautomer or stereoisomer thereof.

24. The compound according to claim 20 of the formula

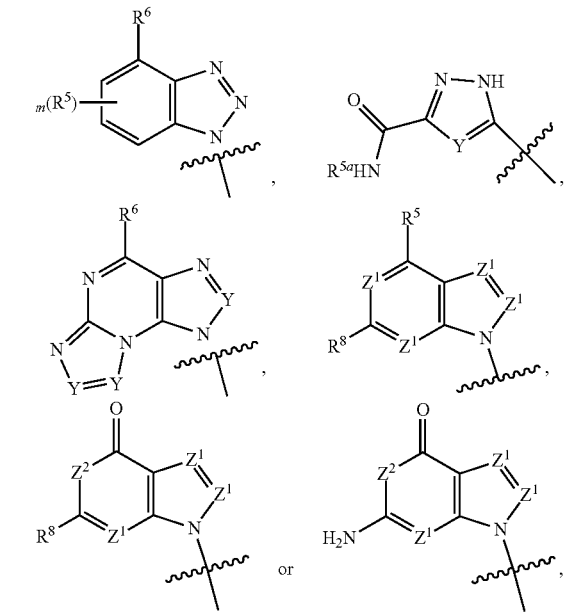

wherein
$X^1$, $X^2$, $X^3$ and $X^4$ are each independently O or NH;
$R^1$ and $R^2$ are each independently

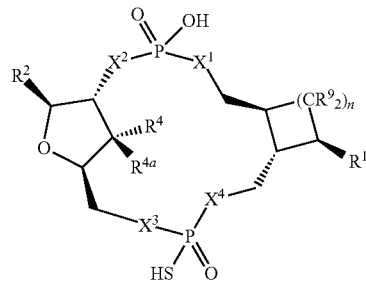

$Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H or $C_{1-3}$ alkyl;

$R^4$ is H, $CH_3$, halogen, $NH_2$ or OH;

$R^{4a}$ is H, $CH_3$, halogen, $NH_2$ or OH; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^9$ is H, halogen or methyl;

Y is $CR^5$ or N;

m is 0, 1, 2 or 3;

n is 0 or 1;

or a pharmaceutically acceptable salt, tautomer or stereoisomer thereof.

25. The compound according to claim 20 of the formula

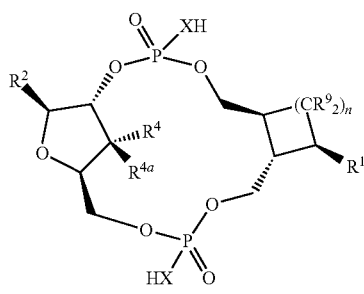

wherein

X is O or S;

$R^1$ and $R^2$ are each independently

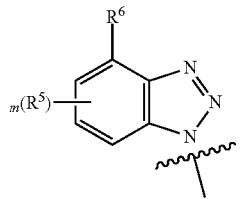 , 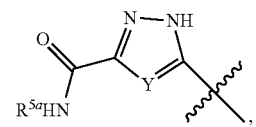 ,

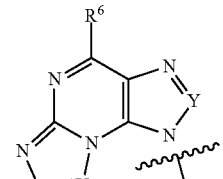 , 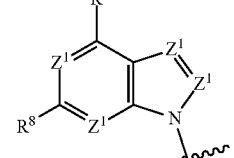 ,

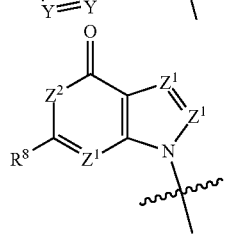 or 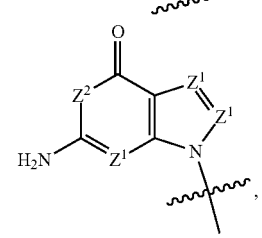 , $Z^1$ is N or $CR^a$;

$Z^2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H or $C_{1-3}$ alkyl;

$R^4$ is H, $CH_3$, halogen, $NH_2$ or OH;

$R^{4a}$ is H, $CH_3$, halogen, $NH_2$ or OH; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1;

or a pharmaceutically acceptable salt, tautomer or stereoisomer thereof.

26. The compound according to claim 20 of the formula

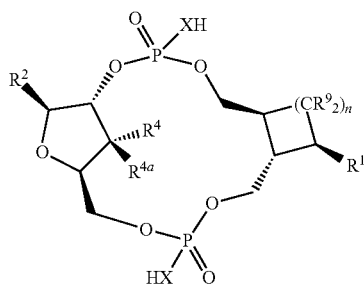

wherein
X is O or S;
X$^1$, X$^2$, X$^3$ and X$^4$ are each independently O or NH;
R$^1$ and R$^2$ are each independently

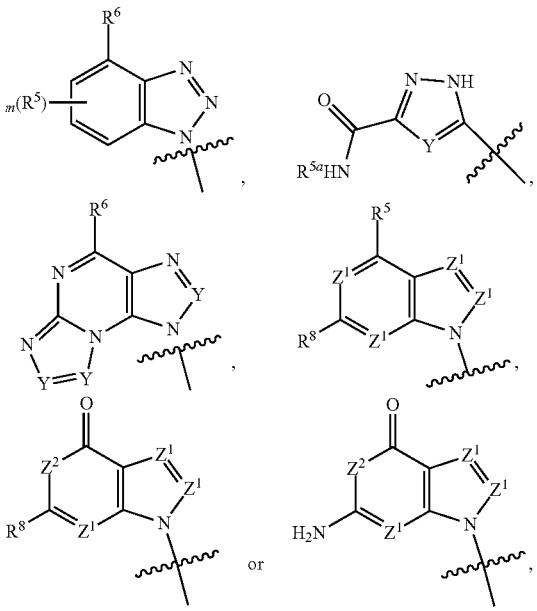

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^4$ is F;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^5$ or N;

m is 0, 1, 2 or 3;

n is 0 or 1;

or a pharmaceutically acceptable salt, tautomer or stereoisomer thereof.

27. The compound according to claim 20 of the formula

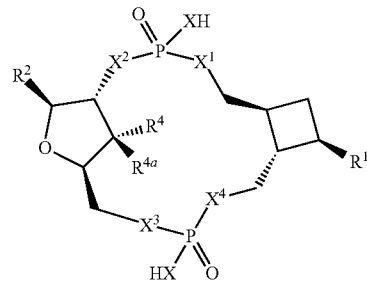

wherein
X is O or S;
X$^1$, X$^2$, X$^3$ and X$^4$ are each independently O or NH;
R$^1$ and R$^2$ are each independently

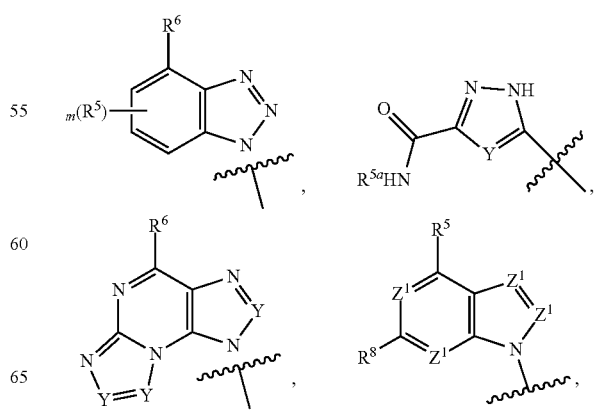

289

-continued

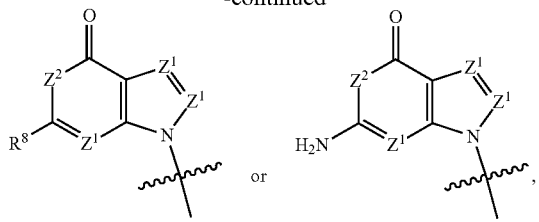

or $Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl;
$R^4$ is H, $CH_3$, halogen, $NH_2$ or OH;
$R^{4a}$ is H, $CH_3$, halogen, $NH_2$ or OH; or
$R^{4a}$ is H, $CH_3$, halogen, $NH_2$ or OH; or
$R^4$ and $R^{4a}$ may be taken together to form a 3-4 membered carbocycle; or
$R^4$ and $R^{4a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
Y is $CR^5$ or N;
m is 0, 1, 2 or 3;
or a pharmaceutically acceptable salt, tautomer or stereoisomer thereof.

28. The compound according to claim 20 of the formula

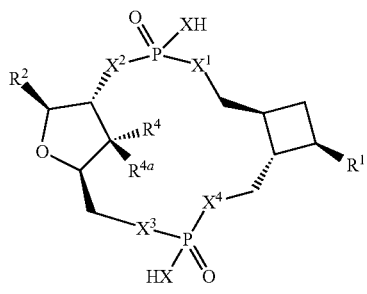

290 wherein
X is S,
$X^1$, $X^2$, $X^3$ and $X^4$ are each independently O or NH;
$R^1$ and $R^2$ are each independently

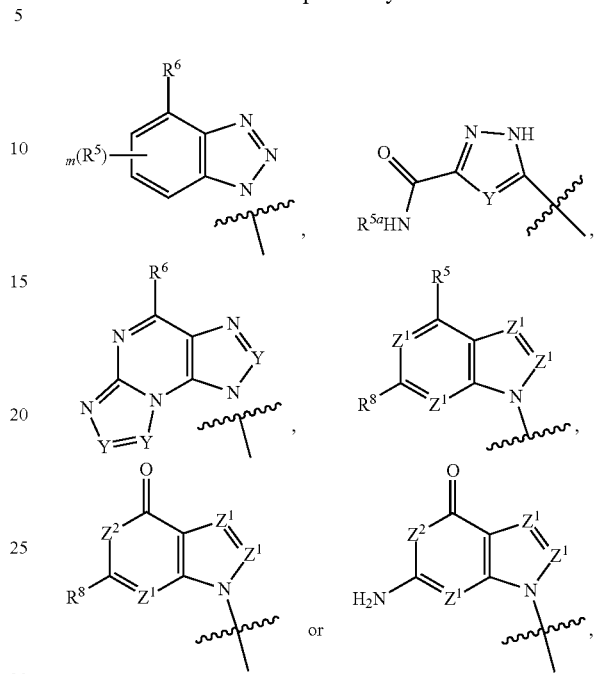

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl;
$R^4$ is H, $CH_3$, halogen, $NH_2$ or OH;
$R^{4a}$ is H, $CH_3$, halogen, $NH_2$ or OH; or
$R^4$ and $R^{4a}$ may be taken together to form a 3-4 membered carbocycle; or
$R^4$ and $R^{4a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

29. The compound according to claim 20 of the formula

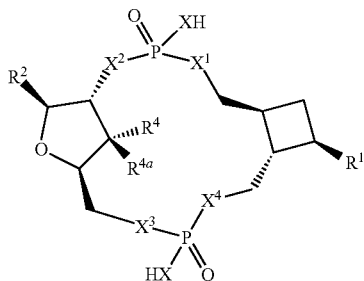

wherein

X is O;

X$^1$, X$^2$, X$^3$ and X$^4$ are each independently O or NH;

R$^1$ and R$^2$ are each independently

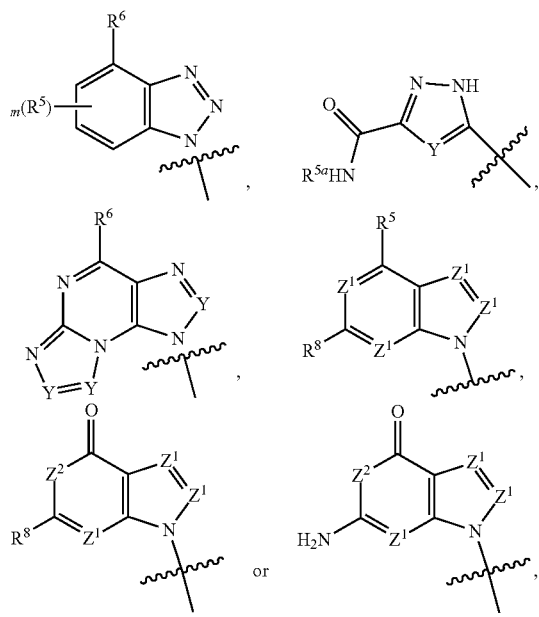

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^4$ is H, CH$_3$, halogen, NH$_2$ or OH;

R$^{4a}$ is H, CH$_3$, halogen, NH$_2$ or OH; or

R$^4$ and R$^{4a}$ may be taken together to form a 3-4 membered carbocycle; or

R$^4$ and R$^{4a}$ may be taken together to form a C═CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

30. The compound according to claim 20 of the formula

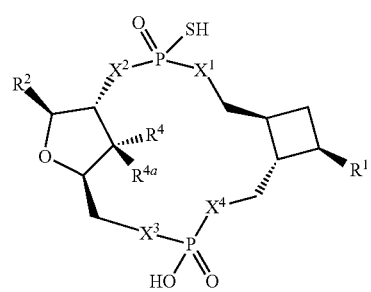

wherein

X$^1$, X$^2$, X$^3$ and X$^4$ are each independently O or NH;

R$^1$ and R$^2$ are each independently

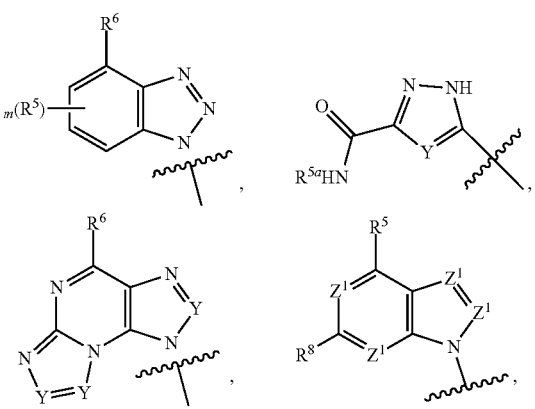

-continued

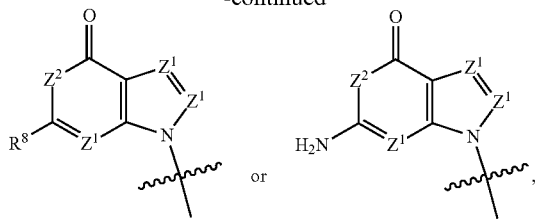

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$ C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;
$R^{a1}$ is H or $C_{1-3}$ alkyl;
$R^4$ is H, $CH_3$, halogen, $NH_2$ or OH;
$R^{4a}$ is H, $CH_3$, halogen, $NH_2$ or OH; or
$R^4$ and $R^{4a}$ may be taken together to form a 3-4 membered carbocycle; or
$R^4$ and $R^{4a}$ may be taken together to form a $C=CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
Y is $CR^5$ or N;
m is 0, 1, 2 or 3;
or a pharmaceutically acceptable salt, tautomer or stereoisomer thereof.

31. The compound according to claim 20 of the formula

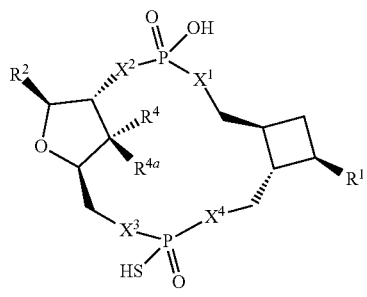

wherein
$X^1$, $X^2$, $X^3$ and $X^4$ are each independently O or NH;
$R^1$ and $R^2$ are each independently

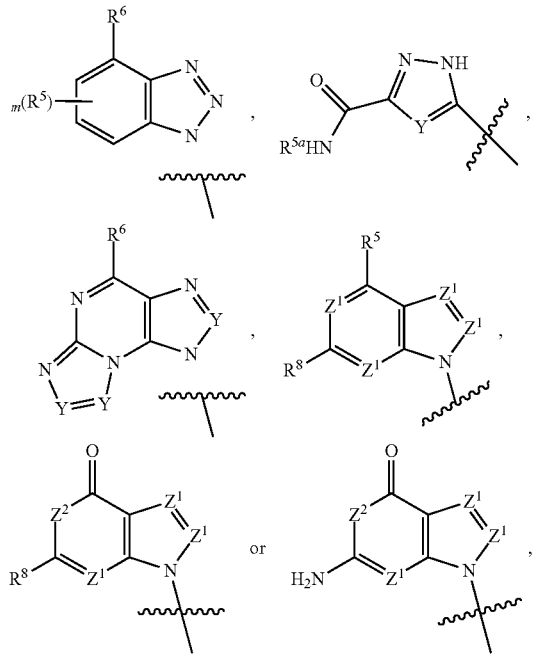

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$ C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;
$R^{a1}$ is H or $C_{1-3}$ alkyl;
$R^4$ is H, $CH_3$, halogen, $NH_2$ or OH;
$R^{4a}$ is H, $CH_3$, halogen, $NH_2$ or OH; or
$R^4$ and $R^{4a}$ may be taken together to form a 3-4 membered carbocycle; or
$R^4$ and $R^{4a}$ may be taken together to form a $C=CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

32. The compound according to claim 20 of the formula

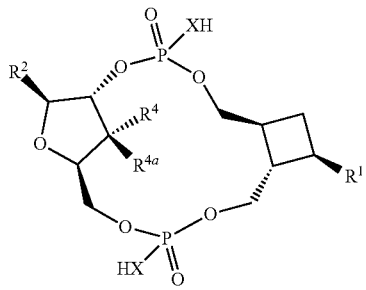

wherein
X is O or S;
R$^1$ and R$^2$ are each independently

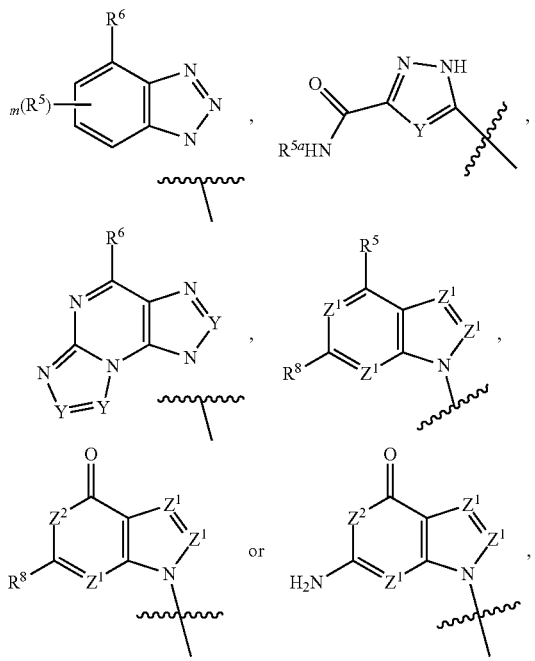

Z$^1$ is N or CR$^a$;
Z$^2$ is NR$^b$;
R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^4$ is H, CH$_3$, halogen, NH$_2$ or OH;

R$^{4a}$ is H, CH$_3$, halogen, NH$_2$ or OH; or

R$^4$ and R$^{4a}$ may be taken together to form a 3-4 membered carbocycle; or

R$^4$ and R$^{4a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

33. The compound according to claim 20 of the formula

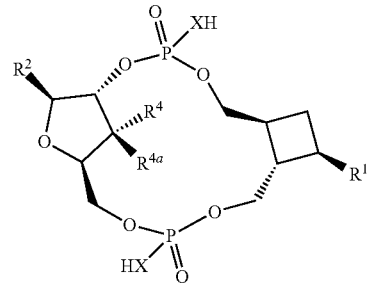

wherein
X is S;
R$^1$ and R$^2$ are each independently

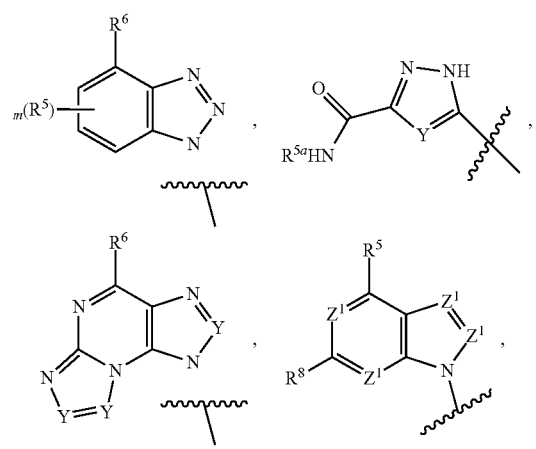

-continued

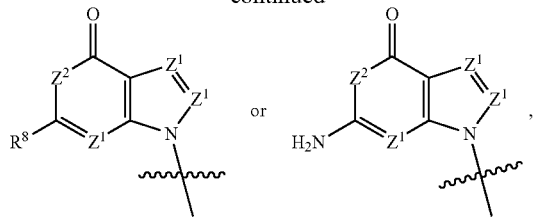

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl;
$R^4$ is H, $CH_3$, halogen, $NH_2$ or OH;
$R^{4a}$ is H, $CH_3$, halogen, $NH_2$ or OH; or
$R^4$ and $R^{4a}$ may be taken together to form a 3-4 membered carbocycle; or
$R^4$ and $R^{4a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
Y is $CR^5$ or N;
m is 0, 1, 2 or 3;
or a pharmaceutically acceptable salt, tautomer or stereoisomer thereof.

34. The compound according to claim 20 of the formula

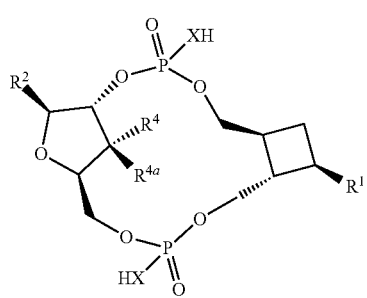

wherein
X is O;
$R^1$ and $R^2$ are each independently

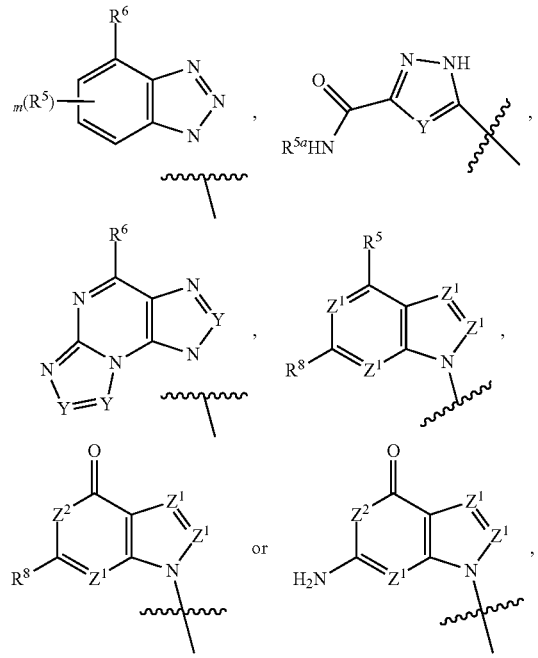

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl;
$R^4$ is H, $CH_3$, halogen, $NH_2$ or OH;
$R^{4a}$ is H, $CH_3$, halogen, $NH_2$ or OH; or
$R^4$ and $R^{4a}$ may be taken together to form a 3-4 membered carbocycle; or
$R^4$ and $R^{4a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

35. The compound according to claim 20 of the formula

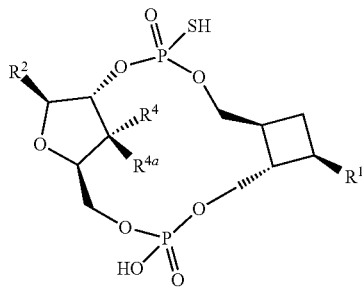

wherein

R$^1$ and R$^2$ are each independently

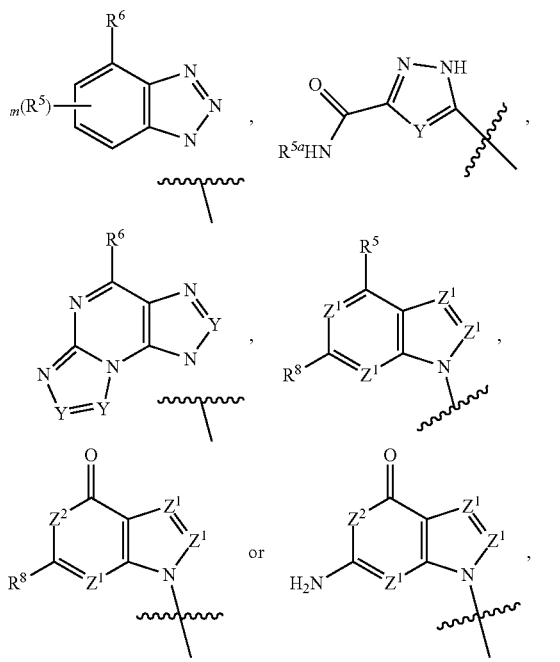

Z$^1$ is N or CR$^a$;

Z$^2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H or C$_{1-3}$ alkyl;

R$^4$ is H, CH$_3$, halogen, NH$_2$ or OH;

R$^{4a}$ is H, CH$_3$, halogen, NH$_2$ or OH; or

R$^4$ and R$^{4a}$ may be taken together to form a 3-4 membered carbocycle; or

R$^4$ and R$^{4a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

Y is CR$^5$ or N;

m is 0, 1, 2 or 3;

or a pharmaceutically acceptable salt, tautomer or stereoisomer thereof.

36. The compound according to claim 20 of the formula

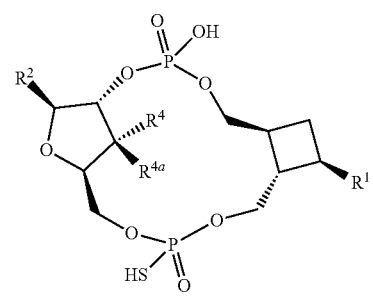

wherein

R$^1$ and R$^2$ are each independently

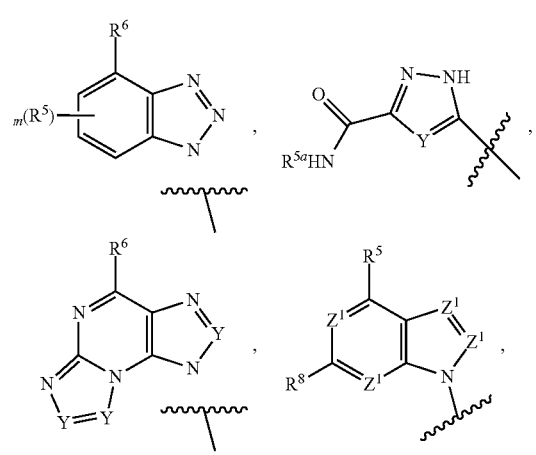

-continued

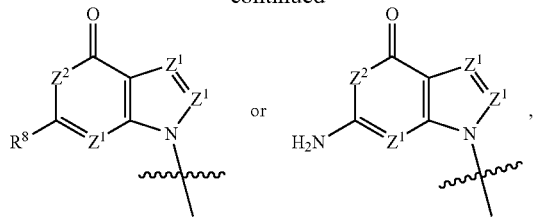

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;
$R^{a1}$ is H or $C_{1-3}$ alkyl;
$R^4$ is H, $CH_3$, halogen, $NH_2$ or OH;
$R^{4a}$ is H, $CH_3$, halogen, $NH_2$ or OH; or
$R^4$ and $R^{4a}$ may be taken together to form a 3-4 membered carbocycle; or
$R^4$ and $R^{4a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
Y is $CR^5$ or N;
m is 0, 1, 2 or 3;
or a pharmaceutically acceptable salt, tautomer or stereoisomer thereof.

37. The compound according to claim 20 of the formula

4

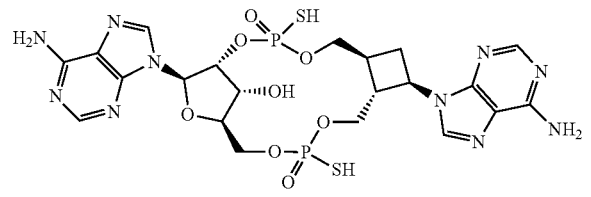

-continued

11

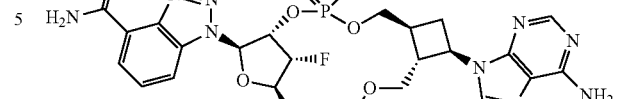

14

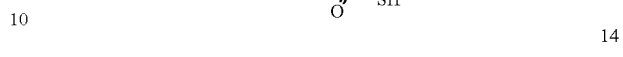

15

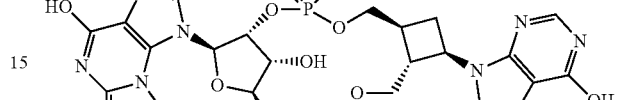

or a pharmaceutically acceptable salt, tautomer or stereoisomer thereof.

38. A compound which is
(1R,6S,8R,9R,15R,17R,18R)-8,17-bis(6-amino-9H-purin-9-yl)-18-fluoro-3,12-disulfanyl-2,4, 11,13,16-pentaoxa-3λ⁵,12λ⁵-diphosphatricyclo[13.3.0.0⁶,⁹]octadecane-3,12-dione;
(1R,6S,8R,9R,15R,17R,18R)-17-(6-amino-9H-purin-9-yl)-18-fluoro-3,12-dihydroxy-8-{4-hydroxy-1H-imidazo[2,1-b]purin-1-yl}-2,4,11,13,16-pentaoxa-3λ⁵, 12λ⁵-diphosphatricyclo[13.3.0.0⁶,⁹]octadecane-3,12-dithione;
(1R,6S,8R,9R,15R,17R,18R)-8,17-bis(6-amino-9H-purin-9-yl)-3,12,18-trihydroxy-2,4,11,13, 16-pentaoxa-3λ²,12λ⁵-diphosphatricyclo[13.2.1.0⁶,⁹]octadecane-3, 12-dithione;
9-[(1R,6 S, 8R, 9R,15R,17R,18R)-17-(6-amino-9H-purin-9-yl)-18-fluoro-3,12-dihydroxy-3,12-disulfanylidene-2,4,11,13,16-pentaoxa-3λ⁵,12λ⁵-diphosphatricyclo[13.3.0.0⁶,⁹]octadecan-8-yl]-6,9-dihydro-1H-purin-6-one;
(1S,6S,8R,9R,15R,17R)-8-(6-amino-9H-purin-9-yl)-17-{4-chloro-7H-pyrrolo[2,3-d]pyrimidin-7-yl}-3-hydroxy-12-sulfanyl-3-sulfanylidene-2,4,11,13,16-pentaoxa-3λ⁵,12λ⁵-diphosphatricyclo[1 3.3.0.0⁶,⁹]octadecan-12-one;
(1R,6S,8R,9R,15R,17R,18S)-8-(6-amino-9H-purin-9-yl)-17-{4-chloro-7H-pyrrolo[2,3-d]pyrimidin-7-yl}-18-fluoro-3,12-dihydroxy-2,4,11,13,16-pentaoxa-3λ⁵, 12λ⁵-diphosphatricyclo[13.3.0.0⁶,⁹]octadecane-3,12-dithione;
(1R,6S,8R,9R,15R,17R,18S)-17-{4-amino-7H-pyrrolo[2,3-d]pyrimidin-7-yl}-8-(6-amino-9H-purin-9-yl)-18-fluoro-3,12-dihydroxy-2,4,11,13,16-pentaoxa-3λ⁵, 12λ⁵-diphosphatricyclo[13.3.0.0⁶,⁹]octadecane-3,12-dithione
1-[(1R,6S,8R,9R,15R,17R,18R)-8-(6-amino-9H-purin-9-yl)-18-fluoro-3,12-dihydroxy-3,12-disulfanylidene-2, 4,11,13,16-pentaoxa-3$\lambda^5$,12$\lambda^5$-diphosphatricyclo [13.3.0.0$^{6,9}$]octadecan-17-yl]-1H,4H,5H-imidazo[2,1-b]purin-4-one;

(1R,6S,8R,9R,15R,17R,18R)-8,17-bis(6-amino-9H-purin-9-yl)-18-fluoro-3,12-dihydroxy-2,4,11,13,16-pentaoxa-3$\lambda^5$,12$\lambda^5$-diphosphatricyclo[13.3.0.0$^{6,9}$]octadecane-3,12-dione;

1-[(1S,6S,8R,9R,15R,17R,18R)-8-(6-amino-9H-purin-9-yl)-18-fluoro-3,12-dihydroxy-3,12-disulfanylidene-2,4,11,13,16-pentaoxa-3$\lambda^5$,12$\lambda^5$-diphosphatricyclo [13.3.0.0$^{6,9}$]octadecan-17-yl]-1H-1,2,3-benzotriazole-4-carboxamide;

1-[(1R,6S,8R,9R,15R,17R,18R)-8-(6-amino-9H-purin-9-yl)-18-fluoro-3,12-dihydroxy-3,12-disulfanylidene-2,4,11,13,16-pentaoxa-3$\lambda^5$,12$\lambda^5$-diphosphatricyclo [13.3.0.0$^{6,9}$]octadecan-17-yl]-1H-1,2,3-benzotriazole-4-carboxamide;

1-[(1R,6S,8R,9R,15R,17R,18R)-17-(6-amino-9H-purin-9-yl)-18-fluoro-3,12-dihydroxy-3,12-disulfanylidene-2,4, 11,13,16-pentaoxa-3$\lambda^5$,12$\lambda^5$-diphosphatricyclo [13.3.0.0$^{6,9}$]octadecan-8-yl]-1H-1,2,3-benzotriazole-4-carboxamide;

(1R,6S,8R,9R,15R,17R,18R)-18-hydroxy-8-(6-hydroxy-9H-purin-9-yl)-17-{4-oxo-1H,4H,5H-imidazo[2,1-b]purin-1-yl}-3,12-disulfanyl-2,4,11,13,16-pentaoxa-3$\lambda^5$,12$\lambda^5$-diphosphatricyclo[13.2.1.0$^{6,9}$]octadecane-3,12-dione;

(1R,6S,8R,9R,15R,17R,18R)-8-(6-amino-9H-purin-9-yl)-3,12,18-trihydroxy-17-{4-hydroxy-1H-imidazo[2,1-b]purin-1-yl}-2,4,11,13,16-pentaoxa-3$\lambda^5$,12$\lambda^5$-diphosphatricyclo[13.2.1.0$^{6,9}$]octadecane-3,12-dithione;

(1S,6S,8R,9R, 15R, 17R, 18R)-8-(6-amino-9H-purin-9-yl)-3,12,18-trihydroxy-17-(6-hydroxy-9H-purin-9-yl)-2,4, 11,13,16-pentaoxa-3$\lambda^5$, 12$\lambda^5$-diphosphatricyclo [13.3.0.0$^{6,9}$]octadecane-3,12-dithione;

(1R,6S,8R,9R,15R,17R,18S)-8,17-bis(6-amino-9H-purin-9-yl)-18-fluoro-3,12-dihydroxy-2,4,11,13,16-pentaoxa-3$\lambda^5$,12$\lambda^5$-diphosphatricyclo[13.3.0.0$^{6,9}$]octadecane-3,12-dithione; and 2-amino-9-[(1R,6S,8R,9R,15R,17R,18R)-17-(6-amino-9H-purin-9-yl)-18-fluoro-3,12-dihydr oxy-3,12-disulfanylidene-2,4,11,13,16-pentaoxa-3$\lambda^5$,12$\lambda^5$-diphosphatricyclo[13.3.0.0$^{6,9}$]octadecan-8-yl]-6,9-dihydro-1H-purin-6-one or a pharmaceutically acceptable salt, tautomer or stereoisomer thereof.

39. The compound according to claim 38 which is
(1R,6S,8R,9R,15R,17R,18R)-8,17-bis(6-amino-9H-purin-9-yl)-18-fluoro-3,12-disulfanyl-2,4,11,13,16-pentaoxa-3$\lambda^5$,12$\lambda^5$-diphosphatricyclo[13.3.0.0$^{6,9}$]octadecane-3,12-di one;

(1R,6S, 8R,9R,15R,17R,18R)-17-(6-amino-9H-purin-9-yl)-18-fluoro-3,12-dihydroxy-8-{4-hydroxy-1 H-imidazo[2,1-b]purin-1-yl}-2,4,11,13,16-pentaoxa-3$\lambda^5$, 12$\lambda^5$-diphosphatricyclo[13.3.0.0$^{6,9}$]octadecane-3,12-dithione;

2-amino-9-[(1R,6S,8R,9R,15R,17R,18R)-17-(6-amino-9H-purin-9-yl)-18-fluoro-3,12-dihydroxy-3,12-disulfanylidene-2,4,11,13,16-pentaoxa-3$\lambda^5$,12$\lambda^5$-diphosphatricyclo[13.3.0.0$^{6,9}$]octadecan-8-yl]-6,9-dihydro-1H-purin-6-one or a pharmaceutically acceptable salt, tautomer or stereoisomer thereof.

40. A compound according to claim 1 wherein the compound has an $EC_{50}$<100 μM in the THP1 IRF3 Reporter Assay.

41. A compound according to claim 20 wherein the compound has an $EC_{50}$<100 μM in the THP1 NFkB Reporter Assay.

42. A pharmaceutical composition comprising a compound according to claim 1 or a pharmaceutically acceptable salt thereof and one or more pharmaceutically acceptable carriers, diluents or excipients.

43. A pharmaceutical composition comprising a compound according to claim 20 or a pharmaceutically acceptable salt thereof and one or more pharmaceutically acceptable carriers, diluents or excipients.

44. A combination pharmaceutical product comprising a compound according to claim 1 or a pharmaceutically acceptable salt thereof and one or more other therapeutically active agents.

45. A combination pharmaceutical product comprising a compound according to claim 20 or a pharmaceutically acceptable salt thereof and one or more other therapeutically active agents.

46. A compound according to claim 1 or a pharmaceutically acceptable salt thereof for use in the treatment of diseases or conditions that may be alleviated by the induction of an immune response via the STING pathway.

47. A compound according to claim 20 or a pharmaceutically acceptable salt thereof for use in the treatment of diseases or conditions that may be alleviated by the induction of an immune response via the STING pathway.

48. A method of treating diseases and conditions in which the modulation of STING is indicated in a subject in need thereof which comprises administering to said subject a therapeutically effective amount of compound according to claim 1 or a pharmaceutically acceptable salt thereof.

49. A method of treating diseases and conditions in which the modulation of STING is indicated in a subject in need thereof which comprises administering to said subject a therapeutically effective amount of compound according to claim 20 or a pharmaceutically acceptable salt thereof.

50. A method of treating cancer wherein the cancer is small cell lung cancer, non-small cell lung cancer, colorectal cancer, melanoma, renal cell carcinoma, head and neck cancer, Hodgkin's lymphoma, bladder cancer, esophageal carcinoma, gastric carcinoma, ovarian carcinoma, cervical carcinoma, pancreatic carcinoma, prostate carcinoma, breast cancers, urinary carcinoma, brain tumors, non-Hodgkin's lymphoma, acute lymphatic leukemia (ALL), chronic lymphatic leukemia (CLL), acute myeloid leukemia (AML), chronic myeloid leukemia (CML), hepatocellular carcinoma, multiple myeloma, gastrointestinal stromal tumors, or mesothelioma comprising administering to a subject in need thereof a therapeutically effective amount of one or more compounds according to claim 1 or a pharmaceutically acceptable salt thereof.

51. A method of treating cancer wherein the cancer is small cell lung cancer, non-small cell lung cancer, colorectal cancer, melanoma, renal cell carcinoma, head and neck cancer, Hodgkin's lymphoma, bladder cancer, esophageal carcinoma, gastric carcinoma, ovarian carcinoma, cervical carcinoma, pancreatic carcinoma, prostate carcinoma, breast cancers, urinary carcinoma, brain tumors, non-Hodgkin's lymphoma, acute lymphatic leukemia (ALL), chronic lymphatic leukemia (CLL), acute myeloid leukemia (AML), chronic myeloid leukemia (CML), hepatocellular carcinoma, multiple myeloma, gastrointestinal stromal tumors, or mesothelioma comprising administering to a subject in need thereof a therapeutically effective amount of one or more compounds according to claim 20 or a pharmaceutically acceptable salt thereof.

52. The method of claim 50 wherein the cancer is small cell lung cancer, non-small cell lung cancer, colorectal cancer, melanoma, renal cell carcinoma, head and neck cancer, Hodgkin's lymphoma or bladder cancer.

53. The method of claim 51 wherein the cancer is small cell lung cancer, non-small cell lung cancer, colorectal cancer, melanoma, renal cell carcinoma, head and neck cancer, Hodgkin's lymphoma or bladder cancer.

54. A compound of formula III

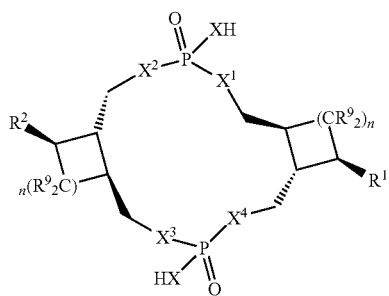

(III)

wherein
X is O or S;
$X^1$, $X^2$, $X^3$ and $X^4$ are each independently O or NH;
$R^1$ and $R^2$ are each independently

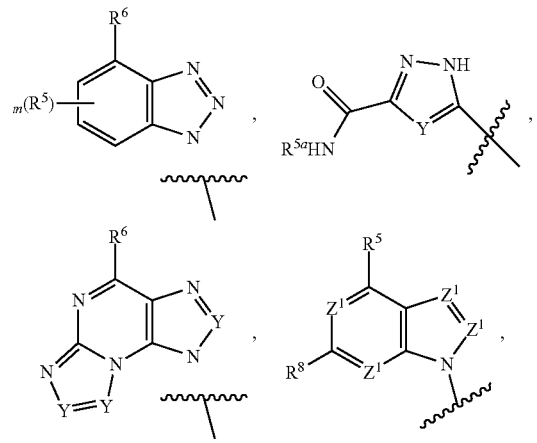

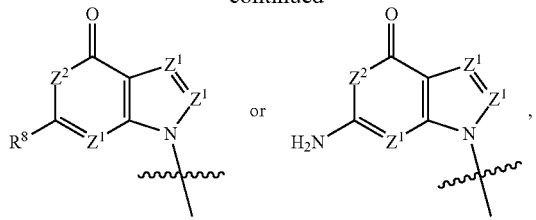

$Z^1$ is N or $CR^a$;
$Z^2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H or $C_{1-3}$ alkyl;
$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, halogen or methyl;
Y is $CR^5$ or N;
m is 0, 1, 2 or 3;
n is 0 or 1;
or a pharmaceutically acceptable salt, tautomer or stereoisomer thereof.

* * * * *

UNITED STATES PATENT AND TRADEMARK OFFICE
CERTIFICATE OF CORRECTION

PATENT NO. : 10,744,150 B2  
APPLICATION NO. : 16/047071  
DATED : August 18, 2020  
INVENTOR(S) : Brian Fink et al.

It is certified that error appears in the above-identified patent and that said Letters Patent is hereby corrected as shown below:

In the Claims

In Claim 1, Column 251, Line 37 (Approx.), delete "0" and insert -- O --, therefor.

In Claim 4, Column 256, Line 16 (Approx.), delete "0" and insert -- O --, therefor.

In Claim 5, Column 257, Line 45 (Approx.), delete "0" and insert -- O --, therefor.

In Claim 6, Column 259, Line 4-13 (Approx.), delete " 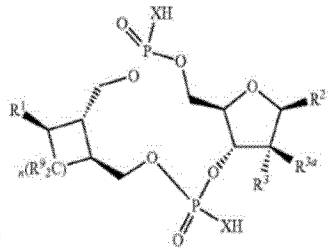 " and insert -- 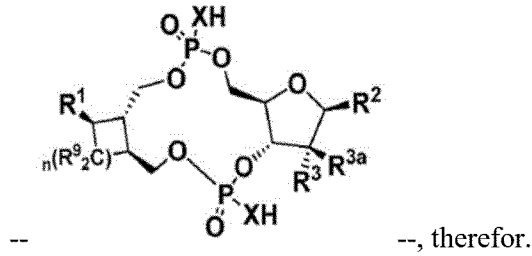 --, therefor.

In Claim 7, Column 261, Line 9-14 (Approx.), delete "$R^3$ is H, $CH_3$, halogen, $NH_2$ or OH;$R^{3a}$ is H, $CH_3$, halogen, $NH_2$ or OH; or $R^3$ and $R^{3a}$ may be taken together to form a 3-4 membered carbocycle; or $R^3$ and $R^{3a}$ may be taken together to form a C =CH2 substituent;" and insert -- $R^3$ is F; --, therefor.

In Claim 18, Column 276, Line 4-11 (Approx.) (Structure 10), delete

Signed and Sealed this  
Fifth Day of October, 2021

Drew Hirshfeld  
*Performing the Functions and Duties of the*  
*Under Secretary of Commerce for Intellectual Property and*  
*Director of the United States Patent and Trademark Office*

" 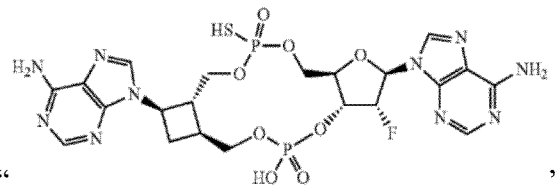 " and insert

-- 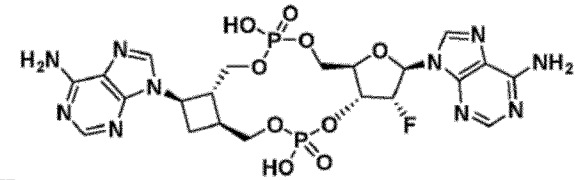 --, therefor.

In Claim 22, Column 281, Line 45 (Approx.), delete "O," and insert -- O; --, therefor.

In Claim 23, Column 283, Line 61, delete "$R^{3a}$" and insert -- $R^{4a}$ --, therefor.

In Claim 23, Column 283, Line 63, delete "$R^{3a}$" and insert -- $R^{4a}$ --, therefor.

In Claim 27, Column 289, Line 26, delete "halogen, NH2" and insert -- halogen --, therefor.

In Claim 28, Column 290, Line 2, delete "S," and insert -- S; --, therefor.

In Claim 38, Column 302, Line 34, delete "4, 11," and insert -- 4,11, --, therefor.

In Claim 38, Column 302, Line 43-44, delete "13, 16-pentaoxa-$3\lambda^2$," and insert -- 13,16-pentaoxa-$3\lambda^5$, --, therefor.

In Claim 38, Column 302, Line 46, delete "6 S," and insert -- 6S, --, therefor.

In Claim 38, Column 302, Line 54, delete "[1 3.3.0.0$^{6,9}$]" and insert -- [13.3.0.0$^{6,9}$] --, therefor.

In Claim 38, Column 302, Line 65, delete "dithione" and insert -- dithione; --, therefor.

In Claim 38, Column 303, Line 20, delete "4, 11," and insert -- 4,11, --, therefor.

In Claim 38, Column 303, Line 33, delete "9R, 15R, 17R, 18R)" and insert -- 9R,15R,17R,18R) --, therefor.

In Claim 38, Column 303, Line 35, delete "4, 11,13,16-pentaoxa-$3\lambda^5$, $12\lambda^5$" and insert -- 4,11,13,16-pentaoxa-$3\lambda^5$,$12\lambda^5$ --, therefor.

In Claim 38, Column 303, Line 42, delete "12-dihydr oxy-3," and insert -- 12-dihydroxy-3, --, therefor.

In Claim 39, Column 303, Line 52, delete "12-di one;" and insert -- 12-dione; --, therefor.

CERTIFICATE OF CORRECTION (continued)
U.S. Pat. No. 10,744,150 B2

In Claim 39, Column 303, Line 53, delete "6S, 8R," and insert -- 6S,8R, --, therefor.

In Claim 39, Column 303, Line 54, delete "4-hydroxy-1 H" and insert -- 4-hydroxy-1H --, therefor.

In Claim 54, Column 305, Line 27 (Approx.), delete "0" and insert -- O --, therefor.

In Claim 54, Column 305, Line 40-47 (Approx.), delete " 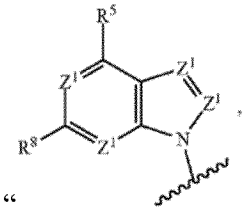 " and insert -- 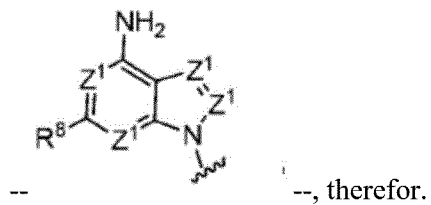 --, therefor.

SEQUENCE LISTING

<160> NUMBER OF SEQ ID NOS: 2

<210> SEQ ID NO 1
<211> LENGTH: 210
<212> TYPE: PRT
<213> ORGANISM: Artificial Sequence
<220> FEATURE:
<223> OTHER INFORMATION: Homosapien

<400> SEQUENCE: 1

Met Gly Ser Ser His His His His His Ser Ser Gly Glu Thr Val
1               5                   10                  15

Arg Phe Gln Gly His Met Ser Val Ala His Gly Leu Ala Trp Ser Tyr
            20                  25                  30

Tyr Ile Gly Tyr Leu Arg Leu Ile Leu Pro Glu Leu Gln Ala Arg Ile
        35                  40                  45

Arg Thr Tyr Asn Gln His Tyr Asn Asn Leu Leu Arg Gly Ala Val Ser
    50                  55                  60

Gln Arg Leu Tyr Ile Leu Leu Pro Leu Asp Cys Gly Val Pro Asp Asn
65              70                  75                  80

Leu Ser Met Ala Asp Pro Asn Ile Arg Phe Leu Asp Lys Leu Pro Gln
            85                  90                  95

Gln Thr Gly Asp Arg Ala Gly Ile Lys Asp Arg Val Tyr Ser Asn Ser
            100                 105                 110

Ile Tyr Glu Leu Leu Glu Asn Gly Gln Arg Ala Gly Thr Cys Val Leu
        115                 120                 125

Glu Tyr Ala Thr Pro Leu Gln Thr Leu Phe Ala Met Ser Gln Tyr Ser
    130                 135                 140

Gln Ala Gly Phe Ser Arg Glu Asp Arg Leu Glu Gln Ala Lys Leu Phe
145             150                 155                 160

Cys Arg Thr Leu Glu Asp Ile Leu Ala Asp Ala Pro Glu Ser Gln Asn
            165                 170                 175

Asn Cys Arg Leu Ile Ala Tyr Gln Pro Ala Asp Asp Ser Ser Phe
            180                 185                 190

Ser Leu Ser Gln Glu Val Leu Arg His Leu Arg Gln Glu Glu Lys Glu
        195                 200                 205

Glu Val
    210

<210> SEQ ID NO 2
<211> LENGTH: 210
<212> TYPE: PRT
<213> ORGANISM: Artificial Sequence
<220> FEATURE:
<223> OTHER INFORMATION: Homosapien

<400> SEQUENCE: 2

Met Gly Ser Ser His His His His His Ser Ser Gly Glu Thr Val
1               5                   10                  15

Arg Phe Gln Gly His Met Ser Val Ala His Gly Leu Ala Trp Ser Tyr
            20                  25                  30

Tyr Ile Gly Tyr Leu Arg Leu Ile Leu Pro Glu Leu Gln Ala Arg Ile
        35                  40                  45

Arg Thr Tyr Asn Gln His Tyr Asn Asn Leu Leu Arg Gly Ala Val Ser
    50                  55                  60

Gln Arg Leu Tyr Ile Leu Leu Pro Leu Asp Cys Gly Val Pro Asp Asn
65              70                  75                  80

Leu Ser Met Ala Asp Pro Asn Ile Arg Phe Leu Asp Lys Leu Pro Gln
            85                  90                  95

Gln Thr Ala Asp Arg Ala Gly Ile Lys Asp Arg Val Tyr Ser Asn Ser
            100                 105                 110

Ile Tyr Glu Leu Leu Glu Asn Gly Gln Arg Ala Gly Thr Cys Val Leu
        115                 120                 125

Glu Tyr Ala Thr Pro Leu Gln Thr Leu Phe Ala Met Ser Gln Tyr Ser

| | | | | | | | | | | |
|---|---|---|---|---|---|---|---|---|---|---|
| | 130 | | | | 135 | | | | 140 | |
| Gln | Ala | Gly | Phe | Ser | Arg | Glu | Asp | Arg | Leu | Glu | Gln | Ala | Lys | Leu | Phe |
| 145 | | | | | 150 | | | | | 155 | | | | | 160 |
| Cys | Gln | Thr | Leu | Glu | Asp | Ile | Leu | Ala | Asp | Ala | Pro | Glu | Ser | Gln | Asn |
| | | | | 165 | | | | | 170 | | | | | 175 | |
| Asn | Cys | Arg | Leu | Ile | Ala | Tyr | Gln | Glu | Pro | Ala | Asp | Asp | Ser | Ser | Phe |
| | | | 180 | | | | | 185 | | | | | 190 | | |
| Ser | Leu | Ser | Gln | Glu | Val | Leu | Arg | His | Leu | Arg | Gln | Glu | Glu | Lys | Glu |
| | | 195 | | | | | 200 | | | | | 205 | | | |
| Glu | Val | | | | | | | | | | | | | | |
| | 210 | | | | | | | | | | | | | | |